US009572815B2

(12) United States Patent
Zuo et al.

(10) Patent No.: US 9,572,815 B2
(45) Date of Patent: Feb. 21, 2017

(54) METHODS AND COMPOSITIONS OF P27$^{KIP1}$ TRANSCRIPTIONAL MODULATORS

(71) Applicant: ST. JUDE CHILDREN'S RESEARCH HOSPITAL, Memphis, TN (US)

(72) Inventors: Jian Zuo, Memphis, TN (US); Taosheng Chen, Germantown, TN (US); Brandon Walters, Memphis, TN (US); Bryan Kuo, Memphis, TN (US); Bradley Walters, Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 14/774,597

(22) PCT Filed: Mar. 15, 2014

(86) PCT No.: PCT/US2014/029927
§ 371 (c)(1),
(2) Date: Sep. 10, 2015

(87) PCT Pub. No.: WO2014/145205
PCT Pub. Date: Sep. 18, 2014

(65) Prior Publication Data
US 2016/0030445 A1 Feb. 4, 2016

Related U.S. Application Data

(60) Provisional application No. 61/787,578, filed on Mar. 15, 2013, provisional application No. 61/938,404, filed on Feb. 11, 2014.

(51) Int. Cl.
*A61K 31/55* (2006.01)
*A61K 45/06* (2006.01)
*A61K 31/05* (2006.01)
*A61K 31/222* (2006.01)
*A61K 31/4418* (2006.01)
*A61K 38/17* (2006.01)
*A61K 35/12* (2015.01)
*A61K 31/44* (2006.01)
*C12N 5/071* (2010.01)

(52) U.S. Cl.
CPC .............. *A61K 31/55* (2013.01); *A61K 31/05* (2013.01); *A61K 31/222* (2013.01); *A61K 31/44* (2013.01); *A61K 31/4418* (2013.01); *A61K 35/12* (2013.01); *A61K 38/17* (2013.01); *A61K 38/1703* (2013.01); *A61K 45/06* (2013.01); *C12N 5/0602* (2013.01)

(58) Field of Classification Search
CPC .................................................... A61K 31/55
USPC ....................................................... 514/394
See application file for complete search history.

(56) References Cited

U.S. PATENT DOCUMENTS

| 5,543,158 | A | 8/1996 | Gref et al. |
|---|---|---|---|
| 7,132,406 | B2 | 11/2006 | Kil et al. |
| 7,206,639 | B2 | 4/2007 | Jacobsen et al. |
| 7,232,814 | B2 | 6/2007 | Meijer et al. |
| 7,470,673 | B2 | 12/2008 | Zoghbi et al. |
| 7,612,196 | B2 | 11/2009 | Khvorova et al. |
| 7,741,303 | B2 | 6/2010 | Kil et al. |
| 8,188,131 | B2 | 5/2012 | Edge et al. |
| 2003/0004351 | A1 | 1/2003 | Davis et al. |
| 2003/0181439 | A1 | 9/2003 | Meijer et al. |
| 2003/0203482 | A1* | 10/2003 | Kil .......................... A61K 31/00 435/325 |
| 2004/0237127 | A1 | 11/2004 | Zoghbi et al. |
| 2006/0002852 | A1 | 1/2006 | Saltzman et al. |
| 2006/0030837 | A1 | 2/2006 | McKenna et al. |
| 2006/0148829 | A1 | 7/2006 | Meijer et al. |
| 2006/0222652 | A1 | 10/2006 | Sebbel et al. |
| 2006/0251677 | A1 | 11/2006 | Bachmann et al. |
| 2007/0093878 | A1 | 4/2007 | Edge et al. |
| 2008/0145441 | A1 | 6/2008 | Penades et al. |
| 2009/0028910 | A1 | 1/2009 | DeSimone et al. |

(Continued)

FOREIGN PATENT DOCUMENTS

| WO | WO-1994/29469 A2 | 12/1994 |
|---|---|---|
| WO | WO-1997/00957 A1 | 1/1997 |

(Continued)

OTHER PUBLICATIONS

U.S. Appl. No. 61/938,404, filed on Feb. 11, 2014, Zuo et al.
PCT/US2014/029927, filed on Mar. 15, 2014, Zuo et al.
Adler Hj, Raphael Y (1996) New hair cells arise from supporting cell conversion in the acoustically damaged chick inner ear. Neuroscience letters vol. 205, 17-20.
Ahmed M, Wong Ey, Sun J, Xu J, Wang F, et al. (2012) Eya1-Six1 interaction is sufficient to induce hair cell fate in the cochlea by activating Atoh1 expression in cooperation with Sox2. Dev Cell vol. 22, 377-390.
Akazawa, C., et al. (1995) A Mammalian Helix-Loop-Helix Factor Structurally Related to the Product of Drosophila Proneural Gene *atonal* Is a Positive Transcriptional Regulator Expressed in the Developing Nervous System, J. Bioi. Chem. 270, 8730-8738.
Aletsee et al. (2001) The Disintegrin Kistrin Inhibits Neurite Extension from Spiral Ganglion Explants Cultured on Laminin, Audiology Neuro-Otology. vol. 6, 57-65.

(Continued)

Primary Examiner — Taofiq A Solola
(74) Attorney, Agent, or Firm — Ballard Spahr LLP

(57) ABSTRACT

In one aspect, the invention relates to pharmaceutical compositions comprising agents that activate the expression of Atoh1, or pharmaceutically acceptable salts, solvates, or polymorphs thereof; and agents that inhibit the expression of p27$^{Kip1}$, or pharmaceutically acceptable salts, solvates, or polymorphs thereof, which are useful for inducing the formation of cochlear hair cells; and methods of treating hearing impairments or disorders using the compositions. In one aspect, the invention relates to pharmaceutical compositions comprising β-catenin; and agents that activate the expression of Atoh1, or pharmaceutically acceptable salts, solvates, or polymorphs thereof. This abstract is intended as a scanning tool for purposes of searching in the particular art and is not intended to be limiting of the present invention.

20 Claims, 28 Drawing Sheets

(56) References Cited

U.S. PATENT DOCUMENTS

| | | | |
|---|---|---|---|
| 2009/0226525 | A1 | 9/2009 | De Los Rios et al. |
| 2009/0232780 | A1 | 9/2009 | Edge et al. |
| 2011/0304574 | A1* | 12/2011 | Harrison ............... G06F 1/1626 345/173 |
| 2011/0305674 | A1 | 12/2011 | Edge et al. |
| 2012/0328580 | A1 | 12/2012 | Edge et al. |
| 2013/0085112 | A1 | 4/2013 | Collard et al. |
| 2013/0210145 | A1 | 8/2013 | Edge |
| 2014/0371213 | A1 | 12/2014 | Berdini et al. |

FOREIGN PATENT DOCUMENTS

| | | |
|---|---|---|
| WO | WO-2006/117212 A2 | 11/2006 |
| WO | WO-2009/06999 A1 | 1/2009 |
| WO | WO-2009/010298 A2 | 1/2009 |
| WO | WO-2009/051837 A2 | 4/2009 |
| WO | WO-2010/047839 A1 | 4/2010 |
| WO | WO-2013/071415 A1 | 5/2013 |

OTHER PUBLICATIONS

Baird RA, Steyger PS, Schuff NR (1996) Mitotic and nonmitotic hair cell regeneration in the bullfrog vestibular otolith organs, Annals of the New York Academy of Sciences 781: 59-70.

Ben-Arie et al. (2000) Functional conservation of atonal and Math1 in the CNS and PNS, Development 127, 1039.

Ben-Arie, N., et al. (1996) Evolutionary conservation of sequence and expression of the bHLH protein Atonal suggests a conserved role in neurogenesis, Human Molecular Genetics, vol. 5, No. 9, 1207-1216.

Berminghan, et al. (1999) Math1: An Essential Gene for the Generation of Inner Ear Hair Cells, Science, vol. 284, 1837-1841.

Bertagnolli, M. M., et al. (2009) p27Kip1 in Stage III Colon Cancer: Implications for Outcome following Adjuvant Chemotherapy in Cancer and Leukemia Group B Protocol 89803, Clinical cancer research : an official journal of the American Association for Cancer Research vol. 15, No. 6, 2116-2122.

Boros et al. (1986) Expression vectors based on the rac fusion promoter, Gene., vol. 42, 97-100.

Bottini, C., et al. (2009) p27Kip1 is inactivated in human colorectal cancer by cytoplasmic localization associated with activation of Akt/PKB, International Journal of Oncology vol. 34, 69-77.

Brigande & Heller (2009) Quo vadis, hair cell regeneration?, Nature Neuroscience, vol. 12, No. 6, 679-685.

Brooker, R., et al. (2006) Notch ligands with contrasting functions: Jagged1 and Delta1 in the mouse inner ear, Development vol. 133, 1277-1286.

Brors, D., et al. (2003) EphA4 provides repulsive signals to developing cochlear ganglion neurites mediated through ephrin-B2 and -B3, Journal of Comparative Neurology vol. 462, 90-100.

Cafaro, et al. (2007) Atoh1 Expression Defines Activated Progenitors and Differentiating Hair Cells During Avian Hair Cell Regeneration, Dev. Dyn. vol. 236, 156-170.

Caiazzo M, et al. (2011) Direct generation of functional dopaminergic neurons from mouse and human fibroblasts. Nature vol. 476, 224-227.

Cariou, S., et al. (2000) Down-regulation of p21WAF1yCIP1 or p27Kip1 abrogates antiestrogenmediated cell cycle arrest in human breast cancer cells, Pnas Usa, vol. 97, No. 16, 9042-9046.

Carmon, K. S., et al. (2011) R-spondins function as ligands of the orphan receptors LGR4 and LGR5 to regulate Wnt/β-catenin signaling, PNAS, U.S.A. vol. 108, No. 28, 11452-11457.

Chai R, et al. (2012) Wnt signaling induces proliferation of sensory precursors in the postnatal mouse cochlea. PNAS U.S.A., vol. 109: 8167-8172.

Chai, R., et al. (2011) Dynamic Expression of Lgr4, a Wnt Target Gene, in the Developing and Mature Mouse Cochlea, JARO, vol. 12, 455-469.

Chang, B. L., et al. (2004) a Polymorphism in the CDKN1B Gene Is Associated with Increased Risk of Hereditary Prostate Cancer, Cancer Research vol. 64, 1997-1999.

Chellappa R, et al. (2008) Barhl1 regulatory sequences required for cell-specific gene expression and autoregulation in the inner ear and central nervous system. Mol Cell Biol Vol. 28, 1905-1914.

Chen P, Segil N (1999) p27(Kip1) links cell proliferation to morphogenesis in the developing organ of Corti. Development vol. 126, 1581-1590.

Chen, et al. (2002) the role of Math1 in inner ear development: Uncoupling the establishment of the sensory primordium from hair cell fate determination, Development vol. 129, 2495-2505.

Chu, I. M., et al. (2008) the Cdk inhibitor p27 in human cancer: prognostic potential and relevance to anticancer therapy, Nature reviews. Cancer vol. 8, 253-267.

Corwin JT, Cotanche DA (1988) Regeneration of sensory hair cells after acoustic trauma. Science vol. 240, 1772-1774.

Cox, et al., (2014) Spontaneous hair cell regeneration in the neonatal mouse cochlea in vivo. Development, vol. 141, 817-829.

Cox B.C., et al (2012) Conditional gene expression in the mouse inner ear using Cre-loxP, JARO vol. 13, 295-322.

Daudet, N., et al. (2002) Expression of members of Wnt and Frizzled gene families in the postnatal rat cochlea, Brain Res. Mol. Brain Res. vol. 105, 98-107.

Diao F, White Bh (2012) A novel approach for directing transgene expression in Drosophila: T2AGal4 in-frame fusion. Genetics vol. 190: 1139-1144.

Doerflinger, N.H., et al. (2003) Inducible Site-Specific Recombination in Myelinating Cells, Genesis vol. 35, 63-72.

Doetzlhofer A, White P, Lee YS, Groves A, Segil N (2006) Prospective identification and purification of hair cell and supporting cell progenitors from the embryonic cochlea. Brain Res vol. 1091, 282-288.

Elbashir, W., et al. (2001) RNA interference is mediated by 21- and 22-nucleotide RNAs, Genes & Development vol. 15, 188-200.

Fekete, et al. (1998) Hair Cells and Supporting Cells Share a Common Progenitor in the Avian Inner Ear, J. Neurosci. vol. 18, No. 19, 7811-7821.

Fire, a., et al. (1998) Potent and specific genetic interference by double-stranded RNA in Caenorhabditis elegans, Nature vol. 391, 806-811.

Flanagan, J. G., et al. (1999) a cytosine analog that confers enhanced potency to antisense oligonucleotides, PNAS USA vol. 96, 3513-3518.

Fujioka M, et al (2011) Generating mouse models of degenerative diseases using Cre/loxmediated in vivo mosaic cell ablation. J Clin Invest vol. 121, 2462-2469.

Gao J, Wu X, Zuo J (2004) Targeting hearing genes in mice, Brain Res Mol Brain Res vol. 132, 192-207.

Garcia, M. I., et al. (2009) LGR5 deficiency deregulates Wnt signaling and leads to precocious Paneth cell differentiation in the fetal intestine, Developmental Biology, vol. 331, 58-67.

Gillespie, L. N., et al. (2001) LIF is more potent than BDNF in promoting neurite outgrowth of mammalian auditory neurons in vitro, Neuro Report vol. 12, No. 2, 275-279.

Golub JS, Tong L, Ngyuen TB, Hume CR, Palmiter RD, et al. (2012) Hair cell replacement in adult mouse utricles after targeted ablation of hair cells with diphtheria toxin. J Neurosci vol. 32, 1509315105.

Gomez-Casati ME, Murtie J, Taylor B, Corfas G (2010) Cell-specific inducible gene recombination in postnatal inner ear supporting cells and glia, JARO vol. 11, 19-26.

Gross J, et al (2011) Expression analysis of prestin and selected transcription factors in newborn rats. Cell Mol Neurobiol vol. 31, 1089-1101.

Gubbels, et al. (2008) Functional auditory hair cells produced in the mammalian cochlea by in utero gene transfer, Nature vol. 455, 537-541.

Harada, N., et al. (1999) Intestinal polyposis in mice with dominant stable muttion of the 13-catenin gene, the EMBO Journal, vol. 18, No. 21, 5931-5942.

Hashimshony T, et al (2012) CEL-Seq: single-cell RNA-Seq by multiplexed linear amplification. Cell Rep vol. 2, 666-673.

(56) References Cited

OTHER PUBLICATIONS

Hayward, et al. (2005) Notch modulates Wnt signalling by associating with Armadillo/beta-catenin and regulating its transcriptional activity, Development vol. 132, 1819-1830.
He DZ, et al. (2010) Changes in plasma membrane structure and electromotile properties in prestin deficient outer hair cells, Cytoskeleton vol. 67, 43-55.
Helms et al. (1998) Progenitors of dorsal commissural interneurons are defined by MATH1 expression, Development vol. 125, 919-928.
Herbst, et al. (2009) Multiplexing a High-Throughput Liability Assay to Leverage Efficiencies, Assay and Drug Development Technologies, vol. 7, 294-303.
Huangfu D, et al. (2008) Induction of pluripotent stem cells by defined factors is greatly improved by small-molecule compounds. Nat Biotechnol vol. 26, 795-797.
Huch, M., et al. (2013) Lgr5+ liver stem cells, hepatic organoids and regenerative medicine, Regen. Med. vol. 8, No. 4, 385-387.
Hudspeth Aj (2000) Hearing and deafness. Neurobiology of Diseases, vol. 7: 511-514.
Ieda M, et al. (2010) Direct reprogramming of fibroblasts into functional cardiomyocytes by defined factors. Cell, vol. 142, 375-386.
Isaka et al. (1999) Short Communication Ectopic expression of the bHLH gene Math1 disturbs neural development, European Journal of Neuroscience. vol. 11, 2582-2588.
Izumikawa M, et al. (2005) Auditory hair cell replacement and hearing improvement by Atoh1 gene therapy in deaf mammals. Nat Med vol. 11, 271-276.
Jahan I, et al (2013) Beyond generalized hair cells: Molecular cues for hair cell types. Hear Res. vol. 297, 30-41.
Jarman, A. P., et al. (1993) atonal Is a Proneural Gene That Directs Chordotonal Organ Formation in the Drosophila Peripheral Nervous System, Cell, vol. 73, 1307-1321.
Jayasena, C. S., et al. (2008) Notch signaling augments the canonical Wnt pathway to specify the size of the otic placode, Development vol. 135, 2251-2261.
Jin, E. J., et al. (2001) Wnt and BMP Signaling Govern Lineage Segregation of Melanocytes in the Avian Embryo, Developmental Biology, vol. 233, 22-37.
Kamezis, a. N., et al. (2001) Loss of p27Kip1 enhances the transplantation efficiency of hepatocytes transferred into diseased livers, Journal of Clinical Investigation vol. 108, No. 3, 383-390.
Kang Sh, et al (2010) NG2+ CNS glial progenitors remain committed to the oligodendrocyte lineage in postnatal life and following neurodegeneration, Neuron, vol. 68, No. 4, 668-681.
Kanzaki S, et al. (2006) p27(Kip1) deficiency causes organ of Cortipathology and hearing loss. Hear Res vol. 214, 28-36.
Kawamoto, K., et al. (2003) Math1 Gene Transfer Generates New Cochlear Hair Cells in Mature Guinea Pigs in Vivo, Journal of Neuroscience vol. 23, No. 11, 4395-4400.
Kelly Mc, et al (2012) Atoh1 directs the formation of sensory mosaics and induces cell proliferation in the postnatal mammalian cochlea in vivo, Journal of Neuroscience vol. 32: 66996710.
Kelley, M. W. (2007) Cellular commitment and differentiation in the organ of Corti, Int. J. Dev. Bioi. vol. 51, 571-583.
Kiernan, a. E. (2013) Notch signaling during cell fate determination in the inner ear, Seminar in Cell Developmental Biology, vol. 24, 470-479.
Kiernan, a. E., et al. (2005) The Notch ligands DLL1 and JAG2 act synergistically to regulate hair cell development in the mammalian inner ear, Development vol. 132, 4353-4362.
Kiernan, a. E., et al. (2006) The Notch Ligand JAG1 Is Required for Sensory Progenitor Development in the Mammalian Inner Ear, PLoS Genetics. vol. 2, Issue 1, 27-38.
Kiernan, a. E., et, al. (2001) The Notch ligand Jagged1 is required for inner ear sensory development, PNAS U.S.A. vol. 98, No. 7, 3873-3878.
Kim K, et al. (2010) Epigenetic memory in induced pluripotent stem cells, Nature vol. 467: 285- 290.
Klisch TJ, et al. (2011) in vivo Atoh1 targetome reveals how a proneural transcription factor regulates cerebellar development. PNAS USA, vol. 108: 3288-3293.
Korrapati, S., et al. (2013) Notch Signaling Limits Supporting Cell Plasticity in the Hair Cell-Damaged Early Postnatal Murine Cochlea, PLoS One vol. 8, Issue 8, e73276, 1-12.
Kunick, C., et al. (2005) Structure-Aided Optimization of Kinase Inhibitors Derived from Alsterpaullone, ChemBioChem vol. 6, 541-549.
Kwon, C., et al. (2011) Notch post-translationally regulates β-catenin protein in stem and progenitor cells, Nature Cell Bioilogy vol. 13, No. 10, 1244-1251.
Lanford, P. J., et al. (1999) Notch signalling pathway mediates hair cell development in mammalian cochlea, Nature Genetics vol. 21, 289-292.
Layman WS, et al. (2013) Epigenetic alterations by NuRD and PRC2 in the neonatal mouse cochlea, Hearing Research, vol. 304:167-78.
Lee, Y. S., et al. (2006) a morphogenetic wave of *p27Kip1* transcription directs cell cycle exit during organ of Corti development, Development vol. 133, 2817 -2826.
Leonardi, et al. (2010) Modulation of Pantothenate Kinase 3 Activity by Small Molecules that Interact with the Substrate/Allosteric Regulatory Domain, Chemistry & Biology, vol. 17, 892-902.
Leost, M., et al. (2000) Paullones are potent inhibitors of glycogen synthase kinase-3β and cyclindependent kinase 5/p25, European Journal of Biochemistry vol. 267, 5983-5994.
Li et al. (2004) Stem cells as therapy for hearing loss Trends in Molecular Medicine vol. 10, No. 7, 309-315.
Li H, Collado M, Villasante A, Matheu A, Lynch CJ, et al. (2012) p27(Kip1) directly represses Sox2 during embryonic stem cell differentiation. Cell Stem Cell vol. 11, 845-852.
Li, H., et al. (2003) Pluripotent stem cells from the adult mouse inner ear, Nature Medicine vol. 9, No. 10, 1293-1299.
Liberman Mc, et al (2006) Deletion of SLC19A2, the high affinity thiamine transporter, causes selective inner hair cell loss and an auditory neuropathy phenotype, JARO, vol. 7: 211-217.
Lin, et al. (2008) Cyclin-dependent Kinase 2 Negatively Regulates Human Pregnane X Receptor-mediated CYP3A4 Gene Expression in HepG2 Liver Carcinoma Cells, J. Biological Chem, vol. 283, No. 45, 30650-30657.
Liu Z, et al. (2012) Age-dependent in vivo conversion of mouse cochlear pillar and Deiters' cells to immature hair cells by Atoh1 ectopic expression, Journal of Neuroscience vol. 32, 6600-6610.
Liu Z, et al. (2012) Regulation of p27Kip1 by Sox2 maintains quiescence of inner pillar cells in the murine auditory sensory epithelium. Journal of Neuroscience, vol. 32, No. 31, 10530-10540.
Liu, J., et al. (2001) Siah-1 Mediates a Novel β-Catenin Degradation Pathway Linking p53 to the Adenomatous Polyposis Coli Protein, Molecular Cell vol. 7, 927 -936.
Liu, Z., et al. (2012) Age-dependent in vivo conversion of mouse cochlear pillar and Deiters' cells to immature hair cells by Atoh1 ectopic expression, Journal of Neuroscience vol. 32, No. 19, 6600-6610.
Liu, Z., et al. (2014) in Vivo Generation of Immature Inner Hair Cells in Neonatal Mouse Cochleae by Ectopic Atoh1 Expression, PloS One vol. 9, Issue 2, e89377, 1-12.
Lou S, et al (2013) Runx1 Controls Terminal Morphology and Mechanosensitivity of VGLUT3-expressing C-Mechanoreceptors, Journal of Neuroscience vol. 33: 870-882.
Lowenheim, H., et al. (1999) Gene disruption of p27(Kip1) allows cell proliferation in the postnatal and adult organ of corti, PNAS USA vol. 96, 4084-4088.
Maas et al. (2013) p27Kip1 Knockdown Induces Proliferation in the Organ of Corti in Culture after Efficient shRNA Lentiviral Transduction, JARO, vol. 14, 495-508.
Mangi, A. A., et al. (2003) Mesenchymal stem cells modified with Akt prevent remodeling and restore performance of infarcted hearts, Nature Medicine, vol. 9, No. 9, 1195-1201.
Mantela, J., et al. (2005) the retinoblastoma gene pathway regulates the postmitotic state of hair cells of the mouse inner ear, Development vol. 132, 2377-2388.

(56) References Cited

OTHER PUBLICATIONS

Marro S, et al. (2011) Direct lineage conversion of terminally differentiated hepatocytes to functional neurons, Cell Stem Cell, vol. 9: 374-382.
Masuda M, et al. (2011) Regulation of POU4F3 gene expression in hair cells by 5' DNA in mice. Neuroscience vol. 197: 48-64.
Masuda M, et al. (2012) TFE2 and GATA3 enhance induction of POU4F3 and myosin VIIa positive cells in nonsensory cochlear epithelium by ATOH1, Developmental Biology, vol. 372: 6880.
Medema, J.P., and Vermeulen, L. (2011) Microenvironmental regulation of stem cells in intestinal homeostasis and cancer, Nature, vol. 474, 318-326.
Mellado Lagarde Mm, et al. (2013) Selective ablation of pillar and deiters' cells severely affects cochlear postnatal development and hearing in mice. Journal of Neuroscience vol. 33: 1564-1576.
Menchon, C., et al., (2011) the cell cycle inhibitor p27KiP1 controls self-renewal and pluripotency of human embryonic stem cells by regulating the cell cycle, Brachyury and Twist, Cell Cycle vol. 109, 1435-1447.
Minoda R, et al. (2007) Manipulating cell cycle regulation in the mature cochlea. Hearing Research vol. 232: 44-51.
Mizutari K, et al. (2013) Notch inhibition induces cochlear hair cell regeneration and recovery of hearing after acoustic trauma. Neuron vol. 77: 58-69.
Mori T, et al. (2006) Inducible gene deletion in astroglia and radial glia—a valuable tool for functional and lineage analysis. Glia vol. 54: 21-34.
Morrison and Boyd, (1987) Organic Chemistry, (5th Ed.), Chapter 13, entitled "Aromaticity," pp. 477-497.
Munnamalai, V. et al. (2013) Wnt Signaling during Cochlear Development, Semin. Cell Dev. Bioi. vol. 24, 480-489.
Nakano Y, et al. (2012) a Mutation in the Srrm4 gene causes alternative splicing defects and deafness in the Bronx waltzer mouse. PLoS Genetics vol. 8 Issue 10, e1002966, 1-17.
Niles, R. M., et al. (2006) Resveratrol is rapidly metabolized in athymic (nu/nu) mice and does not inhibit human melanoma xenograft tumor growth , Journal of Nutrition vol. 136, 2542-2546.
Oesterle EC (2012) Changes in the adult vertebrate auditory sensory epithelium after trauma. Hear Res. vol. 27, 91-98.
Oesterle EC, et al. (2008) Sox2 and JAGGED1 expression in normal and drugdamaged adult mouse inner ear. Jaro vol. 9: 65-89.
Oesterle Ec, et al. (2011) p27(Kip1) is required to maintain proliferative quiescence in the adult cochlea and pituitary, Cell Cycle vol. 10: 1237-1248.
Ohyama, T., et al. (2006) Wnt signals mediate a fate decision between otic placode and epidermis, Development vol. 133, 865-875.
Ohyama, T., et al. (2007) the first steps towards hearing: mechanisms of otic placode induction, Int. J. Dev. Bioi. vol. 51, 463-472.
Ono K, et al. (2009) Silencing p27 reverses post-mitotic state of supporting cells in neonatal mouse cochleae. Mol Cell Neurosci. vol. 42: 391-398.
P. Paolicelli et al. (2010) Surface-modified PLGA-based Nanoparticles that can Efficiently Associate and Deliver Virus-like Particles, Nanomedicine, vol. 5, No. 6, 843-853.
Pan N, et al (2010) Notch signaling is required for the generation of hair cells and supporting cells in the mammalian inner ear, PNAS, vol. 107, No. 36, 15798-15803.
Pan N, et al. (2012) a novel Atoh1 "self-terminating" mouse model reveals the necessity of proper Atoh1 level and duration for hair cell differentiation and viability. PLoS One vol. 7, Issue 1 e30358, 1-12.
Papp B, Plath K (2011) Reprogramming to pluripotency: stepwise resetting of the epigenetic landscape. Cell Res vol. 21, 486-501.
Pellegata, N. S., et al. (2006) Proceedings of the National Academy of Sciences of the United States of America 103, 15558-15563.
Pietrocola, F., et al. (2012) Pro-autophagic polyphenols reduce the acetylation of cytoplasmic proteins, Cell Cycle vol. 11, 3851-3860.
Polyak, K., et al. (1994) Cloning of p27kip1, a Cyclin-Dependent Kinase Inhibitor and a Potential Mediator of Extracellular Antimitogenic Signals, Cell, vol. 78, 59-66.
Rabbani, F., et al. (2007) Prognostic significance of p27Kip1 expression in bladder cancer, BJU International, vol. 100, 259-263.
Ramskold D, et al. (2012) Full-length mRNA-Seq from single-cell levels of RNA and individual circulating tumor cells. Nat Biotechnol vol. 30, 777-782.
Rask-Andersen, H., et al. (2005) Regeneration of human auditory nerve. In vitro/in video demonstration of neural progenitor cells in adult human and guinea pig spiral ganglion, Hearing Research, vol. 203, 180-191.
Riccomagno, M. M., et al. (2005) Wnt-dependent regulation of inner ear morphogenesis is balanced by the opposing and supporting roles of Shh, Genes & Development, vol. 19, 16121623.
Ryals Bm, Rubel EW (1988) Hair cell regeneration after acoustic trauma in adult Coturnix quail, Science, vol. 240: 1774-1776.
Sage C, et al. (2006) Essential role of retinoblastoma protein in mammalian hair cell development and hearing. PNAs USA, vol. 103, No. 19, 7345-7350.
Salt and Plontke (2005) Local inner-ear drug delivery and pharmacokinetics, Drug Discovery Today, vol. 10, No. 19, 1299-1306.
Sato, T. And Clevers, H. (2013) Growing Self-Organizing Mini-Guts from a Single Intestinal Stem Cell: Mechanism and Applications, Science, vol. 340, 1190-1194.
Sato, T., et al. (2009) Single Lgr5 stem cells build crypt-villus structures in vitro without a mesenchymal niche, Nature, vol. 459, 262-265.
Savary E, et al. (2007) Distinct population of hair cell progenitors can be isolated from the postnatal mouse cochlea using side population analysis. Stem Cells, vol. 25, 332-339.
Sharma, V. M., et al. (2008) Semi-empirical calculations on paullones, a promising class of cyclindependent kinase inhibitors, Indian J. Of Biochem. & Biophysics, vol. 45, 416-420.
Shi F, Kempfle Js, Edge As (2012) Wnt-responsive Lgr5-expressing stem cells are hair cell progenitors in the cochlea, J Neurosci, vol. 32, 9639-9648.
Shi, F., et al. (2010) β-Catenin Up-regulates Atoh1 Expression in Neural Progenitor Cells by Interaction with an Atoh1 3' Enhancer, J. Bioi. Chem. vol. 285, 392-400.
Sinkkonen St, et al. (2011) Intrinsic regenerative potential of murine cochlear supporting cells. Scientific Reports, vol. 1, No. 26, 1-8.
Slingerland, J., and Pagano, M. (2000) Regulation of the Cdk Inhibitor p27 and Its Deregulation in Cancer, Journal of cellular physiology vol. 183, 10-17.
So Hs, et al. (2005) Protective effect of T-type calcium channel blocker flunarizine on cisplatin- induced death of auditory cells. Hearing Research, vol. 204: 127-139.
Stevens, C. B., et al. (2003) Forced activation of Wnt signaling alters morphogenesis and sensory organ identity in the chicken inner ear, Dev. Bioi., vol. 261, 149-164.
Takebayashi, S., et al. (2007) Multiple roles of Notch signaling in cochlear development, Dev. Bioi., vol. 307, 165-178.
Taylor Rr,et al. (2012) Defining the cellular environment in the organ of Corti following extensive hair cell loss: a basis for future sensory cell replacement in the Cochlea. PLoS One vol. 7, Issue 1: e30577, 1-21.
Tian, H., et al. (2011) a reserve stem cell population in small intestine renders Lgr5-positive cells dispensable, Nature, vol. 478, 255-259.
Trapp, J., et al. (2006) Adenosine Mimetics as Inhibitors of NAD+-Dependent Histone Deacetylases, from Kinase to Sirtuin Inhibition, J. Med. Chem. vol. 49, 7307-7316.
Vierbuchen T, et al. (2010) Direct conversion of fibroblasts to functional neurons by defined factors. Nature vol. 463, 1035-1041.
Vrijens, et al. (2013) Identification of Small Molecule Activators of BMP Signaling, PloS One, vol. 8, Issue 3, e59045, 1-10.
Walters and Zuo (2013) Postnatal development, maturation and aging in the mouse cochlea and their effects on hair cell regeneration, Hearing Res. vol. 297, 68-83.
Walters B, Zuo J. (2015) a Sox10 rtTA/+ Mouse Line Allows for Inducible Gene Expression in the Auditory and Balance Organs of the Inner Ear, Jaro, vol. 16, No. 3, 331-45.

(56) References Cited

OTHER PUBLICATIONS

Wang Ca, et al. (2012) SIX1 induces lymphangiogenesis and metastasis via upregulation of VEGF-C in mouse models of breast cancer, J Clin Invest. vol. 122: 1895-1906.
Wang, et al. (2007) SIRT2 deacetylates FOXO3a in response to oxidative stress and caloric restriction, Aging Cell, vol. 6, 505-514.
Warchol Me, et al (1996) Regenerative proliferation in organ cultures of the avian cochlea: identification of the initial progenitors and determination of the latency of the proliferative response. Journal of Neuroscience, vol. 16 No. 17, 5466-5477.
Weber T, et al. (2008) Rapid cell-cycle reentry and cell death after acute inactivation of the retinoblastoma gene product in postnatal cochlear hair cells. PNAs, vol. 105, No. 2, 781-785.
Weddell TD, et al. (2011) Prestin links extrinsic tuning to neural excitation in the mammalian cochlea. Current Biology vol. 21, No. 18, R682-R683.
Wennmo et al., (1982) Vestibular Neuronitis, Acta Oto-Laryngologica, vol. 94, 507-515.
White PM, et al (2006) Mammalian cochlear supporting cells can divide and trans-differentiate into hair cells. Nature, vol. 441, 984-987.
Woods, et al., (2004) Math1 regulates development of the sensory epithelium in the mammalian cochlea, Nature Neuroscience, vol. 7, No. 12, 1310-1318.
Xiang M, et al. (1997) Essential role of Pou-domain factor Brn-3c in auditory and vestibular hair cell development. Pns Usa vol. 94, 9445-9450.
Yamamoto, N., et al. (2006) Inhibition of Notch/RBP-J signaling induces hair cell formation in neonate mouse cochleas, J.Mol. Med., vol. 84, 37-45.
Yamashita T, et al. (2012) Normal Hearing Sensitivity at Low-to-Middle Frequencies with 34% Prestin-Charge Density, PLoS One vol. 7, Issue 9, e45453, 1-10.
Yan, K. S., et al. (2012) the intestinal stem cell markers Bmi1 and Lgr5 identify two functionally distinct populations, PNAs U.S.A. vol. 109, No. 2, 466-471.
Yang J, et al. (2012) Functional features of trans-differentiated hair cells mediated by Atoh1 reveals a primordial mechanism. J Neurosci vol. 32, No. 11, 3712-3725.

Yoon, M. K., et al. (2012) Cell cycle regulation by the intrinsically disordered proteins p21 and p27, Biochemical Society Transactions, vol. 40, 981-988.
Yu, Y., et al. (2010) In Vivo Proliferation of Postmitotic Cochlear Supporting Cells by Acute Ablation of the Retinoblastoma Protein in Neonatal Mice J. Neurosci. vol. 30, No. 17, 5927-5936.
Zaharevitz, D., et al. (1999) Discovery and Initial Characterization of the Paullones, a Novel Class of Small-Molecule Inhibitors of Cyclin-dependent Kinases1, Cancer Research, vol. 59, 2566-2569.
Zhang, S., et al., (2013) FOXO3a/p27kip1 Expression and Essential Role After Acute Spinal Cord Injury in Adult Rat, Journal of Cellular Biochemistry vol. 114, 354-365.
Zheng Jl, et al. (2000) Overexpression of Math1 induces robust production of extra hair cells in postnatal rat inner ears, Nature Neuroscience vol. 3, No. 6, 580-586.
Zheng, J. L., et al. (2000) Hes1 is a negative regulator of inner ear hair cell differentiation, Development vol. 127, 4551-4560.
Zilberstein Y, et al. (2012) Inner hair cells are not required for survival of spiral ganglion neurons in the adult cochlea. J Neurosci vol. 32, No. 2, 405-410.
Zine, a., et al. (2001) Hes1 and Hes5 Activities Are Required for the Normal Development of the Hair Cells in the Mammalian Inner Ear, J. Neurosci. vol. 21, No. 13, 4712-4720.
Zuo J, et al. (1999) Visualization of alpha9 acetylcholine receptor expression in hair cells of transgenic mice containing a modified bacterial artificial chromosome, PNAs USA, vol. 96, No. 24, 14100-14105.
International Search Report and Written Opinion were mailed on Oct. 17, 2014 for Application No. PCT/US2014/029927, which was filed on Mar. 15, 2014 and published as WO2014/145205 on Sep. 18, 2014 (Applicant- St. Jude's Children's Hospital) (13 pages).
International Search Report and Written Opinion mailed on Sep. 13, 2016, for Application No. PCT/US2016/038384, which was filed on Jun. 20, 2016 (Applicant- St. Jude's Children's Hospital // Inventor- Zuo, et al.) (10 pages).
Anderson, et al., "Imidazoles: SAR and development of a potent class of cyclin-dependent kinase inhibitors," Bioorganic & Medicinal Chemistry Letters 18 (2008) 5487-5492.
PCT/US/2016/038384, filed Jun. 20, 2014, Zuo et al.

* cited by examiner

```
   1 ATGTCCCGGCC TGCTGCATGC AGAAGAGTGG GCTGAAGTGA AGGAGTTGGG AGACCACCAT
  61 CCCCAGCCCC AGCCGCATCA TCTCCCGGAA CCGCCGCGCC ACCTGCAACT
 121 TTGCAGGCGA GAGAGCATCC CGTCTACCCG CCTGAGCTGT CCCTCCTGGA CAGCACCGAC
 181 CCACGCGCCT GGCTGGCTCC CACTTTGCAG GCCATCTCCA CGGCACGCGC CGGCCAGTAT
 241 TGCTACATT CCCCGGAGCT GGGTGCCTCA GAGGCCGCTG CGCCCGGGGA CGAAGTGGAC
 301 GCCCGGGGG AGCTGGTAAG GAGGAGCAGC GCGGGTGCCA GCAGCAGCAA GAGCCCCGGG
 361 CCGGTGAAAG TGCCGGAACA GCTGTGCAAG CTGAAAGGCG GGGTGGTGGT AGACGAGCTG
 421 GGCTGCAGCC GCCAACGGGC CCCTTCCAGC AGGATGCATG GCTGAACCA GAAGCAGAGA
 481 CGGCTAGCCC CCAACGGGC CCCTTCCAGC AGGATGCATG GCTGAACCA CGCCTTCGAC
 541 CAGCTGCGCA ATGTTATCCC GTCGTTCAAC AACGACAAGA AGCTGTCCAA ATATGAGACC
 601 CTGCAGATGG CCCAAATCTA CATCAACGCC TTGTCCGAGC TGCTACAAAC GCCCAGCGGA
 661 GGGGAACAGC CACCGCCCGG TCCAGCCTCC TGCAAAGCG ACCACCACCA CCTTGCCACC
 721 GCGGCCTCCT ATGAAGGGGG CGCCGGCAAC GCGACCCAG CTGGGCTCA GCAGGCTTCC
 781 GGAGGGAGC AGCCGCGAC CCCGCCCCGG AGTTGCCGGA CTCGCTTCTC AGCCCCAGCT
 841 TCTGCAGGAG GGTACTCGGT GCAGCTGGAC GCTCTGCACT TTGTCTCCTT CGAGGAGAGC
 901 GCCCTGACAG CGATGATGGC GCAAAGAAT CTGTCTCCCG CCCGGG GAGCATCTTG
 961 CAGCCAGTGC AGGAGAAAA CAGCAAAACT TCGCCTCGT CCCACAGAAG CGACGGGGAA
1021 TTTCCCCCC ATTCCCATTA CAGTGACTCG GATGAGGCAA GTTAG
```

FIG. 1A

```
  1 MSRLLHAEEW AEVKELGDHH RQPQPHHLPQ PPPPPQPPAT LQAREHPVYP PELSLLDSTD
 61 PRAWLAPTLQ GICTARAAQY LLHSPELGAS EAAAPRDEVD GKGELVRRSS GGASSKSPG
121 PVKVREQLCK LKGGVVVDEL GCSRQRAPSS KQVNGVQKQR RLAANARERR RMHGLNHAFD
181 QLRNVIPSFN NDKKLSKYET LQMAQIYINA LSELLQTPSG GEQPPPPPAS CKSDHHHLRT
241 AASYEGGAGN ATAAGQQAS GGSQRPTPPG SCRTRFSAPA SAGGYSVQLD ALHFSFFEDS
301 ALTAMMAQKN LSPSLPGSIL QPVQEBNSKT SPRSHRSDGE FSPHSHYSDS DEAS
```

FIG. 1B

```
   1 CTTCTTCGTC AGCCTCCCTT CCACCGCCAT ATTGGGCCAC TAAAAAAAGG GGGCTCGTCT
  61 TTTCGGGGTG TTTTTCTCCC CCTCCCTGT GCCCGCTTGC TCACGGCTCT GCGACTCCGA
 121 CGCCCGCAAG GTTTCGAGAG CCGCTGGGTT CGCGGGACCC GCGGGCTTGC ACCCGCCCAG
 181 ACTCGGACGG GCTTTGCCAC CCTCTCCGCT TGCCTGGTCC CCTCTCCTCT CCGGCCCTCCC
 241 GCTCGCCAGT CCATTTGATC AGCGGAGACT CGGCGGCCGG GCCGGGCTT CCCCGCAGCC
 301 CCTGCGCGCT CCTAGAGCTC GGGCCGTGGC TCGTCGGGGT CTGNNCTTT TGGCTCCGAG
 361 GGCAGTCGCT GGGCTTCCGA GAGGGGTTCG GGCTGCGTAG GGGCGCTTTG TTTTGTTCGG
 421 TTTTCTTTTT TTCAGAGTGC GAGAGAGGCG GTCGTGCAGA CCCGGGAGAA AGATGTCAAA
 481 CGTGCGAGTG TCTAACGGGA GCCCTAGCCT GGAGCGGATG GACGCCAGGC AGGCGGAGCA
 541 CCCCAAGCCC TCGGCCTGCA GGAACCTCTT CGGCCCGGTG GACCACGAAG AGTTAACCCG
 601 GGACTTGGAG AAGCACTGCA GAGACATGGA AGAGGCGAGC CAGCGCAAGT GGAATTTCGA
 661 TTTTCAGAAT CACAAACCCC TAGAGGGCAA GTACGAGTGG CAAGAGGTGG AGAAGGGCAG
 721 CTTGCCCGAG TTCTACTACA GACCCCCGCG GCCCCCCAAA GGTGCCTGCA AGGTGCCGGC
 781 GCAGGAGAGC CAGGATGTCA GCGGGAGCCG CCCCGGCGGCG CCTTAATTG GGGCTCCGGC
 841 TAACTCTGAG GACACGCATT TGGTGCACCC AAAGACTGAT CCGTCGGACA GCCAGACGGG
 901 GTTAGCGGAG CAATGCGCAG GAATAAGGAA GCGACCTGCA ACCGACGATT CTTCTACTCA
 961 AAACAAAAGA GCCAACAGAA CAGAAGAAAA TGTTTCAGAC GGTTCCCCAA ATGCCGGTTC
1021 TGTGGAGCAG ACGCCCAAGA AGCCTGGCCT CAGAAGACGT CAAACGTAAA CAGCTCGAAT
1081 TAAGAATATG TTTCCTTGTT TATCAGATAC ATCACTGCTT GATGAAGCAA GGAAGATATA
1141 CATGAAAATT TTAAAATAC ATATCGCTGA CTTCATGGAA TGGACATCTT GTATAAGCAC
1201 TGAAAAACAA CAACACAATA ACACTAAAAT TTTAGGCACT CTTAAATGAT CTGCCTCTAA
1261 AAGCGTTGGA TGTAGCATTA TGCAATTAGG TTTTTCCTTA TTTGCTTCAT TGTACTACCT
1321 GTGTATATAG TTTTTACCTT TTATGTAGCA CATAAACTTT GGGGAAGGGA GGGCAGGGTG
1381 GGGCTGAGGA ACTGACGTGG AGCGGGGTAT GAAGAGCTTG CTTTGATTTA CAGCAAGTAG
1441 ATAAATATTT GACTTGCATG AAGAGAAGCA ATTTTGGGGA AGGGTTTGAA TTGTTTTCTT
1501 TAAAGATGTA ATGTCCCTTT CAGAGACAGC TGATACTTCA TTTAAAAAAA TCACAAAAAT
1561 TTGAACACTG GCTAAAGATA ATTGCTATTT ATTTTTACAA GAAGTTTATT CTCATTTGGG
1621 AGATCTGGTG ATCTCCCAAG CTATCTAAAG TTTGTTAGAT AGCTGCATGT GGCTTTTTTA
1681 AAAAAGCAAC AGAAACCTAT CCTCACTGCC CTCCCCAGTC TCTCTTAAAG TTGGAATTTA
1741 CCAGTTAATT ACTCAGCAGA ATGGTGATCA CTCCAGGTAG TTTGGGCAA AAATCCGAGG
1801 TGCTTGGGAG TTTTGAATGT TAAGAATTGA CCATCTGCTT TTATTAAATT TGTTGACAAA
1861 ATTTCTCAT TTTCTTTTCA CTTCGGGCTG TGTAAACACA GTCAAAATAA TTCTAAATCC
1921 CTCGATATTT TTAAAGATCT GTAAGTAACT TCACATTAAA AAATGAAATA TTTTTTAATT
1981 TAAAGCTTAC TCTGTCCATT TATCCACAGG AAAGTGTTAT TTTCAAGGA AGGTTCATGT
2041 AGAGAAAAGC ACACTTGTAG GATAAGTGAA ATGGATACTA CATCTTTAAA CAGTATTTCA
2101 TTGCCTGTGT ATGGAAAAAC CATTTGAAGT GTACCTGTGT ACATAACTCT GTAAAAACAC
2161 TGAAAAATTA TACTAACTTA TTTATGTTAA AAGATTTTTT TTAATCTAGA CAATATACAA
2221 GCCAAGTGG CATGTTTTGT GCATTTGTAA ATGCTGTGTT GGGTAGAATA GGTTTTCCCC
2281 TCTTTTGTTA AATAATATGG CTATGCTTAA AAGGTTGCAT ACTGAGCCAA GTATAATTTT
2341 TTGTAATGTG TGAAAAAGAT GCCAATTATT GTTACACATT AACTAATCAA TAAAGAAAAC
2401 TTCCATAGCT ATT
```

FIG. 2A

```
  1 MSNVRVSNGS PSLERMDARQ AEHPKPSACR NLFGPVDHEE LTRDLEKHCR DMEEASQRKW
 61 NFDFQNHKPL EGKYEWQEVE KGSLPEFYYR PPRPPKGACK VPAQESQDVS GSRPAAPLIG
121 APANSEDTHL VDPKTDPSDS QTGLAEQCAG IRKRPATDDS STQNKRANRT EENVSDGSPN
181 AGSVEQTPKK PGLRRRQT
```

FIG. 2B

METHODS AND COMPOSITIONS OF P27$^{KIP1}$ TRANSCRIPTIONAL MODULATORS

CROSS-REFERENCE TO RELATED APPLICATIONS

This application claims the benefit of U.S. Provisional Application No. 61/787,578, filed on Mar. 15, 2013 and U.S. Provisional Application No. 61/938,404 filed on Feb. 11, 2014, which are incorporated herein by reference in their entirety.

STATEMENT REGARDING FEDERALLY SPONSORED RESEARCH

This invention was made with U.S. Government support under grant numbers GM086415, DC06471, and CA21765 awarded by the National Institutes of Health (NIH) and grant numbers N000140911014, N000141210191, and N000141210775, awarded by the Office of Naval Research. The U.S. Government has certain rights in the invention.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named "191160025P1Seq_ST25.txt," created on Mar. 15, 2014, and having a size of 12,288 bytes and is filed concurrently with the specification. The sequence listing contained in this ASCII formatted document is part of the specification and is herein incorporated by reference in its entirety.

BACKGROUND

Hearing loss in humans and other mammals, whether congenital, as a result of loud noise exposure or due to ototoxic drugs, or age-related, is permanent. According to the World Health Organization (WHO), hearing loss affects 5% of the world's population (360 million people), while the current production of hearing aids only meet 10% of the demand. In the U.S., approximately 36 million adults report some degree of hearing loss, and two to three out of 1,000 babies born each year have detectable hearing loss according to the Center for Disease Control (CDC). In both cases, the social, emotional, and economic impacts affect the individuals' ability to communicate, resulting in reduced function in the workforce, isolation and depression, as well as increased financial costs.

The auditory sensory epithelium of the cochlea, also known as the organ of Corti, contains one row of inner hair cells (IHCs) and three rows of outer hair cells (OHCs), as well as surrounding supporting cells (SCs), including the several SC subtypes: Inner Border cells (IBs), Inner Phalangeal cells (IPhs), pillar cells (PCs) and Deiters' cells (DCs), which are directly underneath hair cells (HCs). During cochlear development, HCs and SCs are believed to share the same prosensory progenitors (Fekete, et al. (1998) *J. Neurosci.* 18:7811-21). Atonal protein homologue 1 (Atoh1) is a basic helix-loop-helix transcription factor required for HC development (Chen, et al. (2002) *Development* 129:2495-2505; Woods, et al. (2004) *Nat. Neurosci.* 7:1310-1318); no HCs appear in Atoh1 germline knock-out mice (Bermingham, et al. (1999) *Science* 284: 1837-1841).

When HC damage occurs in non-mammalian vertebrates, including birds and fish, their SCs spontaneously turn on Atoh1, and some change cell fate to become new HCs (Cafaro, et al. (2007) *Dev. Dyn.* 236:156-170); however, mammals have lost this capacity and suffer permanent deafness after HC damage (Brigande & Heller (2009) *Nat. Neurosci.* 12:679-685). In vitro ectopic expression of Atoh1 in the nonsensory greater epithelial ridge (GER) of neonatal rat cochlear explants generates ectopic HCs (Zheng & Gao (2000) *Nat. Neurosci.* 3:580-586), suggesting the sufficiency of Atoh1 in specifying a HC fate in a permissive cellular environment. In addition, in vivo overexpression of Atoh1 in mouse otocysts by electroporation (Gubbels, et al. (2008) *Nature* 455:537-541) and in the adult cochlea of guinea pigs by viral transduction (Izumikawa, et al. (2005) Nat. Med. 11:271-276) also leads to new HCs. However, this analysis did not indicate whether various postmitotic mouse SC subtypes, at different postnatal ages, are able to respond to ectopic Atoh1 expression and be converted into HCs. Recently, delivery of an γ-secretase inhibitor (LY411575) to noise-damaged adult mouse cochleae reportedly caused regeneration of functional hair cells and partial hearing recovery and this effect was reported to be linked to Atoh1 activation in the treated cochleae (Mizutari, et al. (2013) *Neuron* 77:58-69). However, it was not demonstrated whether these effects were specific to Atoh1 and supporting cells.

Ectopic expression of Atoh1 in mice has shown that PCs and DCs from neonatal and juvenile mice can be converted into HCs (Liu, et al. (2012) *J. Neurosci.* 32:6600-10). While these data demonstrate that neonatal and juvenile PCs and DCs can be converted into immature HCs, overexpression of Atoh1 alone was insufficient to complete the maturation of new HCs. Moreover, expression of Atoh1 in a spatially and temporally specific manner in the postnatal mammalian cochlea indicates that Atoh1 can generate cells in young animals with morphological, molecular, and physiological properties reminiscent of hair cells (Kelly, et al. (2012) *J. Neurosci.* 32:6699-6710). However, this competency is cell type specific and progressively restricted with age.

Screening assays for identifying Atoh1 activators and use of such activators for hair cell regeneration have been suggested (see U.S. Pat. No. 8,188,131). This patent describes small organic compounds that increase mouse Atoh1 expression and increase hair cell differentiation. Furthermore, U.S. Ser. No. 10/860,724 describes nucleic acids encoding Atoh1 for increasing Atoh1 expression and for the treatment of deafness, osteoarthritis, and abnormal cell proliferation.

It has also been reported that virus-mediated overexpression of Atoh1 and SKP2 (a presumed inhibitor of p27$^{Kip1}$) induced ectopic HC formation in areas flanking the mature organ of Corti, although it was not demonstrated whether new HCs were generated from infected cells (Minoda, et al. (2007) *Hearing Research* 232:44-51). Similar inactivation of p27$^{Kip1}$ in neonatal and juvenile SCs in mice resulted in their proliferation without transdifferentiation to HCs; such effect however failed in adult *cochleae* (Liu, et al. (2012) *J. Neuroscience* 32:10530-40; Oesterle, et al. (2011) *Cell Cycle* 10:1237-48).

p27$^{Kip1}$ (also known as Cdkn1B) is a member of the Cip/Kip family of cell cycle inhibitors that are characterized by their ability to bind and inhibit cyclin dependent kinases (CDK)/cyclin complexes halting cell cycle progression in the G1 phase (Yoon, M. K., et al. (2012) *Biochemical Society Transactions* 40, 981-988). Because p27$^{Kip1}$ inhibits the cell cycle, loss of p27$^{Kip1}$ has been associated with some forms of cancer in humans and germline p27$^{Kip1}$ deletion in mice results in sporadic pituitary tumors at old ages (Bertagnolli, M. M., et al. (2009) *Clinical cancer research: an official journal of the American Association for Cancer Research* 15, 2116-2122; Bottini, C., et al. (2009) *International journal of oncology* 34, 69-77; Chang, B. L., et al. (2004) *Cancer research* 64, 1997-1999; Slingerland, J., and Pagano, M. (2000) *Journal of cellular physiology* 183, 10-17; Pellegata, N. S., et al. (2006) *Proceedings of the National Academy of Sciences of the United States of America* 103, 15558-15563). Although, mutations in p27$^{Kip1}$ may not always be causative of cancer, it is often dysregulated and associated with a poor prognosis (Chu, I. M., et al. (2008) *Nature reviews. Cancer* 8, 253-267; Rabbani, F., et al. (2007) *BJU international* 100, 259-263). Despite this, recent experiments have cast a light on how p27$^{Kip1}$ may antagonize stem cells pluripotency (Menchon, C., et al., (2011) *Cell Cycle* 10, 1435-1447), and regenerative processes within certain tissue types giving some impetus to identification of small molecules to decrease the levels of p27$^{Kip1}$. Specifically, loss of p27$^{Kip1}$ has been associated with regenerative phenotypes in spinal cord injuries (Zhang, S., et al. (2013) *J. Cellular Biochem.* 114, 354-365), hepatocyte transplantation (Karnezis, A. N., et al. (2001) *J of Clinical Investigation* 108, 383-390), and in the inner ear (Liu, Z., et al. (2012) *J. of Neuroscience: The Official J. of the Soc. for Neuroscience* 32, 10530-10540; Oesterle, E. C., et al. (2011) *Cell Cycle* 10, 1237-1248; White, P. M., et al. (2011) *Nature* 441, 984-987; Mantela, J., et al. (2005) *Development* 132, 2377-2388). Interestingly, p27$^{Kip1}$ initiates its expression during embryonic development coinciding with the exit of HCs and SCs within the organ of Corti from the cell cycle, and the beginning of quiescence during embryonic development (Chen, P. and Segil, N. (1999) *Development* 126, 1581-1590; Lee, Y. S., et al. (2006) *Development* 133, 2817-2826), implying a pivotal role for p27$^{Kip1}$ in these post-mitotic cells. In vivo and explant studies in postnatal mouse cochleae revealed that removal of p27$^{Kip1}$ from normally quiescent supporting cells forced these cells to re-enter the cell cycle (Liu, Z., et al. (2012) *J. of Neuroscience: The Official J. of the Soc. for Neuroscience* 32, 10530; Oesterle, E. C., et al. (2011) *Cell Cycle* 10, 1237-1248; Maas et al. (2013) *JARO* 14, 495), the first step towards replacing lost sensory cells. Similarly, multiple cell cycle inhibitors are up-regulated in older cells (Walters, B. J. and Zuo, J. (2013) *Hearing Research* 297, 68-83), implying that a cocktail of cell cycle inhibitors, including p27$^{Kip1}$ may need to be developed to force proliferation to occur in older quiescent tissues.

Despite advances in research directed to inhibition of p27$^{Kip1}$, there remains a significant need for compounds capable of inhibiting p27$^{Kip1}$ expression for use in proliferation of cells, specifically hair cells, and methods of identifying and preparing same. These needs and other needs are satisfied by the present invention.

SUMMARY

In accordance with the purpose(s) of the invention, as embodied and broadly described herein, the invention, in one aspect, relates to pharmaceutical compositions comprising at least one agent that activates the expression of Atoh1, or a pharmaceutically acceptable salt, solvate, or polymorph thereof; at least one agent that inhibits the expression of p27$^{Kip1}$ or a pharmaceutically acceptable salt, solvate, or polymorph thereof; and a pharmaceutically acceptable carrier.

Also disclosed are pharmaceutical compositions comprising β-catenin and at least one agent that activates the expression of Atoh1, or a pharmaceutically acceptable salt, solvate, or polymorph thereof.

Also disclosed are pharmaceutical compositions comprising β-catenin; at least one agent that activates the expression of Atoh1, or a pharmaceutically acceptable salt, solvate, or polymorph thereof; at least one agent that inhibits the expression of p27$^{Kip1}$, or a pharmaceutically acceptable salt, solvate, or polymorph thereof; and a pharmaceutically acceptable carrier.

Also disclosed are methods of preparing a pharmaceutical composition, the method comprising the step of combining at least one agent that activates the expression of Atoh1, or a pharmaceutically acceptable salt, solvate, or polymorph thereof; at least one agent that inhibits the expression of p27$^{Kip1}$, or a pharmaceutically acceptable salt, solvate, or polymorph thereof; wherein at least one is present in an effective amount; and a pharmaceutically acceptable carrier.

Also disclosed are methods of preparing a pharmaceutical composition, the method comprising the step of combining β-catenin and at least one agent that synergistically activates the expression of Atoh1, or a pharmaceutically acceptable salt, solvate, or polymorph thereof; and a pharmaceutically acceptable carrier; wherein the β-catenin and the agent are present in an effective amount.

Also disclosed are methods of treating hearing impairment associated with loss of cochlear hair cells in a subject, the method comprising the step of co-administering to the subject a therapeutically effective amount of at least one agent that activates the expression of Atoh1, or a pharmaceutically acceptable salt, solvate, or polymorph thereof; and at least one agent that inhibits the expression of p27$^{Kip1}$ or a pharmaceutically acceptable salt, solvate, or polymorph thereof.

Also disclosed are methods of treating hearing impairment associated with loss of cochlear hair cells in a subject, the method comprising the step of co-administering to the subject a therapeutically effective amount of β-catenin and at least one agent that synergistically activates the expression of Atoh1, or a pharmaceutically acceptable salt, solvate, or polymorph thereof.

Also disclosed are methods of treating a subject who has a hearing impairment associated with loss of cochlear hair cells, the method comprising: a) obtaining a population of cells capable of differentiating into cochlear hair cells; b) contacting the population of cells with an effective amount of at least one agent that activates the expression of Atoh1, or a pharmaceutically acceptable salt, solvate, or polymorph thereof; and at least one agent that inhibits the expression of p27$^{Kip1}$, or a pharmaceutically acceptable salt, solvate, or polymorph thereof; and c) administering the population of cells, or a subset thereof, to the subject's ear, thereby treating the subject.

Also disclosed are methods of treating a subject who has a hearing impairment associated with loss of cochlear hair cells, the method comprising: a) obtaining a population of cells capable of differentiating into cochlear hair cells; b) contacting the population of cells with an effective amount of β-catenin and at least one agent that synergistically activates the expression of Atoh1, or a pharmaceutically acceptable salt, solvate, or polymorph thereof; and c) administering the population of cells, or a subset thereof, to the subject's ear, thereby treating the subject.

Also disclosed are methods of increasing the number of cells with the characteristics of cochlear hair cells, the method comprising: a) obtaining a population of cells capable of differentiating into cochlear hair cells; b) contacting the population of cells with an effective amount of at least one agent that activates the expression of Atoh1, or a pharmaceutically acceptable salt, solvate, or polymorph thereof; and at least one agent that inhibits the expression of p27$^{Kip1}$ or a pharmaceutically acceptable salt, solvate, or polymorph thereof, for a period of time sufficient to increase the number of cells with the characteristics of cochlear hair cells in the population of cells.

Also disclosed are methods of increasing the number of cells with the characteristics of cochlear hair cells, the method comprising: a) obtaining a population of cells capable of differentiating into cochlear hair cells; b) contacting the population of cells with an effective amount of β-catenin and at least one agent that synergistically activates the expression of Atoh1, or a pharmaceutically acceptable salt, solvate, or polymorph thereof, for a period of time sufficient to increase the number of cells with the characteristics of cochlear hair cells in the population of cells.

Also disclosed are compositions comprising a population of cells made by a disclosed method.

Also disclosed are kits comprising at least one agent that activates the expression of Atoh1, or a pharmaceutically acceptable salt, solvate, or polymorph thereof; at least one agent that inhibits the expression of p27$^{Kip1}$ or a pharmaceutically acceptable salt, solvate, or polymorph thereof; and one or more of: a) at least one agent known to treat a hearing impairment; b) at least one agent known to regenerate tissue; c) at least one chemotherapeutic agent; d) at least one ototoxic agent; e) a device suitable for administration of the at least one agent that activates the expression of Atoh1 and at least one agent that inhibits the expression of p27$^{Kip1}$ to the inner ear of a subject; f) instructions for treating a hearing impairment or imbalance disorder; and g) instructions for regenerating tissue.

Also disclosed are kit comprising β-catenin and at least one agent that synergistically activates the expression of Atoh1, or a pharmaceutically acceptable salt, solvate, or polymorph thereof; and one or more of: a) at least one agent that inhibits the expression of p27$^{Kip1}$ or a pharmaceutically acceptable salt, solvate, or polymorph thereof; b) at least one agent known to treat a hearing impairment; c) at least one agent known to regenerate tissue; d) at least one chemotherapeutic agent; e) at least one ototoxic agent; f) a device suitable for administration of the at least one agent that activates the expression of Atoh1 and at least one agent that inhibits the expression of p27$^{Kip1}$ to the inner ear of a subject; g) instructions for treating a hearing impairment or imbalance disorder; and h) instructions for regenerating tissue.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

FIG. 1A shows the nucleotide (SEQ ID NO:1) sequence of human Atoh1.

FIG. 1B shows the amino acid (SEQ ID NO: 2) sequence of human Atoh1.

FIG. 2A shows the nucleotide (SEQ ID NO: 3) sequence of human p27$^{Kip1}$

FIG. 2B shows the amino acid (SEQ ID NO: 4) sequence of human p27Kip1.

FIG. 3 shows representative data pertaining to the design of a high throughput screen to antagonize p27$^{Kip1}$ transcription. Specifically.

FIG. 4A shows the performance of the p27$^{Kip1}$-luciferase assay against negative controls (DMSO, triangle) and titrating amount of the positive control (cyclohexamide, circle). FIG. 4B shows Z' factor calculations for assay performance over 35 plates from the primary screen (Mean Z' factor=0.74±0.06).

FIG. 7 shows representative data pertaining to the secondary screen of primary hits. Specifically.

FIG. 17 shows representative data pertaining to the mechanism by which alsterpaullone, 2-cyanoethyl prevents FoxO3a from binding to the p27$^{Kip1}$ promoter. Specifically.

FIG. 18 shows additional representative data pertaining to the mechanism by which alsterpaullone, 2-cyanoethyl prevents FoxO3a from binding to the p27$^{Kip1}$ promoter. Specifically.

FIG. 21 shows representative data pertaining to the effect of concurrent ectopic expression of β-catenin and Atoh1 in the inner hair cell region in postnatal mouse cochleae. Specifically.

FIG. 22 shows representative data pertaining to the effect of Atoh1 alone, or both Atoh1 and β-catenin in the 3$^{rd}$ Deiters region in postnatal mouse cochleae. Specifically.

FIG. 23 shows representative data pertaining to the effect of ectopic expression of Atoh1 alone, or both Atoh1 and β-catenin on inner phalangeal supporting cells. Specifically.

Figure 3A:
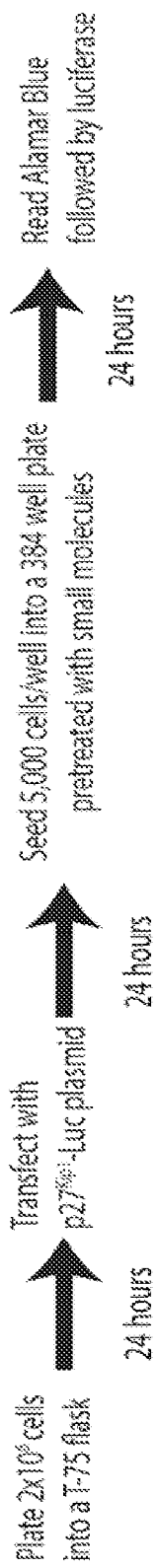
FIG. 3A shows a schematic of the p27$^{Kip1}$ promoter driven luciferase plasmid used herein.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Unless defined otherwise, all technical and scientific terms used herein have the same meaning as commonly understood by one of ordinary skill in the art to which this invention belongs. In this specification and in the claims which follow, reference will be made to a number of terms which shall be defined herein.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of".

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage forms can comprise inventive a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "encapsulate in a nanocarrier" or "encapsulate in a synthetic nanocarrier" both refer to enclosing at least a portion of a substance within a synthetic nanocarrier. For example, the substance can be enclosed completely within a synthetic nanocarrier. Alternatively, most or all of a substance that is encapsulated is not exposed to the local environment external to the synthetic nanocarrier. In the context where some of a substance is not exposed to the local environment external to the synthetic nanocarrier, this can mean that no more than 50%, 40%, 30%, 20%, 10% or 5% is exposed to the local environment. Encapsulation is distinct from absorption, which places most or all of a substance on a surface of a synthetic nanocarrier, and leaves the substance exposed to the local environment external to the synthetic nanocarrier.

As used herein, "synthetic nanocarrier" refers to a discrete object that is not found in nature, and that possesses at least one dimension that is less than or equal to 5 microns in size. A synthetic nanocarrier can be, but is not limited to, one or a plurality of lipid-based nanoparticles, polymeric nanoparticles, metallic nanoparticles, surfactant-based emulsions, dendrimers, buckyballs, nanowires, peptide or protein-based particles (such as albumin nanoparticles) and/or nanoparticles that are developed using a combination of nanomaterials such as lipid-polymer nanoparticles. Synthetic nanocarriers may be a variety of different shapes, including but not limited to spheroidal, cuboidal, pyramidal, oblong, cylindrical, toroidal, and the like. Synthetic nanocarriers according to the invention comprise one or more surfaces. Exemplary synthetic nanocarriers include: (1) the biodegradable nanoparticles disclosed in U.S. Pat. No. 5,543,158 to Gref et al., (2) the polymeric nanoparticles of Published US Patent Application 20060002852 to Saltzman et al., (3) the lithographically constructed nanoparticles of Published US Patent Application 20090028910 to DeSimone et al., (4) the disclosure of WO 2009/051837 to von Andrian et al., or (5) the nanoparticles disclosed in Published US Patent Application 2008/0145441 to Penades et al., (6) the protein nanoparticles disclosed in Published US Patent Application 20090226525 to de los Rios et al., (7) the virus-like particles disclosed in published US Patent Application 20060222652 to Sebbel et al., (8) the nucleic acid coupled virus-like particles disclosed in published US Patent Application 20060251677 to Bachmann et al., (9) the virus-like particles disclosed in WO2010047839A1 or WO2009106999A2, or (10) the nanoprecipitated nanoparticles disclosed in P. Paolicelli et al., "Surface-modified PLGA-based Nanoparticles that can Efficiently Associate and Deliver Virus-like Particles" Nanomedicine. 5(6):843-853 (2010). In embodiments, synthetic nanocarriers may possess an aspect ratio greater than 1:1, 1:1.2, 1:1.5, 1:2, 1:3, 1:5, 1:7, or greater than 1:10.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internes website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14$^{th}$ edition), the Physicians' Desk Reference (64$^{th}$ edition), and The Pharmacological Basis of Therapeutics (12$^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

The term "hearing impairment" as used herein refers to a neurologic disorder, oto-neurological in nature, typically sensorineural, but including composite loss (both sensorineural and conductive loss), preferably either a sensory or a neural (8$^{th}$ nerve related) hearing lost, and most preferably a sensory loss (cochlear related), in which the patient will display, complain of, or is diagnosed to have a hearing loss. Conductive hearing loss is typically related to the external or middle ear. These impairments of interest to the present invention are those associated with hair cell damage. Less preferably such impairments can occur along with conductive hearing loss damage or damage, loss, or degeneration of a neuron of the auditory system. Hair cells are epithelial cells possessing fine projections and located in the maculae and the organ of Corti.

Examples of hearing impairments and situations in which such hearing impairments can occur encompassed by the term "hearing impairment," as used herein, include sensory hearing loss due to end-organ lesions, e.g., acoustic trauma, viral endolymphatic labyrinthitis, and Meniere's disease.

The impairment can also be a neural hearing loss due to events including cerebellopontine angle tumors of the 8$^{th}$ nerve. Hearing impairments include tinnitus, this is a perception of sound in the absence of an acoustic stimulus, and may be intermittent or continuous, wherein there is a diagnosed sensorineural loss. Hearing loss may be due to bacterial or viral infection of the 8$^{th}$ nerve ganglia, such as in herpes zoster oticus, purulent labyrinthitis arising from acute otitis media, purulent meningitis, chronic otitis media, sudden deafness including that of viral origin, e.g., viral endolymphatic labyrinthitis caused by viruses including mumps, measles, influenza, chickenpox, mononucleosis, and adenoviruses. The hearing loss can be congenital, such as that caused by rubella, anoxia during birth, bleeding into the inner ear due to trauma during delivery, ototoxic drugs administered to the mother, erythroblastosis fetalis, and hereditary conditions including Waardenburg's syndrome and Hurler's syndrome. The hearing loss can be noise-induced, generally due to a noise greater than 85 decibels (db) that damages the inner ear. Hearing loss includes presbycusis, which is a sensorineural hearing loss occurring as a normal part of aging, fractures of the temporal bone extending into the middle ear and rupturing the tympanic membrane and possibly the ossicular chain, fractures affecting the cochlea, and acoustic neurinoma, which are tumors generally of Shwann cell origin that arise from either the auditory or vestibular divisions of the 8$^{th}$ nerve. In various aspects, the hearing loss is caused by an obotoxic drug that affects the auditory portion of the inner ear, particularly the organ of Corti. Incorporated herein by reference are Chapters 196, 197, 198, and 199 of The Merck Index, 14$^{th}$ Edition (1982), Merck Sharp & Dome Research Laboratories, N.J. and related chapters in the most recent edition, relating to description and diagnosis of hearing impairments.

Tests are known and available for diagnosing hearing impairments. Neuro-otological, neuro-ophthalmological, neurological examinations, and electra-oculography can be used (Wennmo et al., *Acta Otolaryngol* 1982, 94, 507). Sensitive and specific measures are available to identify patients with auditory impairments. For example, tuning fork tests can be used to differentiate a conductive from a sensorineural hearing loss and determine whether the loss is unilateral. An audiometer is used to quantitate hearing loss, measured in decibels. With this device the hearing for each ear is measured, typically from 125 to 8000 Hz, and plotted as an audiogram. Speech audiometry can also be performed. The speech recognition threshold, the intensity at which speed is recognized as a meaningful symbol, can be determined at various speech frequencies. Speech or phoneme discrimination can also be determined and used as an indicator of sensorineural hearing loss since analysis of speech sounds relies upon the inner ear and 8$^{th}$ nerve. Tympanometry can be used to diagnose conductive hearing loss and aid in the diagnosis of those patients with sensorineural hearing loss. Electrocochleography, measuring the cochlear microphonic response and action potential of the 8$^{th}$ nerve, and evoked response audiometry, measuring evoked response from the brainstem and auditory cortex, to acoustic stimuli can be used in patients, particularly infants and children or patients with sensorineural hearing loss of obscure etiology. These tests serve a diagnostic function as well as a clinical function in assessing response to therapy.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —NH$_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein. A specific example of amino is —NH$_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "Rn," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —$O(CH_2)_{0-4}R^\circ$; —$O(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; CH=CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ C(S)R^\circ$; —$(CH_2)_{0-4}N(R^\circ C(O)NR^\circ_2$; —$N(R^\circ C(S)NR^\circ)_2$; —$(CH_2)_{0-4}N(R^\circ C(O)OR^\circ$; —$N(R^\circ)N(R^\circ)C(O)R^\circ$; —$N(R^\circ N(R^\circ C(O)NR^\circ_2$; —$N(R^\circ N(R^\circ C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$(CH_2)_{0-4}OC(O)NR^\circ_2$; —$C(O)N(OR^\circ)R^\circ$; —$C(O)C(O)R^\circ$; —$C(O)CH_2C(O)R^\circ$;

—C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°S(O)$_2$NR°$_2$; —N(R°S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_1$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

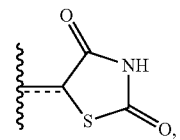

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

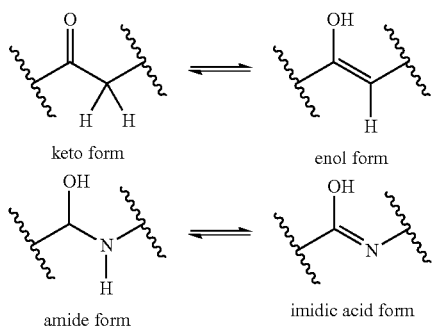

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

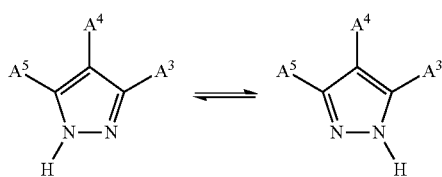

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

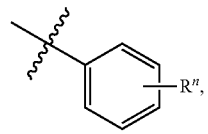

which is understood to be equivalent to a formula:

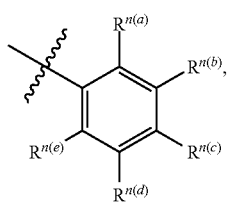

wherein n is typically an integer. That is, $R^n$ is understood to represent five independent substituents, $R^{n\,(a)}$, $R^{n\,(b)}$, $R^{n\,(c)}$, $R^{n\,(d)}$, $R^{n\,(e)}$. By "independent substituents," it is meant that each R substituent can be independently defined. For example, if in one instance $R^{n\,(a)}$ is halogen, then $R^{n\,(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein.

These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Pharmaceutical Compositions

In one aspect, the invention relates to pharmaceutical compositions comprising at least one agent that activates the expression of Atoh1, or a pharmaceutically acceptable salt, solvate, or polymorph thereof; at least one agent that inhibits the expression of p27$^{Kip1}$, or a pharmaceutically acceptable salt, solvate, or polymorph thereof; and a pharmaceutically acceptable carrier.

In one aspect, the invention relates to pharmaceutical compositions comprising β-catenin and at least one agent that activates the expression of Atoh1, or a pharmaceutically acceptable salt, solvate, or polymorph thereof.

In one aspect, the invention relates to pharmaceutical compositions comprising β-catenin; at least one agent that activates the expression of Atoh1, or a pharmaceutically acceptable salt, solvate, or polymorph thereof; at least one agent that inhibits the expression of p27$^{Kip1}$, or a pharmaceutically acceptable salt, solvate, or polymorph thereof; and a pharmaceutically acceptable carrier.

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, Pa. 1990.

In a further aspect, the pharmaceutical composition is used to treat hearing impairment.

In a further aspect, the pharmaceutical composition comprises a population of cells made by a disclosed method.

1. Inhibitors of p27$^{Kip1}$ Expression

In various aspects, the invention relates to pharmaceutical compositions comprising at least one agent that inhibits the expression of p27$^{Kip1}$ or a pharmaceutically acceptable salt, solvate, or polymorph thereof.

An agent that decreases or inhibits the expression or activity of p27$^{Kip1}$ is an agent that measurably decreases or reduces the amount of mRNA encoding p27$^{Kip1}$ the amount of p27$^{Kip1}$ protein, or the activity of p27$^{Kip1}$ as compared to a cell not contacted with the inhibitory agent. In various aspects, the inhibitory agent results in at least a 2-fold, 3-fold, 4-fold, 5-fold, or 10-fold decrease in p27$^{Kip1}$ expression or activity.

p27$^{Kip1}$ is an enzyme that in humans is encoded by the CDKN1B gene (Polyak, K., et al. (1994) Cell 78, 59-66). p27$^{Kip1}$ belongs to the Cip/Kip family of cyclin-dependent kinase (Cdk) inhibitor proteins and binds to and prevents the activation of cyclin E-CDK2 or cyclin D-CDK4 complexes, thereby controlling the cell cycle progression at G1. The inhibition of p27$^{Kip1}$ expression is disclosed in U.S. Pat. No. 7,741,303 and U.S. Pat. No. 7,132,406, wherein antisense nucleic acid molecules are described for use in stimulating the formation of an inner ear sensory hair cell from an inner ear support cell, and improving auditory function. The nucleotide and amino acid sequences of p27$^{Kip1}$ are known in the art and include, but are not limited to, those available under GENBANK Accession Nos. NM_004064 and NP_004055 (Homo sapiens, FIGS. 2A and 2B, respectively) and NM_009875 and NP_034005 (Mus musculus).

In a further aspect, the agent that inhibits expression of p27$^{Kip1}$ inhibits transcription from a p27$^{Kip1}$ promoter by at least about 50% in a cell-based transcriptional assay. In a still further aspect, the cell-based transcriptional assay comprises a plasmid comprising the p27$^{Kip1}$ promoter linked to a reporter gene. In yet a further aspect, the reporter gene codes for a luciferase. In an even further aspect, the agent that inhibits the transcription from the p27$^{Kip1}$ promoter inhibits transcription from an SV40 promoter linked to a reporter gene by less than about 30%.

a. Examples

In various aspects, the p27$^{Kip1}$ inhibitor downregulates transcription or translation of CDKN1B gene. The downregulation of transcription or translation includes downregulation of transcription by binding to the CDKN1B promoter, degradation of mRNA after transcription, interruption of translation, or any other downregulation.

Examples of agents that inhibit p27$^{Kip1}$ expression include antisense or ribozyme molecules, e.g., the antisense molecule 5'-TGGCTCTCXTGCGCC-3' (SEQ ID NO:5; Cariou, S., et al. (2000) Proc. Natl. Acad. Sci. USA 97, 9042-9046), wherein X indicates a G clamp modification (Flanagan, J. G., et al. (1999) Proc. Natl. Acad. Sci. USA 96, 3513-3518). Moreover, exemplary antisense nucleic acid molecules for inhibiting the expression of p27$^{Kip1}$ are described in, e.g., U.S. Pat. No. 7,741,303 and U.S. Pat. No. 7,132,406, each of which is incorporated by reference in its entirety.

Other p27$^{Kip1}$ inhibitors include siRNA (short interfering RNA) using RNA interference of CDKN1B gene or shRNA (short hairpin RNA). RNA interference (hereinafter, "RNAi") is a mechanism that inhibits gene expression after transcription in many eukaryotes. RNAi is induced by short double-stranded RNA ("dsRNA") molecules existing in cells (Fire, A., et al. (1998) Nature 391, 806-811). These short dsRNA molecules, also known as the "siRNA," are separated into single strands and bind to RNA-induced silencing complex (RISC), thereby cleaving target mRNA or interfering translation (Elbashir, W., et al. (2001) Genes Dev. 15, 188-200).

Thus, the present invention provides a siRNA composed of short double-stranded RNA of from about 17 to about 25 nucleotides that target mRNA of the CDKN1B gene. The siRNA includes a sense RNA strand and its complementary antisense RNA strand. These two strands bind (anneal) with each other through Watson-Crick base pairing interaction. The sense strand includes the same nucleotide sequence in the target sequence of the target mRNA. The target sequence of siRNA may be selected by a method published in the literature.

The sense and antisense strands of the siRNA of the present invention may include two complementary, single-stranded RNA molecules, or a molecule wherein two complementary moieties are base-paired and covalently bonded by a single-stranded "hairpin" domain. The latter is called shRNA (short hairpin RNA). shRNA is a single strand, about 50-70 nucleotides in length, having a stem-loop structure in vivo. On both sides of 5-10 nucleotide loop portion, long RNA of 19-29 nucleotides are base-paired to form a double-stranded stem.

The siRNA of the present invention may be obtained and synthesized chemically or produced by recombinant techniques using methods well-known in the related art. Preferably, the siRNA of the present invention may be synthesized chemically using adequately protected ribonucleoside phosphoramidites and a commonly used DNA/RNA synthesizer. The siRNA may be synthesized as two separated complementary RNA molecules or as an RNA molecule having two complementary domains. Alternatively, the siRNA may be expressed from a recombinant DNA plasmid using an adequate promoter. Examples of the adequate promoter for expressing the siRNA of the present invention from plasmid may include U6 or H1 RNA pol III promoter and cytomegalovirus promoter. Further, the recombinant plasmid may include an inducing promoter or a controllable promoter so that the siRNA can be expressed under a specific tissue or cell environment.

The siRNA of the present invention may be expressed from the recombinant plasmid as two separated complementary RNA molecules or as an RNA molecule having two complementary domains. Selection of adequate plasmid for expressing the siRNA of the present invention, insertion of nucleotide sequence for expressing the siRNA into the plasmid, and transfer of the recombinant plasmid to target cells are disclosed in the related art (see, i.e., Tuschl, T., et al. (2002) Nat. Biotechnol. 20, 446-448; Brummelkamp, T. R., et al. (2002) Science 296, 550-553; Miyagishi, K., et al. (2002) Nat. Biotechnol. 20, 497-500; Paddison, P. J., et al. (2002) Genes Dev. 16, 948-958; Lee, N. S., et al. (2002) Nat. Biotechnol. 20, 500-505; Paul, C. P., et al. (2002) Nat. Biotechnol. 20, 505-508).

Exemplary siRNA targeting CDKN1B are described in U.S. Pat. No. 7,612,196, incorporated herein by reference in its entirety.

In addition to inhibiting expression, the present invention also includes agents that inhibit the activity of p27$^{Kip1}$. Inhibition of p27$^{Kip1}$ activity includes inhibition of protein activity and interruption of protein interaction with other proteins, e.g., using a peptide or small molecule compound that binds specifically to a p27$^{Kip1}$ binding or active domain or a neutralizing polyclonal or monoclonal antibody against p27$^{Kip1}$.

Neutralizing antibodies may be prepared by injecting the immunogen p27$^{Kip1}$ protein or its fragment into a host by methods well-known to those skilled in the art. The host may include, but are not limited to mammals such as mouse, rat, sheep or rabbit. The immunogen may be injected intramuscularly, intra-abdominally or subcutaneously. An adjuvant may be administered together in order to enhance antigenicity. Blood is taken from the host at predetermined intervals to collect the serum showing improved titer or antigen specificity, and antibodies are isolated and purified therefrom.

A monoclonal antibody may be prepared by fusion with an immortalized cell line as is well-known in the related art (Koehler, G. and Milstein, C. (1975) Nature 256, 495-497). The procedure typically includes immunizing a mouse with p27$^{Kip1}$ protein, isolating antigen-producing lymphocytes from the mouse and fusing the lymphocytes with human or mouse myeloma cells to produce immortalized hybridomas. Hybridoma cells producing monoclonal antibody are selected and proliferated by ELISA, and monoclonal antibody is isolated and purified therefrom. The ability of the antibody to neutralize p27$^{Kip1}$ can be assessed by determining whether the antibody blocks activation of cyclin E-CDK2 or cyclin D-CDK4 complexes.

In a further aspect, the agent that inhibits the expression of p27$^{Kip1}$ is selected from a compound having a structure represented by a formula:

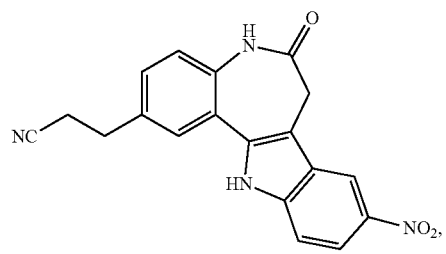

-continued

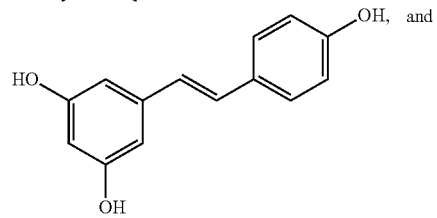

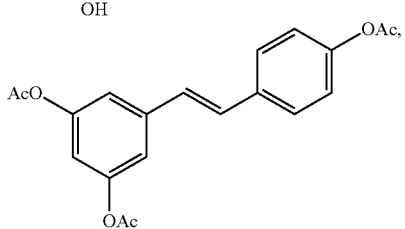

or a pharmaceutically acceptable salt, solvate, or polymorph thereof.

i. Paullone Derivatives

In various aspects, the agent that inhibits the expression of p27$^{Kip1}$ is a paullone derivative, or a pharmaceutically acceptable solvate, salt, or polymorph thereof. Paullones are a family of benzazepinones characterized by a core framework represented by a structure:

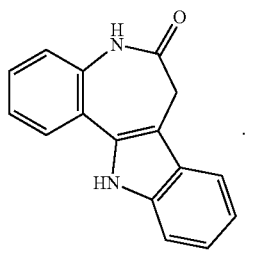 [SMILES: O=C1Cc2c([nH]c3ccccc23)-c2ccccc2N1]

Paullones constitute a well-established class of cyclin-dependent kinase (CDK) inhibitors. CDK's are a family of serine/threonine protein kinases known to play a central role in the normal growth and life cycle of eukaryotic cells. Inhibitors of CDK could potentially serve as pharmacological agents to treat diseases of proliferation such as cancer, psoriasis, and restenosis (Sharma, V. M., et al. (2008) *Indian J. of Biochem. & Biophysics* 45, 416; Leost, M., et al. (2000) *Eur. J. Biochem.* 267, 5983-5994).

Paullone derivatives have been previously described in, for example, US 2003/0181439 A1; U.S. Pat. No. 7,232,814 B2; Kunick, C., et al. (2005) *ChemBioChem* 6, 541-549; Zaharevitz, D., et al. (1999) *Cancer Res.* 59, 2566-2569; Leost, M., et al. (2000) *Eur. J. Biochem.* 267, 5983-5994; WO 2006/117212 A2; WO 2009/010298 A2; Sharma, V. M., et al. (2008) *Indian J. of Biochem. & Biophysics* 45, 416; Pies, T. (2003) *Dissertation*, Hamburg University, Hamburg, GER, which are herein incorporated by reference.

In a further aspect, the paullone derivative is selected from a compound having a structure represented by a formula:

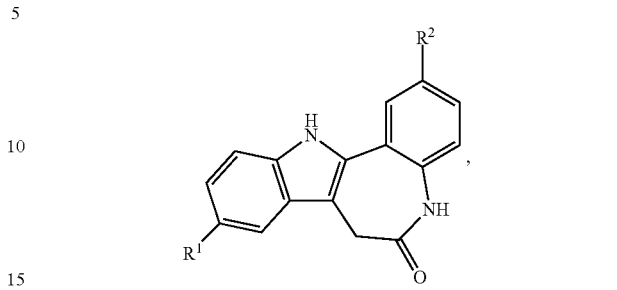

wherein $R^1$ is selected from hydrogen, halogen, —OH, —CN, —NO$_2$, —NH$_2$, —(S═O)—R$^3$, —SO$_2$—R$^3$, C1-C6 monohaloalkyl, C1-C6 polyhaloalkyl, C1-C6 alkoxy, C1-C6 cyanoalkyl, C1-C6 aminoalkyl, C1-C6 hydroxyalkyl, C1-C6 monoalkylamino, and C1-C6 dialkylamino; wherein $R^3$ is selected from hydrogen, —CH$_3$, —CFH$_2$, —CF$_2$H, —CF$_3$, —NH$_2$, —NH(CH$_3$), and —N(CH$_3$)$_2$; wherein $R^2$ is selected from hydrogen, halogen, —OH, —CN, —NO$_2$, —NH$_2$, —(S═O)—R$^4$, —SO$_2$—R$^4$, C1-C6 monohaloalkyl, C1-C6 polyhaloalkyl, C1-C6 alkoxy, C1-C6 cyanoalkyl, C1-C6 aminoalkyl, C1-C6 hydroxyalkyl, C1-C6 monoalkylamino, and C1-C6 dialkylamino; wherein $R^4$ is selected from hydrogen, —CH$_3$, —CFH$_2$, —CF$_2$H, —CF$_3$, —NH$_2$, —NH(CH$_3$), and —N(CH$_3$)$_2$; or a pharmaceutically acceptable solvate, salt, or polymorph thereof.

In a further aspect, $R^1$ is selected from hydrogen, —F, —Cl, —Br, —OH, —CN, —NO$_2$, —NH$_2$, —(S═O)—CF$_2$H, —(S═O)—CF$_3$, —(S═O)—NH$_2$, —SO$_2$CF$_2$H, —SO$_2$CF$_3$, —SO$_2$NH$_2$, —SO$_2$—R$^3$, —CH$_3$, —CFH$_2$, —CF$_2$H, —CF$_3$, —OCH$_3$, —NH(CH$_3$), and —N(CH$_3$)$_2$; and wherein $R^2$ is selected from —CN, cyanomethyl, cyanoethyl, and cyanopropyl. In a still further aspect, $R^1$ is selected from hydrogen, —F, —CN, —NO$_2$, and —CF$_3$; and wherein $R^2$ is selected from —CN, cyanomethyl, cyanoethyl, and cyanopropyl.

In a further aspect, the paullone derivative is selected from a compound having a structure represented by a formula:

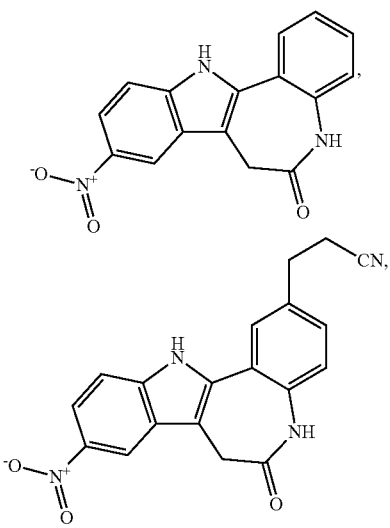

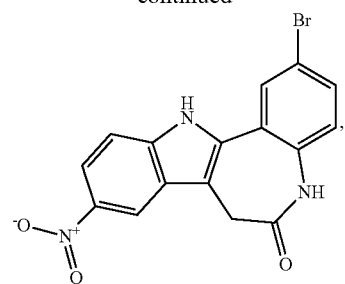
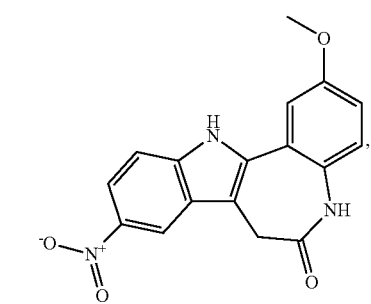
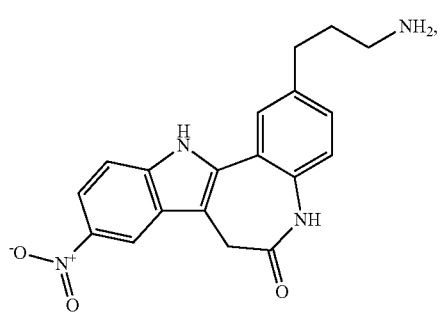
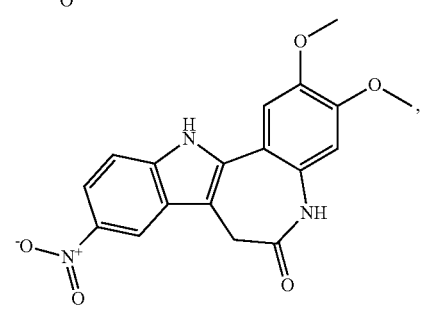
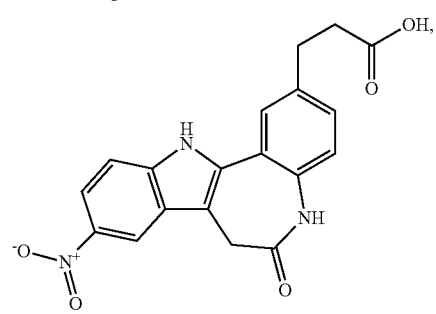
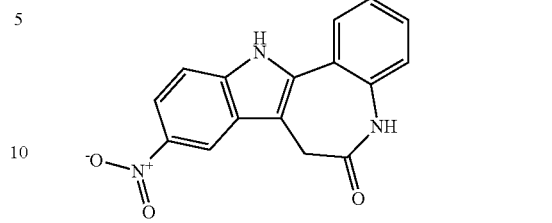
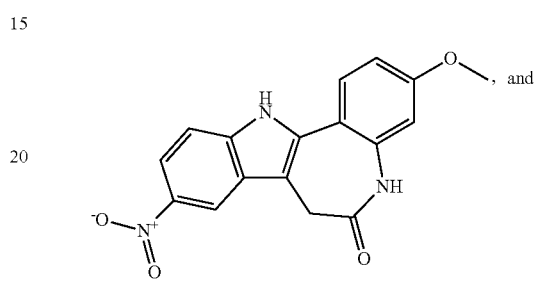
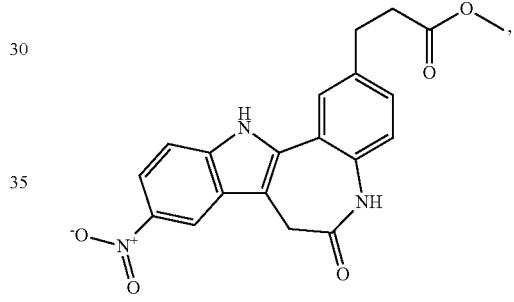
or a pharmaceutically acceptable salt, solvate, or polymorph thereof.
In a further aspect, the paullone derivative is selected from a compound having a structure represented by a formula:
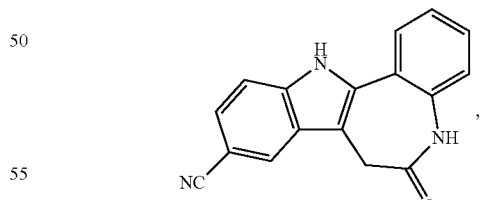
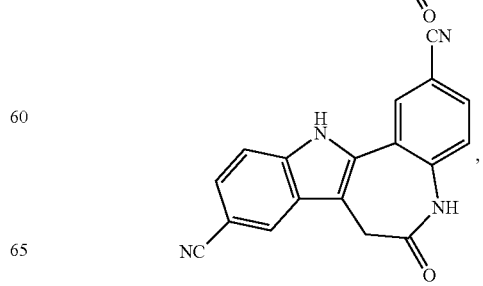

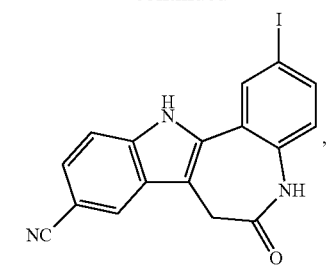
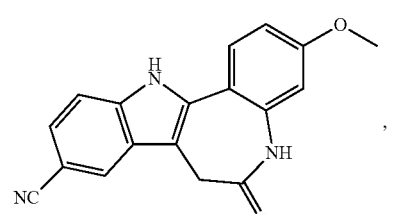
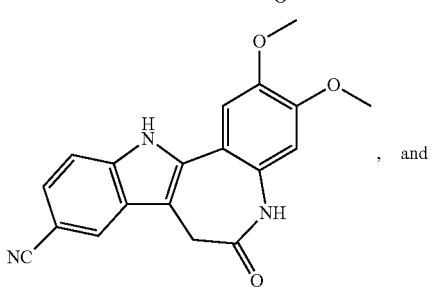
, and
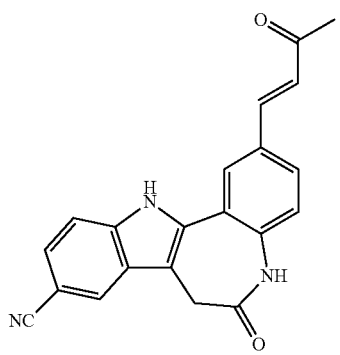
or a pharmaceutically acceptable salt, solvate, or polymorph thereof.
In a further aspect, the paullone derivative is selected from a compound having a structure represented by a formula:
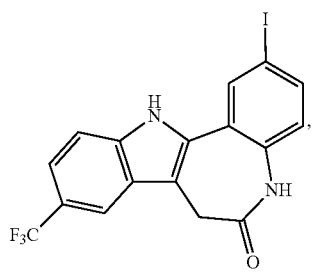
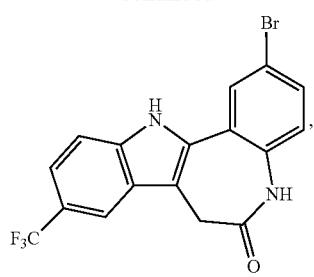
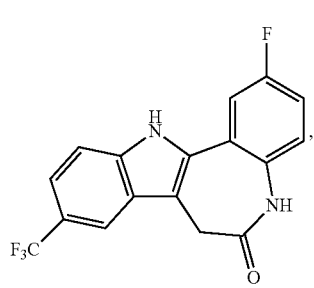
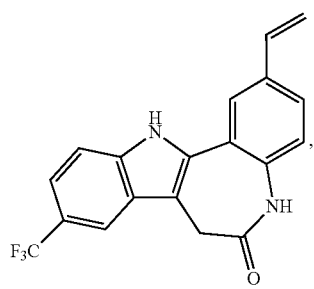
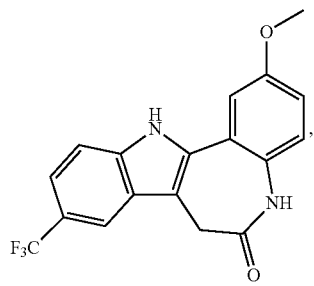
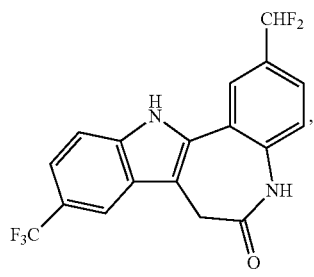
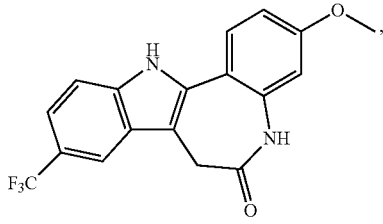

39
-continued
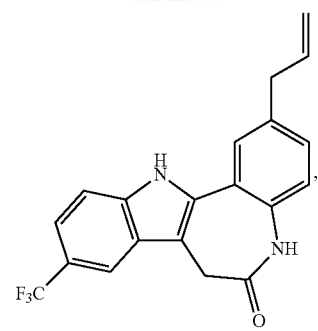
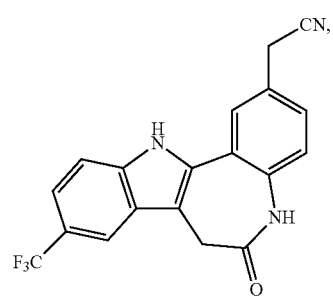
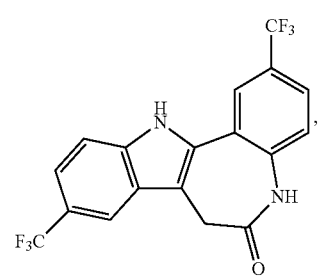
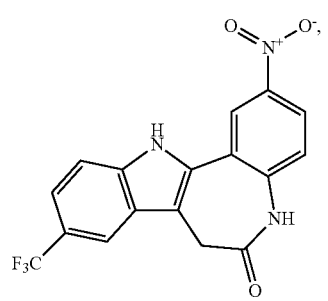
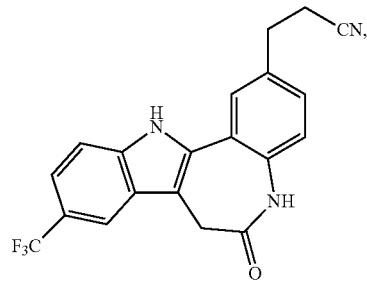
40
-continued
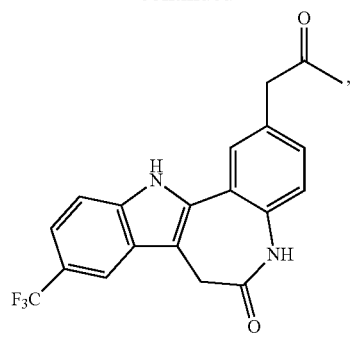
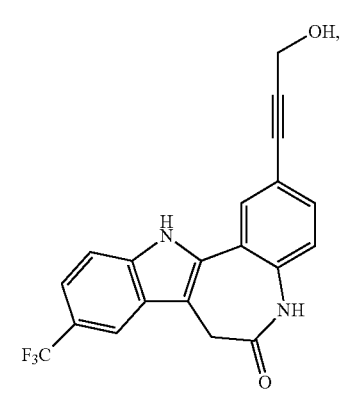
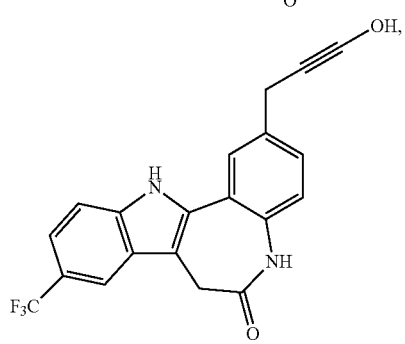
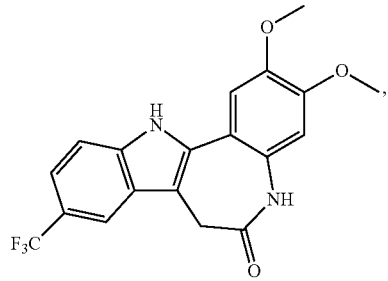
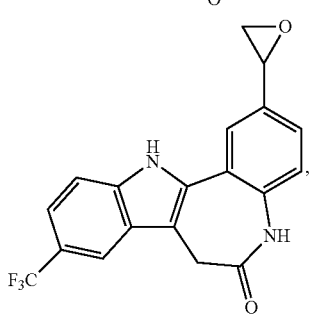

-continued
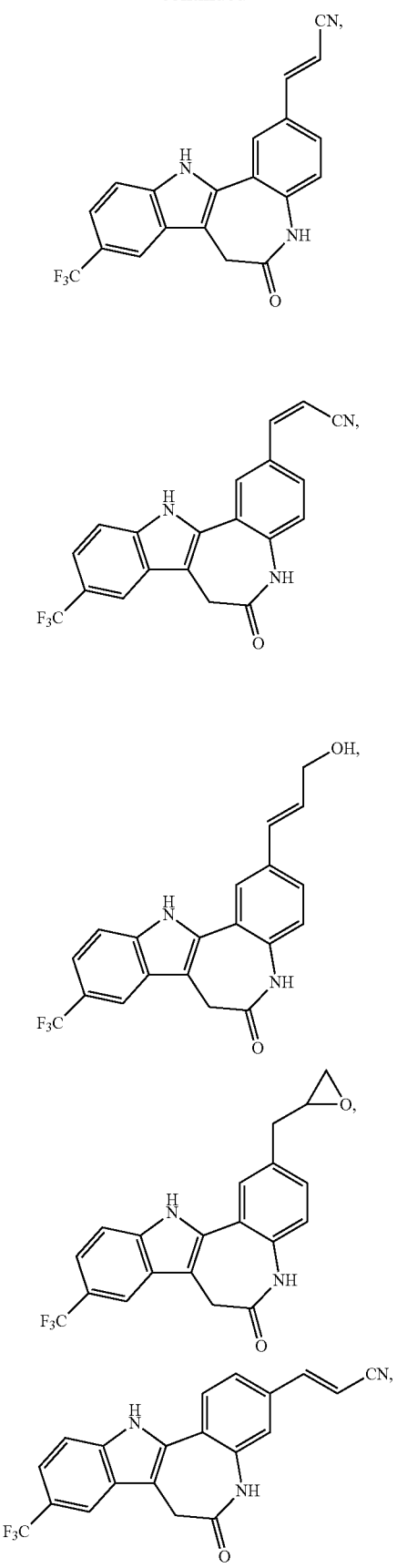
-continued
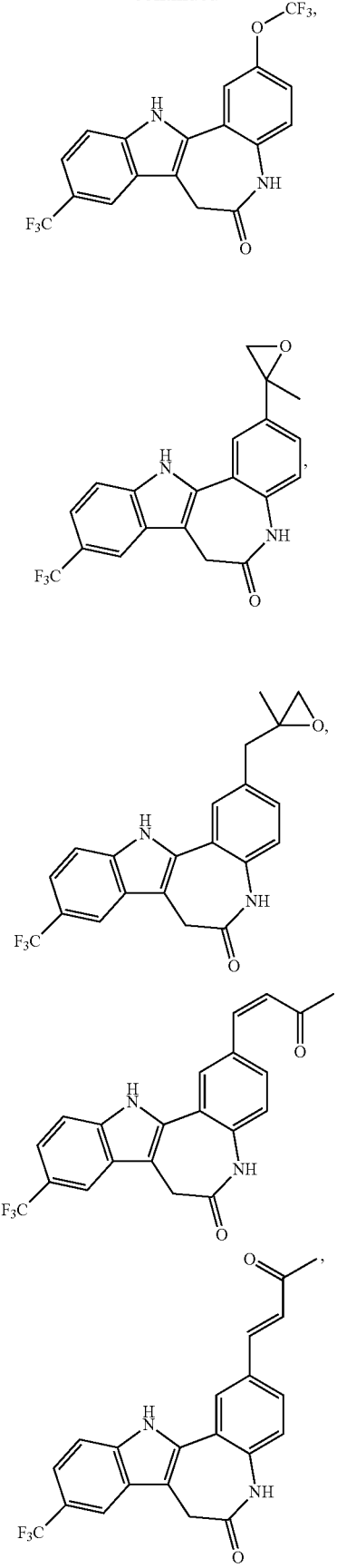

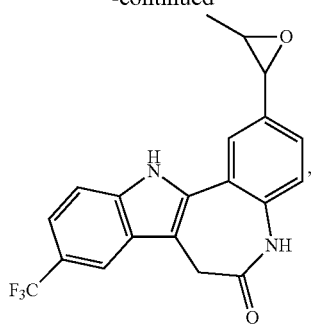
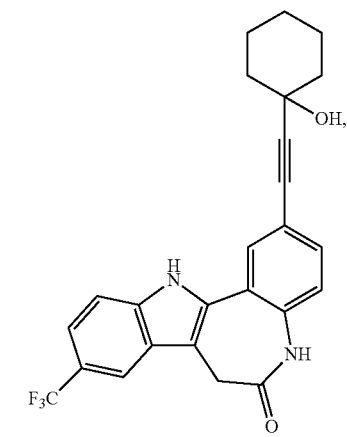
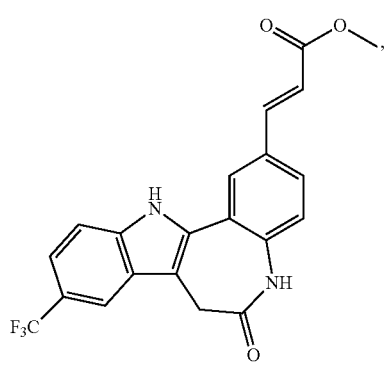
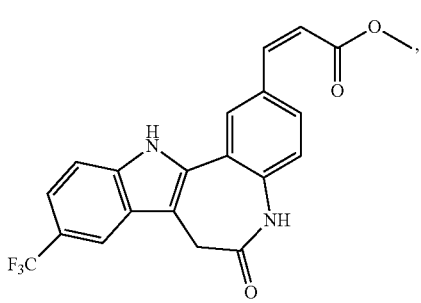
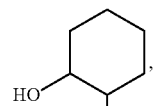
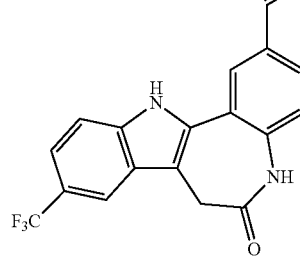
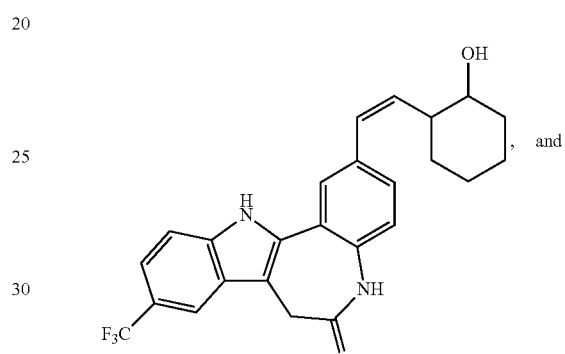
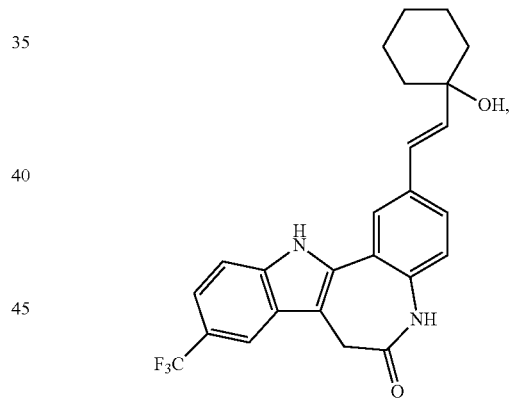
or a pharmaceutically acceptable salt, solvate, or polymorph thereof.
In a further aspect, the paullone derivative is selected from a compound having a structure represented by a formula:
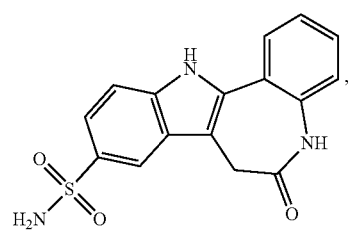

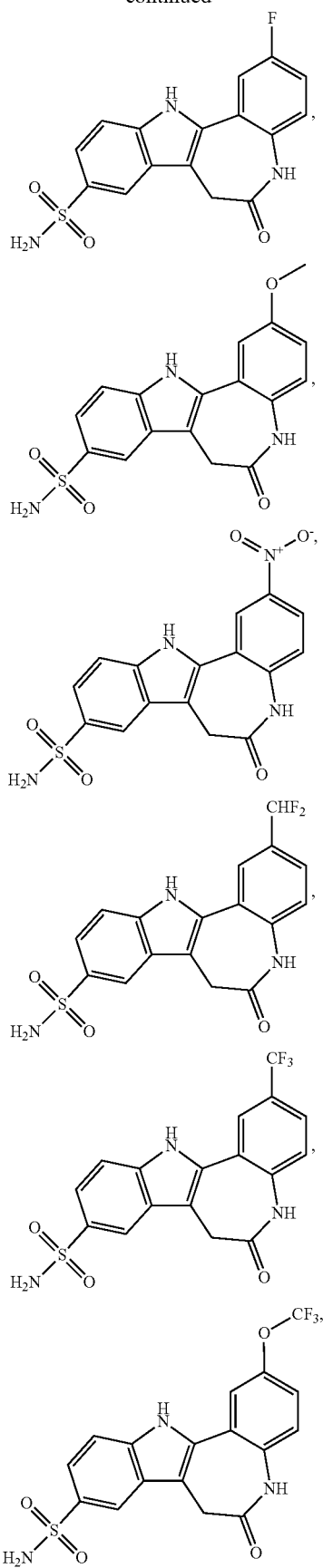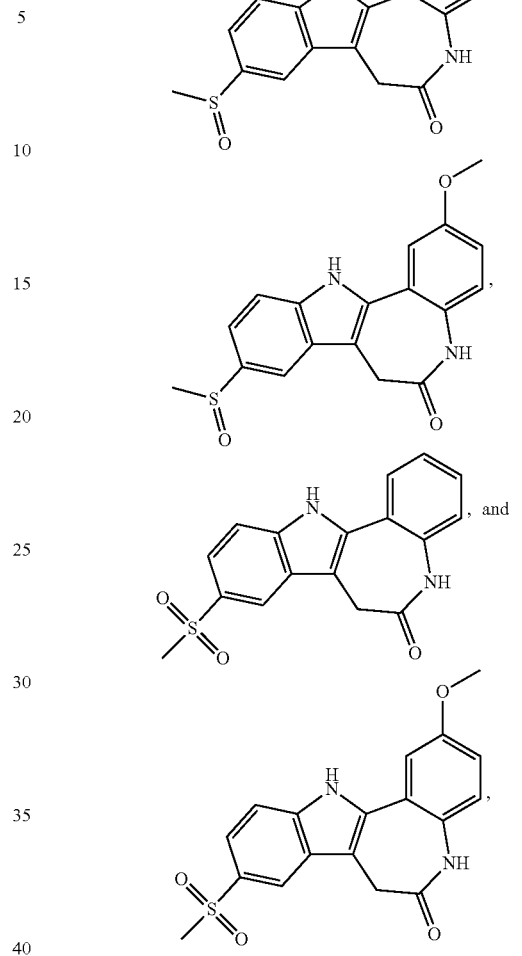

or a pharmaceutically acceptable salt, solvate, or polymorph thereof.

In a further aspect, the paullone derivative is a compound having a structure represented by a formula:

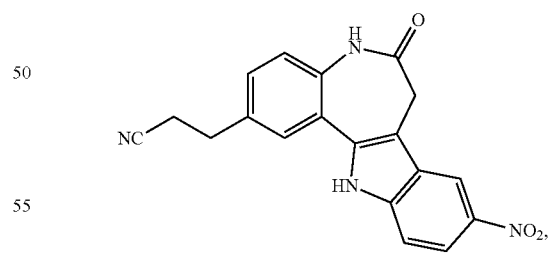

or a pharmaceutically acceptable solvate, salt, or polymorph thereof.

2. Activators of Atoh1 Expression

In various aspects, the invention relates to pharmaceutical compositions comprising at least one agent that activates the expression of Atoh1, or a pharmaceutically acceptable salt, solvate, or polymorph thereof.

An agent that stimulates the expression or activity of Atoh1 is an agent that measurably increases or elevates the amount of mRNA encoding Atoh1, the amount of Atoh1 protein or the activity of Atoh1 in a cell or tissue as compared to a cell or tissue not contacted with the stimulatory agent. Exemplary activators of Atoh1 expression have been previously described (see, i.e., U.S. Pat. No. 8,188,131; US 2013/0085112; US 2011/0305674; US 2013/0210145; US 2012/0328580). In various aspects, the stimulatory agent results in at least a 2-fold, 3-fold, 4-fold, 5-fold, or 10-fold increase in Atoh1 expression or activity.

Atonal protein homologue 1 (Atoh1 or atonal) is a proneural gene that encodes a basic helix-loop-helix (bHLH) domain-containing protein that appears to play an important role in cell fate determination in the development of the *Drosophila* nervous system (Jarman, A. P., et al. (1993) *Cell* 73, 1307-1321). Atoh1 is evolutionarily conserved, with homologs identified in *Tribolium castenium* (the red flour beetle), *Fugu rubripes* (puffer fish), chicken (Cath1), mouse (Math1), and human (Hath1) (Ben-Arie, N., et al. (1996) *Hum. Mol. Gene* 5, 1207-1216). Each of these homologs contains a bHLH domain that is identical in length and has high sequence identity to the Atoh1 bHLH domain. For example, the Hath1 and Math1 genes are almost identical in length. These molecules also have highly similar nucleotide sequences (86% identity) and highly similar bHLH amino acid sequences (89%). The bHLH domain of Cath1 is 97% and 95% identical to the bHLH domain of Hath1 and Math1, respectively. The bHLH of Cath1 is 67% identical to the Atoh1 bHLH domain. In contrast, the bHLH domains of other *Drosophila* encoded proteins share only 40-50% sequence identity.

Each of the mammalian Atoh1 homologs functions as a transcription factor that activates E box-dependent transcription (Ben-Arie, N., et al. (1996) *Hum. Mol. Gene* 5, 1207-1216; Akazawa, C., et al. (1995) *J. Biol. Chem.* 270, 8730-8738) and functions as a critical positive regulator of cell fate determination in neural tissue and the gastrointestinal (GI) tract (Helms et al. (1998) *Development* 125, 919; Isaka et al. (1999) *Eur. J. Neurosci.* 11, 2582; Ben-Arie et al. (2000) *Development* 127, 1039).

a. Examples

In various aspects, the methods of the invention include stimulating the expression of Atoh1. In accordance with this aspect, stimulating expression of Atoh1 can include providing an agent that increases Atoh1 transcription and/or increases synthesis of Atoh1 protein. Agents that can increase Atoh1 expression and/or synthesis include, but are not limited to, small organic compounds, nucleic acids encoding Atoh1, and the Atoh1 protein itself.

Examples of small organic compounds capable of increasing Atoh1 expression in a cell include, but are not limited to, the phenolic compounds (or sulfur analogs), benzamide compounds, heterocyclic compounds, benzothiazole-containing compounds, quinoline-containing compounds, benzoxazole-containing compounds, quinazolinone-containing compounds, and benzimidazopyrimidine-containing compounds described in, e.g., U.S. Pat. No. 8,188,131, which is incorporated herein by reference in its entirety. Such compounds have been shown to increase Atoh1 expression and promote the differentiation of a progenitor or stem cell toward an auditory hair cell.

In various aspects, an Atoh1 nucleic acid or polypeptide is used to increase the expression of Atoh1. As used herein, "Atoh1" refers to any and all Atoh1-associated nucleic acid or protein sequences and includes any sequence that is orthologous or homologous to, or has significant sequence similarity to, an Atoh1 nucleic acid or amino acid sequence, respectively, and thus the term "Atoh1" includes other mammalian homologues, e.g., human, mouse, rat, etc. The sequence can be present in any animal including mammals (e.g., humans). Examples of Atoh1 nucleic acid and amino acid sequences include, but are not limited to, those listed in Table 1, as well as other synonyms that may be used to refer to this protein, e.g., atonal, atonal homolog 1, Atoh1, and helix-loop-helix protein Hath1.

TABLE 1

| Organism | Ortholog | Sequence Identity to Hath1 Protein | | GENBANK Accession Nos. |
|---|---|---|---|---|
| Homo sapiens | Hath1 | 100% | Nucleotide | NM_005172.1[a] |
| | | | Protein | NP_005163.1[b] |
| Pan troglodytes | Atoh1 | 99.7% | Nucleotide | NM_001012432.1 |
| | | | Protein | NP_001012434.1 |
| Mus Musculus | Math1 | 89.2% | Nucleotide | NM_007500.4 |
| | | | Protein | NP_031526.1 |
| Rattus norvegicus | Atoh1 | 89.2% | Nucleotide | NM_001109238.1 |
| | | | Protein | NP_001102708.1 |
| Macaca mulatta | Atoh1 | 97.7% | Nucleotide | XM_001102247.1 |
| | | | Protein | XP_001102247.1 |
| Bos taurus | Atoh1 | 94.6% | Nucleotide | NM_001098099.1 |
| | | | Protein | NP_001091568.1 |
| Canis lupus | Atoh1 | 92.3% | Nucleotide | XM_544986.2 |
| | | | Protein | XP_544986.2 |

[a]See FIG. 1A;
[b]See FIG. 1B.

Furthermore, multiple homologous or similar sequences can exist in an animal (See, e.g., GeneID: 474 (*Homo sapiens*); GeneID: 11921 (*Mus musculus*); GeneID: 461380 (Pan troglodytes); GeneID: 500156 (*Rattus norvegicus*); GeneID: 704893 (*Macaca mulatta*); GeneID: 539158 (*Bos taurus*); and GeneID: 487864 (*Canis lupus familiaris*)).

Any sequence with significant sequence similarity (i.e., similarity greater than 80%, e.g., is at least 85%, 90%, 95%, 99%, or more, across the entire sequence) to the human Atoh1 sequence (available under GENBANK Accession Nos. NM_005172.1 and NP_005163.1) can be used in the present methods. To determine the percent identity of two nucleic acid sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 80% (in some embodiments, about 85%, 90%, 95%, or 100% of the length of the reference sequence) is aligned. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can be determined using the Needleman & Wunsch (*J. Mol. Biol.* 1970, 48, 444) algorithm which has been incorporated into the GAP program in the GCG software package, using a Blossum 62 scoring matrix with a gap penalty of 12, a gap extend penalty of 4, and a frameshift gap penalty of 5.

In various aspects, this invention embraces the use of a vector harboring and capable of expressing a nucleic acid encoding an Atoh1 protein as described above. Such a vector can be an expression vector and/or a gene delivery vector. Expression vectors are in this context meant for use in ex vivo gene therapy techniques, i.e., suitable host cells are transfected outside the body and then administered to the subject. Gene delivery vectors are referred to herein as vectors suited for in vivo gene therapeutic applications, i.e., the vector is directly administered to the subject, either systemically or locally. The vectors referred to herein may only be composed of nucleic acid or may be complexed with additional compounds that enhance, for instance, transfer into the target cell, targeting, stability and/or bioavailability, e.g., in the circulatory system. Examples of such additional compounds are lipidic substances, polycations, membrane-disruptive peptides or other compounds, antibodies or fragments thereof or receptor-binding molecules specifically recognizing the target cell, etc.

Expression or gene delivery vectors may preferably be derived from viruses such as retroviruses, vaccinia virus, adeno-associated virus, herpes viruses, or bovine papilloma virus, and may be used for delivery into a targeted cell population. Methods which are well known to those skilled in the art can be used to construct recombinant expression or gene delivery vectors; see, for example, the techniques described in Sambrook & Russell (2001) *Molecular Cloning: A Laboratory Manual*, Cold Spring Harbor Laboratory N.Y. and Ausubel (1989) *Current Protocols in Molecular Biology*, Green Publishing Associates and Wiley Interscience, N.Y. Alternatively, the vectors can be reconstituted into liposomes for delivery to target cells. The vectors containing Atoh1-encoding polynucleotide can be transferred into a host cell by well-known methods, which vary depending on the type of cellular host. For example, calcium chloride transfection is commonly utilized for prokaryotic cells, whereas calcium phosphate treatment or electroporation may be used for other cellular hosts.

Suitable vectors and methods for ex vivo or in vivo gene therapy are described in the literature and are known to the person skilled in the art (see, e.g., Giordano, F. J., et al. (1996) *Nature Medicine* 2, 534-539; Schaper, W., et al. (1996) *Circ. Res.* 79, 911-919; Anderson, W. F., (1992) *Science* 256, 808-813; Isner, J. M., et al. (1996) *Lancet* 348, 370-374; Muhlhauser et al. (1995) *Circ. Res.* 77, 1077-1086; Wang et al. (1996) *Nature Medicine* 2, 714-716; WO 94/29469; WO 97/00957; Schaper et al. (1996) *Curr. Opin. Biotech.* 7, 635-640, and references cited therein). The vectors for use in this embodiment of the invention may be designed for direct introduction or for introduction via liposomes or viral vectors (e.g., adenoviral, retroviral) into the cell. Preferred gene delivery vectors include baculovirus-, adenovirus- and vaccinia virus-based vectors, which are preferably non-replicating vectors. Exemplary nucleic acids encoding Atoh1 to increase Atoh1 expression are described in, e.g., US 2004/0237127.

As indicated, some aspects of the invention include the use of the Atoh1 protein itself. The Atoh1 protein can be obtained by conventional methods, including chemical synthesis or recombinant protein production. Any suitable expression vector can be used to overexpress Atoh1 for recombinant protein production. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence.

It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance *E. coli, S. cerevisiae*) are sufficiently described in the literature. Promoters permitting a particularly high expression of a downstream sequence are for instance the T7 promoter (Studier, F. W., et al. (1990) *Meth. Enzymol.* 185, 60-69), lacUVS, trp, trp-lacUVS (DeBoer, et al. (1982) in Rodriguez and Chamberlin (Eds) Promoters, Structure and Function, Praeger, New York, 462-481; DeBoer, H. A., et al. (1983) *Proc. Natl. Aced. Sci. USA* 80, 21-25), lp1, rac (Boros et al. (1986) *Gene* 42, 97-100). Inducible promoters are preferably used for the synthesis of proteins. These promoters often lead to higher protein yields than do constitutive promoters. Termination signals for transcription are also described in the literature. Transformation or transfection of suitable host cells can be carried out according to conventional methods.

The transformation of the host cell with a nucleic acid molecule or vector according to the invention can be carried out by standard methods, as for instance described in Sambrook & Russell (2001) supra; *Methods in Yeast Genetics, A Laboratory Course Manual*, Cold Spring Harbor Laboratory Press (1990). The host cell is cultured in nutrient media meeting the requirements of the particular host cell used, in particular in respect of the pH value, temperature, salt concentration, aeration, antibiotics, vitamins, trace elements etc. The Atoh1 protein can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, and lectin chromatography. Depending on whether the protein is expressed intra- or extracellularly, the protein can be recovered from the cultured cells and/or from the supernatant of the medium. Protein refolding steps can be used, as necessary, in completing configuration of the protein. Finally, high performance liquid chromatography (HPLC) can be employed for final purification steps.

Alternatively, the Atoh1 protein may be produced by any standard peptide synthesis procedure as described in the art (see, e.g., Merrifield, B., et al. (1997) *Methods Enzymol.* 289, 3-13; Hancock et al. (1995) *Mol. Biotechnol.* 4, 73; Merrifield, R. B., et al. (1969) *Adv. Enzymol. Relat. Areas Mol. Biol.* 32, 221-296).

In various aspects, the agent that activates the expression of Atoh1 is selected from 4-(4-chlorophenyl)-1-(5H-pyrimido[5,4-b]indol-4-yl)-1H-pyrazol-3-amine; 6-chloro-1-(2-chlorobenzyloxy)-2-phenyl-1H-benzo[d]imidazole; 6-chloro-1-(2-chlorobenzyloxy)-2-(4-methoxyphenyl)-1H-benzo[d]imidazole; 6-chloro-2-(4-methoxyphenyl)-1-(4-methylbenzyloxy)-1H-benzo[d]imidazole; 6-chloro-1-(3,5-dimethylbenzyloxy)-2-(4-methoxyphenyl)-1H-benzo[d]imidazo-le; 6-chloro-1-(4-methoxybenzyloxy)-2-(4-methoxyphenyl)-1H-benzo[d]imidazo-le; 1-(4-methylbenzyloxy)-6-nitro-2-phenyl-1H-benzo[d]imidazole; 4-(1H-benzo[d]imidazol-2-yl)phenol; 2,5-dichloro-N4-(1-methyl-1H-benzo[d]imidazol-2-yl)methyl)aniline; 4-(2-(1-methyl-1H-benzo[d]imidazol-2-yl)ethyl)aniline; 2-((2-methoxyphenoxy)methyl)-1H-benzo[d]imidazole; 2-((4- fluorophenoxy)methyl)-1-methyl-1H-benzo[d]imidazole; 2-(phenylthiomethyl)-1H-benzo[d]imidazole; 3-(6-methyl-1H-benzo[d]imidazol-2-yl)-2H-chromen-2-imine; 2-(o-tolyloxymethyl)-1H-benzo[d]imidazole; 2-(4-methoxyphenyl)-1-phenethyl-1H-benzo[d]imidazole; N-(6-bromobenzo[d]thiazol-2-yl)thiophene-2-carboxamide; N-(benzo[d]thiazol-2-yl)-1-methyl-1H-pyrazole-5-carboxamide; 2-(4-fluorobenzylthio)benzo[d]thiazole; 5-chloro-N-methylbenzo[d]thiazol-2-amine; N-(2-(1H-benzo[d]imidazol-2-yl)phenyl)isobutyramide; N-(6-acetamidobenzo[d]thiazol-2-yl)furan-2-carboxamide; N-(6-fluorobenzo[d]thiazol-2-yl)-3-methoxybenzamide; 2-(benzo[d]oxazol-2-ylthio)-N-(2-chlorophenyl)acetamide; 5-chloro-2-phenylbenzo[d]oxazole; 5-methyl-2-m-tolylbenzo[d]oxazole; 2-(4-isobutoxyphenyl)-3-(naphthalen-2-yl)-2,3-dihydroquinazolin-4(1H)-one-; N-(2-(2-(4-fluorophenyl)-2-oxoethylthio)-4-oxoquinazolin-3(4H)-yl)benzamide; 2-(4-chlorophenyl)-4-(4-methoxyphenyl)-1,4-dihydrobenzo[4,5]imidazo[1-,2-a]pyrimidine; 2-(3-pyridyl)-4-(4-bromophenyl)-1,4-dihydrobenzo[4,5]imidazo[1,2-a]pyrimidine; N-sec-butyl-1,7,7-trimethyl-9-oxo-8,9-dihydro-7H-furo[3,2-f]chromene-2-carboxamide; N-(3-carbamoyl-5,6-dihydro-4H-cyclopenta[b]thiophen-2-yl)benzofuran-2-carboxamide; 3-chloro-N-(5-chloropyridin-2-yl)benzo[b]thiophene-2-carboxamide-; 3-chloro-N-((tetrahydrofuran-2-yl)methyl)benzo[b]thiophene-2-carboxamide-; N-(3-(5-chloro-3-methylbenzo[b]thiophen-2-yl)-1H-pyrazol-5-yl)acetamide; 2-(naphthalen-2-yl)-1H-indole; 2-(pyridin-2-yl)-1H-indole; N-(2-chlorophenyl)-2-(1H-indol-3-yl)-2-oxoacetamide; 2-m-tolylquinoline; 2-(4-(2-methoxyphenyl)piperazin-1-yl)quinoline; 2-(1H-benzo[d][1,2,3]triazol-1-yl)-N-(2,3-dihydro-1H-inden-2-yl)acetamide-; 1-phenethyl-1H-benzo[d][1,2,3]triazole; 7-(4-fluorobenzyloxy)-2H-chromen-2-one; N-(2,4-dichlorophenyl)-8-methoxy-2H-chromene-3-carboxamide; N-(3-chlorophenyl)-8-methyl-3,4-dihydroquinoline-1(2H)-carbothioamide; 7-methoxy-5-methyl-2-phenyl-4H-chromen-4-one; 2-(3,4-dimethylphenyl)quinoxaline; 4-bromo-N-(5-chloropyridin-2-yl)benzamide; 3-amino-6,7,8,9-tetrahydro-5H-cyclohepta[e]thieno[2,3-b]pyridine-2-carbox-amide; (Z)-3-methyl-N'-(nicotinoyloxy)benzimidamide; N,N-diethyl-6-methoxythieno[2,3-b]quinoline-2-carboxamide; 6-(4-methoxyphenyl)-1,2,3,4-tetrahydro-1,5-naphthyridine; 5-bromo-N-(2-(phenylthio)ethyl)nicotinamide; N-(6-methylpyridin-2-yl)-2,3-dihydrobenzo[b][1,4]dioxine-6-carboxamide; 2-(4-methylbenzylthio)oxazolo[4,5-b]pyridine; N-(2-methoxyethyl)-5-p-tolylpyrimidin-2-amine; 4-(5-(benzo[b]thiophen-2-yl)pyrimidin-2-yl)morpholine; 4-(5-(4-fluorophenyl)pyrimidin-2-yl)morpholine; N-(4-bromo-3-methylphenyl)quinazolin-4-amine; N-(4-methoxyphenyl)quinazolin-4-amine; N-(3-methoxyphenyl)-9H-purin-6-amine; N,N-diethyl-1-m-tolyl-1H-pyrazolo[3,4-d]pyrimidin-4-amine; (5-(4-bromophenyl)furan-2-yl)(morpholino)methanone; (Z)-4-bromo-N'-(furan-2-carbonyloxy)benzimidamide; N-(4-iodophenyl)furan-2-carboxamide; 5-(5-(2,4-difluorophenyl)furan-2-yl)-1-(methylsulfonyl)-1H-pyrazole; 1-(3-amino-5-(4-tert-butylphenyl)thiophen-2-yl)ethanone; N-(3-cyano-4,5,6,7-tetrahydrobenzo[b]thiophen-2-yl)-2-fluorobenzamide; N-(5-chloropyridin-2-yl)thiophene-2-carboxamide; N-(2-(4-fluorophenoxy)ethyl)thiophene-2-carboxamide; 2,5-dimethyl-N-phenyl-1-(thiophen-2-ylmethyl)-1H-pyrrole-3-carboxamide; N-(3-cyanothiophen-2-yl)-4-isopropoxybenzamide; 2-(4-methoxyphenoxy)-N-(thiazol-2-yl)acetamide; 4-(4-methoxyphenyl)-N-(3-methylpyridin-2-yl)thiazol-2-amine; 4-(biphenyl-4-yl)thiazol-2-amine; 4-(4-(4-methoxyphenyl)thiazol-2-yl)-3-methylisoxazol-5-amine; N-(2-methoxyphenyl)-4-phenylthiazol-2-amine; 1-(4-amino-2-(m-tolylamino)thiazol-5-yl)-2-methylpropan-1-one; 4-(4-chlorophenyl)-1-(5H-pyrimido[5,4-b]indol-4-yl)-1H-pyrazol-3-amine; 2-(4-chlorophenyl)-6-ethyl-5-methylpyrazolo[1,5-a]pyrimidin-7(4H)-one; 5-methoxy-2-(5-phenyl-1H-pyrazol-3-yl)phenol; (3-(4-bromophenyl)-1-phenyl-1H-pyrazol-4-yl)methanol; N-(2,5-dichlorophenyl)-1-ethyl-1H-pyrazole-3-carboxamide; 4-chloro-1-methyl-N-(2-oxo-2-phenylethyl)-1H-pyrazole-3-carboxamide; N-(3-(5-tert-butyl-2-methylfuran-3-yl)-1H-pyrazol-5-yl)benzamide; N-(5-methylisoxazol-3-yl)benzo[d][1,3]dioxole-5-carboxamide; (5-(4-bromophenyl)isoxazol-3-yl)(morpholino)methanone; N-(4-bromophenyl)-5-isopropylisoxazole-3-carboxamide; 5-((4-chloro-2-methylphenoxy)methyl)-3-(pyridin-4-yl)-1,2,4-oxadiazole; 5-(2-methoxyphenyl)-3-p-tolyl-1,2,4-oxadiazole; 5-(phenoxymethyl)-3-(pyridin-2-yl)-1,2,4-oxadiazole; 5-(2-chloro-4-methylphenyl)-3-(pyridin-3-yl)-1,2,4-oxadiazole; 3-(2-chlorophenyl)-5-p-tolyl-1,2,4-oxadiazole; 5-(piperidin-1-ylmethyl)-3-p-tolyl-1,2,4-oxadiazole; 5-(4-bromophenyl)-3-(pyridin-3-yl)-1,2,4-oxadiazole; 5-(2-bromophenyl)-3-(4-bromophenyl)-1,2,4-oxadiazole; 5-(2-bromo-5-methoxyphenyl)-3-(thiophen-2-yl)-1,2,4-oxadiazole; 3-(2-fluorophenyl)-N-(3-(piperidin-1-yl)propyl)-1,2,4-oxadiazol-5-amine; 2-(2-chlorobenzoyl)-N-(4-fluorophenyl)hydrazinecarbothioamide; 2-(methylamino)-N-phenethylbenzamide; 4-tert-butyl-N-((tetrahydrofuran-2-yl)methyl)benzamide; 2-phenyl-5-o-tolyl-1,3,4-oxadiazole; 4-(3-(4-chlorophenyl)-4,5-dihydro-1H-1,2,4-triazol-5-yl)-N,N-dimethylanil-ine; 7-methoxy-2-(4-methoxyphenyl)-1,10b-dihydrospiro[benzo[e]pyrazolo[1,5-c][1,3]oxazine-5,1'-cyclohexane]; 6-oxo-2-(4-(3-(trifluoromethyl)phenoxy)phenyl)-1,4,5,6-tetrahydropyridine-3-carbonitrile; 6-(4-methoxyphenyl)imidazo[2,1-b]thiazole; 2-(2-bromophenoxy)-N-(4H-1,2,4-triazol-3-yl)acetamide; 1-(indolin-1-yl)-2-phenoxyethanone; and 2-(4-chlorophenyl)-6,7,8,9-tetrahydrobenzo[e]imidazo[1,2-b][1,2,4]triazine, or a pharmaceutically acceptable solvate, salt, or polymorph thereof. In a still further aspect, the agent that activates the expression of Atoh1 is selected from 5-(4-chloro-2-methylphenoxy)methyl)-3-(pyridin-4-yl)-1,2,4-oxadiazole, 5-(2-methoxyphenyl)-3-p-tolyl-1,2,4-oxadiazole, 5-(phenoxymethyl)-3-(pyridin-2-yl)-1,2,4-oxadiazole, 5-(2-chloro-4-methylphenyl)-3-(pyridin-3-yl)-1,2,4-oxadiazole, 3-(2-chlorophenyl)-5-p-tolyl-1,2,4-oxadiazole, 5-(piperidin-1-ylmethyl)-3-p-tolyl-1,2,4-oxadiazole, 5-(4-bromophenyl)-3-(pyridin-3-yl)-1,2,4-oxadiazole, 5-(2-bromophenyl)-3-(4-bromophenyl)-1,2,4-oxadiazole, 5-(2-bromo-5-methoxyphenyl)-3-(thiophen-2-yl)-1,2,4-oxadiazole, and 3-(2-fluorophenyl)-N-(3-(piperidin-1-yl)propyl)-1,2,4-oxadiazol-5-amine, or a pharmaceutically acceptable solvate, salt, or polymorph thereof.

In a further aspect, the agent that activates the expression of Atoh1 is a β-catenin protein or a compound that activates a β-catenin protein.

In a further aspect, the agent that activates the expression of Atoh1 comprises one or more compounds that increase the expression of a β-catenin protein from the endogenous β-catenin gene. In a still further aspect, the compound that increases β-catenin expression comprises one or more Wnt/β-catenin pathway agonists, one or more glycogen synthase kinase 3β (GSK3β) inhibitors, or one or more casein kinase 1 (CK1) inhibitors. In yet a further aspect, the Wnt/β-catenin pathway agonist comprises a Wnt protein, a nucleotide encoding a Wnt protein, or an activator of a Wnt protein. In an even further aspect, the Wnt protein is selected from Wnt1, Wnt2, Wnt2b/13, Wnt3, Wnt3a, Wnt4, Wnt5a, Wnt5b, Wnt6, Wnt7a, Wnt7b, Wnt7c, Wnt8, Wnt8a, Wnt8b, Wnt8c, Wnt10a, Wnt10b, Wnt11, Wnt14, Wnt15, Wnt16, and Wnt17. In a still further aspect, the Wnt protein is the human homolog thereof. In yet a further aspect, the Wnt protein is selected from Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11, and Wnt16.

In a further aspect, the Wnt/β-catenin pathway agonist is an agent that promotes signaling in the Wnt/β-catenin pathway. In a still further aspect, the agent that promotes signaling in the Wnt/β-catenin pathway is a polypeptide selected from a Dkk polypeptide, a crescent polypeptide, a cerberus polypeptide, an axin polypeptide, a Frzb polypeptide, a glycogen synthase kinase polypeptide, a T-cell factor polypeptide, and a dominant negative disheveled polypeptide, or a fragment thereof.

In a further aspect, the Wnt/β-catenin pathway agonist comprises one or more compounds having the structure:

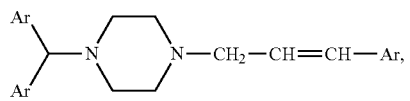

wherein each occurrence of Ar is independently selected from phenyl and fluorophenyl. In a still further aspect, at least one occurrence of the Ar group is fluorophenyl. In yet a further aspect, the fluorophenyl is para-fluorophenyl. In an even further aspect, the compound has the structure:

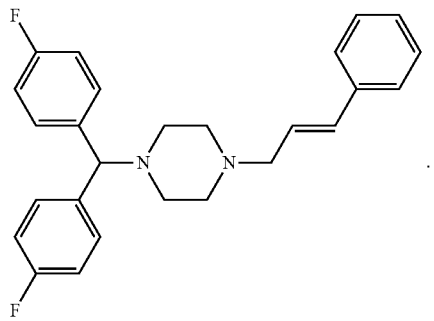 [SMILES: Fc1ccc(C(c2ccc(F)cc2)N2CCN(C/C=C/c3ccccc3)CC2)cc1]

In a further aspect, the Wnt/β-catenin pathway agonist comprises one or more compounds having the structure:

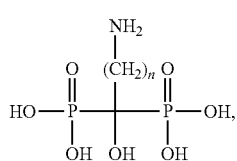

wherein n is an integer from 3 to 5. In a still further aspect, the compound has the structure:

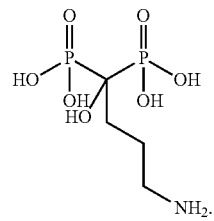

In a further aspect, the Wnt/β-catenin pathway agonist comprises one or more compounds having the structure:

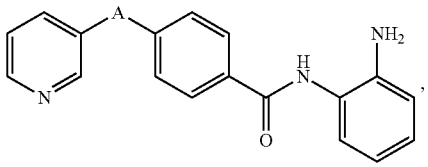

wherein A is selected from a moiety having the structure:

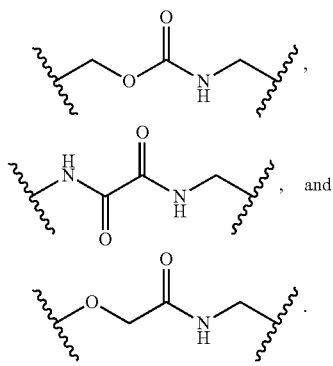

In a still further aspect, the compound has the structure:

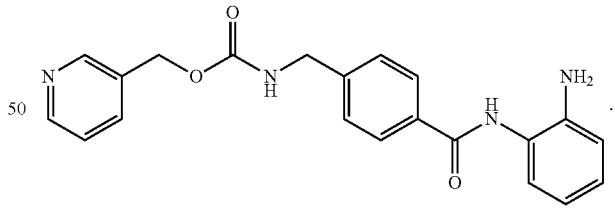

In a further aspect, the Wnt/β-catenin pathway agonist comprises one or more compounds having the structure:

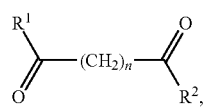

wherein n is an integer from about 4 to about 8; wherein each of R1 and R2 are the same and selected from an optionally substituted cycloalkylamino, pyridineamino, piperidino, 9-purine-6-amine, or thiazoleamino group; or wherein R1 is R3-N—R4, wherein each of R3 and R4 is independently selected from hydrogen, hydroxyl, and an optionally substituted group selected from alkyl, alkenyl, cycloalkyl, aryl, alkyloxy, aryloxy, arylalkyloxy, and pyridine group; and wherein R2 is selected from hydroxylamino, hydroxyl, amino, alkylamino, and alkyloxy group. In a still further aspect, the compound has the structure:

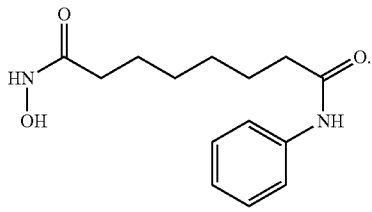 [SMILES: O=C(CCCCCCC(=O)Nc1ccccc1)NO]

In a further aspect, the Wnt/β-catenin pathway agonist comprises one or more compounds having the structure:

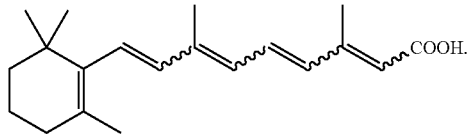 [SMILES: CC(C=CC1=C(C)CCCC1(C)C)=CC=CC(C)=CC(=O)O]

In a further aspect, the compound has the structure:

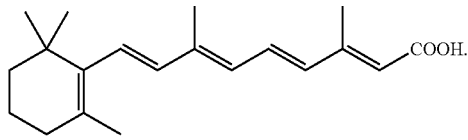 [SMILES: CC1=C(/C=C/C(C)=C/C=C/C(C)=C/C(=O)O)C(C)(C)CCC1]

In a further aspect, the Wnt/β-catenin pathway agonist has the structure:

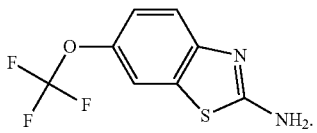 [SMILES: Nc1nc2ccc(OC(F)(F)F)cc2s1]

In a further aspect, the one or more glycogen synthase kinase 3β (GSK3β) inhibitors is an indirubin analog. In a still further aspect, the indirubin analog is selected from indirubin-5-sulfonamide; indirubin-5-sulfonic acid (2-hydroxyethyl)-amide indirubin-3'-monoxime; 5-iodo-indirubin-3'-monoxime; 5-fluoroindirubin; 5,5'-dibromoindirubin; 5-nitroindirubin; 5-chloroindirubin; 5-methylindirubin; 5-bromoindirubin; and 6,6'-dibromoindirubin. In yet a further aspect, the glycogen synthase kinase 3r3 (GSK3β) inhibitor is selected from lithium chloride; purvalanol A; olomoucine; alsterpaullone; kenpaullone; benzyl-2-methyl-1,2,4-thiadiazolidine-3,5-dione; 2-thio(3-iodobenzyl)-5-(1-pyridyl)-[1,3,4]-oxadiazole; 2,4-dibenzyl-5-oxothiadiazolidine-3-thione; (2'Z,3'E)-6-Bromoindirubin-3'-oxime; α-4-dibromoacetophenone; 2-Chloro-1-(4,5-dibromo-thiophen-2-yl)-ethanone; N-(4-methoxybenzyl)-N'-(5-nitro-1,3-thiazol-2-yl)urea; indirubin-5-sulfonamide; indirubin-5-sulfonic acid (2-hydroxyethyl)-amide; indirubin-3'-monoxime; 5-iodo-indirubin-3'-monoxime; 5-fluoroindirubin; 5,5'-dibromoindirubin; 5-nitroindirubin; 5-chloroindirubin; 5-methylindirubin, 5-bromoindirubin; 4-benzyl-2-methyl-1,2,4-thiadiazolidine-3,5-dione; 2-thio(3-iodobenzyl)-5-(1-pyridyl)-[1,3,4]-oxadiazole; 2,4-dibenzyl-5-oxothiadiazolidine-3-thione; (2'Z,3'E)-6-Bromoindirubin-3'-oxime; α-4-dibromoacetophenone; 2-Chloro-1-(4,5-dibromo-thiophen-2-yl)-ethanone; N-(4-methoxybenzyl)-N'-(5-nitro-1,3-thiazol-2-yl)urea; H-KEAPPAPPQSpP-NH2; and Myr-N-GKEAPPAP-PQSpP-NH2.

In a further aspect, the agent that activates the expression of Atoh1 comprises a nucleotide encoding a β-catenin protein. In a still further aspect, the nucleotide encoding 3-catenin is operably linked to a transcriptional promoter.

In a further aspect, the composition further comprises an inhibitor of the Notch signaling pathway. In a still further aspect, the inhibitor of the Notch signaling pathway is a gamma secretase inhibitor. In yet a further aspect, the gamma secretase inhibitor is selected from N-[N-(3,5-difluorophenacetyl)-L-alanyl]-S-phenylglycine-t-butylester; (2 S)-2-hydroxy-3-methyl-N-[(1S)-1-methyl-2-oxo-2-[[(1S)-2,3,4,5-tetrahydro-3-methyl-2-oxo-1H-3-benzazepin-1-yl] amino]ethyl]butanamide; N2-[(2S)-2-(3,5-difluorophenyl)-2-hydroxyethanoyl]-N1-[(7S)-5-methyl-6-oxo-6,7-dihydro-5H-dibenzo[b,d]azepin-7-yl]-L-alaninamide; [(2S)-2-{[(3, 5-difluorophenyl)acetyl]amino}-N-[(3S)-1-methyl-2-oxo-5-phenyl-2,3-dihydro-1H-1,4-benzodiazepin-3-yl] propanamide]; 4-chloro-N-(2,5-difluorophenyl)-N-((1R)-{4-fluoro-2-[3-(1H-imidazol-1-yl)propyl]phenyl}ethyl) benzenesulfonamide hydrochloride; 4-[2-((1R)-1-{[(4-chlorophenyl)sulfonyl]-2,5-difluoroanilino}ethyl)-5-fluorophenyl]butanoic acid; R-flurbiprofen ([1,1'-biphenyl]-4-acetic acid, 2-fluoro-alpha-methyl); (5S)-(t-butoxycarbonylamino)-6-phenyl-(4R)hydroxy-(2R) benzylhexanoyl)-L-leu-L-phe-amide (L-685,458); 5-chloro-N-[(1S)-3,3,3-trifluoro-1-(hydroxymethyl)-2-(trifluoromethyl)propyl]thiophene-2-sulfonamide; 4-fluoro-N-[(1R,2R,4S)-1,3,3-trimethylbicyclo[2.2.1]hept-2-yl] benzenesulfonamide; (2R)-2-{[5-chloro-2-(hydroxymethyl) phenyl][(4-chlorophenyl)sulfonyl] amino}propylpropylcarbamate; 5-chloro-N-[(1S,2R)-4,4,4-trifluoro-1-(hydroxymethyl)-2-methylbutyl]thiophene-2-sulfonamide; N-{(2R,4R,5 S)-2-benzyl-5-[(tert-butoxycarbonyl)amino]-4-hydroxy-6-phenylhexanoyl}-L-leucyl-L-phenylalaninamide; L-852,647; MW167, WPE-III-31; MK0752; MRK-003; NGX-555, CZC-1040, E2012, NIC5-15, BACE Inhibitor, and CI-IF-5074.

3. B-Catenin

In various aspects, the invention relates to pharmaceutical compositions comprising β-catenin. In a further aspect, β-catenin is a β-catenin protein or fragment thereof. In a still further aspect, β-catenin is a nucleotide encoding a β-catenin protein. In yet a further aspect, the nucleotide encoding β-catenin is operably linked to a transcriptional promoter.

C. Methods of Preparing a Composition

In one aspect, the invention relates to methods of preparing a pharmaceutical composition, the method comprising the step of combining at least one agent that activates the expression of Atoh1, or a pharmaceutically acceptable salt, solvate, or polymorph thereof; at least one agent that inhibits the expression of p27$^{Kip1}$, or a pharmaceutically acceptable salt, solvate, or polymorph thereof; wherein at least one is present in an effective amount; and a pharmaceutically acceptable carrier. In a further aspect, the effective amount is a prophylactically effective amount. In a still further aspect, the effective amount is a therapeutically effective amount.

In a further aspect, combining is co-formulation of the agent that activates the expression of Atoh1 and the agent that inhibits the expression of $p27^{Kip1}$ with the pharmaceutically acceptable carrier. In a still further aspect, co-formulation provides an oral solid dosage form comprising the agent that activates the expression of Atoh1, the agent that inhibits the expression of $p27^{Kip1}$ and the pharmaceutically acceptable carrier. In yet al further aspect, the solid dosage form is a tablet. In an even further aspect, the solid dosage form is a capsule.

In a further aspect, co-formulation provides an inhaled dosage form comprising the agent that activates the expression of Atoh1, the agent that inhibits the expression of $p27^{Kip1}$, and the pharmaceutically acceptable carrier.

In a further aspect, co-formulation provides an injectable dosage form comprising the agent that activates the expression of Atoh1, the agent that inhibits the expression of $p27^{Kip1}$, and the pharmaceutically acceptable carrier.

In a further aspect, the pharmaceutical composition is used to treat hearing impairment.

In one aspect, the invention relates to methods of preparing a pharmaceutical composition, the method comprising the step of combining β-catenin and at least one agent that synergistically activates the expression of Atoh1, or a pharmaceutically acceptable salt, solvate, or polymorph thereof; and a pharmaceutically acceptable carrier; wherein the β-catenin and the agent are present in an effective amount. In a further aspect, the effective amount is a prophylactically effective amount. In a still further aspect, the effective amount is a therapeutically effective amount.

In a further aspect, combining is co-formulation of the β-catenin and the agent that activates the expression of Atoh1. In a still further aspect, co-formulation is an inhaled dosage form comprising the β-catenin and the agent that activates the expression of Atoh1, and the pharmaceutically acceptable carrier. In yet a further aspect, co-formulation is an injectable dosage form comprising the β-catenin and the agent that activates the expression of Atoh1, and the pharmaceutically acceptable carrier.

In a further aspect, the pharmaceutical composition is used to treat hearing impairment.

D. Methods of Using the Compositions

Also provided are methods of use of a disclosed composition or medicament. In one aspect, the method of use is directed to the treatment of a disorder. In a further aspect, the disclosed compounds can be used as single agents or in combination with one or more other drugs in the treatment, prevention, control, amelioration, or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

The pharmaceutical compositions and methods of the present invention can further comprise other therapeutically active compounds as noted herein which are usually applied in the treatment of the above mentioned pathological conditions.

In addition to activating Atoh1 and inhibiting $p27^{Kip1}$, a combination of genetic manipulations of more than one gene (pathway) could effectively be used to regenerate hair cells in adult deafened cochleae. For example, Atoh1 activation plus inhibition of the Notch or Wnt signaling pathway simultaneously could be effective as well.

1. Treatment Methods

In one aspect, the compounds and compositions disclosed herein are useful for treating, preventing, ameliorating, controlling or reducing the risk of a variety of hearing impairments and disorders, including hearing loss, deafness, tinnitus, ringing, Presbyacusis, auditory neuropathy, acoustic trauma, acoustic neuroma, Pendred syndrome, Usher syndrome, Wardenburg syndrome, non-syndromic sensorineural deafness, otitis media, otosclerosis, Meniere's disease, ototoxicity, labyrinthitis, as well as hearing impairments caused by infection (i.e. measles, mumps, or meningitis), medicines such as antibiotics, and some cancer treatments (i.e. chemotherapy and radiation therapy). For example, a treatment can include increasing the number of cochlear hair cells in a subject.

In various aspects, the invention relates to a method of inducing the formation of cochlear hair cells and treating hearing loss, hearing impairment or an imbalance disorder associated with loss of auditory hair cells by modulating the expression or activity of Atoh1 and $p27^{Kip1}$. In a further aspect, the invention relates to a method comprising administering to a subject an agent that stimulates the expression or activity of Atoh1 and an agent that inhibits the expression or activity of $p27^{Kip1}$. In a still further aspect, the invention relates to a method for contacting one or more target cells in vitro with an agent that stimulates the expression or activity of Atoh1 and an agent that inhibits the expression or activity of $p27^{Kip1}$, thereby promoting complete or partial differentiation of the target cells to or toward a mature cell type, e.g., a hair cell. Cells contacted in vitro with the agents described herein can be administered to a subject in need thereof to treat hearing loss, hearing impairment, or an imbalance disorder associated with a loss of auditory hair cells.

It has been suggested that although cells capable of generating hair cells are present in the inner ear, natural hair cell regeneration in the inner ear is low (Li et al. (2004) *Trends Mol. Med.* 10, 309-315; Li et al. (2003) *Nat. Med.* 9, 1293-1299; Rask-Andersen, H., et al. (2005) *Hear. Res.* 203, 180-191). As a result, lost or damaged hair cells may not be adequately replaced by natural physiological processes (e.g., cell differentiation) and a loss of hair cells occurs. In many individuals, such hair cell loss can result in sensorineural hearing loss, hearing impairment, and/or imbalance disorders. Therapeutic strategies that increase the number of hair cells in the inner ear may benefit a patient with hair cell loss, e.g., with one or more of these conditions.

The compounds and compositions are further useful in methods for the prevention, treatment, control, amelioration, or reduction of risk of the hearing impairments and disorders noted herein. The compounds and compositions are further useful in a method for the prevention, treatment, control, amelioration, or reduction of risk of the aforementioned hearing impairments and disorders in combination with other agents.

In one aspect, the disclosed compounds can be used in combination with one or more other drugs in the treatment, prevention, control, amelioration, or reduction of risk of hearing impairments and disorders for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Accordingly, the pharmaceutical compositions include those that contain one or more other active ingredients, in addition to a compound of the present invention.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the bacterial infections for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

Where appropriate, following treatment, the subject (e.g., human or other animal) can be tested for an improvement in hearing or in other symptoms related to inner ear disorders. Methods for measuring hearing are well-known and include pure tone audiometry, air conduction, and bone conduction tests. These exams measure the limits of loudness (intensity) and pitch (frequency) that a human can hear. Hearing tests in humans include behavioral observation audiometry (for infants to seven months), visual reinforcement orientation audiometry (for children 7 months to 3 years) and play audiometry for children older than 3 years. Oto-acoustic emission testing can be used to test the functioning of the cochlear hair cells, and electro-cochleography provides information about the functioning of the cochlea and the first part of the nerve pathway to the brain. In various aspects, treatment can be continued with or without modification or can be stopped.

a. Treating Hearing Impairment

In one aspect, the invention relates methods of treating hearing impairment associated with loss of cochlear hair cells in a subject, the method comprising the step of co-administering to the subject a therapeutically effective amount of at least one agent that activates the expression of Atoh1, or a pharmaceutically acceptable salt, solvate, or polymorph thereof; and at least one agent that inhibits the expression of $p27^{Kip1}$, or a pharmaceutically acceptable salt, solvate, or polymorph thereof.

The importance of Atoh1 in hair cell genesis has been documented. For example, Math1 is required for hair cell development and the differentiation of inner ear progenitor cells to inner ear support cells and/or hair cells (Bermingham, N. A., et al. (1999) *Science* 284, 1837-1841). In addition, adenovirus-mediated Math1 overexpression in the endolymph of the mature guinea pig results in the differentiation of non-sensory cells in the mature cochlea into immature hair cells (Kawamoto, K., et al. (2003) *J. Neurosci.* 23, 4395-4400). The implications of these studies are two-fold. First, they demonstrate that non-sensory cells of the mature cochlear retain the ability to differentiate into sensory cells, e.g., hair cells. Second, they demonstrate that Math1 overexpression can direct hair cell differentiation from non-sensory cells. A later study furthered these findings by demonstrating that adenovirus-mediated Atoh1 overexpression induces hair cell regeneration and substantially improves hearing thresholds in an experimentally deafened animal model (Izumikawa, M., et al. (2005) *Nat. Med.* 11, 271-276).

Analysis of $p27^{Kip1-/-}$ and $p27^{Kip1+/-}$ mice has shown qualitative evidence of supernumerary hair cells in both inner hair cell and outer hair cell regions (Chen, P. and Segil, N. (1999) *Development* 126, 1581-1590; Lowenheim, H., et al. (1999) *Proc. Natl. Acad. Sci. USA* 96, 4084-4088). Further, it has been demonstrated that Sox2 plays a novel role as a key upstream regulator of $p27^{Kip1}$ to maintain the quiescent state of postmitotic inner pillar cells (Liu et al. (2012) *J. Neurosci.* 32, 10530-10540). In addition, inhibition of the $p27^{Kip1}$ gene product in $p27^{Kip1+/+}$ cochlea has indicated that terminally mitotic cells in a terminally differentiated organ can reenter the cell-cycle (U.S. Pat. No. 7,741, 303).

Therefore, the combination of agents described herein are of use in methods of treating patients who have, or who are at risk for developing, an auditory disorder resulting from a loss of hair cells. Administration of an agent that stimulates the expression or activity of Atoh1 and an agent that inhibits the expression or activity of $p27^{Kip1}$ to a subject promotes the formation of auditory hair cells, e.g., in the ear of the patient (e.g., the inner ear) and/or increases the number of auditory hair cells in the ear (e.g., the inner ear) by promoting complete or partial auditory hair cell differentiation from non-hair cell types naturally present in the inner ear of a subject.

In a further aspect, the cochlear hair cells are outer or inner cochlear hair cells. Examples of cells that are capable of differentiating into hair cells (e.g., inner and/or outer hair cells) include but are not limited to inner ear stem cells, iPS cells, progenitor cells, and/or support cells (e.g., Deiters' cells, pillar cells, inner phalangeal cells, inner border cells, tectal cells and Hensen's cells).

In a further aspect, the subject is a mammal. In a still further aspect, the subject is human.

In a further aspect, the subject has been diagnosed with a need for treatment of hearing impairment associated with loss of cochlear hair cells prior to the administering step. In a still further aspect, the subject is at risk for developing a hearing impairment associated with loss of cochlear hair cells prior to the administering step.

In a further aspect, the agent that activates the expression of Atoh1 and the agent that inhibits the expression of $p27^{Kip1}$ are administered locally to the inner ear of the subject. In a still further aspect, the agent that activates the expression of Atoh1 and the agent that inhibits the expression of $p27^{Kip1}$ are administered via injection into one or more of the scala tympani, cochlear duct, scala vestibule of the cochlea, into the auditory nerve trunk in the internal auditory meatus, or into the middle ear space across the transtympanic membrane/ear drum.

In a further aspect, the agent that activates the expression of Atoh1 and the agent that inhibits the expression of $p27^{Kip1}$ are co-formulated. In a still further aspect, the agent that activates the expression of Atoh1 and the agent that inhibits the expression of $p27^{Kip1}$ are co-packaged.

In a further aspect, the method further comprises identifying a subject in need of treatment for hearing impairment associated with loss of cochlear hair cells.

In one aspect, the invention relates to methods of treating hearing impairment associated with loss of cochlear hair cells in a subject, the method comprising the step of co-administering to the subject a therapeutically effective amount of β-catenin and at least one agent that synergistically activates the expression of Atoh1, or a pharmaceutically acceptable salt, solvate, or polymorph thereof.

In a further aspect, the β-catenin and the agent that activates the expression of Atoh1 are administered locally to the inner ear of the subject. In a still further aspect, the β-catenin and the agent that activates the expression of Atoh1 are administered via injection into one or more of the scala tympani, cochlear duct, scala vestibule of the cochlea, into the auditory nerve trunk in the internal auditory meatus, or into the middle ear space across the transtympanic membrane/ear drum.

In a further aspect, the β-catenin and the agent that activates the expression of Atoh1 are co-formulated. In a still further aspect, the β-catenin and the agent that activates the expression of Atoh1 are co-packaged.

In a further aspect, the cochlear hair cells are outer or inner cochlear hair cells. Examples of cells that are capable of differentiating into hair cells (e.g., inner and/or outer hair cells) include but are not limited to inner ear stem cells, iPS cells, progenitor cells, and/or support cells (e.g., Deiters' cells, pillar cells, inner phalangeal cells, inner border cells, tectal cells and Hensen's cells).

In a further aspect, the subject is a mammal. In a still further aspect, the subject is human.

In a further aspect, the subject has been diagnosed with a need for treatment of hearing impairment associated with loss of cochlear hair cells prior to the administering step. In a still further aspect, the subject is at risk for developing a hearing impairment associated with loss of cochlear hair cells prior to the administering step.

In a further aspect, the method further comprises identifying a subject in need of treatment for hearing impairment associated with loss of cochlear hair cells.

b. Treating a Subject Who has a Hearing Impairment

In one aspect, the invention relates to methods of treating a subject who has a hearing impairment associated with loss of cochlear hair cells, the method comprising: a) obtaining a population of cells capable of differentiating into cochlear hair cells; b) contacting the population of cells with an effective amount of at least one agent that activates the expression of Atoh1, or a pharmaceutically acceptable salt, solvate, or polymorph thereof; and at least one agent that inhibits the expression of $p27^{Kip1}$ or a pharmaceutically acceptable salt, solvate, or polymorph thereof; and c) administering the population of cells, or a subset thereof, to the subject's ear, thereby treating the subject.

In a further aspect, the subject is a mammal. In a still further aspect, the subject is a human.

In a further aspect, the subject has been diagnosed with a need for treatment of hearing impairment associated with loss of cochlear hair cells prior to the administering step.

In a further aspect, the method further comprises identifying a subject in need of treatment for hearing impairment associated with loss of cochlear hair cells. In a still further aspect, the cochlear hair cells are outer or inner cochlear hair cells. In yet a further aspect, the cochlear hair cells are outer cochlear hair cells. In an even further aspect, the cochlear hair cells are inner cochlear hair cells.

In a further aspect, the population of cells includes cells selected from stem cells, progenitor cells, support cells, Deiters' cells, pillar cells, inner phalangeal cells, inner border cells, tectal cells, Hensen's cells, Boettcher cells, Claudius cells, tympanic border cells, lesser epithelial ridge (LER) cells, greater epithelial ridge (GER) cells, and germ cells, or a combination thereof. In a still further aspect, the stem cells are adult stem cells. In yet a further aspect, the adult stem cells are derived from inner ear, bone marrow, mesenchyme, skin, fat, liver, muscle, or blood. In an even further aspect, the stem cells are embryonic stem cells, or stem cells obtained from a placenta or umbilical cord. In a still further aspect, the progenitor cells are derived from the inner ear, bone marrow, mesenchyme, skin, fat, liver, muscle, or blood.

In a further aspect, administering the population of cells comprises: a) injecting the cells into the scala tympani, the luminae of the cochlea, the auditory nerve trunk in the internal auditory meatus, or the middle ear space across the transtympanic membrane/ear drum; or b) implanting the cells within a cochlear implant.

In a further aspect, the method further comprises administering to the subject a therapeutically effective amount of at least one agent that activates the expression of Atoh1, or a pharmaceutically acceptable salt, solvate, or polymorph thereof; and at least one agent that inhibits the expression of $p27^{Kip1}$, or a pharmaceutically acceptable salt, solvate, or polymorph thereof. In a still further aspect, the agent that activates the expression of Atoh1 and the agent that inhibits the expression of $p27^{Kip1}$ are administered locally to the subject's ear. In yet a further aspect, the agent that activates the expression of Atoh1 and the agent that inhibits the expression of $p27^{Kip1}$ are administered via injection into the scala tympani, the luminae of the cochlea, to the auditory nerve trunk in the internal auditory meatus, or the middle ear space across the transtympanic membrane/ear drum; or, if present, into a cochlear implant.

In a further aspect, the agent that activates the expression of Atoh1 and the agent that inhibits the expression of p27$^{Kip1}$ are co-formulated. In a still further aspect, the agent that activates the expression of Atoh1 and the agent that inhibits the expression of p27$^{Kip1}$ are co-packaged.

In one aspect, the invention relates to methods of treating a subject who has a hearing impairment associated with loss of cochlear hair cells, the method comprising: a) obtaining a population of cells capable of differentiating into cochlear hair cells; b) contacting the population of cells with an effective amount of β-catenin and at least one agent that synergistically activates the expression of Atoh1, or a pharmaceutically acceptable salt, solvate, or polymorph thereof; and c) administering the population of cells, or a subset thereof, to the subject's ear, thereby treating the subject.

In a further aspect, the subject is a mammal. In a still further aspect, the subject is a human.

In a further aspect, the subject has been diagnosed with a need for treatment of hearing impairment associated with loss of cochlear hair cells prior to the administering step.

In a further aspect, the method further comprises identifying a subject in need of treatment for hearing impairment associated with loss of cochlear hair cells. In a still further aspect, the cochlear hair cells are outer or inner cochlear hair cells. In yet a further aspect, the cochlear hair cells are outer cochlear hair cells. In an even further aspect, the cochlear hair cells are inner cochlear hair cells.

In a further aspect, the population of cells includes cells selected from stem cells, progenitor cells, support cells, Deiters' cells, pillar cells, inner phalangeal cells, inner border cells, tectal cells, Hensen's cells, Boettcher cells, Claudius cells, tympanic border cells, lesser epithelial ridge (LER) cells, greater epithelial ridge (GER) cells, and germ cells, or a combination thereof. In a still further aspect, the stem cells are adult stem cells. In yet a further aspect, the adult stem cells are derived from inner ear, bone marrow, mesenchyme, skin, fat, liver, muscle, or blood. In an even further aspect, the stem cells are embryonic stem cells, or stem cells obtained from a placenta or umbilical cord. In a still further aspect, the progenitor cells are derived from the inner ear, bone marrow, mesenchyme, skin, fat, liver, muscle, or blood.

In a further aspect, administering the population of cells comprises: a) injecting the cells into the scala tympani, the luminae of the cochlea, the auditory nerve trunk in the internal auditory meatus, or the middle ear space across the transtympanic membrane/ear drum; or b) implanting the cells within a cochlear implant.

In a further aspect, the method further comprises administering to the subject a therapeutically effective amount of β-catenin and the agent that synergistically activates the expression of Atoh1, or a pharmaceutically acceptable salt, solvate, or polymorph thereof. In a still further aspect, the β-catenin and the agent that synergistically activates the expression of Atoh1 are administered locally to the subject's ear. In yet a further aspect, the β-catenin and at least one agent that synergistically activates the expression of Atoh1 are administered via injection into the scala tympani, the luminae of the cochlea, to the auditory nerve trunk in the internal auditory meatus, or the middle ear space across the transtympanic membrane/ear drum; or, if present, into a cochlear implant.

In a further aspect, the at least one agent that activates the expression of Atoh1 and at least one agent that inhibits the expression of p27$^{Kip1}$ are co-formulated. In a still further aspect, the at least one agent that activates the expression of Atoh1 and at least one agent that inhibits the expression of p27$^{Kip1}$ are co-packaged.

In a further aspect, the method further comprises administering to the subject a therapeutically effective amount of at least one agent that inhibits the expression of p27$^{Kip1}$, or a pharmaceutically acceptable salt, solvate, or polymorph thereof.

c. Increasing the Number of Cells with the Characteristics of Cochlear Hair Cells In one aspect, the invention relates to methods of increasing the number of cells with the characteristics of cochlear hair cells, the method comprising: a) obtaining a population of cells capable of differentiating into cochlear hair cells; b) contacting the population of cells with an effective amount of at least one agent that activates the expression of Atoh1, or a pharmaceutically acceptable salt, solvate, or polymorph thereof; and at least one agent that inhibits the expression of p27$^{Kip1}$, or a pharmaceutically acceptable salt, solvate, or polymorph thereof, for a period of time sufficient to increase the number of cells with the characteristics of cochlear hair cells in the population of cells.

In one aspect, the invention relates to methods of increasing the number of cells with the characteristics of cochlear hair cells, the method comprising: a) obtaining a population of cells capable of differentiating into cochlear hair cells; b) contacting the population of cells with an effective amount of β-catenin and at least one agent that synergistically activates the expression of Atoh1, or a pharmaceutically acceptable salt, solvate, or polymorph thereof, for a period of time sufficient to increase the number of cells with the characteristics of cochlear hair cells in the population of cells.

For ex vivo applications, one or more cells capable of differentiating completely or partially into a hair cell are contacted, e.g., in vitro, with an agent that stimulates the expression or activity of Atoh1 and an agent that inhibits the expression or activity of p27$^{Kip1}$, thereby promoting complete or partial differentiation of those cells to or toward a mature cell type of the inner ear, e.g., a hair cell (e.g., an inner and/or outer hair cell).

In various aspects, the invention relates to a method of obtaining tissue from the inner ear of the animal, where the tissue includes at least a portion of the utricular maculae. The animal can be a mammal, such as a mouse, rat, pig, rabbit, goat, horse, cow, dog, cat, primate, or human. The isolated tissue can be suspended in a neutral buffer, such as phosphate-buffered saline (PBS), and subsequently exposed to a tissue-digesting enzyme (e.g., trypsin, leupeptin, chymotrypsin, and the like) or a combination of enzymes, or a mechanical (e.g., physical) force, such as trituration, to break the tissue into smaller pieces. Alternatively, or in addition, both mechanisms of tissue disruption can be used. For example, the tissue can be incubated in about 0.05% enzyme (e.g., about 0.001%, 0.01%, 0.03%, 0.07%, or 1.0% of enzyme) for about 5, 10, 15, 20, or 30 minutes, and following incubation, the cells can be mechanically disrupted. The disrupted tissue can be passed through a device, such as a filter or bore pipette, that separates a stem cell or progenitor cell from a differentiated cell or cellular debris. The separation of the cells can include the passage of cells through a series of filters having progressively smaller pore size. For example, the filter pore size can range from about 80 μm or less, about 70 μm or less, about 60 μm or less, about 50 μm or less, about 40 μm or less, about 30 μm or less, about 35 μm or less, or about 20 μm or less.

The cells obtained may constitute an enriched population of stem cells and/or progenitor cells; isolation from all (or essentially all) differentiated cells or other cellular material within the tissue may be achieved but is not required to meet the definition of "isolated." Absolute purity is not required. The invention encompasses cells obtained by the isolation procedures described herein. The cells may be mixed with a cryoprotectant and stored or packaged into kits. Once obtained, the stem cells and/or progenitor cells can be expanded in culture.

Where a mixed population of cells is used, the proportion of stem cells within the test population can vary. For example, the population can contain few stem cells (e.g., about 1-10%), a moderate proportion of stem cells (e.g., about 10-90% (e.g., about 20, 25, 30, 40, 50, 60, 70, 75, 80, or 85% stem cells), or many stem cells (e.g., at least 90% of the population (e.g., 92, 94, 96, 97, 98, or 99%) can be stem cells). The cells will have the potential to differentiate into a completely or partially differentiated cell of the inner ear (e.g., the cell can be a pluripotent stem cell that differentiates into a cell that expresses one or more auditory proteins). Partially differentiated cells are useful in the treatment methods (whether therapeutic or prophylactic) as long as they express a sufficient number and type of auditory-specific proteins to confer a benefit on the patient (e.g., improved hearing).

Cells that have been contacted with the agents disclosed herein may be analyzed to determine if complete or partial differentiation has occurred. Such a determination can be performed by analyzing the presence or absence of tissue-specific genes. Alternatively, or in addition, a hair cell can be identified by physiological testing to determine if the cells generate conductance channels characteristic of mature hair or spiral ganglion cells. Cells that are confirmed to have undergone complete or partial differentiation toward an inner ear sensory cell, e.g., a hair cell can be transplanted or implanted into a patient.

Partially and/or fully differentiated cells, e.g., generated by the methods described above, can be transplanted or implanted, such as in the form of a cell suspension, into the ear by injection, such as into the luminae of the cochlea. Injection can be, for example, through the round window of the ear or through the bony capsule surrounding the cochlea. The cells can be injected through the round window into the auditory nerve trunk in the internal auditory meatus or into the scala tympani.

In order to improve the ability of transplanted or implanted cells to engraft, cells can be modified prior to differentiation. For example, the cells can be engineered to overexpress one or more anti-apoptotic genes in the progenitor or differentiated cells. The Fak tyrosine kinase or Akt genes are candidate anti-apoptotic genes that can be useful for this purpose; overexpression of FAK or Akt can prevent cell death in spiral ganglion cells and encourage engraftment when transplanted into another tissue, such as an explanted organ of Corti (see, for example, Mangi, A. A., et al. (2003) *Nat. Med.* 9, 1195-1201). Neural progenitor cells overexpressing 03 integrin may have an enhanced ability to extend neurites into a tissue explant, as the integrin has been shown to mediate neurite extension from spiral ganglion neurons on laminin substrates (Aletsee et al. (2001) *Audiol. Neurootol.* 6, 57-65). In another example, ephrinB2 and ephrinB3 expression can be altered, such as by silencing with RNAi or overexpression with an exogenously expressed cDNA, to modify EphA4 signaling events. Spiral ganglion neurons have been shown to be guided by signals from EphA4 that are mediated by cell surface expression of ephrin-B2 and -B3 (Brors, D., et al. (2003) *J. Comp. Neurol.* 462, 90-100).

Inactivation of this guidance signal may enhance the number of neurons that reach their target in an adult inner ear. Exogenous factors such as the neurotrophins BDNF and NT3, and LIF can be added to tissue transplants to enhance the extension of neurites and their growth towards a target tissue in vivo and in ex vivo tissue cultures. Neurite extension of sensory neurons can be enhanced by the addition of neurotrophins (BDNF, NT3) and LIF (Gillespie, L. N., et al. (2001) NeuroReport 12, 275-279).

In various aspects, the cells described herein can be used in a cochlear implant, for example, as described in US 2007/0093878. A cochlear implant is an electronic device that is used to improve hearing in humans who have experienced hearing loss, particularly severe to profound hearing loss.

In a further aspect, the population of cells capable of differentiating into cochlear hair cells comprises cells selected from stem cells, inner ear stem cells, adult stem cells, bone marrow derived stem cells, embryonic stem cells, mesenchymal stem cells, skin stem cells, fat derived stem cells, progenitor cells, inner ear progenitor cells, support cells, Deiters' cells, pillar cells, inner phalangeal cells, inner border cells, tectal cells, Hensen's cells, Boettcher cells, Claudius cells, tympanic border cells, lesser epithelial ridge (LER) cells, greater epithelial ridge (GER) cells, and germ cells, or a combination thereof. In a still further aspect, the stem cells are adult stem cells. In yet a further aspect, the adult stem cells are derived from inner ear, bone marrow, mesenchyme, skin, fat, liver, muscle, or blood. In an even further aspect, the stem cells are embryonic stem cells, or stem cells obtained from a placenta or umbilical cord. In a still further aspect, the progenitor cells are derived from the inner ear, bone marrow, mesenchyme, skin, fat, liver, muscle, or blood.

2. Manufacture of a Medicament

In one aspect, the invention relates to a medicament comprising one or more compounds that inhibit the expression of $p27^{Kip1}$, or a pharmaceutically acceptable salt, hydrate, solvate, or polymorph thereof; and one or more compounds that activate the expression of Atoh1, or a pharmaceutically acceptable salt, solvate, or polymorph thereof.

In one aspect, the invention relates to a medicament comprising β-catenin, or a pharmaceutically acceptable salt, hydrate, solvate, or polymorph thereof; and one or more compounds that activate the expression of Atoh1, or a pharmaceutically acceptable salt, solvate, or polymorph thereof.

In various aspect, the invention relates methods for the manufacture of a medicament for treating hearing impairment comprising combining one or more disclosed compounds, products, or compositions or a pharmaceutically acceptable salt, solvate, hydrate, or polymorph thereof, with a pharmaceutically acceptable carrier. It is understood that the disclosed methods can be performed with the disclosed compounds, products, and pharmaceutical compositions. It is also understood that the disclosed methods can be employed in connection with the disclosed methods of using.

3. Use of Compounds and Compositions

Also provided are the uses of the disclosed compounds and compositions. Thus, in one aspect, the invention relates to the uses of at least one agent that activates the expression of Atoh1, or a pharmaceutically acceptable salt, solvate, or polymorph thereof; and at least one agent that inhibits the expression of $p27^{Kip1}$ or a pharmaceutically acceptable salt, solvate, or polymorph thereof.

In a further aspect, the invention relates to the use of at least one agent that activates the expression of Atoh1, or a pharmaceutically acceptable salt, solvate, or polymorph thereof; and at least one agent that inhibits the expression of $p27^{Kip1}$, or a pharmaceutically acceptable salt, solvate, or polymorph thereof in the manufacture of a medicament for the treatment of a hearing impairment or disorder.

In a further aspect, the use relates to a process for preparing a pharmaceutical composition comprising a therapeutically effective amount of at least one agent that activates the expression of Atoh1, or a pharmaceutically acceptable salt, solvate, or polymorph thereof; and at least one agent that inhibits the expression of $p27^{Kip1}$ or a pharmaceutically acceptable salt, solvate, or polymorph thereof, for use as a medicament.

In a further aspect, the use relates to a process for preparing a pharmaceutical composition comprising a therapeutically effective amount of at least one agent that activates the expression of Atoh1, or a pharmaceutically acceptable salt, solvate, or polymorph thereof; and at least one agent that inhibits the expression of $p27^{Kip1}$ or a pharmaceutically acceptable salt, solvate, or polymorph thereof, wherein a pharmaceutically acceptable carrier is intimately mixed with a therapeutically effective amount of the at least one agent that activates the expression of Atoh1 or at least one agent that inhibits the expression of $p27^{Kip1}$.

In one aspect, the invention relates to the uses of at least one agent that activates the expression of Atoh1, or a pharmaceutically acceptable salt, solvate, or polymorph thereof; and β-catenin, or a pharmaceutically acceptable salt, solvate, or polymorph thereof.

In a further aspect, the invention relates to the use of at least one agent that activates the expression of Atoh1, or a pharmaceutically acceptable salt, solvate, or polymorph thereof; and β-catenin, or a pharmaceutically acceptable salt, solvate, or polymorph thereof in the manufacture of a medicament for the treatment of a hearing impairment or disorder.

In a further aspect, the use relates to a process for preparing a pharmaceutical composition comprising a therapeutically effective amount of at least one agent that activates the expression of Atoh1, or a pharmaceutically acceptable salt, solvate, or polymorph thereof; and β-catenin, or a pharmaceutically acceptable salt, solvate, or polymorph thereof, for use as a medicament.

In a further aspect, the use relates to a process for preparing a pharmaceutical composition comprising a therapeutically effective amount of at least one agent that activates the expression of Atoh1, or a pharmaceutically acceptable salt, solvate, or polymorph thereof; and β-catenin, or a pharmaceutically acceptable salt, solvate, or polymorph thereof, wherein a pharmaceutically acceptable carrier is intimately mixed with a therapeutically effective amount of the at least one agent that activates the expression of Atoh1 or β-catenin.

In various aspects, the use relates to the treatment of a hearing impairment or disorder in a vertebrate animal. In a further aspect, the use relates to the treatment of a hearing impairment or disorder in a human subject.

In a further aspect, the use is the treatment of a hearing impairment or disorder. In a still further aspect, the use is the treatment of a hearing impairment. In yet a further aspect, the use is the treatment of a hearing disorder.

It is understood that the disclosed uses can be employed in connection with the disclosed compounds, methods, compositions, and kits. In a further aspect, the invention relates to the use of a disclosed compound or composition of a medicament for the treatment of a hearing impairment or disorder in a mammal.

In a further aspect, the invention relates to the use of a disclosed compound or composition in the manufacture of a medicament for the treatment of a hearing impairment or disorder selected from hearing loss, deafness, tinnitus, ringing, Presbyacusis, auditory neuropathy, acoustic trauma, acoustic neuroma, Pendred syndrome, Usher syndrome, Wardenburg syndrome, non-syndromic sensorineural deafness, otitis media, otosclerosis, Meniere's disease, ototoxicity, labyrinthitis, as well as hearing impairments caused by infection (i.e. measles, mumps, or meningitis), medicines such as antibiotics, and some cancer treatments (i.e. chemotherapy and radiation therapy).

In a further aspect, the invention relates to the use of a disclosed compound or composition in the manufacture of a medicament for the treatment of a hearing impairment or disorder.

In a further aspect, the invention relates to the use of a disclosed compound or composition in the treatment of hair cell loss and any disorder that arises as a consequence of cell loss in the ear, such as hearing impairments (e.g., because of trauma or prolonged exposure to loud noises), deafness (e.g., because of a genetic or congenital defect), and vestibular disorders (e.g., including bilateral and unilateral vestibular dysfunction), for example, by promoting differentiation (e.g., complete or partial differentiation) of one or more cells into one or more cells capable of functioning as sensory cells of the ear, e.g., hair cells. Subjects benefiting from such treatment include those at risk of hair cell loss and/or a patient with hair cell loss. For example, a subject having or at risk for developing a hearing loss can hear less well than the average subject (e.g., an average human being), or less well than a subject before experiencing the hearing loss. For example, hearing can be diminished by at least 5%, 10%, 30%, 50% or more.

In various aspects, the methods described herein can be used to generate hair cell growth in the ear and/or to increase the number of hair cells in the ear (e.g., in the inner, middle, and/or outer ear). In this respect, an effective amount of a stimulatory agent and an inhibitory agent described herein is an amount that increases the number of hair cells in the ear by about 2-, 3-, 4-, 6-, 8-, or 10-fold, or more, as compared to the number of hair cells before treatment. This new hair cell growth can effectively restore or establish at least a partial improvement in the subject's ability to hear. For example, administration of a stimulatory agent and an inhibitory agent of this invention can improve hearing loss by about 5, 10, 15, 20, 40, 60, 80, 100% or more.

In various aspects, the agents and methods described herein can be used prophylactically, such as to prevent, reduce or delay progression of hearing loss, deafness, or other auditory disorders associated with loss of inner ear function.

4. Kits

In one aspect, the invention relates to a kit comprising at least one agent that activates the expression of Atoh1, or a pharmaceutically acceptable salt, solvate, or polymorph thereof; at least one agent that inhibits the expression of $p27^{Kip1}$, or a pharmaceutically acceptable salt, solvate, or polymorph thereof; and one or more of: a) at least one agent known to treat a hearing impairment; b) at least one agent known to regenerate tissue; c) at least one chemotherapeutic agent; d) at least one ototoxic agent; e) a device suitable for administration of the at least one agent that activates the expression of Atoh1 and at least one agent that inhibits the expression of p27$^{Kip1}$ to the inner ear of a subject; f) instructions for treating a hearing impairment or imbalance disorder; and g) instructions for regenerating tissue.

In various aspects, the agents and pharmaceutical compositions described herein can be provided in a kit, as can cells that have been induced to differentiate (e.g., stem cells, progenitor cells, and/or support cells that have differentiated into, for example, hair cells or hair-like cells) and/or that are capable of differentiating into hair cells. The kit can also include combinations of the agents and pharmaceutical compositions described herein and such cells. The kit can include: a) one or more agents, such as in a composition that includes the agents; b) cells that have been induced to differentiate (e.g., stem cells, progenitor cells, and/or support cells that have differentiated into, for example, hair cells or hair-like cells) and/or that are capable of differentiating into hair cells; c) informational material; and any combination of a), b), and c). In various aspects, a) and/or b) can be provided in a syringe (e.g., a preloaded disposable single dose syringe) suitable for the direct administration of a) and/or b) directly into the ear (e.g., the middle or inner ear) of a patient. In various aspects, a) and/or b) can be provided in a catheter and pump system, as described above, suitable for the direct administration of a) and/or b) directly into the ear (e.g., the middle or inner ear) of a patient. The informational material can be descriptive, instructional, marketing or other material that relates to the methods described herein and/or to the use of the agents for the methods described herein. For example, the informational material relates to the use of the agents herein to treat a subject who has, or who is at risk for developing, an auditory hair cell loss hearing and/or abnormal cell proliferation. The kits can also include paraphernalia for administering the agents of this invention to a cell (in culture or in vivo) and/or for administering a cell to a patient.

In various aspects, the informational material can include instructions for administering the pharmaceutical composition and/or cell(s) in a suitable manner to treat a human, e.g., in a suitable dose, dosage form, or mode of administration (e.g., a dose, dosage form, or mode of administration described herein). In a further aspect, the informational material can include instructions to administer the pharmaceutical composition to a suitable subject, e.g., a human having, or at risk for developing, auditory hair cell loss and/or abnormal cell proliferation.

In various aspects, the composition of the kit can include other ingredients, such as a solvent or buffer, a stabilizer, a preservative, a fragrance or other cosmetic ingredient. In such aspects, the kit can include instructions for admixing the agent and the other ingredients, or for using one or more compounds together with the other ingredients.

In a further aspect, the agent that activates the expression of Atoh1 and the agent that inhibits the expression of p27$^{Kip1}$ are co-formulated. In a still further aspect, the agent that activates the expression of Atoh1 and the agent that inhibits the expression of p27$^{Kip1}$ are co-packaged.

In a further aspect, the agent known to treat a hearing impairment is selected from an antiepileptic drug blocking T-type calcium channels; an anticonvulsant; a synthetic glucocorticoid; a loop diuretic; an anti-oxidant; a proton pump inhibitor; a PDE5 inhibitor; and a mGluR7 inhibitor. In a still further aspect, the agent known to treat a hearing impairment is selected from trimethadione; mibefrabil; ethosuximide; 3,5-dichloro-N-[1-(2,2-dimethyl-tetrahydro-pyran-4-ylmethyl)-4-fluoro-piperidin-4-ylmethyl]-benzamide (TTA-P2); NNC 55-0396; ML 218; nilvadipine; valproic acid; oxcarbazepine; phenobarbital; phenytoin; zonisamide; nicardipine; chlordiazepoxide; sipatrigine; halothane; octanol; pimozide; penfluridol; fluspirilene; thioridazine; clozapine; haloperidol; tetramethrin; tetrandrine; amiodarone; bepridil; cinnarizine; flunarizine; amiloride; anandamide; dexamethasone; methylprednisolone; N2-[(2S)-2-(3,5-Difluorophenyl)-2-hydroxyethanoyl]-N1-[(7S)-5-methyl-6-oxo-6,7-dihydro-5H-dibenzo[b,d]azepin-7-yl]-L-alaninamide; 2-phenyl-1,2-benzisoselenazol-3-one (ebselen); sodium thiosulfate; D-methionine; furosemide; N-acetyl-L-cysteine; vitaminsA; vitamin C; vitamin E; vigabatrin; omeprazole; lansoprazole; pantoprazole; rabeprazole; esomerprazole; pariprazole; leminoprazole; 3,3'-diindolylmethane; vardenafil; sildenafil; tadalafil; udenafil; dasantafil; avanafil; SLx2101; LAS34179; N,N'-dibenzhydrylethane-1,2-diamine dihydrochloride; R(+)-N-propargyl-1-aminoindan; and L-carnitine.

In a further aspect, the chemotherapeutic agent is a platinum-based agent. In a still further aspect, the platinum-based agent is selected from carboplatin, cisplatin, transplatin, nedaplatin, oxaliplatin, picoplatin, satraplatin, transplatin, and triplatin. In yet a further aspect, the platinum-based agent is cisplatin.

In a further aspect, the ototoxic agent is selected from one or more of an antibiotic, a loop diuretic, an antimetabilite, and a salicyclate. In a still further aspect, the antibiotic agent is selected from one or more of daunorubicin, doxorubicin, epirubicin, idarubicin, actinomycin-D, bleomycin, and mitomycin-C, or a pharmaceutically acceptable salt thereof. In yet a further aspect, the antibiotic agent is an aminoglycoside. In yet a further aspect, the aminoglycoside is selected from one or more of amikacin, apramycin, arbekacin, astromicin, bekanamycin, dibekacin, framycetin, gentamicin, hygromycin B, isepamicin, kanamycin, neomycin, netilmicin, paromomycin, rhodostreptomycin, ribostamycin, sisomicin, spectinomycin, streptomycin, tobramycin, and verdamicin, or a pharmaceutically acceptable salt thereof.

In a further aspect, the loop diuretic is selected from one or more of furosemide; ethacrynic acid; or bumetanide, or a pharmaceutically acceptable salt thereof.

In a further aspect, the antimetabilite is selected one or more of an anti-folate, a fluoropyridimidine, a deoxynucleoside analogue, and a thiopurine. In a still further aspect, the antimetabolite is selected from one or more of methotrexate, pemetrexed, fluorouracil, capecitabine, cytarabine, gemcitabine, decitabine, 5-azacytidine, fludarabine, nelarabine, cladribine, clofarabine, pentostatin, thioguanine, and mercaptopurine, or a pharmaceutically acceptable salt thereof.

In a further aspect, the salicylate is selected from one or more of salicylic acid, methyl salicylate, and trolamine salicylate, or pharmaceutically acceptable salts thereof.

In a further aspect, the device is a flexible cannula or a preloaded single dose syringe.

In a further aspect, the kit further comprises a plurality of dosage forms, the plurality comprising one or more doses; wherein each dose comprises an effective amount of the agent that activates the expression of Atoh1 and the agent that inhibits the expression of p27$^{Kip1}$. In a still further aspect, the effective amount is a therapeutically effective amount. In yet a further aspect, the effective amount is a prophylactically effective amount. In an even further aspect, each dose of the agent that activates the expression of Atoh1 and the agent that inhibits the expression of p27$^{Kip1}$ are co-packaged. In a still further aspect, each dose of the agent that activates the expression of Atoh1 and the agent that inhibits the expression of p27$^{Kip1}$ are co-formulated.

In a further aspect, the dosage forms are formulated for topical administration. In a still further aspect, the dosage forms are formulated for injection into the luminae of the cochlea, the auditory nerve trunk in the internal auditory meatus, the scala tympani, or the middle ear space across the transtympanic membrane/ear drum; or, if present, into a cochlear implant.

In a further aspect, the agent that activates the expression of Atoh1 is formulated for topical administration; and wherein the agent that inhibits the expression of p27$^{Kip1}$ is formulated for injection into the luminae of the cochlea, the auditory nerve trunk in the internal auditory meatus, the scala tympani, or the middle ear space across the transtympanic membrane/ear drum; or, if present, into a cochlear implant. In a still further aspect, the agent that activates the expression of Atoh1 is formulated for injection into the luminae of the cochlea, the auditory nerve trunk in the internal auditory meatus, the scala tympani, or the middle ear space across the transtympanic membrane/ear drum; or, if present, into a cochlear implant; and wherein the agent that inhibits the expression of p27$^{Kip1}$ is formulated for topical administration.

In a further aspect, the kit further comprises a plurality of dosage forms, the plurality comprising one or more doses; wherein each dose comprises the agent that activates the expression of Atoh1, the agent that inhibits the expression of p27$^{Kip1}$, and the at least one agent known to treat a hearing impairment; wherein at least one is present in an effective amount. In a still further aspect, the effective amount is a therapeutically effective amount. In yet a further aspect, the effective amount is a prophylactically effective amount. In an even further aspect, each dose of the agent that activates the expression of Atoh1, the agent that inhibits the expression of p27$^{Kip1}$, and the agent known to treat a hearing impairment are co-packaged. In a still further aspect, each dose of the agent that activates the expression of Atoh1, the agent that inhibits the expression of p27$^{Kip1}$, and the agent known to treat a hearing impairment are co-formulated.

In a further aspect, the dosage forms are formulated for topical administration. In a still further aspect, the dosage forms are formulated for injection into the luminae of the cochlea, the auditory nerve trunk in the internal auditory meatus, the scala tympani, the middle ear space across the transtympanic membrane/ear drum; or, if present, into a cochlear implant.

In a further aspect, the agent that activates the expression of Atoh1 is formulated for topical administration; and wherein the agent that inhibits the expression of p27$^{Kip1}$ and the agent known to treat a hearing impairment are formulated for injection into the luminae of the cochlea, the auditory nerve trunk in the internal auditory meatus, the scala tympani, the middle ear space across the transtympanic membrane/ear drum; or, if present, into a cochlear implant. In a still further aspect, the agent that activates the expression of Atoh1 is formulated for injection into the luminae of the cochlea, the auditory nerve trunk in the internal auditory meatus, the scala tympani, the middle ear space across the transtympanic membrane/ear drum; or, if present, into a cochlear implant; and wherein the agent that inhibits the expression of p27$^{kip1}$ and the at least one agent known to treat a hearing impairment are formulated for topical administration. In yet a further aspect, the agent that activates the expression of Atoh1 and the agent known to treat a hearing impairment are formulated for topical administration; and wherein the agent that inhibits the expression of p27$^{Kip1}$ is formulated for injection to the luminae of the cochlea, to the auditory nerve trunk in the internal auditory meatus, to the scala tympani, the middle ear space across the transtympanic membrane/ear drum; or, if present, into a cochlear implant. In an even further aspect, the agent that activates the expression of Atoh1 and the agent known to treat a hearing impairment are formulated for injection to the luminae of the cochlea, to the auditory nerve trunk in the internal auditory meatus, to the scala tympani, the middle ear space across the transtympanic membrane/ear drum; or, if present, into a cochlear implant; and wherein the agent that inhibits the expression of p27$^{kip1}$ is formulated for topical administration.

In a further aspect, the kit further comprises a plurality of dosage forms, the plurality comprising one or more doses; wherein each dose comprises the agent that activates the expression of Atoh1, the agent that inhibits the expression of p27$^{Kip1}$, and the agent known to regenerate tissue; wherein at least one is present in an effective amount. In a still further aspect, the effective amount is a therapeutically effective amount. In yet a further aspect, the effective amount is a prophylactically effective amount. In an even further aspect, each dose of the agent that activates the expression of Atoh1, the agent that inhibits the expression of p27$^{Kip1}$, and the agent known to regenerate tissue are co-packaged. In a still further aspect, each dose of the agent that activates the expression of Atoh1, the agent that inhibits the expression of p27$^{Kip1}$, and the agent known to regenerate tissue are co-formulated.

In a further aspect, the dosage forms are formulated for topical administration. In a still further aspect, the dosage forms are formulated for injection to the luminae of the cochlea, to the auditory nerve trunk in the internal auditory meatus, to the scala tympani; or, if present, into a cochlear implant.

In a further aspect, the agent that activates the expression of Atoh1 is formulated for topical administration; and wherein the agent that inhibits the expression of p27$^{Kip1}$ and the agent known to regenerate tissue are formulated for injection to the luminae of the cochlea, to the auditory nerve trunk in the internal auditory meatus, to the scala tympani; or, if present, into a cochlear implant. In a still further aspect, the agent that activates the expression of Atoh1 is formulated for injection to the luminae of the cochlea, to the auditory nerve trunk in the internal auditory meatus, to the scala tympani; or, if present, into a cochlear implant; and wherein the agent that inhibits the expression of p27$^{Kip1}$ and the agent known to regenerate tissue are formulated for topical administration. In yet a further aspect, the agent that activates the expression of Atoh1 and the agent known to regenerate tissue are formulated for topical administration; and wherein the agent that inhibits the expression of p27$^{Kip1}$ is formulated for injection to the luminae of the cochlea, to the auditory nerve trunk in the internal auditory meatus, to the scala tympani; or, if present, into a cochlear implant. In an even further aspect, the agent that activates the expression of Atoh1 and the agent known to regenerate tissue are formulated for injection to the luminae of the cochlea, to the auditory nerve trunk in the internal auditory meatus, to the scala tympani; or, if present, into a cochlear implant; and wherein the agent that inhibits the expression of p27$^{kip1}$ is formulated for topical administration.

In a further aspect, the kit further comprises a plurality of dosage forms, the plurality comprising one or more doses; wherein each dose comprises the agent that activates the expression of Atoh1, the agent that inhibits the expression of p27$^{Kip1}$, and the chemotherapeutic agent; wherein at least one is present in an effective amount. In a still further aspect, the effective amount is a therapeutically effective amount. In yet a further aspect, the effective amount is a prophylactically effective amount. In an even further aspect, each dose of the agent that activates the expression of Atoh1, the agent that inhibits the expression of $p27^{Kip1}$ and the chemotherapeutic agent are co-packaged. In a still further aspect, each dose of the agent that activates the expression of Atoh1, the agent that inhibits the expression of $p27^{Kip1}$ and the chemotherapeutic agent are co-formulated.

In a further aspect, the dosage forms are formulated for intravenous or oral administration. In a still further aspect, the dosage forms are formulated for intravenous administration. In yet a further aspect, the dosage forms are formulated for oral administration.

In a further aspect, the agent that activates the expression of Atoh1 is formulated for intravenous administration; and wherein the agent that inhibits the expression of $p27^{kip1}$ and the chemotherapeutic agent are formulated for oral administration. In a still further aspect, the agent that activates the expression of Atoh1 is formulated for oral administration; and wherein the agent that inhibits the expression of $p27^{Kip1}$ and the chemotherapeutic agent are formulated for intravenous administration. In yet a further aspect, the agent that activates the expression of Atoh1 and the chemotherapeutic agent are formulated for intravenous administration; and wherein the agent that inhibits the expression of $p27^{kip1}$ is formulated for oral administration. In an even further aspect, the agent that activates the expression of Atoh1 and the chemotherapeutic agent are formulated for oral administration; and wherein the agent that inhibits the expression of $p27^{kip1}$ is formulated for intravenous administration.

In a further aspect, the kit further comprises a plurality of dosage forms, the plurality comprising one or more doses; wherein each dose comprises the agent that activates the expression of Atoh1, the agent that inhibits the expression of $p27^{Kip1}$, and the antibiotic agent; wherein at least one is present in an effective amount. In a still further aspect, the effective amount is a therapeutically effective amount. In yet a further aspect, the effective amount is a prophylactically effective amount. In an even further aspect, each dose of the agent that activates the expression of Atoh1, the agent that inhibits the expression of $p27^{Kip1}$, and the antibiotic agent are co-packaged. In a still further aspect, each dose of the agent that activates the expression of Atoh1, the agent that inhibits the expression of $p27^{Kip1}$, and the antibiotic agent are co-formulated.

In a further aspect, the dosage forms are formulated for intravenous or oral administration. In a still further aspect, the dosage forms are formulated for intravenous administration. In yet a further aspect, the dosage forms are formulated for oral administration.

In a further aspect, the agent that activates the expression of Atoh1 is formulated for intravenous administration; and wherein the agent that inhibits the expression of $p27^{kip1}$ and the antibiotic agent are formulated for oral administration. In a still further aspect, the agent that activates the expression of Atoh1 is formulated for oral administration; and wherein the agent that inhibits the expression of $p27^{kip1}$ and the antibiotic agent are formulated for intravenous administration. In yet a further aspect, the agent that activates the expression of Atoh1 and the antibiotic agent are formulated for intravenous administration; and wherein the agent that inhibits the expression of $p27^{kip1}$ is formulated for oral administration. In an even further aspect, the agent that activates the expression of Atoh1 and the antibiotic agent are formulated for oral administration; and wherein the agent that inhibits the expression of $p27^{kip1}$ is formulated for intravenous administration.

In one aspect, the invention relates to a kit comprising (β-catenin and at least one agent that synergistically activates the expression of Atoh1, or a pharmaceutically acceptable salt, solvate, or polymorph thereof; and one or more of: a) at least one agent that inhibits the expression of $p27^{Kip1}$ or a pharmaceutically acceptable salt, solvate, or polymorph thereof; b) at least one agent known to treat a hearing impairment; c) at least one agent known to regenerate tissue; d) at least one chemotherapeutic agent; e) at least one ototoxic agent; f) a device suitable for administration of the at least one agent that activates the expression of Atoh1 and at least one agent that inhibits the expression of $p27^{Kip1}$ to the inner ear of a subject; g) instructions for treating a hearing impairment or imbalance disorder; and h) instructions for regenerating tissue.

In a further aspect, the β-catenin and the agent that activates the expression of Atoh1 are co-formulated. In a still further aspect, the β-catenin and the agent that activates the expression of Atoh1 are co-packaged.

In a further aspect, the agent known to treat hearing impairment is selected from an antiepileptic drug blocking T-type calcium channels; an anticonvulsant; a synthetic glucocorticoid; a loop diuretic; an anti-oxidant; a proton pump inhibitor; a PDE5 inhibitor; and a mGluR7 inhibitor. In a still further aspect, the agent known to treat a hearing impairment is selected from trimethadione; mibefrabil; ethosuximide; 3,5-dichloro-N-[1-(2,2-dimethyl-tetrahydro-pyran-4-ylmethyl)-4-fluoro-piperidin-4-ylmethyl]-benzamide (TTA-P2); NNC 55-0396; ML 218; nilvadipine; valproic acid; oxcarbazepine; phenobarbital; phenytoin; zonisamide; nicardipine; chlordiazepoxide; sipatrigine; halothane; octanol; pimozide; penfluridol; fluspirilene; thioridazine; clozapine; haloperidol; tetramethrin; tetrandrine; amiodarone; bepridil; cinnarizine; flunarizine; amiloride; anandamide; dexamethasone; methylprednisolone; N2-[(2S)-2-(3,5-Difluorophenyl)-2-hydroxyethanoyl]-N1-[(7S)-5-methyl-6-oxo-6,7-dihydro-5H-dibenzo[b,d]azepin-7-yl]-L-alaninamide; 2-phenyl-1,2-benzisoselenazol-3-one (ebselen); sodium thiosulfate; D-methionine; furosemide; N-acetyl-L-cysteine; vitaminsA; vitamin C; vitamin E; vigabatrin; omeprazole; lansoprazole; pantoprazole; rabeprazole; esomerprazole; pariprazole; leminoprazole; 3,3'-diindolylmethane; vardenafil; sildenafil; tadalafil; udenafil; dasantafil; avanafil; SLx2101; LAS34179; N,N'-dibenzhydrylethane-1,2-diamine dihydrochloride; R(+)-N-propargyl-1-aminoindan; and L-carnitine.

In a further aspect, the chemotherapeutic agent is a platinum-based agent. In a still further aspect, the platinum-based agent is selected from carboplatin, cisplatin, transplatin, nedaplatin, oxaliplatin, picoplatin, satraplatin, transplatin, and triplatin. In yet a further aspect, the platinum-based agent is cisplatin.

In a further aspect, ototoxic agent is selected from one or more of an antibiotic, a loop diuretic, an antimetabilite, and a salicyclate. In a still further aspect, the antibiotic agent is selected from one or more of daunorubicin, doxorubicin, epirubicin, idarubicin, actinomycin-D, bleomycin, and mitomycin-C, or a pharmaceutically acceptable salt thereof. In yet a further aspect, the antibiotic agent is an aminoglycoside. In an even further aspect, the aminoglycoside is selected from one or more of amikacin, apramycin, arbekacin, astromicin, bekanamycin, dibekacin, framycetin, gentamicin, hygromycin B, isepamicin, kanamycin, neomycin, netilmicin, paromomycin, rhodostreptomycin, ribostamycin, sisomicin, spectinomycin, streptomycin, tobramycin, and verdamicin, or a pharmaceutically acceptable salt thereof.

In a further aspect, the loop diuretic is selected from one or more of furosemide; ethacrynic acid; or bumetanide, or a pharmaceutically acceptable salt thereof.

In a further aspect, the antimetabilite is selected one or more of an anti-folate, a fluoropyridimidine, a deoxynucleoside analogue, and a thiopurine. In a still further aspect, the antimetabolite is selected from one or more of methotrexate, pemetrexed, fluorouracil, capecitabine, cytarabine, gemcitabine, decitabine, 5-azacytidine, fludarabine, nelarabine, cladribine, clofarabine, pentostatin, thioguanine, and mercaptopurine, or a pharmaceutically acceptable salt thereof.

In a further aspect, the salicylate is selected from one or more of salicylic acid, methyl salicylate, and trolamine salicylate, or pharmaceutically acceptable salts thereof.

In a further aspect, the device is a flexible cannula or a preloaded single dose syringe.

In a further aspect, the kit further comprises a plurality of dosage forms, the plurality comprising one or more doses; wherein each dose comprises an effective amount of the β-catenin and the agent that synergistically activates the expression of Atoh1. In a still further aspect, the effective amount is a therapeutically effective amount. In yet a further aspect, the effective amount is a prophylactically effective amount.

5. Subjects

In various aspects, the subject of the herein disclosed methods is a vertebrate, e.g., a mammal Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In some aspects of the disclosed methods, the subject has been diagnosed with a need for treatment prior to the administering step. In some aspects of the disclosed method, the subject has been diagnosed with a hearing impairment or disorder prior to the administering step. In some aspects of the disclosed methods, the subject has been identified with a need for treatment prior to the administering step. In one aspect, a subject can be treated prophylactically with a compound or composition disclosed herein, as discussed herein elsewhere.

a. Dosage

Toxicity and therapeutic efficacy of the agents and pharmaceutical compositions described herein can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio $LD_{50}/ED_{50}$. Polypeptides or other compounds that exhibit large therapeutic indices are preferred.

Data obtained from cell culture assays and further animal studies can be used in formulating a range of dosage for use in humans. The dosage of such compounds lies preferably within a range of circulating concentrations that include the $ED_{50}$ with little or no toxicity, and with little or no adverse effect on a human's ability to hear. The dosage may vary within this range depending upon the dosage form employed and the route of administration utilized. For any agents used in the methods described herein, the therapeutically effective dose can be estimated initially from cell culture assays. A dose can be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Exemplary dosage amounts of a differentiation agent are at least from about 0.01 to 3000 mg per day, e.g., at least about 0.00001, 0.0001, 0.001, 0.01, 0.1, 1, 2, 5, 10, 25, 50, 100, 200, 500, 1000, 2000, or 3000 mg per kg per day, or more.

The formulations and routes of administration can be tailored to the disease or disorder being treated, and for the specific human being treated. For example, a subject can receive a dose of the agent once or twice or more daily for one week, one month, six months, one year, or more. The treatment can continue indefinitely, such as throughout the lifetime of the human. Treatment can be administered at regular or irregular intervals (once every other day or twice per week), and the dosage and timing of the administration can be adjusted throughout the course of the treatment. The dosage can remain constant over the course of the treatment regimen, or it can be decreased or increased over the course of the treatment.

In various aspects, the dosage facilitates an intended purpose for both prophylaxis and treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., (1990) Chapter 27 in Remington's Pharmaceutical Sciences, 18th Ed., Gennaro, ed., Mack Publishing Co., Easton, Pa.). In general, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., (1996) Chapter 3, In: Goodman & Gilman's The Pharmacological Basis of Therapeutics, 9th Ed., Hardman et al., eds., McGraw-Hill, New York, N.Y.).

b. Routes of Administration

Also provided are routes of administering the disclosed compounds and compositions. The compounds and compositions of the present invention can be administered by direct therapy using systemic administration and/or local administration. In various aspects, the route of administration can be determined by a patient's health care provider or clinician, for example following an evaluation of the patient. In various aspects, an individual patient's therapy may be customized, e.g., the type of agent used, the routes of administration, and the frequency of administration can be personalized. Alternatively, therapy may be performed using a standard course of treatment, e.g., using pre-selected agents and pre-selected routes of administration and frequency of administration.

Systemic routes of administration can include, but are not limited to, parenteral routes of administration, e.g., intravenous injection, intramuscular injection, and intraperitoneal injection; enteral routes of administration e.g., administration by the oral route, lozenges, compressed tablets, pills, tablets, capsules, drops (e.g., ear drops), syrups, suspensions and emulsions; rectal administration, e.g., a rectal suppository or enema; a vaginal suppository; a urethral suppository; transdermal routes of administration; and inhalation (e.g., nasal sprays).

In various aspects, the compounds and compositions described herein can be administered to a patient, e.g., a patient identified as being in need of treatment for hair cell loss, using a local route of administration. Such local routes of administration include administering the agents described herein into the ear of a patient and/or the inner ear of a patient, for example, by injection and/or using a pump.

In various aspects, a pharmaceutical composition can be injected into the ear (e.g., auricular administration), such as into the luminae of the cochlea (e.g., the Scala media, Sc vestibulae, and Sc tympani), e.g., using a syringe, e.g., a single-dose syringe. For example, the compounds and compositions described herein can be administered by intratympanic injection (e.g., into the middle ear), and/or injections into the outer, middle, and/or inner ear. Such methods are routinely used in the art, for example, for the administration of steroids and antibiotics into human ears. Injection can be, for example, through the round window of the ear or through the cochlear capsule. Other inner ear administration methods are known in the art (see, e.g., Salt and Plontke, *Drug Discovery Today* 2005, 10, 1299).

In various aspects, the pharmaceutical composition can be administered in situ, via a catheter or pump. A catheter or pump can, for example, direct a pharmaceutical composition into the cochlear luminae or the round window of the ear and/or the lumen of the colon. Exemplary drug delivery apparatus and methods suitable for administering one or more of the compounds described herein into an ear, e.g., a human ear, are described in US 2006/0030837 and U.S. Pat. No. 7,206,639. In a further aspect, a catheter or pump can be positioned, e.g., in the ear (e.g., the outer, middle, and/or inner ear) of a patient during a surgical procedure. In a still further aspect, a catheter or pump can be positioned, e.g., in the ear (e.g., the outer, middle, and/or inner ear) of a patient without the need for a surgical procedure.

In various aspects, one or more of the compounds and compositions described herein can be administered in combination with a mechanical device such as a cochlear implant or a hearing aid, which is worn in the outer ear. An exemplary cochlear implant that is suitable for use with the present invention is described in US 2007/0093878.

In various aspects, the modes of administration described above may be combined in any order. In this respect one or more agents that stimulate expression or activity of Atoh1 can be administered before, after, or simultaneously with one or more agents that inhibit the expression or activity of $p27^{Kip1}$.

In various aspects, the compounds and compositions described herein can be administered via cell therapy, wherein cells are contacted ex vivo with the combination of agents described herein to promote complete or partial differentiation of the cells to or toward a mature cell type of the inner ear (e.g., a hair cell) in vitro. Cells resulting from such methods can then be transplanted or implanted into a patient in need of such treatment.

In various aspects, suitable cells can be derived from a mammal, such as a human, mouse, rat, pig, sheep, goat, or non-human primate. For example, stem cells have been identified and isolated from the mouse utricular macula (Li, H., et al. (2003) *Nature Medicine* 9, 1293-1299). The cells can also be obtained from a patient to whom they will subsequently be re-administered.

In various aspects, suitable cells (e.g., a stem cell, progenitor cell, and/or support cell) may be isolated from the inner ear of an animal. Specifically, suitable cells can be obtained from the cochlear organ of Corti, the modiolus (center) of the cochlea, the spiral ganglion of the cochlea, the vestibular sensory epithelia of the saccular macula, the utricular macula, or the cristae of the semicircular canals.

The stem cell, progenitor cell, and/or supporting cells can also be obtained, however, from other tissues such as bone marrow, blood, skin, or an eye. The cells employed can be obtained from a single source (e.g., the ear or a structure or tissue within the ear) or a combination of sources (e.g., the ear and one or more peripheral tissues (e.g., bone marrow, blood, skin, or an eye).

E. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Experimental Methods a. Cell Culture

HeLa and HEK-293 cells were obtained from ATCC (HeLa #CCL-2, HEK #CRL-1573). 3T3-J2 (Swiss) cells were a generous gift from Dr. Richard Schlegel. All cell types were grown in DMEM supplemented with 10% FBS (Life Tech, #16000044), 1×penicillin/streptomycin mix (Life Tech, 15140148). Cells were grown in a tissue incubator at 37° C., 5% $CO_2$, 95% relative humidity. Transfections were carried out using lipofectamine LTX transfection reagent (Life Tech, $15338100) following the manufacturers protocol.

b. Plasmids

The luciferase vector was obtained from Dr. Sakai, the $p27^{Kip1}$ promoter was excised, and cloned into BamH1 sites from pGL4.17 (Promega). Cloning was verified by both restriction enzyme digests and DNA sequencing. The nonspecific plasmid (SV40-LacZ) was obtained from Addgene (#188116).

c. Assay Optimization

The number of cells transfected, amount of lipofectamine transfection reagent, and plasmid DNA were all optimized for maximal endogenous luciferase activity prior to screening. The $2\times10^6$ cells plated into a T75 flask (Corning, #3776) plate, followed by transfection utilizing 30 μL of transfection reagent and 5 μg of plasmid DNA gave optimal luciferase values.

d. High Throughput Screening

HeLa cells transiently transfected with the $p27^{Kip1}$-Luciferase plasmid were seeded into white, solid-bottom, tissue culture-treated, 384-well polystyrene plates (Corning, #8804BC) at a density of $5\times10^3$ cells per well in 25 μL ledia. Compounds, including those previously described (8.904 with 4,359 unique) (Leonardi, et al. (2010) *Chemistry & Biology* 17, 892; Vrijens, et al. (2013) *PloS one* 8, e59045), cycloheximide (Sigma, #C7698) (positive control; non-specific inhibition), titrations of cycloheximide (1- to 2-dilutions from 200 μM to 6.1 nM) or DMSO (Fisher Scientific, D128-1) (negative control) were transferred with a V&P 384-well pintool at 30 nL/well to give a final compound concentration of 12 μM in each individual well. The final cycloheximide concentration was 200 μM and the final DMSO concentration was 0.12%. The assay plates were then incubated overnight at 37° C., 5% $CO_2$, 95% relative humidity followed by alamar blue cytotoxicity assay (Life Tech, #DAL1100) and luminescence luciferase reporter activity assay (Envision HTS microplate reader, PerkinElmer, Model 2102) with SteadyLite HTS reagent (PerkinElmer, #6016981) (Herbst, et al. (2009) *Assay and drug development technologies* 7, 294; Lin, et al. (2008) *J. Biological Chem.* 283, 30650). Briefly, after overnight incubation, each well of the assay plates received diluted alamar blue reagent (1-to-12 dilution with DPBS (Life Tech, #14190) at 5 µL/well and incubated for an additional hour at 37° C., followed by 5 minute room temperature incubation to cool down. The assay plates were then read for fluorescent signals (excitation wavelength of 492 nm and emission wavelength of 590 nm) with an Envision plate reader. Next, SteadyLite HTS reagent (25 µL/well) was dispensed into each well followed by 20 minute room temperature incubation. The luminescence signals for individual wells were then measured with an Envision plate reader. Compound activity was normalized to that of 200 µM of cycloheximide (as 100% inhibition) and 0.12% DMSO (as 0% inhibition). Primary hits were compounds with luciferase inhibitory activity >50% and the activity difference between luciferase inhibition and alamar blue inhibition (% luciferase inhibition–% alamar blue inhibition) >20%. One hundred and eleven primary hits were further tested in a dose response analysis (10 compound concentrations, following a 3-fold dilution scheme with final concentration ranged from 56 µM to 2.8 nM, except for A2CE which ranged from 100 µM to 1 nM) in triplicate. Similarly, 200 µM of cycloheximide and 0.56% DMSO were included as positive and negative controls, respectively. The final DMSO concentration was 0.56% in the dose response assays, in order to achieve the highest compound concentration at 56 µM. The activity data for individual chemicals were fit into sigmoidal dose-response curves, if applicable, to derive $IC_{50}$ values with GraphPad Prism 6.01.

e. Chromatin Immunoprecipitation (ChIP)

ChIP was performed on $5\times10^7$ HeLa treated for 1 day with 10 µM A2CE or DMSO using the simple ChIP kit from Cell signaling (#9003). ChIP's were quantitated by real-time PCR (Eppendorf, Realplex$^2$ #) using Syber Green (Biorad #170880). Results are displayed as percent enrichment compared to the input. Primers for the p27$^{Kip1}$ promoter are from (Wang, et al. (2007) *Aging Cell* 6, 505) p27-FP: 5'-acacacacatcctggcaaag-3'; p27-RP: 5'-agtgtcccaaagaagcatgg-3'.

f. LacZ Luminescence

Figure 3B:
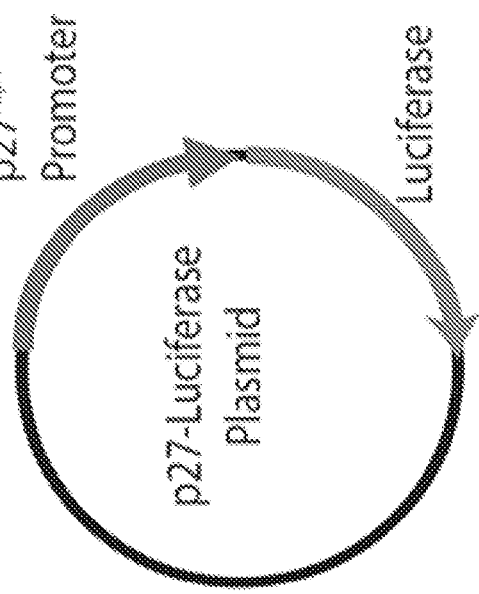
FIG. 3B shows the workflow for the primary screen.

Luminescence of LacZ was measured using the duel light luminescence kit from Life Technologies (#T1003) following the workflow diagrammed in FIG. 3B, and the same conditions optimized for p27$^{Kip1}$-luciferase transfections. Luminescence was quantified on either a GloMax Multi+ (Promega) or the Envision HTS microplate reader.

g. mRNA Isolation

HeLa cells were grown to ~50% confluence at which time A2CE was added. 16-24 h later cells were harvested in RNA stat 60 (Tel-Test, #CS-112) and mRNA harvested following the manufacturer's protocol. The resulting mRNA was quantified (Thermo, NanoDrop 2000), and further used to generate cDNA (Life Technologies, #4368813). qPCR was performed on 2 ng of cDNA run in multiplex against human p27$^{Kip1}$ (Life Tech, Hs01597588), or mouse p27$^{Kip1}$ (Life Tech, 4310893E) as the internal control.

h. Cochlear Explants

Organs of Corti were harvested from P1-P4 mice, plated on Matrigel (BD bioscience, #356234), and grown in DMEM (supplemented with 1% FBS, 10 µg/µL ciprofloxin). A2CE (10 µM) was added after 24 h, and explants were harvested after additional 24 h incubation. Isolation and quantification of mRNA was done the same as described above herein.

i. Immunoblot

HeLa cells were harvested and homogenized in RIPA buffer (10 mM Tris (pH 7.4), 100 mM NaCl, 1 mM EDTA, 1 mM EGTA, 0.1% SDS, 1% Triton-X100, 0.5% sodium deoxycholate, 10% glycerol, + protease and phosphatase inhibitors) and total protein was quantitated using a BCA assay (Thermo scientific, #23225). Samples were boiled for 5 min with SDS sample loading buffer prior to loading. Samples were run on 4-20% precast polyacrylamide gels (Bio-Rad, 456-1096) after which they were transferred to a polyvinylidene difluoride membrane (Millipore, #IPHVH07850). Membranes were blocked in 5% (w/v) fat-free milk-PBST (phosphate buffer with 0.05% Tween 20) for 1 h at r.t. after which the membranes were incubated with rabbit anti-p27$^{Kip1}$ polyclonal antibody (#06-445, Upstate) or anti-(3-actin antibody (#3700, cell signaling) in PBST overnight at 4° C. The membrane was washed three times with PBST followed by incubation in HRP-anti-mouse IgG or HRP-anti-rabbit IgG secondary antibodies diluted 1:5000 in PBST for 1 h at rt. After washing three times with PBST, the specific bands were developed on the films using SuperSignal West Pico Chemiluminescent Substrate (Thermo Scientific). Densitometry was performed using ImageJ (U.S. National Institutes of Health).

j. Isolation of Full Length p27Kip1

Full-length p27$^{Kip1}$ protein was expressed in *Escherichia Coli* as 6xHis fusion constructs. The protein was purified by nickel affinity chromatography and then digested with thrombin to remove the fusion tag. Further purification by reverse-phase high performance liquid chromatography (HPLC) using a C4 column (Vydac) and 0.1% trifluoroacetic acid-containing water/acetonitrile solvent system yielded high purity protein. Protein concentration was determined by UV absorbance at 280 nm using a molar extinction coefficient of 15,470 $M^{-1}*cm^{-1}$.

k. Mouse Models

Lgr5EGFP-IRES-CreERT2/+ and PlpCreER mice were purchased from the Jackson Laboratory (stock no. 008875 and 005975, respectively; Bar Harbor, Me.). Catnb1exon3$^{flox}$ mouse was obtained from Dr. Taketo and described in Harada et al., 1999. Atoh1-HA mouse is described in Liu et al., 2012.

Tamoxifen (T5648-5G, Sigma) (3 mg/40 g body weight) was given by intraperitoneal injections (IP) at postnatal (P) day 0 (P0) and 1 (P1). All animal work conducted during the course of this study was approved by the Institutional Animal Care and Use Committee at St. Jude Children's Research Hospital and was performed according to NIH guidelines.

l. Tissue Preparation, Immunofluorescence and Analysis

Isolated cochlea were fixed in 2% PFA for 3-4 hours at room temperature, and subsequently washed in phosphate buffer saline (PBS) (P3813, Sigma) 3 times for 5 minutes. Whole mount preparations were performed as described previously (Liu et al., 2010). Briefly, the whole mounts were blocked/permeabilized in 10% Bovine serum albumin (BP1600-100, Fischer scientific), 1% Triton X (BP151-500, Fischer scientific), and PBS for 1 h at rt, then washed 3 times in PBS, and incubated with the appropriate primary and secondary antibodies in 5% normal horse serum, 0.1% Triton X, and PBS overnight at 4° C. The following primary antibodies were used: anti-Myosin-VII (rabbit, 1:200, 25-6790, Proteus Biosciences), anti-HA (rat, 1:100, 11867423001, Roche), anti-Ctbp2 (mouse, 1:500, 612044, BD Transduction), anti-GFP (chicken, 1:1000, ab13970, Abcam), anti-GLUR2 (mouse, 1:200, MAB397, Millipore), anti-TUJ1 (mouse, 1:1000, MMS-435P, Covance), anti-prestin (1:200, sc-22692, Santa Cruz Biotechnology), and anti-Sox2 (goat, 1:1000, sc-17320, Santa Cruz Biotechnology). All secondary antibodies were purchased from Invitrogen and used at 1:1000 except for Alexa Fluor 405 goat anti-rabbit IgG (1:500) and Alexa Fluor 647 goat anti-rat IgG (1:500). Confocal imaging was performed on a Zeiss LSM 700 and analyzed with Photoshop CS4 (Adobe Systems, San Jose, Calif.).

m. Quantification of Ectopic Hair Cells

After the whole mounts were stained with the appropriate antibodies, the samples were cut into two parts with the cut site close to the end of the first apical turn. The apical, middle and base regions were first imaged under 20× to identify regions of interest. Z-stacks were then obtained for each turn using the 40× objective (1 μm step). Zeiss LSM image browser was then used to analyze the Z-stacks. The number of ectopic hair cells was determined by scoring Atoh1-ATOH1-HA+/Myosin7a+ cells along the Z-axis and normalized to 100 μm sections. Subsequently, the rate of trans-differentiation was determined as the ratio of ectopic hair cells over the total number of Atoh1-ATOH1-HA+ cells.

n. Statistical Analysis

Statistical analysis was performed using OriginLab 8.5. Where applicable, one-way ANOVAs with Bonferroni were run to test for mean difference, or a two sample T-test if two conditions were compared.

Alternatively, statistical analysis was performed using the GraphPad Prism 5.0 software package (GraphPad Software). One-way ANOVA with Bonferroni correction was used to determine statistical significance ($P<0.05$ was considered significant).

Figure 4A:
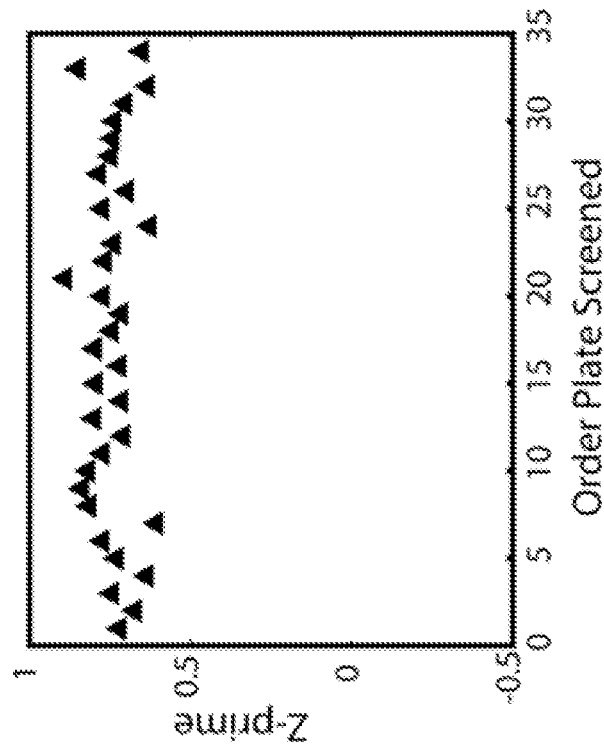
FIG. 4A and FIG. 4B show representative data pertaining to the validation of a high throughput screen to antagonize p27$^{Kip1}$ transcription. Specifically.
Figure 4B:
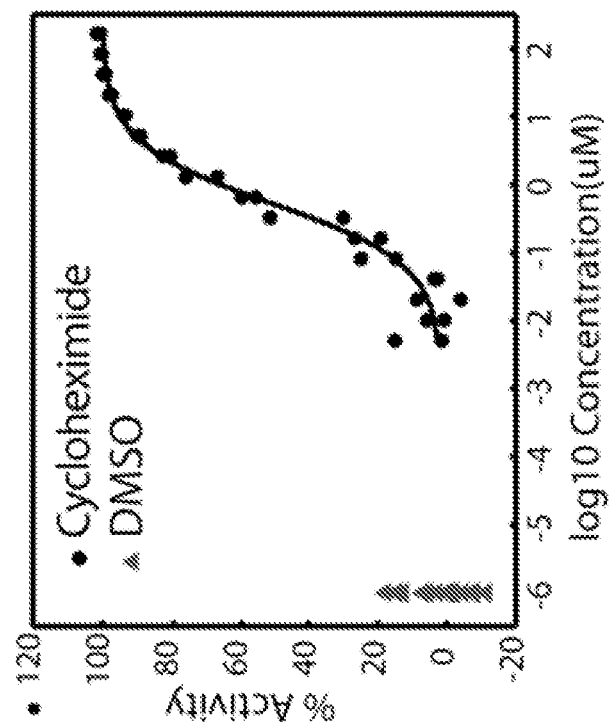

2. Creation and Validation of p27Kip1-Luciferase Assay for High Throughput Screening A transfection and screening procedure was optimized (diagrammed in FIG. 3A) using $p27^{Kip1}$-luciferase plasmid transfected into HeLa cells. The $p27^{Kip1}$ plasmid has been previously described (Liu, et al. (2012) J. Neuroscience 32, 10530), but the backbone was not suitable for high throughput screening (HTS). The 4-kb human $p27^{Kip1}$ promoter was cloned into the BamHI site of the pGL4.17 commercially available luciferase backbone (FIG. 3B). To ensure a robust assay, the generalized translation inhibitor cycloheximide was chosen as a positive control that should maximally repress the luciferase signal in each plate. Titration of cyclohexamide produced optimal repression of luciferase at 200 μM and was then defined as 100% luciferase inhibition (FIG. 3B). Z' factor (measure of robustness of a HTS) was calculated for each plate run in the HTS and is displayed in FIG. 4A. The overall mean of the Z' factor from the assay was 0.74±0.06, demonstrating that the assay is well suited for HTS. Cell viability was monitored during the HTS, since inhibition of luciferase could be due to cell death and not repression of $p27^{Kip1}$. Alamar blue, an oxidation-reduction indicator, which is converted to a fluorescent form proportionally to cellular metabolism and is commonly used in HTS as a measure of cell viability, was chosen (FIG. 4B).

Figure 5:
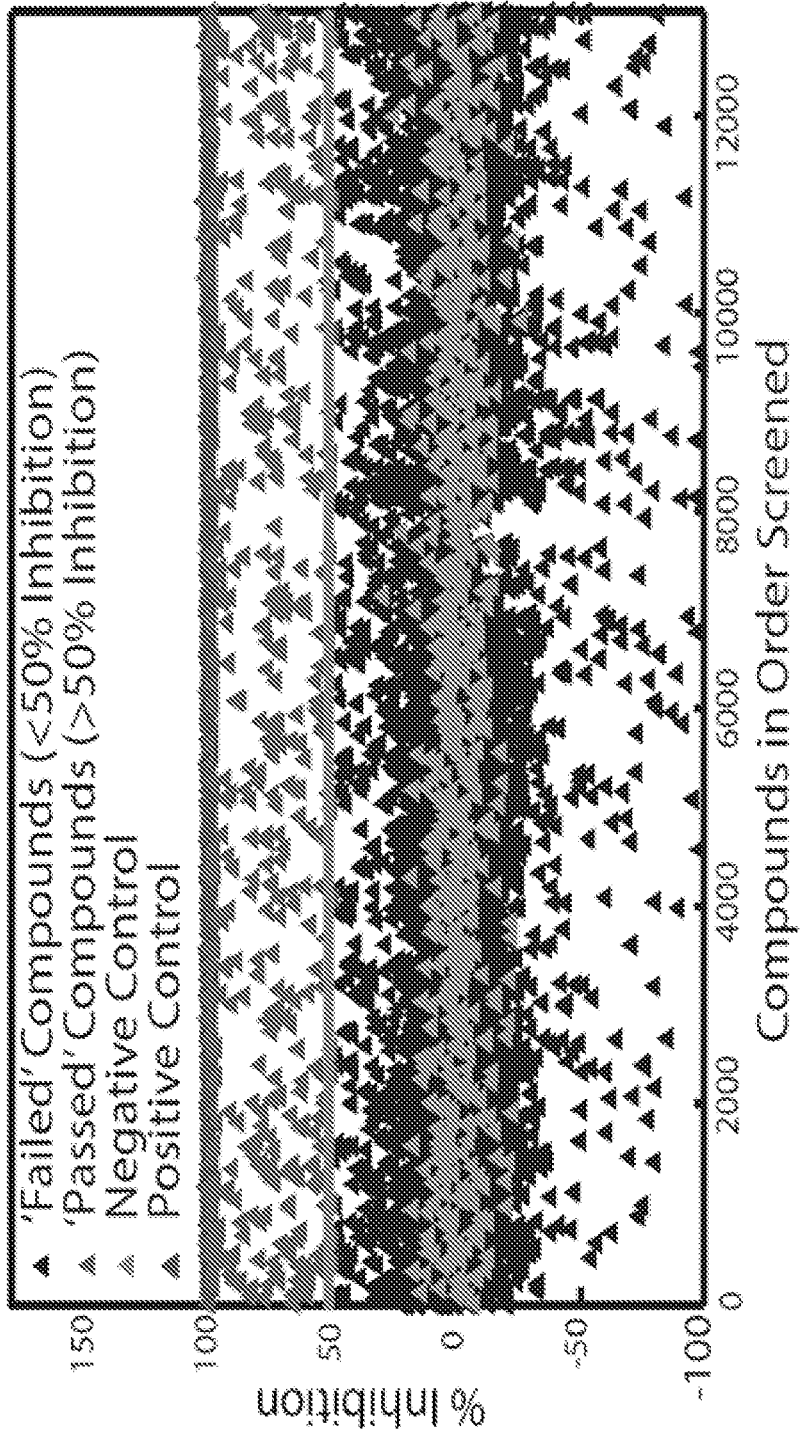
FIG. 5 shows representative data pertaining to the primary screen for inhibition of p27$^{Kip1}$-luciferase.
Figure 6:
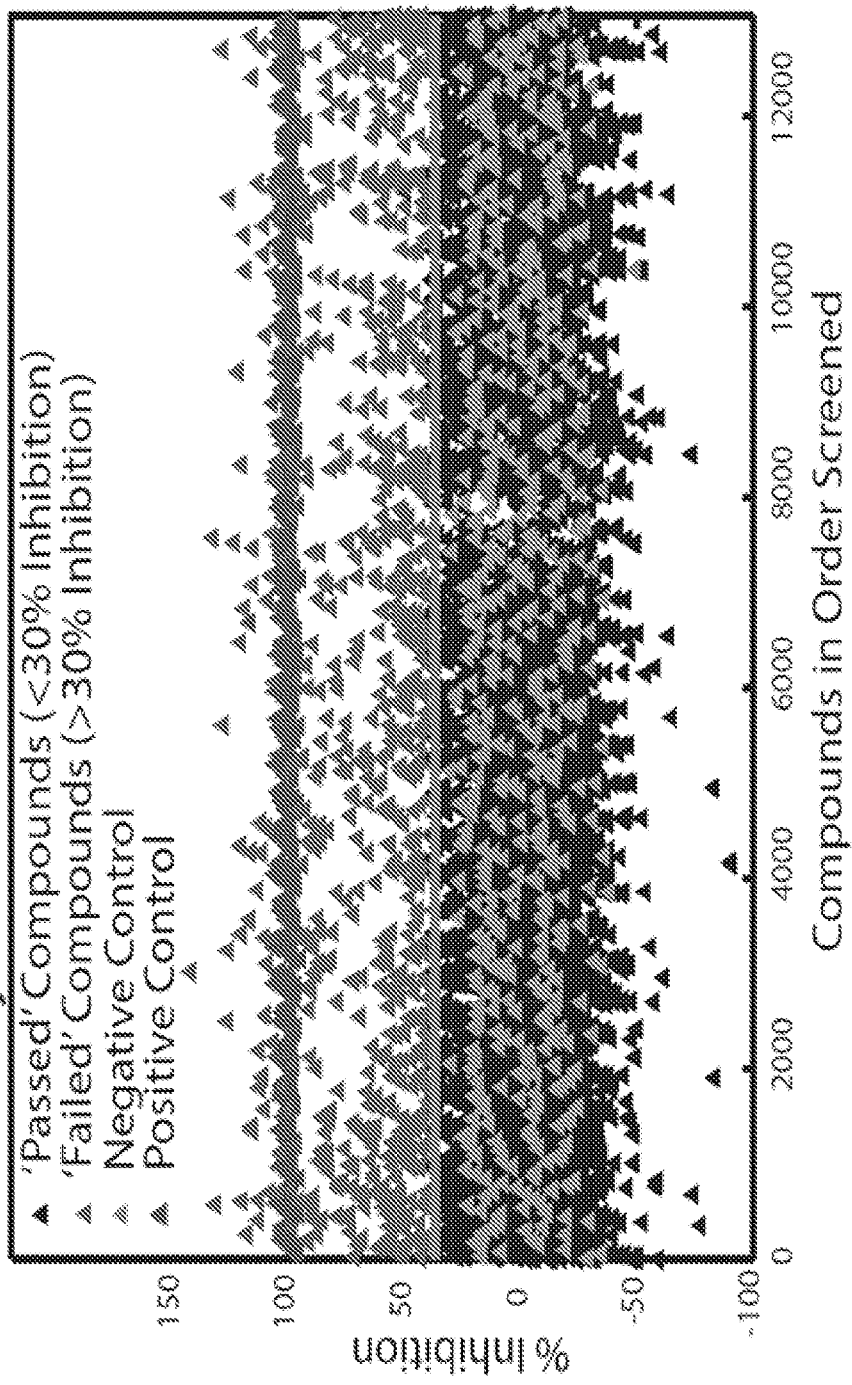
FIG. 6 shows representative data pertaining to the effect of small molecule application (12 μM) on alamar blue fluorescence.

3. High Throughput Screening of the Combined FDA/Bioactive Libraries Reveals 111 Primary Hits Once the primary assay was validated, the primary screen of the "bioactive" library was performed. Small molecules were added to a final concentration of 12 μM (following the workflow from FIG. 3A). Alamar blue signal was measured first for cell viability, followed by luciferase activity. Any compound which demonstrated at least 50% luciferase inhibition (FIG. 5, when compared to 200 μM cycloheximide) but less than a 30% drop in cell viability (FIG. 6) were considered primary hits, and passed on to the first of the secondary screens. 111 primary hits were obtained, representing 2.5% hit rate.

4. Secondary Screening Validated Four p27Kip1 Transcriptional Inhibitors

Figure 7A:
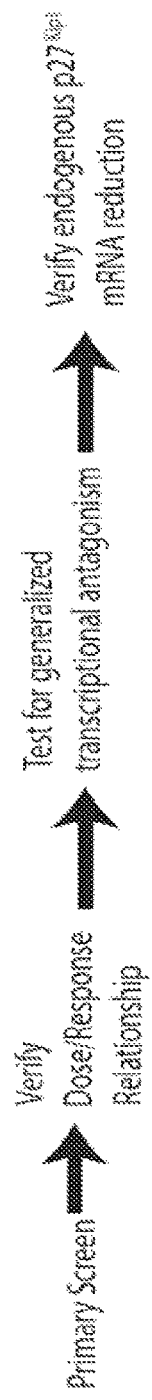
FIG. 7A shows the workflow of the secondary screening procedures.
Figure 7B:
FIG. 7B shows the remaining hits after each step of the secondary screen.
Figure 8B:
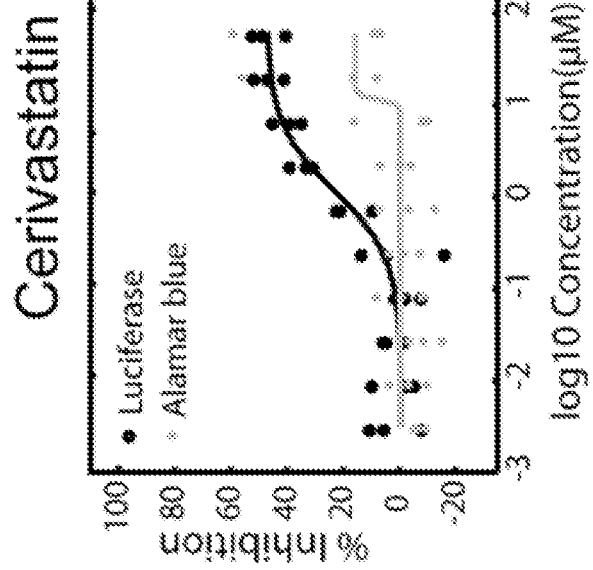
FIG. 8 shows representative data pertaining to the dose-dependent luciferase inhibition (black) and alamar blue inhibition (gray) of A2CE (8A) and cerivastatin sodium (8B).
Figure 8A:
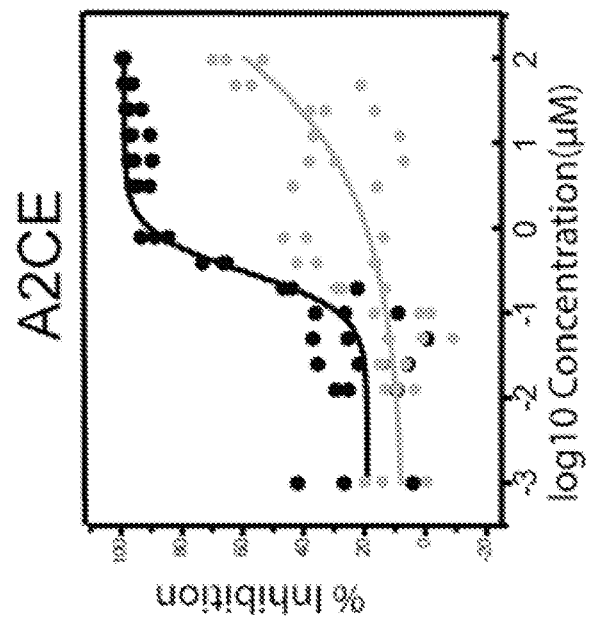
Figure 9B:
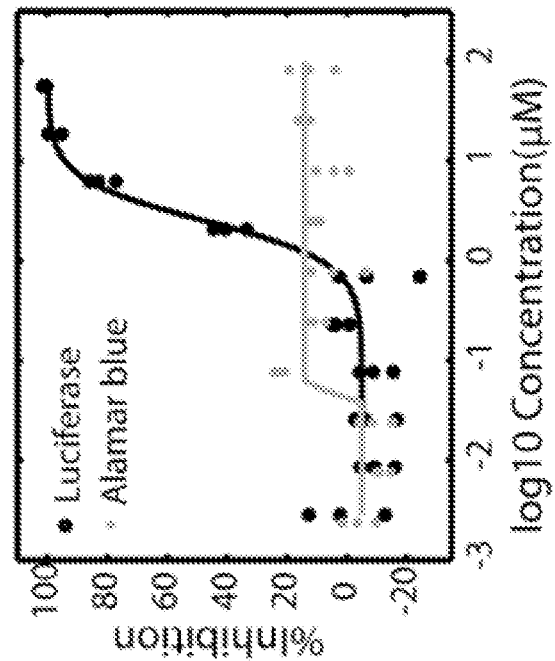
FIG. 9 shows representative data pertaining to the dose-dependent luciferase inhibition (black) and alamar blue inhibition (gray) of resveratrol (9A) and triacetylresveratrol (9B).
Figure 9A:
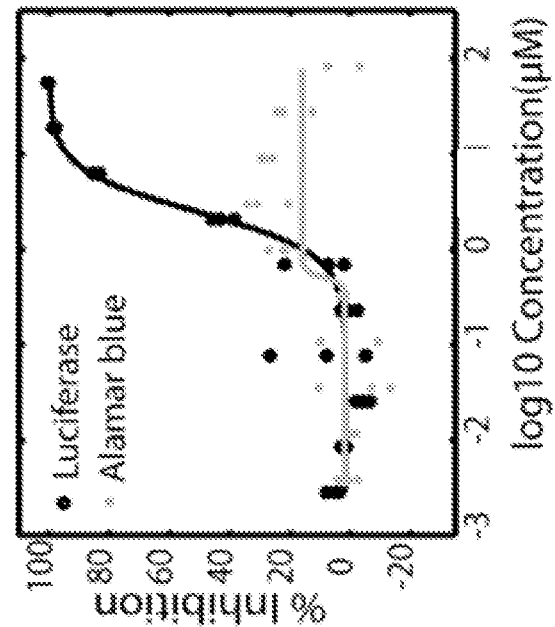
Figure 10B:
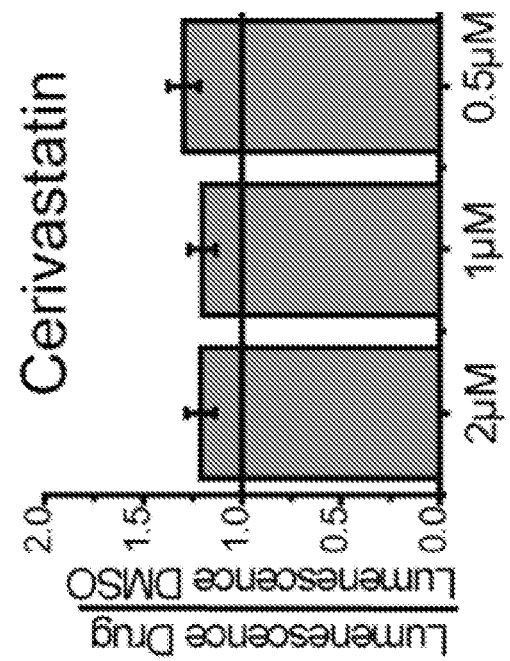
FIG. 10 shows representative data pertaining to the luciferase levels (normalized to DMSO) over 3 doses of A2CE (10A) and cerivastatin sodium (10B) showing no effect on SV-40 driven luciferase (n=3).
Figure 10A:
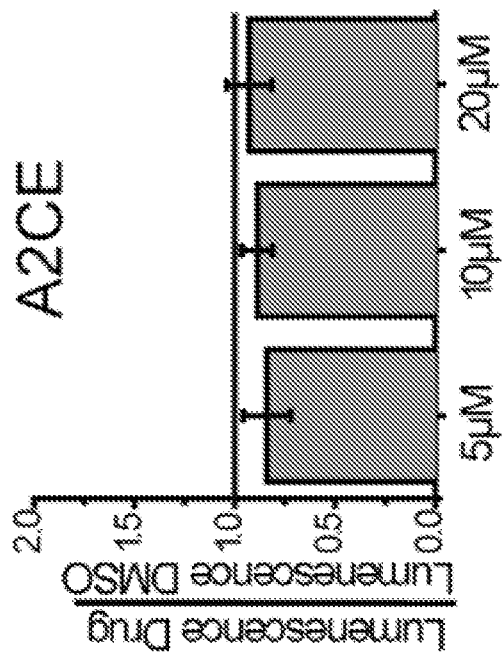
Figure 11B:
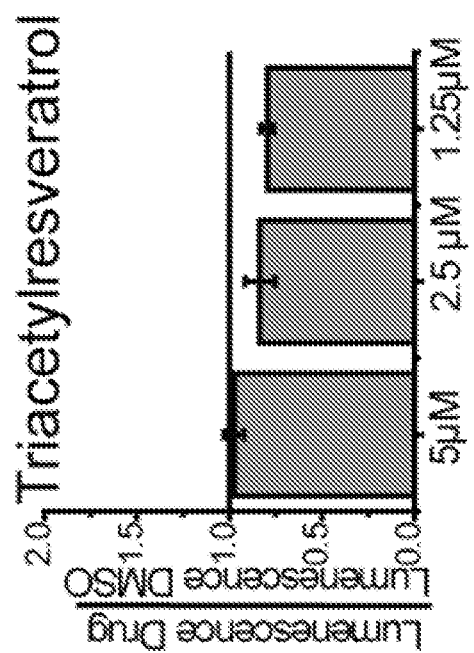
FIG. 11 shows representative data pertaining to the luciferase levels (normalized to DMSO) over 3 doses of resveratrol (11A) and triacetylresveratrol (11B) showing no effect on SV-40 driven luciferase (n=3).
Figure 11A:
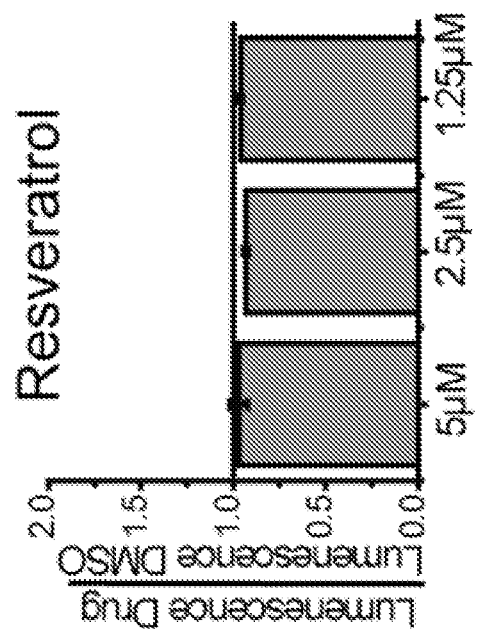
Figure 12B:
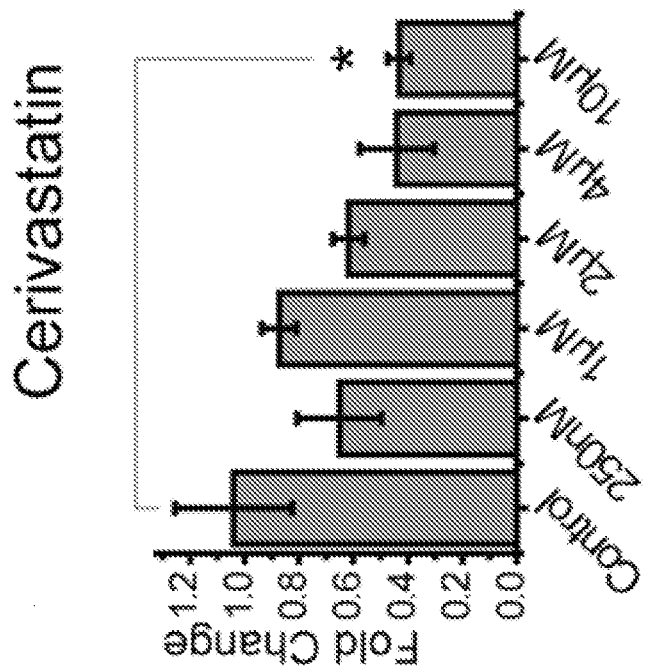
FIG. 12 shows representative data pertaining to a dose-dependent decrease in endogenous p27$^{Kip1}$ mRNA of A2CE (12A) and cerivastatin sodium (12B) normalized to that in DMSO control (RT-qPCR) in HeLa cells (n=3).
Figure 12A:
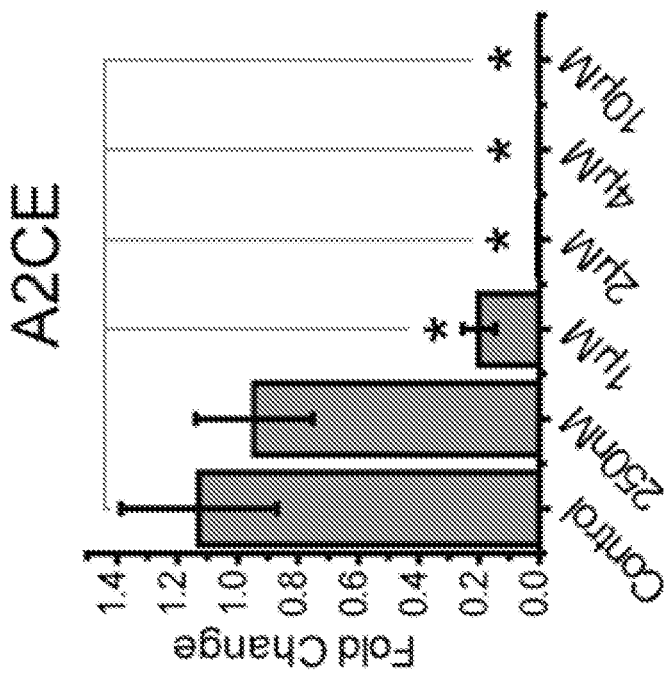
Figure 13B:
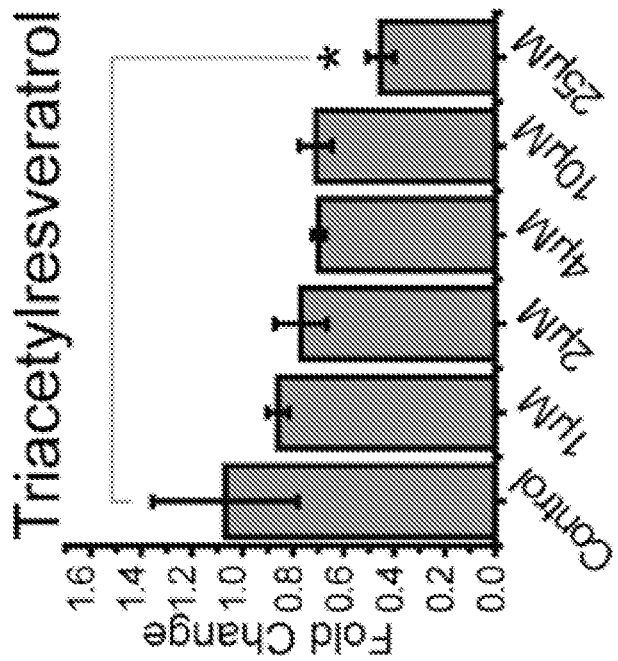
FIG. 13 shows representative data pertaining to a dose-dependent decrease in endogenous p27$^{Kip1}$ mRNA of resveratrol (13A) and triacetylresveratrol (13B) normalized to that in DMSO control (RT-qPCR) in HeLa cells (n=3).
Figure 13A:
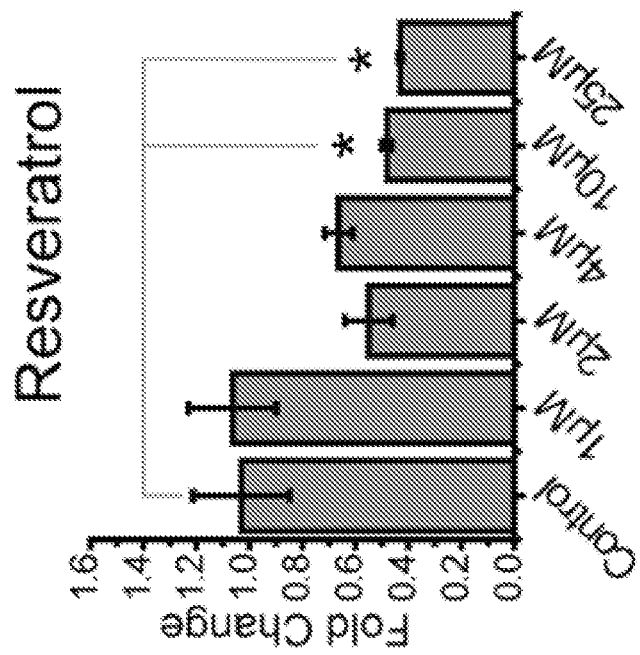

Primary hits from HTS may contain "false-positives" ranging from toxic compounds to naturally fluorescence-quenching molecules. To help remove these false-positive hits, three progressively more restrictive secondary screens were designed (FIG. 7A). To confirm the effect of these compounds on inhibiting the activity of the $p27^{Kip1}$-luciferase reporter, all primary hits were tested in a dose response analysis and assayed not only the luciferase response for $p27^{Kip1}$ inhibition, but also for the alamar blue levels for cell survival. $IC_{50}$ values were calculated from each luciferase response and are displayed for each final compound in Table 2 below. Only compounds that demonstrated a robust dose response relationship with the luciferase values, and no noticeable effect on alamar blue over the effective doses (FIGS. 8A, 8B, 9A, and 9B) were passed to the next secondary screen.

Since it is possible that any positive hits obtained from the primary screen could represent generalized transcriptional inhibitors that are non-specific to $p27^{Kip1}$, an independent plasmid utilizing the SV40 promoter to drive LacZ expression was used (FIGS. 10A, 10B, 11A, and 11B). LacZ expression was measured in a luminescent assay over 3 concentration points of the compound, and any reduction in luminescence would reflect a generalized transcriptional repression, and would eliminate the compound.

After the first two phases of secondary screens, the ability of the remaining compounds to repress endogenous $p27^{Kip1}$ expression (measured by quantitative real time PCR) of HeLa cells instead of the transient transfected reporter plasmid was investigated (FIGS. 12A, 12B, 13A, and 13B). Table 2 describes the full list of compounds that passed both the primary and secondary screens, as well as calculated $IC_{50}$ value.

TABLE 2

| Name | Calculated $IC_{50}$ (μM) | 95% Confidence Interval |
| --- | --- | --- |
| Alsterpaullone, 2-Cyanoethyl | 0.2 | −0.129, 0.530 |
| Cerivastatin Sodium | 1 | 0.5, 2.0 |
| Resveratrol | 2.49 | 2.10, 2.94 |
| Triacetylresveratrol | 2.5 | 1.9, 3.3 |

5. Alsterpaullone, 2-Cyanoethyl Treatment Reduces p27Kip1 Protein Levels

Figure 14:
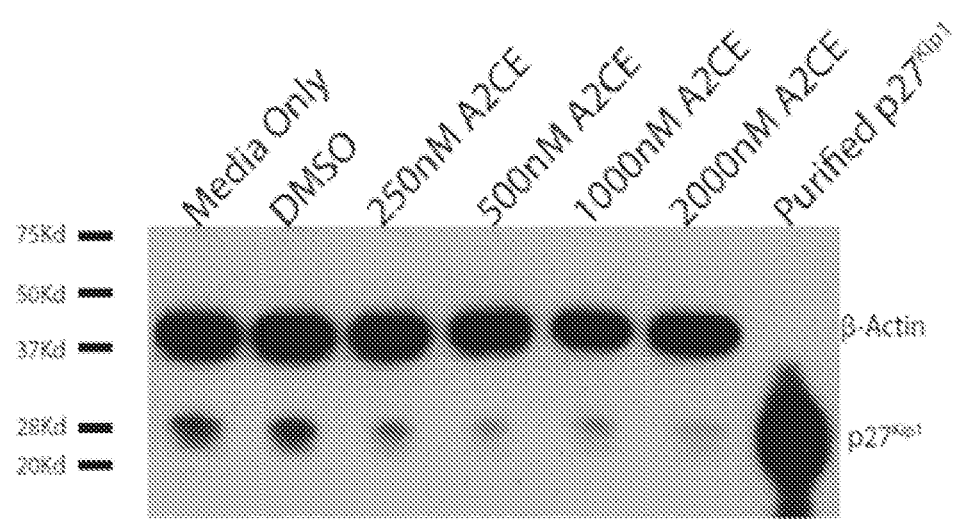
FIG. 14 shows representative data demonstrating that alsterpaullone, 2-cyanoethyl reduces p27$^{Kip1}$ protein levels.
Figure 15A:
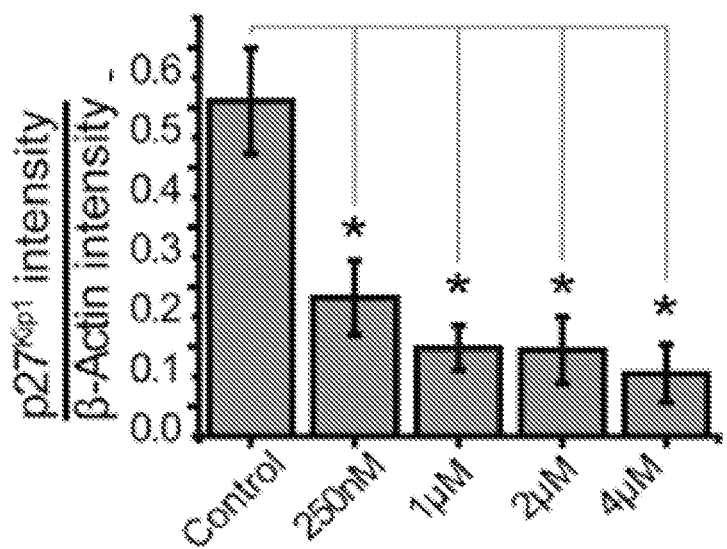
FIG. 15 shows representative data demonstrating that alsterpaullone, 2-cyanoethyl reduces p27$^{Kip1}$ protein levels (15A) and inhibits p27$^{Kip1}$ transcription in HEK cells (15B).

After validation of these four compounds as $p27^{Kip1}$ transcription antagonists, A2CE was focused on because the other three compounds demonstrated only a modest reduction on the level of $p27^{Kip1}$ mRNA. First, the effect of A2CE treatment on endogenous $p27^{Kip1}$ at the protein level was evaluated in HeLa cells. $p27^{Kip1}$ protein levels were assayed using an immunoblot procedure as described herein. Progressively higher doses of A2CE were added, resulting in the formation of an immune positive band at 28 kDa when proved with $p27^{Kip1}$ specific antisera that decreased in intensity with higher treatment concentrations of A2CE (FIG. 14). β-actin was used as a loading control. Band intensities were quantified using densitometry (FIG. 15A) and displayed as average $p27^{Kip1}$ intensity normalized to β-actin intensity. These results confirm that A2CE's inhibitory effects on p27$^{Kip1}$ transcription eventually led to a reduction at the protein level.

Figure 15B:
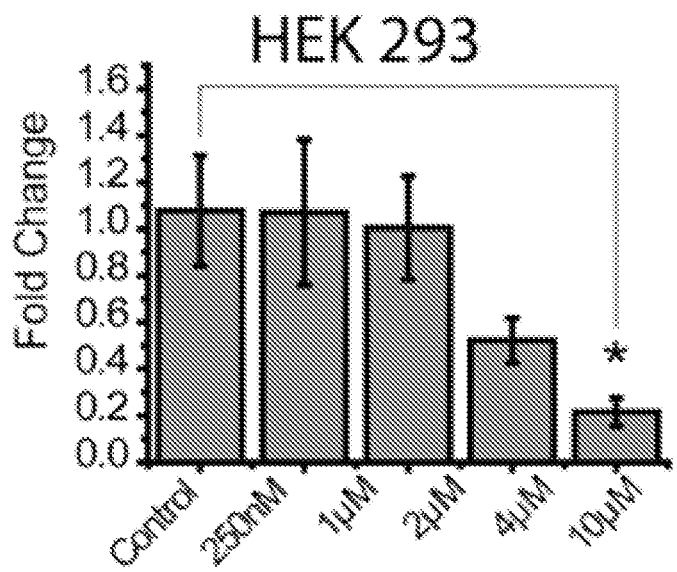
Figure 16A:
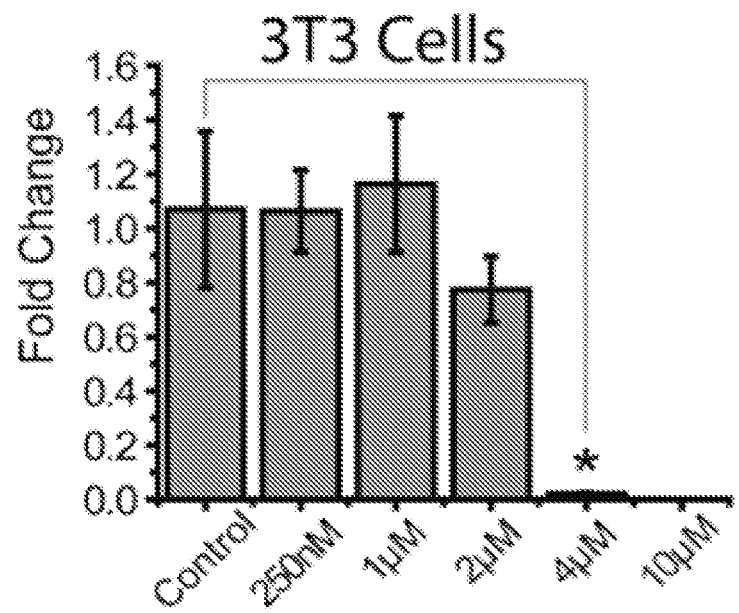
FIG. 16 shows representative data demonstrating that alsterpaullone, 2-cyanoethyl inhibits p27$^{Kip1}$ transcription in 3T3 cells (16A) and cochlear explants (16B).
Figure 16B:
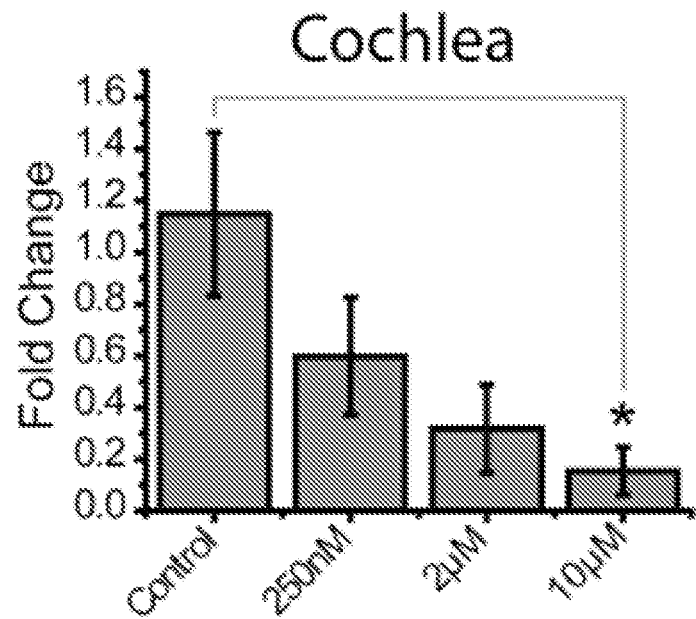

6. Alsterpaullone, 2-Cyanoethyl Treatment Reduces p27Kip1 mRNA Across Diverse Cell Lines and in Cochlear Explants To determine whether addition of A2CE was only relevant in HeLa cells, both HEK-293 and 3T3 cells were treated with 10 µM A2CE and assayed for p27$^{Kip1}$ transcript. Significantly less p27$^{Kip1}$ mRNA was detected in both HEK-293 and 3T3 cells when assayed by quantitative PCR (qPCR) (FIGS. 15B and 16A). Finally, the effect of A2CE treatment on p27$^{Kip1}$ transcription in a cochlear explant was evaluated using one of the tissue types where repression of p27$^{Kip1}$ may be beneficial. Postnatal (P1) 1-P4 cochleae were isolated, and after 1 day were treated with 10 µM A2CE. One day after treatment, whole cochlear mRNA was harvested. FIG. 16B demonstrates a significant reduction of p27$^{Kip1}$ mRNA after treatment with 10 µM A2CE.

7. Alsterpaullone, 2-Cyanoethyl Inhibits FoxO3a Binding to the p27Kip1 Promoter

Figure 17A:
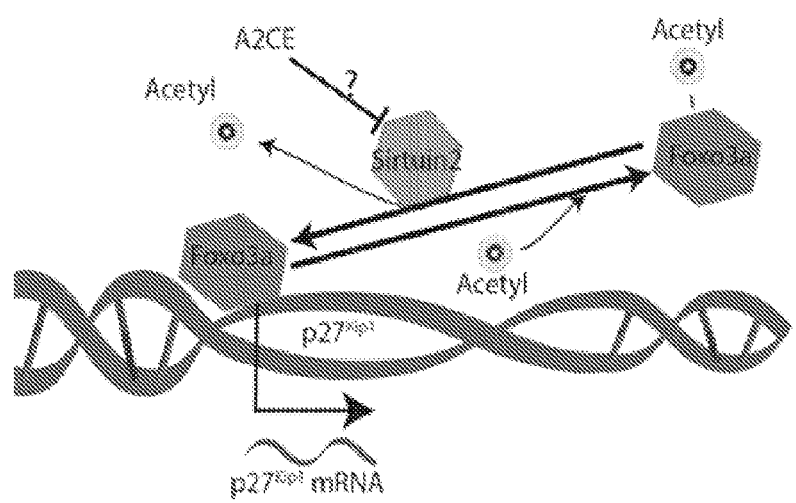
FIG. 17A shows a proposed schematic for how FoxO3a interacts with the p27$^{Kip1}$ promoter, and where A2CE is hypothesized to interact with it.
Figure 17B:
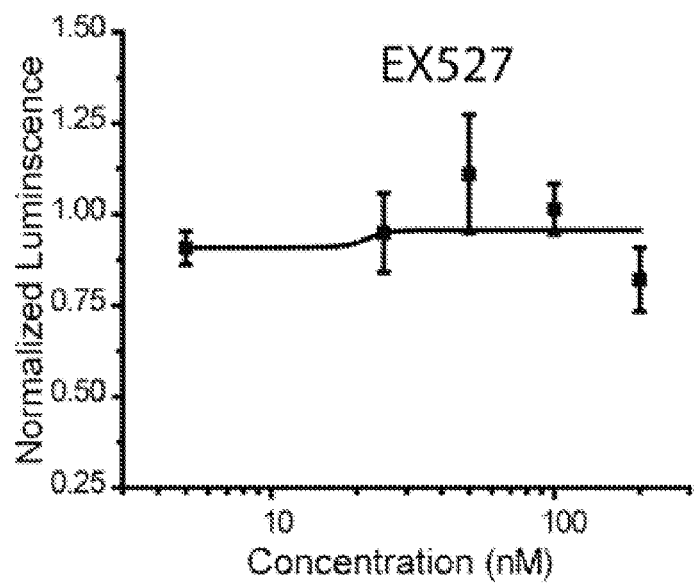
FIG. 17B shows p27$^{Kip1}$-luciferase levels upon application of the Sirtuin 1 inhibitor EX527 (IC$_{50}$=100 nM, n=3).
Figures 18A, 18B:
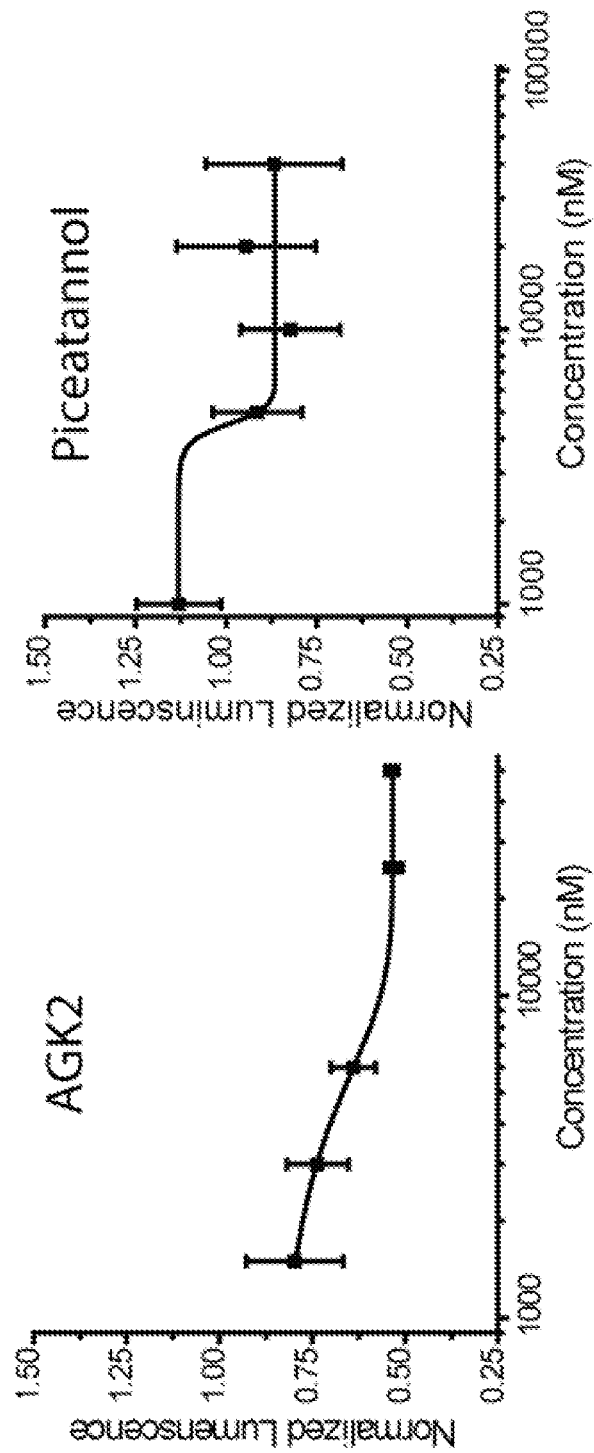
FIG. 18A shows p27$^{Kip1}$-luciferase levels upon application of the Sirtuin 2 inhibitor AGK2 (IC$_{50}$=3.5 µM, n=3).
FIG. 18B shows p27$^{Kip1}$-luciferase levels upon application of the resveratrol metabolite piceatenol (n=3).
Figure 19:
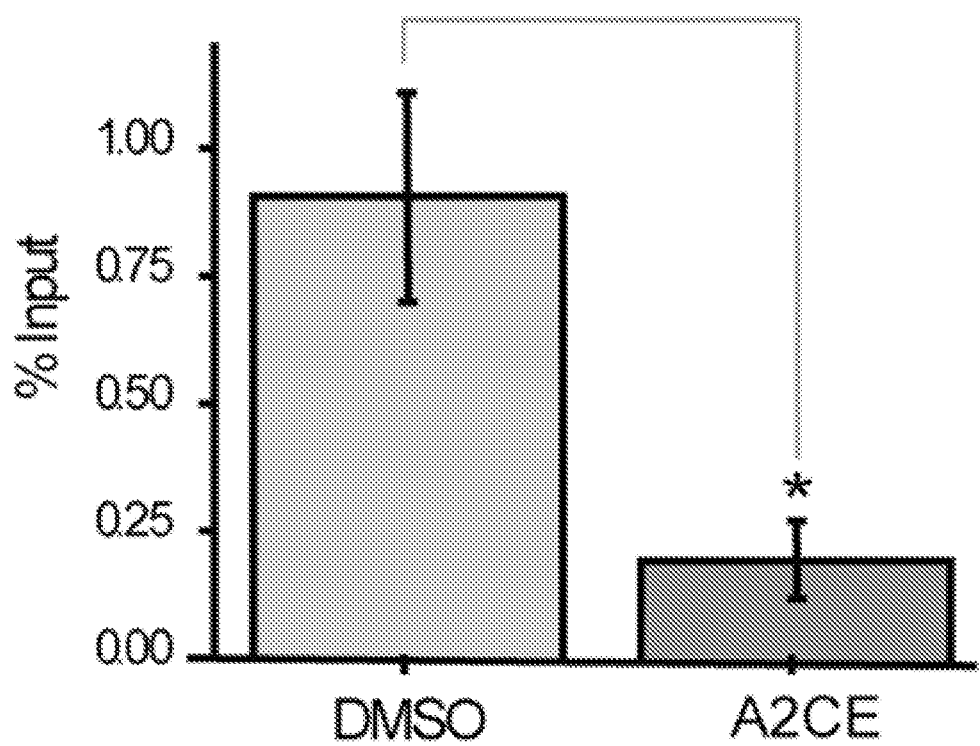
FIG. 19 shows representative data demonstrating that alsterpaullone, 2-cyanoethyl prevents FoxO3a from binding to the p27$^{Kip1}$ promoter.

A2CE has never been described as having an effect on p27$^{Kip1}$ levels, but other types of paullones have demonstrated inhibitory effect on certain types of NAD+ dependent deacetylases, primarily the Sirtuins (Trapp, J., et al. (2006) *J. Med. Chem.* 49, 7307-7316), which are known to deacetylate FoxO3a and regulate p27$^{Kip1}$ transcription (FIG. 17A). To ascertain if Sirtuin inhibition could phenocopy the A2CE inhibition in the p27$^{Kip1}$-luciferase assay to different doses of a known Sirtuin 1 (Sirt1) inhibitor (EX527, IC$_{50}$=100 nM, FIG. 17B), and a known Sirt2 inhibitor (AGK2, IC$_{50}$=3.5 µM, FIG. 18A) in HeLa cells. Treatment with the Sirt2 specific inhibitor phenocopied the results with A2CE, while the addition of the Sirt1 specific inhibitor had no effect, suggesting that Sirt2 is responsible for A2CE effects on p27$^{Kip1}$ transcription. Resveratrol is a known Sirtuin agonist, and confusingly was also one of the hits from the screen (see Table 2 above). To understand if resveratrol was exerting its effects on p27$^{Kip1}$ by agonizing Sirtuin, piceatenol, a metabolite of resveratrol (Niles, R. M., et al. (2006) *J. Nutrition* 136, 2542-2546) which also promotes protein deacetylation (Pietrocola, F., et al. (2012) *Cell Cycle* 11, 3851-3860) was added. Piceatenol did not phenocopy the inhibition of p27$^{Kip1}$-luciferase by A2CE (FIG. 18B), suggesting that promotion of deacetylation was not responsible for the observed p27$^{Kip1}$ transcriptional antagonism. Finally, the downstream effects of Sirt2 antagonism were examined (diagrammed in FIG. 17A) by assaying for FoxO3a's ability to bind to the p27$^{Kip1}$ promoter after 10 µM A2CE treatment by chromatin immune-precipitation (ChIP) followed by qPCR. A significant decrease in FOXO3a binding to the p27$^{Kip1}$ promoter was observed upon addition of 10 µM A2CE (FIG. 19), demonstrating that p27$^{Kip1}$ transcriptional repression by A2CE is through lack of FOXO3a binding.

8. Ectopic Atoh1 and B-Catenin Co-Expression Induces Lgr5+ Proliferating Neonatal Cochlear Non-Sensory Scs Trans-Differentiation The expression of β-catenin in Lgr5+ non-sensory SCs results in a transient proliferative response with the formation of replication foci closely abutting the inner HCs. However, there is no ectopic HC formation; although cultured isolated Lgr5+ SCs can proliferate and trans-differentiate upon Wnt activation (Chai, R., et al. (2012) *Proc. Natl. Acad. Sci. USA* 109, 8167-8172). Since Atoh1 plays a crucial role in HC fate determination and ectopic Atoh1 expression induces the trans-differentiation of SCs in mice (Liu, Z., et al. (2012) *J. Neuroscience* 32, 10530-10540; Kelley, M. C., et al. (2012) *J. Neurosci.* 32, 6699-6710), a LgrSCreER; β-catenin f/+; Atoh1-HA (Lgr5; (β-catenin; Atoh1-HA) mouse model was generated to address whether the β-catenin-mediated proliferating Lgr5+ SCs can trans-differentiate into HCs in vivo. The HA tag in Atoh1-HA transgenic mice allowed lineage tracing of Atoh1-HA expressing SCs to distinguish between Atoh1-HA transgene and endogenous Atoh1 (Liu, Z., et al. (2012) *J. Neuroscience* 32, 10530-10540). As previously described (Chai, R., et al. (2012) *Proc. Natl. Acad. Sci. USA* 109, 8167-8172), Tamoxifen induction was performed at postnatal day 0 and 1 (P0-1), while the analysis was done at P8, P15 and P21 in Lgr5; β-cat; Atoh1-HA mice as well as Lgr5; 3-cat and Lgr5; Atoh1-HA control littermates (FIGS. 21 and 22). At P8, ectopic HCs expressing both the HA tag and myosin7a (thereafter referred to as AtOH1-HA+/myo7a+ hair cells) were present in the inner and outer HC regions along the cochleae of Lgr5; β-catenin; Atoh1-HA mice. These ectopic HCs were present at P15 and remained at least until P21.

Figure 21A:
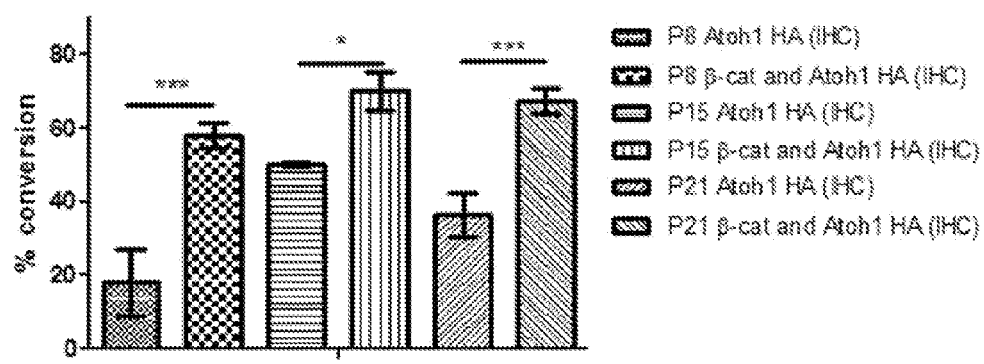
FIG. 21A shows representative data pertaining to the rate of supporting cell to hair cell conversion in response to concurrent ectopic expression of β-catenin and Atoh1 in the inner hair cell region.
Figure 21B:
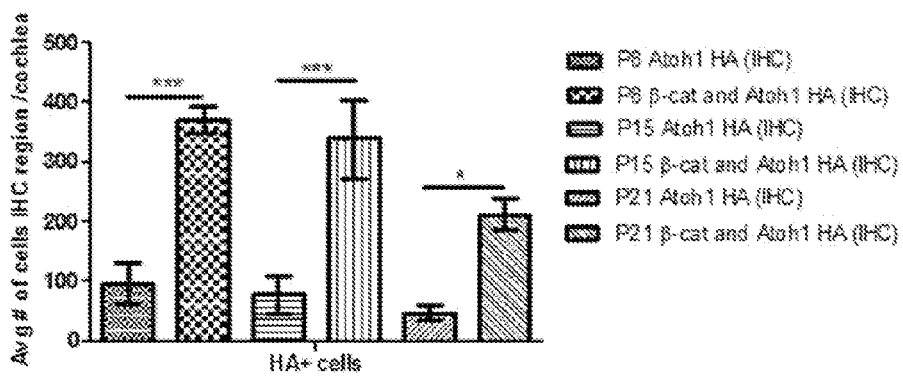
FIG. 21B shows representative data pertaining to the number of Atoh1-ATOH1-HA+ cells transdifferentiated from supporting cells in response to the ectopic expression of Atoh1 alone, or both Atoh1 and β-catenin in the inner hair cell region.
Figure 21C:
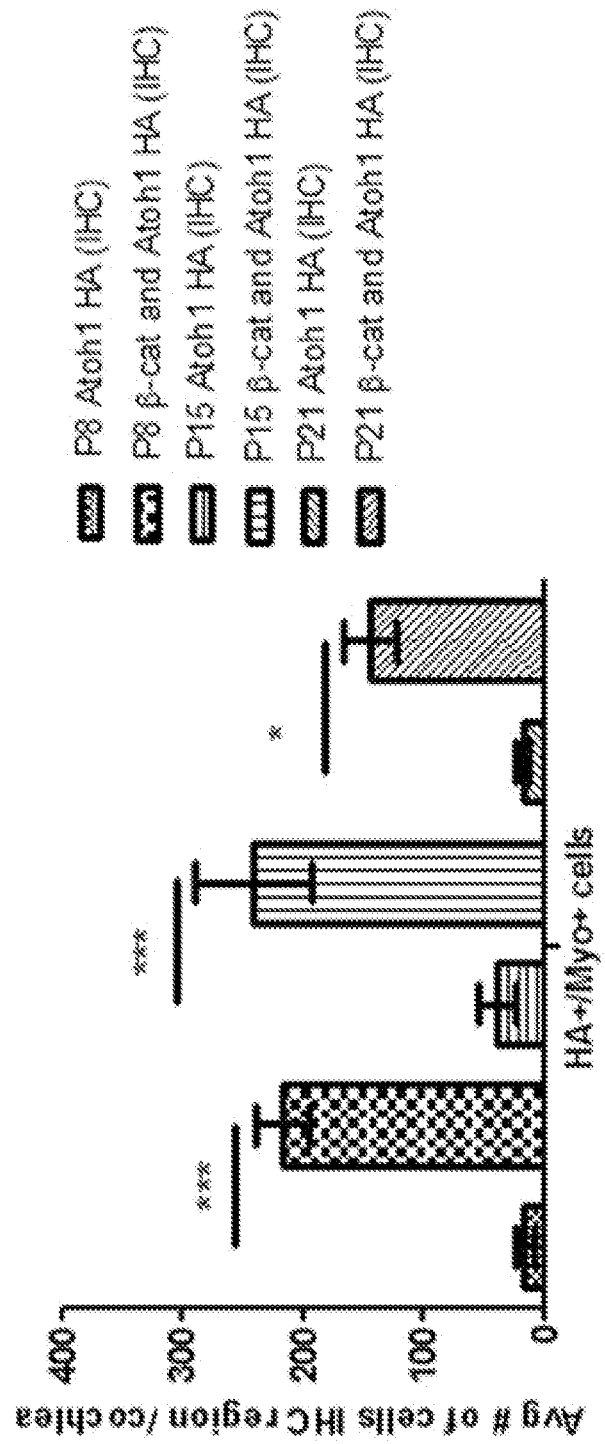
FIG. 21C shows representative data pertaining to the number of Atoh1-ATOH1-HA+/Myosin7a+ cells transdifferentiated from supporting cells in response to the ectopic expression of Atoh1 alone, or both Atoh1 and β-catenin in the inner hair cell region.

Next, the rate of conversion of Lgr5+ SCs was analyzed by counting the number of ATOH1-HA+/myo7a+ cells and comparing that to the total number of ATOH1-HA+ cells. The rates of conversion significantly increased in the presence of β-catenin and Atoh1 compared to Atoh1 alone. These increases are distributed as followed: 20% to 60% at P8, 45% to 68% at P15 and 40% to 65% at P21 (FIG. 21A). A significant increase was observed in the number of ATOH1-HA+ and ATOH1-HA+/myo7a+ HCs abutting the inner HC (IHCs) at P8, P15 and P21 (FIGS. 21B and 21C). Without wishing to be bound by theory, this may suggest a synergistic role for β-catenin and Atoh1-HA on trans-differentiation for the Lgr5+ SCs abutting the endogenous IHC.

Figure 22A:
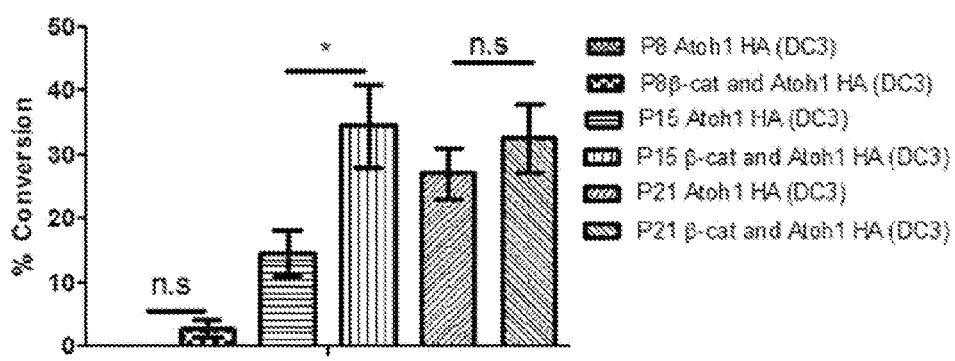
FIG. 22A shows representative data pertaining to the percent conversion of Lgr5+ supporting cells to hair cells in response to the ectopic expression of Atoh1 alone, or both Atoh1 and 3-catenin in the 3$^{rd}$ Deiters region.
Figure 22B:
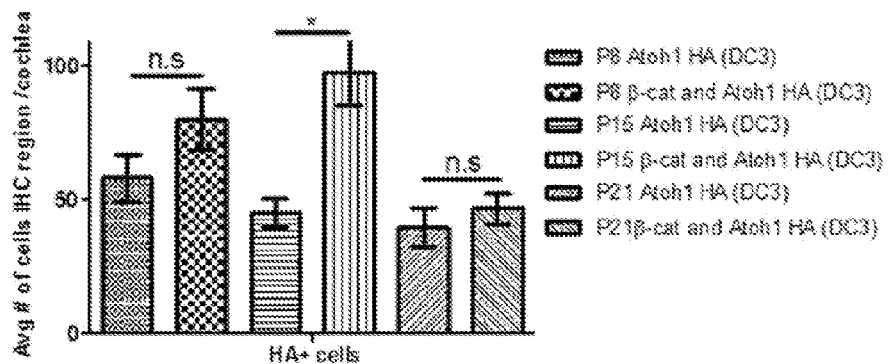
FIG. 22B shows representative data pertaining to the number of Atoh1-ATOH1-HA+ cells transdifferentiated from supporting cells in response to the ectopic expression of Atoh1 alone, or both Atoh1 and β-catenin in the 3$^{rd}$ Deiters region.
Figure 22C:
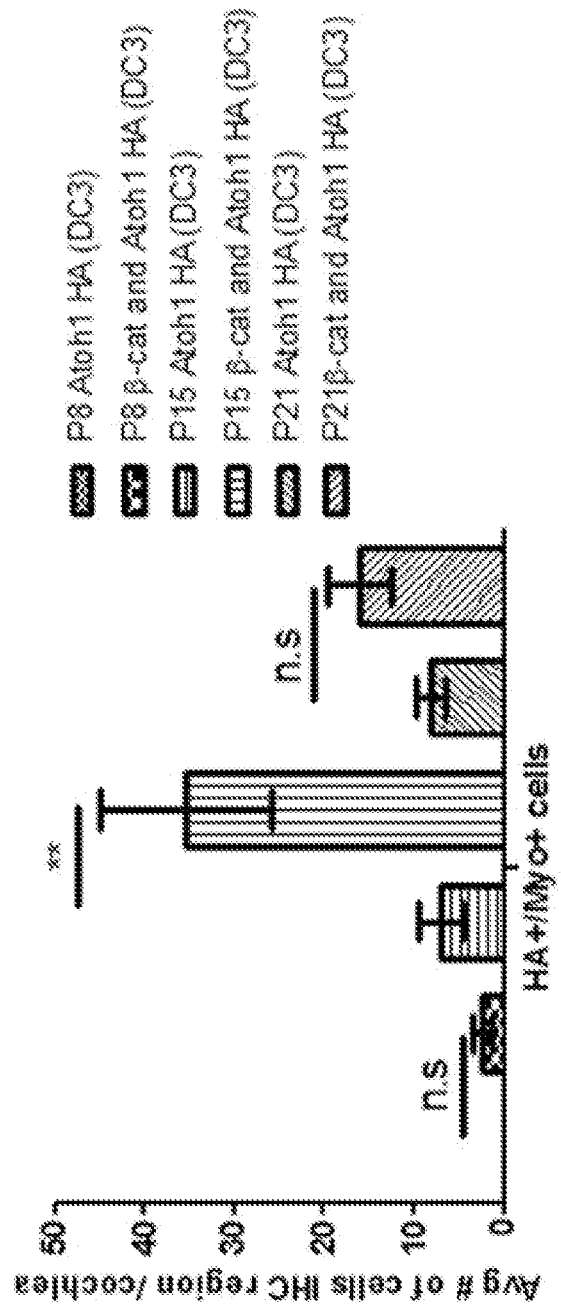
FIG. 22C shows representative data pertaining to the number of Atoh1-ATOH1-HA+/Myosin7a+ cells transdifferentiated from supporting cells in response to the ectopic expression of Atoh1 alone, or both Atoh1 and β-catenin in the 3$^{rd}$ Deiters region.

An effect on the timing of the trans-differentiation which occurs at P8 was observed upon analyzing the 3$^{rd}$ Deiters' SCs in the presence of β-catenin and Atoh1-HA via immunohistology. The trans-differentiation of these SCs were previously reported to occur by P22 when Atoh1-HA was ectopically expressed in similar SCs under the control of Prox1CreER (Liu, Z., et al. (2012) *J. Neuroscience* 32, 10530-10540). In addition, the formation of ectopic HCs from these SCs was observed by P15 (FIGS. 22A and 22B). Without wishing to be bound by theory, this may suggest that β-catenin and Atoh1-HA accelerated the conversion of the 3$^{rd}$ Deiters' cells. Unlike the medial SCs (described herein above), a similar synergistic effect was not observed on the rate transdifferentiation or significant increases in the number of ATOH1-HA+ and ATOH1-HA+/myo7a+ (FIG. 22A-C), and this deficiency may attributed to, for example, the presumed higher expression of Lgr5 in the 3$^{rd}$ Deiters cells, as reflected by EGFP expression (Chai, R., et al. (2011) *J. Assoc. Res. Otolaryngol.* 12, 455-469), which could prevent HC trans-differentiation. In support of this, very few GFP positive ATOH1-HA+/Myo7a+ HCs were observed in this system. In addition, isolated Lgr5+ SCs cultured in the presence of Wnt3a transdifferentiated into HCs do not express EGFP (Chai, R., et al. (2012) *Proc. Natl. Acad. Sci. USA* 109, 8167-8172).

To address the level of maturation for these ectopic HCs, the expression of various HC markers and synaptic components was analyzed via immunohistology. In addition to myosin7a, these ectopic HCs were found to express Otoferlin, but do not express the mature/terminal HC differentiation markers vGlut3 or prestin in the inner or outer HC regions. The synaptic ribbon component Ctbp2 and the vesicular glutamate transporter GluR2 were both found to be expressed in a matching pattern in the endogenous HCs. In the new HCs, some GluR2 puncta matches that of Ctbp2, while others do not. The presence of Tuj1+ projections on the basolateral sides of the ectopic HCs was observed, suggesting they are innervated. Lastly, the presence of stereocillia hair bundles with Phalloidin labeling in the inner and outer HC region was analyzed. The immunohistology results indicate that the hair bundles form in the ectopic HCs abutting the inner HCs, but their morphology differs from that of the endogenous inner and outer HCs. The medially-located ectopic HCs were found to display either a bent, splayed or perpendicular morphology. The ectopic HCs located on the lateral side of the Organ of Corti also were found to display a peculiar hair cell bundle morphology which does not resemble that of the traditional "V" shape found in normal endogenous outer HCs. Instead, there appears to be an accumulation of actin at the cuticular plate. Without wishing to be bound by theory, these data suggest that the Lgr5-derived ectopic HCs generated from β-catenin and Atoh1 expression are immature at P21.

9. B-Catenin and Atoh1-HA Synergistic Effect on Proliferation

In an immunohistology assay, a proliferative response was still observed from the Lgr5+ SCs at P8 when β-catenin and Atoh1-HA were concurrently expressed. However, an increase in the size of the replication foci and a much closer proximity between adjacent foci were present, suggestive of a more pronounced proliferative response than expression of β-catenin alone (as compared to FIGS. 1 and 2 from Chai, R., et al. (2012) *Proc. Natl. Acad. Sci. USA* 109, 8167-8172). This was further confirmed independently by the increase in the number of ATOH1-HA+ cells (~2 cells/100 nm with Atoh1-HA alone vs. 5 cells/100 nm with β-cat and Atoh1-HA at P21) and the number of ATOH1-HA+/myo7a+ hair cells (~2 cells/100 μm with Atoh1 alone vs. ~10 cells/100 μm with β-cat and Atoh1-HA at P21) (FIGS. 21A and 21B). Without wishing to be bound by theory, this may suggest a synergism between β-cat and Atoh1-HA on the proliferative response of Lgr5+ SCs.

Figure 23A:
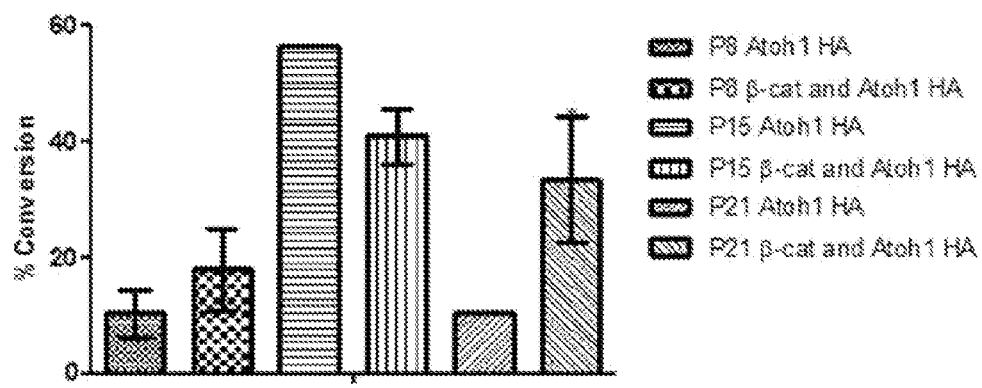
FIG. 23A shows representative data pertaining to the rate of conversion of inner phalangeal supporting cells in response to the ectopic expression of Atoh1 alone, or both Atoh1 and β-catenin.
Figure 23B:
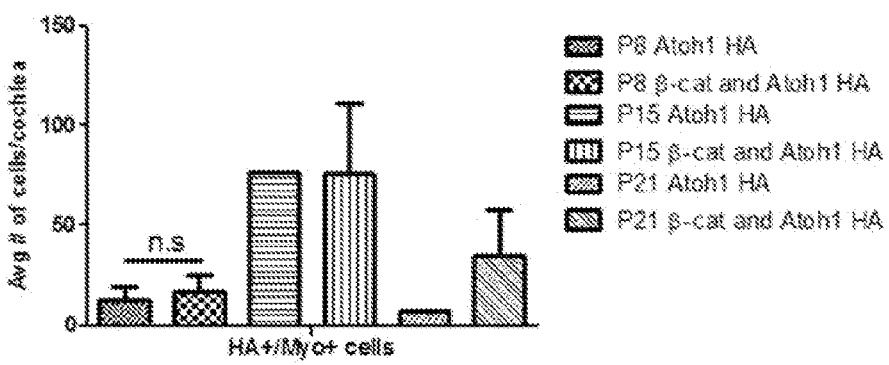
FIG. 23B shows representative data pertaining to the number of Atoh1-ATOH1-HA+/Myosin7a+ cells transdifferentiated from inner phalangeal supporting cells in response to ectopic expression of Atoh1 alone, or both Atoh1 and β-catenin.
Figure 23C:
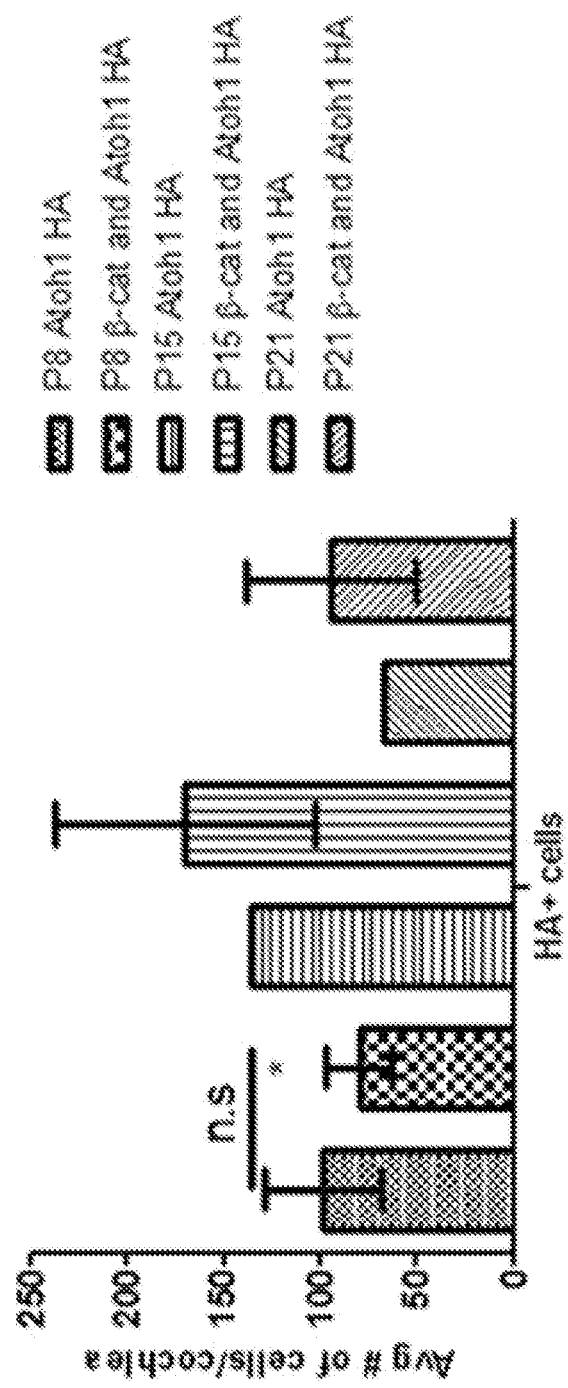
FIG. 23C shows representative data pertaining to the number of Atoh1-ATOH1-HA+ cells transdifferentiated from inner phalangeal supporting cells in response to ectopic expression of Atoh1 alone, or both Atoh1 and β-catenin.
Figure 24:
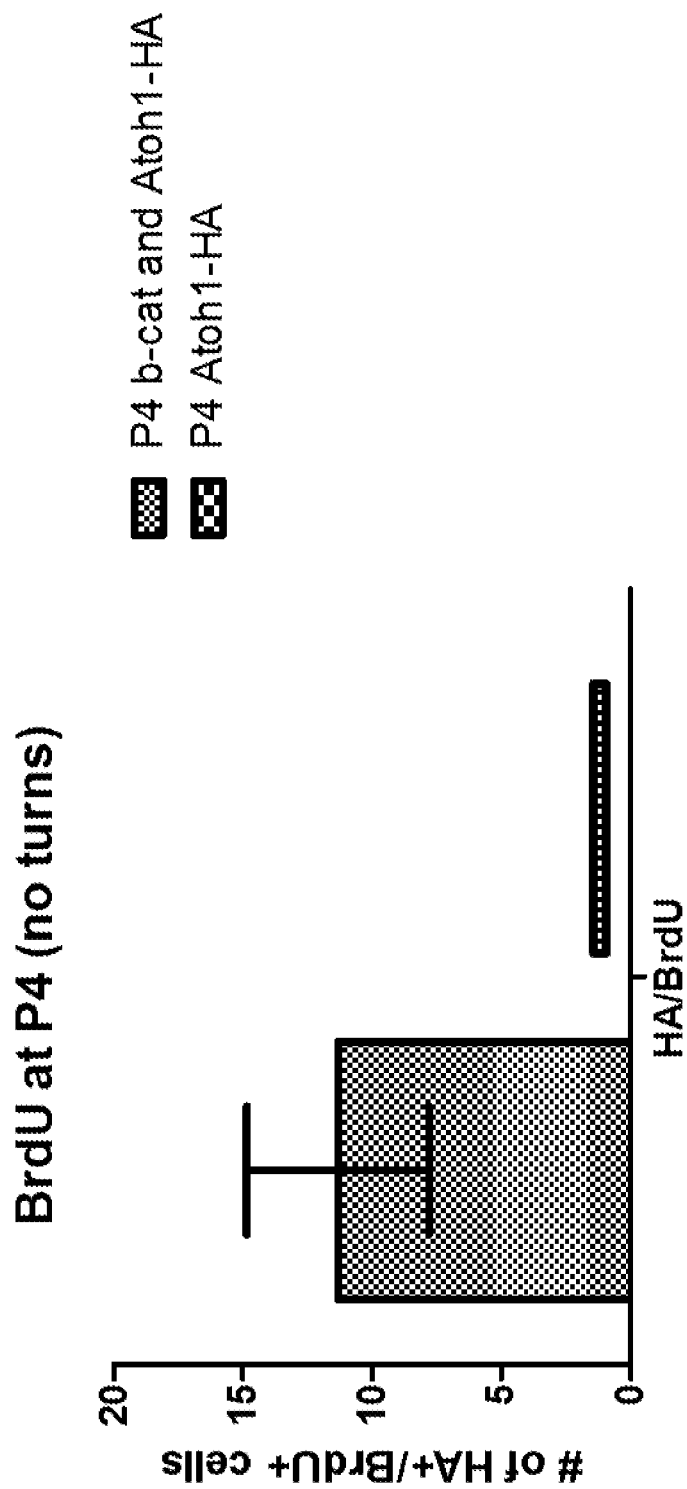
FIG. 24 shows representative data pertaining to the number of Atoh1-ATOH1-HA+/BrdU+ cells transdifferentiated from supporting cells in response to the ectopic expression of Atoh1 alone, or both Atoh1 and β-catenin at P4.

10. Inner Phalangeal Cells Exhibit Increased Trans-Differentiation By Co-Expression of B-Catenin and Atoh1-HA Next the inner phalangeal (IPh) cells, a specific subtype within SCs that Lgr5-CreER targets, were targeted using another independent CreER line, P1pCreER (Doerflinger, N. H., et al. (2003) *Genesis* 35, 63-72; Liu, Z., et al. (2014) *PloS One* 9, e89377). The formation of replication foci similar to those observed in the Lgr5CreER; β-catenin model was not observed, to suggest an absence of a proliferative response at P8, P15 (not shown) or P21 in all 3 genotypes: P1pCreER; β-catenin, P1pCreER; Atoh1-HA, and P1pCreER; β-catenin; Atoh1-HA. Ectopic ATOH1-HA+/Myo7a+ HCs were present when either Atoh1 or β-catenin and Atoh1-HA were ectopically expressed (FIG. 23A-C). However, the increases in the cell counts for ATOH1-HA+ and ATOH1-HA+/Myosin7a+ were not significant (FIG. 23B) suggesting an absence of synergistic effect, similar to the one previously observed in the Lgr5+SCs. Nonetheless, the rate of conversion at P8 and P21 are higher than that reported in a previous study (17%) targeting the inner-phalangeal SCs using the P1pCreER; Atoh1-HA model (Liu, Z., et al. (2014) *PloS One* 9, e89377). Without wishing to be bound by theory, this data suggests that the combination of β-catenin and Atoh1 targeting the IPh cells results in ectopic HC formation without apparent proliferation.

Herein the concurrent expression of β-catenin and Atoh1 has been shown to result in a proliferative and trans-differentiation response from neonatal Lgr5+ SCs, where β-catenin alone could only elicit a transient proliferative response (Chai, R., et al. (2012) *Proc. Natl. Acad. Sci. U.S.A.* 109, 8167-8172) and Atoh1 alone could convert SCs in vivo, albeit less efficiently (Liu, Z., et al. (2012) *J. Neurosci.* 32, 6600-6610). There is also a synergistic effect of this combination on the rate of trans-differentiation of Lgr5+ SCs, but not on the IPh SCs (a subtype of Lgr5+ SCs), even though they trans-differentiate in response to this combination. Overall, the ectopic HCs remain immature as reflected by the lack of mature IHC and OHC markers, notably VGLUT3 and Prestin, respectively. Pre- and post-synaptic markers, Ctbp2 and GluR2, respectively, are present, but they were not completely matched. Nonetheless, a paradigm has been established that can elicit both a proliferative and a trans-differentiation response from the Lgr5+ SCs which may represent a platform from which to build on in the overarching goal of achieving HC mitotic regeneration.

Lgr5+ SCs were targeted since they have been proposed to represent an in vivo source of progenitors for HC regeneration in neonatal cochleae. In addition, Lgr5+ cells have the ability to differentiate into organs from which they were isolated from. For example, intestinal- and liver-derived Lgr5+ cells give rise to "mini-gut" and liver organoid, respectively. Furthermore, transplanted Lgr5+ cells successfully engraft to damage areas in host intestines and allow for the recovery of that organ after damage (Sato, T., et al. (2009) *Nature* 459, 262-265; Huch, M., et al. (2013) *Regen. Med.* 8, 385-387; Sato, T. and Clevers, H. (2013) *Science* 340, 1190-1194). In the cochlea, isolated and cultured Lgr5+ SCs show an increased ability to proliferate and differentiate into HCs (Chai, R., et al. (2012) *Proc. Natl. Acad. Sci. U.S.A.* 109, 8167-8172), compared to isolated p27$^{Kip1}$+ SCs (White, P. M., et al. (2006) *Nature* 441, 984-987). Without wishing to be bound by theory, this may suggest that these cochlear progenitors hold tremendous regenerative potential compared to the other SCs. It therefore becomes subsequently important to determine whether this paradigm would also result in the formation of ectopic HCs, similar to the neonatal response reported herein, in adult animals. More importantly, it may be crucial to determine the degree of recovery after HC damage using this paradigm. However, based on the restriction of the expression of Lgr5-EGFP-CreER to the 3$^{rd}$ Deiters' SCs (Chaff, R., et al. (2011) *J. Assoc. Res. Otolaryngol.* 12, 455-469) after the first week of postnatal development, other CreER lines may be required to target similar SCs targeted herein. Alternatively, determining whether the pattern of expression of Lgr5 changes after damage, and is re-expressed in similar SCs as in the neonates may be critical to address how these progenitor SCs would respond to β-catenin and Atoh1 after damage. If Lgr5 expression returns to the Organ of Corti after damage in the adults, this may suggest that they respond similarly to intestinal Lgr5+ cells (Tian, H., et al. (2011) *Nature* 478, 255-259; Yan, K. S., et al. (2012) *Proc. Natl. Acad. Sci. U.S.A.* 109, 466-471). Without wishing to be bound by theory, this may help to understand the regulation and the function of Lgr5 in the cochlea.

Since Atoh1 has been shown to be important for HC differentiation (Bermingham, N. A., et al (1999) *Science* 284, 1837-1841; Chen, P., et al. (2002) *Development* 129, 2495-2505), and since its ectopic expression yielded to the formation of supernumerary HCs in vivo (Kelly, M. C., et al. (2012) *J. Neurosci.* 32, 6699-6710; Liu, Z., et al. (2012) *J. Neurosci.* 32, 6600-6610), it was predicted that its expression, in conjunction to β-catenin, may trigger HC differentiation in proliferating Lgr5+ SCs. An effect on HC maturation was also predicted due to the potential activation of β-catenin target genes that can promote HC maturation independently of ectopic Atoh1 expression. Such an additive effect of (β-catenin to Atoh1 pro-HC is supported by the following: 1) β-catenin plays a role during embryonic HC development (Ohyama, T., et al. (2007) *Int. J. Dev. Biol.* 51, 463-472; Jayasena, C. S., et al. (2008) *Development* 135, 2251-2261; Munnamalai, V. and Fekete, D. M. (2013) *Semin. Cell Dev. Biol.* 24, 480-489); 2) over-expression of β-catenin in the chick basilar papilla results in the formation of ectopic HCs (Stevens, C. B., et al. (2003) *Dev. Biol.* 261, 149-164); 3) one of β-catenin's targets is Atoh1 (Shi, F., et al. (2010) *J. Biol. Chem.* 285, 392-400), and 4) β-catenin has been reported to play a role in differentiation including, but not limited to, melanogenesis (Jin, E. J., et al. (2001) *Dev. Biol.* 233, 22-37) and skeletal/cardiac myogenesis (Jin, E. J., et al. (2001) *Dev. Biol.* 233, 22-37). Contrary to what was predicted, the ectopic HCs still remained immature (i.e. lack of VGLUT3 and Prestin). Without wishing to be bound by theory, the following explanations are offered for the lack of terminal differentiation. The constitutive expression of β-catenin and/or Atoh1 is/are unnatural to HC terminal differentiation, as their expression is normally down-regulated during development (Chen, P., et al. (2002) *Development* 129, 2495-2505; Daudet, N., et al. (2002) *Brain Res. Mol. Brain Res.* 105, 98-107; Riccomagno, M. M., et al. (2005) *Genes Dev.* 19, 1612-1623; Ohyama, T., et al. (2006) *Development* 133, 865-875). Briefly, β-catenin is expressed during the stages of the otic placode induction and becomes restricted to the dorsal region by E9.5, while Atho1 is first expressed at E12 in the sensory region of the future organ of Corti, and becomes restricted to HCs by E17.5. Conversely, β-catenin expression might still be down-regulated even though the ectopic form expressed here is impervious to GSK3β-dependent degradation. For instance, the E3 ligase Siah1 has been shown to mediate β-catenin degradation independently of the GSK3β-mediated phosphorylation (Liu, J., et al. (2001) *Mol. Cell* 7, 927-936), and it could act as a negative regulator for this form stable of 3-catenin. Lgr5 itself may also act as a negative regulator of β-catenin ectopic expression (Garcia, M. I., et al. (2009) *Dev. Biol.* 331, 58-67; Carmon, K. S., et al. (2011) *Proc. Natl. Acad. Sci. U.S.A.* 108, 11452-11457).

HC patterning in the cochlea has been shown to involve Notch lateral inhibition by inhibiting Atoh1 (Lanford, P. J., et al. (1999) *Nat. Genet.* 21, 289-292; Kiernan, A. E., et al. (2001) *Proc. Natl. Acad. Sci. U.S.A.* 98, 3873-3878; Kiernan, A. E., et al. (2005) *Development* 132, 4353-4362; Kiernan, A. E., et al. (2006) *PloS Genet.* 2, e4; Kelley, M. W. (2007) *Int. J. Dev. Biol.* 51, 571-583; Kiernan, A. E. (2013) *Semin. Cell Dev. Biol.* 24, 470-479; Pan, W., et al. (2010) *Proc. Natl. Acad. Sci. U.S.A.* 107, 15798-15803). Notch has also been shown to be a target of the Wnt signaling in the ear (Jayasena, C. S., et al. (2008) *Development* 135, 2251-2261) and the intestine (Medema, J. P., and Vermeulen, L. (2011) *Nature* 474, 318-326). Without wishing to be bound by theory, it is therefore possible that the ectopic Atoh1 expression performed herein may be repressed by Notch up-regulation mediated by ectopic β-catenin expression. In addition, the Notch Intracellular Domain (NICD) has been shown to sequester and promote β-catenin degradation by direct interaction with its Armadillo repeats in the cytoplasm and the nucleus (Hayward, P., et al. (2005) *Development* 132, 1819-1830; Kwon, C., et al. (2011) *Nat. Cell Biol.* 13, 1244-1251), independently of the well-described GSK3β-mediated degradation pathway. This is important because the stable form of β-catenin expressed in the model described herein appears to remain unaffected by the aforementioned degradation pathway (Harada, N., et al. (1999) *EMBO J.* 18, 5931-5942) and can presumably freely diffuse to the nucleus to activate its targets. Finally, as mentioned herein above, Lgr5 has been shown to down-regulate 3-catenin (Garcia, M. I., et al. (2009) *Dev. Biol.* 331, 58-67; Carmon, K. S., et al. (2011) *Proc. Natl. Acad. Sci. U.S.A.* 108, 11452-11457), possibly in conjunction with Notch, to decreased levels below a threshold necessary to trigger the expression of pro-HC target genes. Given the relative success of Notch repression by genetic manipulation and by using 2-secretase inhibitors to promote HC formation and maturation (Zheng, J. L., et al. (2000) *Development* 127, 4551-4560; Zine, A., et al. (2001) *J. Neurosci.* 21, 4712-4720; Yamamoto, N., et al. (2006) *J. Mol. Med. (Berl.)* 84, 37-45; Takebayashi, S., et al. (2007) *Dev. Biol.* 307, 165-178; Mizutari, K., et al. (2013) *Neuron* 77, 58-69; Korrapati, S., et al. (2013) *PLoS One* 8, e73276; Kiernan, A. E., et al. (2005) *Development* 132, 4353-4362; Brooker, R., et al. (2006) *Development* 133, 1277-1286), the impact of its repression, if present, would greatly impact the future of the paradigm described herein. Thus, without wishing to be bound by theory, targeting the interactions between Notch, Wnt (i.e. (β-catenin) and pro-HC gene (i.e. Atoh1) could potentially be an important avenue for HC regeneration strategies.

F. Prophetic Examples

1. Regeneration of Outer Hair Cells in Mature Cochleae

Figure 20:
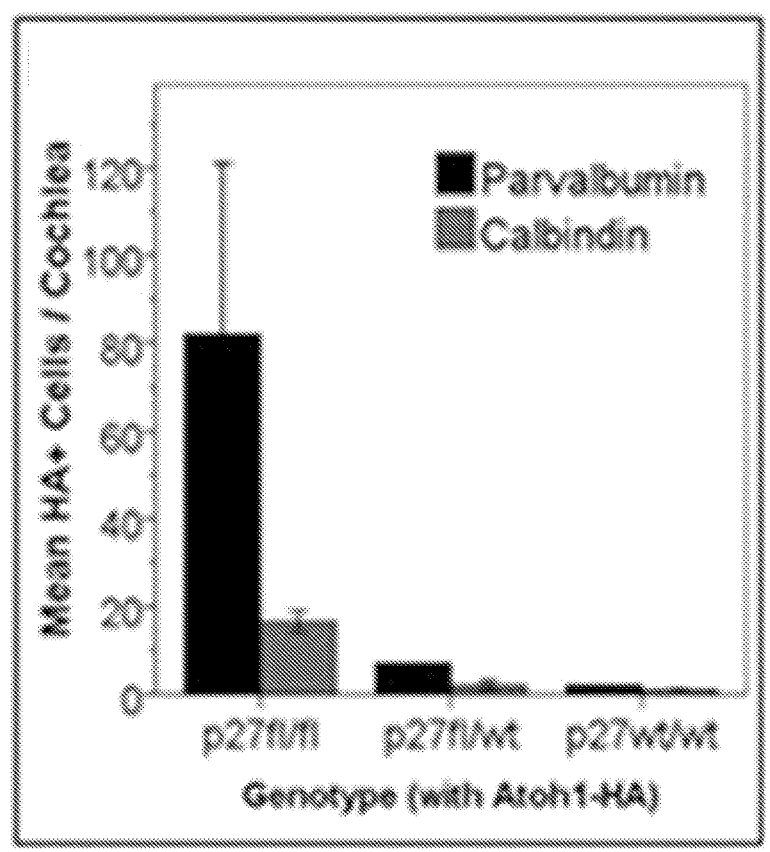
FIG. 20 shows representative data pertaining to the effect of the combination of ectopic Atoh1 expression and p27$^{Kip1}$ deletion on Atoh1-ATOH1-HA+ cells that co-label with the hair cell markers Parvalbumin (Parv) and Calbindin (Calb) in mature mouse cochleae.

It remains unclear why the mature cochlea is unable to elicit proliferation and trans-differentiation in vivo in the presence of either Atoh1 ectopic expression or $p27^{Kip1}$ deletion (Liu, Z., et al. (2012) *J. Neurosci.* 32, 10530-10540; Oesterle, E. C., et al. (2011) *Cell Cycle* 10, 1237-1248; Liu, Z., et al. (2012) *J. Neurosci.* 32, 6600-6610; Kelly, M. C., et al. (2012) *J. Neurosci.* 32, 6699-6710; Walters and Zuo (2013) *Hearing Res.* 297: 68-83). It is hypothesized that when combined, these two manipulations may synergistically convert SCs to HCs in the mature cochlea. This combinatory strategy is commonly used in studies of iPS cell and hepatocyte reprogramming, and CNS and cardiac regeneration, which require multiple factors (Marro, S., et al. (2011) *Cell Stem Cell* 9, 374-382; Caiazzo, M., et al. (2011) *Nature* 476, 224-227; Vierbuchen, T., et al. (2010) *Nature* 463, 1035-1041; Ieda, M., et al. (2010) *Cell* 142, 375-386). Preliminary studies support this hypothesis (FIG. 20) and have identified a novel, Atoh1-dependent regulatory pathway/mechanism for HC regeneration in mature cochleae. It is also hypothesized that Deiters' cells and pillar cells surrounding outer HCs are the SCs responsible for outer HC regeneration in situ in mature cochleae.

Therefore, in one prophetic example, a 3 locus-compound mouse model (Fgfr3-iCreER [Fgfr3-CreER]; p27-floxed/floxed; cytomegalovirus (CMV) early enhancer element and chicken β-actin promoter [CAG]-stop-floxed-Atoh1-hemagglutinin tag [HA]) is used to study proliferation and trans-differentiation of mature Deiters' cells/pillar cells (DCs/PCs) induced by tamoxifen. When induced at P30, Fgfr3-CreER specifically labels most cochlear DCs/PCs, but not HCs (Liu, Z., et al. (2012) *J. Neurosci.* 32, 10530-10540; Liu, Z., et al. (2012) *J. Neurosci.* 32, 6600-6610; Cox, B. C., et al. (2012) *J. Assoc. Res. Otolaryngol.* 13, 295-322), allowing the DC/PC-specific Cre-mediated excision of DNA flanked by two loxP sites in both the $p27^{Kip1}$-floxed and CAG-stop-floxed-Atoh1-HA loci. The HA tag in the Atoh1-HA line is also used to fate-map these Cre+; ATOH1-HA+ DCs/PCs at the time of induction (P30).

To determine the efficiency of conversion of DCs/PCs to HCs and maturation of the HCs at various time-points after P30 induction, the expression of a battery of hair cell differentiation markers, including the Atoh1-GFP transgene, myo7a, calretinin, calbindin, parvalbumin, espin, the α9 nAChR-GFP transgene, Cbtp2, prestin, and oncomodulin, is quantified among Atoh1-ATOH1-HA+ cells.

To measure the proliferation rate of these DCs/PCs and regenerated hair cells, 5-ethynyl-2-deoxyuridine (EdU) and/or 5-bromo-2-deoxyuridine (BrdU) is delivered to the mice at various time-points post-induction and Atoh1-ATOH1-HA+ and/or myo7a+ cells that are EdU+ and/or BrdU+ can be quantified. Ki67 and PCNA labeling is used to confirm the proliferation of Cre+ cells and assess the viability of Cre+; ATOH1-HA+ cells by Caspase3 staining (Yu, Y., et al. (2010) *J. Neurosci.* 30, 5927-5936; Liu, Z., et al. (2012) *J. Neurosci.* 32, 6600-6610).

To determine whether the new HCs are mature and functional, the hearing of the mice can be tested by measuring auditory brainstem response (ABR), distortion products otoacoustic emission (DPOAE) thresholds, and input-output functions at various levels of stimuli (Liu, Z., et al. (2012) *J. Neurosci.* 32, 6600-6610; Yamashita, T., et al. (2012) *PLoS One* 7, e45453).

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A pharmaceutical composition comprising at least one agent that activates the expression and/or activity of Atoh1, or a pharmaceutically acceptable salt thereof, wherein the agent that activates the expression and/or activity of Atoh1 is a β-catenin protein or a compound selected from 4-(4-chlorophenyl)-1-(5H-pyrimido[5,4-b]indol-4-yl)-1H-pyrazol-3-amine; 6-chloro-1-(2-chlorobenzyloxy)-2-phenyl-1H-benzo[d]imidazole; 6-chloro-1-(2-chlorobenzyloxy)-2-(4-methoxyphenyl)-1H-benzo[d]imidazole; 6-chloro-2-(4-methoxyphenyl)-1-(4-methylbenzyloxy)-1H-benzo[d]imidazole; 6-chloro-1-(3,5-dimethylbenzyloxy)-2-(4-methoxyphenyl)-1H-benzo[d]imidazole; 6-chloro-1-(4-methoxybenzyloxy)-2-(4-methoxyphenyl)-1H-benzo[d]imidazole; 1-(4-methylbenzyloxy)-6-nitro-2-phenyl-1H-benzo[d]imidazole; 4-(1H-benzo[d]imidazol-2-yl)phenol; 2,5-dichloro-N-((1-methyl-1H-benzo[d]imidazol-2-yl)methyl)aniline; 4-(2-(1-methyl-1H-benzo[d]imidazol-2-yl)ethyl)aniline; 2-((2-methoxyphenoxy)methyl)-1H-benzo[d]imidazole; 2-((4-fluorophenoxy)methyl)-1-methyl-1H-benzo[d]imidazole; 2-(phenylthiomethyl)-1H-benzo[d]imidazole; 3-(6-methyl-1H-benzo[d]imidazol-2-yl)-2H-chromen-2-imine; 2-(o-tolyloxymethyl)-1H-benzo[d]limidazole; 2-(4-methoxyphenyl)-1-phenethyl-1H-benzo[d]imidazole; N-(6-bromobenzo[d]thiazol-2-yl)thiophene-2-carboxamide; N-(benzo[d]thiazol-2-yl)-1-methyl-1H-pyrazole-5-carboxamide; 2-(4-fluorobenzylthio)benzo[d]thiazole; 5-chloro-N-methylbenzo[d]thiazol-2-amine; N-(2-(1H-benzo[d]imidazol-2-yl)phenyl)isobutyramide; N-(6- acetamidobenzo[d]thiazol-2-yl)furan-2-carboxamide; N-(6-fluorobenzo[d]thiazol-2-yl)-3-methoxybenzamide; 2-(benzo[d]oxazol-2-ylthio)-N-(2-chlorophenyl)acetamide; 5-chloro-2-phenylbenzo[d]oxazole; 5-methyl-2-m-tolylbenzo[d]oxazole; 2-(4-isobutoxyphenyl)-3-(naphthalen-2-yl)-2,3-dihydroquinazolin-4 (1H)-one-; N-(2-(2-(4-fluorophenyl)-2-oxoethylthio)-4-oxoquinazolin-3(4H)-yl)benzam-ide; 2-(4-chlorophenyl)-4-(4-methoxyphenyl)-1,4-dihydrobenzo[4,5]imidazo[1-,2-a]pyrimidine; 2-(3-pyridyl)-4-(4-bromophenyl)-1,4-dihydrobenzo[4,5]imidazo[1,2-a]pyrimi-dine; N-sec-butyl-1,7,7-trimethyl-9-oxo-8,9-dihydro-7H-furo[3,2-f]chromene-2-carboxamide; N-(3-carbamoyl-5,6-dihydro-4H-cyclopenta[b]thiophen-2-yl)benzofuran-2-car-boxamide; 3-chloro-N-(5-chloropyridin-2-yl)benzo[b]thiophene-2-carboxamide-; 3-chloro-N-((tetrahydrofuran-2-yl)methyl)benzo[b]thiophene-2-carboxamide-; N-(3-(5-chloro-3-methylbenzo[b]thiophen-2-yl)-1H-pyrazol-5-yl) acetamide; 2-(naphthalen-2-yl)-1H-indole; 2-(pyridin-2-yl)-1H-indole; N-(2-chlorophenyl)-2-(1H-indol-3-yl)-2-oxoacetamide; 2-m-tolylquinoline; 2-(4-(2-methoxyphenyl)piperazin-1-yl)quinoline; 2-(1H-benzo[d][1,2,3]triazol-1-yl)-N-(2,3-dihydro-1H-inden-2-yl) acetamide-; 1-phenethyl-1H-benzo[d][1,2,3]triazole; 7-(4-fluorobenzyloxy)-2H-chromen-2-one; N-(2,4-dichlorophenyl)-8-methoxy-2H-chromene-3-carboxamide; N-(3-chlorophenyl)-8-methyl-3,4-dihydroquinoline-1(2H)-carbothioamide; 7-methoxy-5-methyl-2-phenyl-4H-chromen-4-one; 2-(3,4-dimethylphenyl) quinoxaline; 4-bromo-N-(5-chloropyridin-2-yl)benzamide; 3-amino-6,7,8,9-tetrahydro-5H-cyclohepta[e]thieno[2,3-b]pyridine-2-carbox-amide; (Z)-3-methyl-N'-(nicotinoyloxy)benzimidamide; N,N-diethyl-6-methoxythieno[2,3-b]quinoline-2-carboxamide; 6-(4-methoxyphenyl)-1,2,3,4-tetrahydro-1,5-naphthyridine; 5-bromo-N-(2-(phenylthio)ethyl)nicotinamide; N-(6-methylpyridin-2-yl)-2,3-dihydrobenzo[b][1,4]dioxine-6-carboxamide; 2(4-methylbenzylthio)oxazolo[4,5-b]pyridine; N-(2-methoxyethyl)-5-p-tolylpyrimidin-2-amine; 4-(5-(benzo[b]thiophen-2-yl)pyrimidin-2-yl)morpholine; 4-(5-(4-fluorophenyl)pyrimidin-2-yl)morpholine; N-(4-bromo-3-methylphenyl)quinazolin-4-amine; N-(4-methoxyphenyl)quinazolin-4-amine; N-(3-methoxyphenyl)-9H-purin-6-amine; N,N-diethyl-1-m-tolyl-1H-pyrazolo[3,4-d]pyrimidin-4-amine; (5-(4-bromophenyl)furan-2-yl)(morpholino)methanone; (Z)-4-bromo-N'-(furan-2-carbonyloxy)benzimidamide; N-(4-iodophenyl)furan-2-carboxamide; 5(5-(2,4-difluorophenyl)furan-2-yl)-1-(methylsulfonyl)-1H-pyrazole; 1-(3-amino-5-(4-tert-butylphenyl)thiophen-2-yl) ethanone; N-(3-cyano-4,5,6,7-tetrahydrobenzo[b]thiophen-2-yl)-2-fluorobenzamide; N-(5-chloropyridin-2-yl)thiophene-2-carboxamide; N-(2-(4-fluorophenoxy)ethyl)thiophene-2-carboxamide; 2,5-dimethyl-N-phenyl-1-(thiophen-2-ylmethyl)-1H-pyrrole-3-carboxamide; N-(3-cyanothiophen-2-yl)-4-isopropoxybenzamide; 2-(4-methoxyphenoxy)-N-(thiazol-2-yl)acetamide; 4-(4-methoxyphenyl)-N-(3-methylpyridin-2-yl)thiazol-2-amine; 4-(biphenyl-4-yl)thiazol-2-amine; 4-(4-(4-methoxyphenyl)thiazol-2-yl)-3-methylisoxazol-5-amine; N-(2-methoxyphenyl)-4-phenylthiazol-2-amine; 1-(4-amino-2-(m-tolylamino)thiazol-5-yl)-2-methylpropan-1-one; 4-(4-chlorophenyl)-1-(5H-pyrimido[5,4-b]indol-4-yl)-1H-pyrazol-3-amine; 2-(4-chlorophenyl)-6-ethyl-5-methylpyrazolo[1,5-a]pyrimidin-7(4H)-one; 5-methoxy-2-(5-phenyl-1H-pyrazol-3-yl)phenol; (3-(4-bromophenyl)-1-phenyl-1H-pyrazol-4-yl)methanol; N-(2,5-dichlorophenyl)-1-ethyl-1H-pyrazole-3-carboxamide; 4-chloro-1-methyl-N-(2-oxo-2-phenylethyl)-1H-pyrazole-3-carboxamide; N-(3-(5-tert-butyl-2-methylfuran-3-yl)-1H-pyrazol-5-yl)benzamide; N-(5-methylisoxazol-3-yl)benzold[d][1,3]dioxole-5-carboxamide; (5-(4-bromophenyl)isoxazol-3-yl)(morpholino)methanone; N-(4-bromophenyl)-5-isopropylisoxazole-3-carboxamide; 5-((4-chloro-2-methylphenoxy)methyl)-3-(pyridin-4-yl)-1,2,4-oxadiazole; 5-(2-methoxyphenyl)-3-p-tolyl-1,2,4-oxadiazole; 5-(phenoxymethyl)-3-(pyridin-2-yl)-1,2,4-oxadiazole; 5-(2-chloro-4-methylphenyl)-3-(pyridin-3-yl)-1,2,4-oxadiazole; 3-(2-chlorophenyl)-5-p-tolyl-1,2,4-oxadiazole; 5-(piperidin-1-ylmethyl)-3-p-tolyl-1,2,4-oxadiazole; 5-(4-bromophenyl)-3-(pyridin-3-yl)-1,2,4-oxadiazole; 5-(2-bromophenyl)-3-(4-bromophenyl)-1,2,4-oxadiazole; 5-(2-bromo-5-methoxyphenyl)-3-(thiophen-2-yl)-1,2,4-oxadiazole; 3-(2-fluorophenyl)-N-(3-(piperidin-1-yl)propyl)-1,2,4-oxadiazol-5-amine; 2-(2-chlorobenzoyl)-N-(4-fluorophenyl)hydrazinecar-bothioamide; 2-(methylamino)-N-phenethylbenzamide; 4-tert-butyl-N-((tetrahydrofuran-2-yl)methyl) benzamide; 2-phenyl-5-o-tolyl-1,3,4-oxadiazole; 4-(3-(4-chlorophenyl)-4,5-dihydro-1H-1,2,4-triazol-5-yl)-N,N-dimethylanil-ine; 7-methoxy-2-(4-methoxyphenyl)-1,10b-dihydrospiro[benzo[e]pyrazolo[1,5-c][1,3]oxazine-5,1'-cyclohexane]; 6-oxo-2-(4-(3-(trifluoromethyl)phenoxy)phenyl)-1,4,5,6-tetrahydropyridine-3-carbonitrile; 6-(4-methoxyphenyl)imidazo[2,1-b]thiazole; 2-(2-bromophenoxy)-N-(4H-1,2,4-triazol-3-yl)acetamide; 1-(indolin-1-yl)-2-phenoxyethanone; and 2-(4-chlorophenyl)-6,7,8,9-tetrahydrobenzo[e]imidazo[1,2-b][1,2,4]triazine;

at least one agent that inhibits the expression and/or activity of p27$^{Kip1}$, or a pharmaceutically acceptable salt thereof, wherein the agent that inhibits the expression and/or activity of p27$^{Kip1}$ is a compound having a structure represented by a formula:

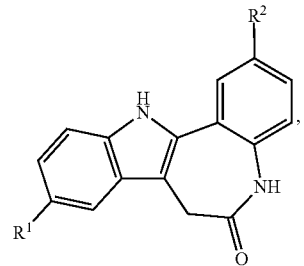

wherein $R^1$ is selected from hydrogen, halogen, —OH, —CN, —NO$_2$, —NH$_2$, —(S=O)—R$^3$, —SO$_2$—R$^3$, C1-C6 monohaloalkl, C1-C6 polyhaloalkyl, C1-C6 alkoxy, C1-C6 cyanoalkyl, C1-C6 aminoalkyl, C1-C6 hydroxyalkyl, C1-C6 monoalkylamino, and C1-C6 dialkylamino; wherein $R^3$ is selected from hydrogen, —CH$_3$, —CFH$_2$, —CF$_2$H, —CF$_3$, —NH$_2$, —NH (CH$_3$), and —N(CH$_3$)$_2$; wherein $R^2$ is selected from hydrogen, halogen, —OH, —CN, —NO$_2$, —NH$_2$, —(S=O)—R$^4$, —SO$_2$—R$^4$, C1-C6 monohaloalkyl, C1-C6 polyhaloalkyl, C1-C6 alkoxy, C1-C6 cyanoalkyl, C1-C6 aminoalkyl, C1-C6 hydroxyalkyl, C1-C6 monoalkylamino, and C1-C6 dialkylamino; wherein R⁴ is selected from hydrogen, —CH₃, —CFH₂, —CF₂H, —CF₃, —NH₂, —NH(CH₃), and —N(CH₃)₂; or a pharmaceutically acceptable salt thereof, or a compound selected from

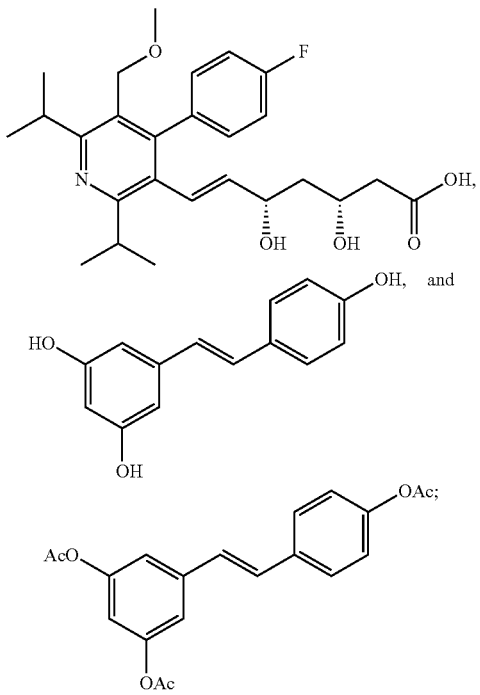

and a pharmaceutically acceptable carrier.

2. The composition of claim 1, wherein the agent that activates the expression and or activity of Atoh1 is selected from 4-(4-chlorophenyl)-1-(5H-pyrimido[5,4-b]indol-4-yl)-1H-pyrazol-3-amine; 6-chloro-1-(2-chlorobenzyloxy)-2-phenyl-1H-benzo[d]imidazole; 6-chloro-1-(2-chlorobenzyloxy)-2-(4-methoxyphenyl)-1H-benzo[d]imidazole; 6-chloro-2-(4-methoxyphenyl)-1-(4-methylbenzyloxy)-1H-benzo[d]imidazole; 6-chloro-1-(3,5-dimethylbenzyloxy)-2-(4-methoxyphenyl)-1H-benzo[d]imidazo-le; 6-chloro-1-(4-methoxybenzyloxy)-2-(4-methoxyphenyl)-1H-benzo[d]imidazo-le; 1-(4-methylbenzyloxy)-6-nitro-2-phenyl-1H-benzo[d]imidazole; 4-(1H-benzo[d]imidazol-2-yl)phenol; 2,5-dichloro-N-((1-methyl-1H-benzo[d]imidazol-2-yl)methyl)aniline; 4-(2-(1-methyl-1H-benzo[d]imidazol-2-yl)ethyl)aniline; 2-((2-methoxyphenoxy)methyl)-1H-benzo[d]imidazole; 2-(4-fluorophenoxy)methyl)-1-methyl-1H-benzo[d]imidazole; 2-(phenylthiomethyl)-1H-benzo[d]imidazole; 3-(6-methyl-1H-benzo[d]imidazol-2-yl)-2H-chromen-2-imine; 2-(o-tolyloxymethyl)-1H-benzo[d]imidazole; 2-(4-methoxyphenyl)-1-phenethyl-1H-benzo[d]imidazole; N-(6-bromobenzo[d]thiazol-2-yl)thiophene-2-carboxamide; N-(benzo[d]thiazol-2-yl)-1-methyl-1H-pyrazole-5-carboxamide; 2-(4-fluorobenzylthio)benzo[d]thiazole; 5-chloro-N-methylbenzo[d]thiazol-2-amine; N-(2-(1H-benzo[d]imidazol-2-yl)phenyl)isobutyramide; N-(6-acetamidobenzo[d]thiazol-2-yl)furan-2-carboxamide; N-(6-fluorobenzo[d]thiazol-2-yl)-3-methoxybenzamide; 2-(benzo[d]oxazol-2-ylthio)-N-(2-chlorophenyl)acetamide; 5-chloro-2-phenylbenzo[d]oxazole; 5-methyl-2-m-tolylbenzo[d]oxazole; 2-(4-isobutoxyphenyl)-3-(naphthalen-2-yl)-2,3-dihydroquinazolin-4(1H)-one-; N-(2-(2-(4-fluorophenyl)-2-oxoethylthio)-4-oxoquinazolin-3(4H)-yl)benzam-ide; 2-(4-chlorophenyl)-4-(4-methoxyphenyl)-1,4-dihydrobenzo[4,5]imidazo[1-,2-a]pyrimidine; 2-(3-pyridyl)-4-(4-bromophenyl)-1,4-dihydrobenzo[4,5]imidazo[1,2-a]pyrimidine; N-sec-butyl-1,7,7-trimethyl-9-oxo-8,9-dihydro-7H-furo[3,2-f]chromene-2-carboxamide; N-(3-carbamoyl-5,6-dihydro-4H-cyclopenta[b]thiophen-2-yl)benzofuran-2-carboxamide; 3-chloro-N-(5-chloropyridin-2-yl)benzo[b]thiophene-2-carboxamide-; 3-chloro-N-((tetrahydrofuran-2-yl)methyl)benzo[b]thiophene-2-carboxamide-; N-(3-(5-chloro-3-methylbenzo[b]thiophen-2-yl)-1H-pyrazol-5-yl)acetamide; 2-(naphthalen-2-yl)-1H-indole; 2-(pyridin-2-yl)-1H-indole; N-(2-chlorophenyl)-2-(1H-indol-3-yl)-2-oxoacetamide; 2-m-tolylquinoline; 2-(4-(2-methoxyphenyl)piperazin-1-yl)quinoline; 2-(1H-benzo[d][1,2,3]triazol-1-yl)-N-(2,3-dihydro-1H-inden-2-yl)acetamide-; 1-phenethyl-1H-benzo[d][1,2,3]triazole; 7-(4-fluorobenzyloxy)-2H-chromen-2-one; N-(2,4-dichlorophenyl)-8-methoxy-2H-chromene-3-carboxamide; N-(3-chlorophenyl)-8-methyl-3,4-dihydroquinoline-1(2H)-carbothioamide; 7-methoxy-5-methyl-2-phenyl-4H-chromen-4-one; 2-(3,4-dimethylphenyl)quinoxaline; 4-bromo-N-(5-chloropyridin-2-yl)benzamide; 3-amino-6,7,8,9-tetrahydro-5H-cyclohepta[e]thieno[2,3-b]pyridine-2-carbox-amide; (Z)-3-methyl-N'-(nicotinoyloxy)benzimidamide; N,N-diethyl-6-methoxythieno[2,3-b]quinoline-2-carboxamide; 6-(4-methoxyphenyl)-1,2,3,4-tetrahydro-1,5-naphthyridine; 5-bromo-N-(2-(phenylthio)ethyl)nicotinamide; N-(6-methylpyridin-2-yl)-2,3-dihydrobenzo[b][1,4]dioxine-6-carbox-amide; 2-(4-methylbenzylthio)oxazolo[4,5-b]pyridine; N-(2-methoxyethyl)-5-p-tolylpyrimidin-2-amine; 4-(5-(benzo[b]thiophen-2-yl)pyrimidin-2-yl)morpholine; 4-(5-(4-fluorophenyl)pyrimidin-2-yl)morpholine; N-(4-bromo-3-methylphenyl)quinazolin-4-amine; N-(4-methoxyphenyl)quinazolin-4-amine; N-(3-methoxyphenyl)-9H-purin-6-amine; N,N-diethyl-1-m-tolyl-1H-pyrazolo[3,4-d]pyrimidin-4-amine; (5-(4-bromophenyl)furan-2-yl)(morpholino)methanone; (Z)-4-bromo-N'-(furan-2-carbonyloxy)benzimidamide; N-(4-iodophenyl)furan-2-carboxamide; 5-(5-(2,4-difluorophenyl)furan-2-yl)-1-(methylsulfonyl)-1H-pyrazole; 1-(3-amino-5-(4-tert-butylphenyl)thiophen-2-yl)ethanone; N-(3-cyano-4,5,6,7-tetrahydrobenzo[b]thiophen-2-yl)-2-fluorobenzamide; N-(5-chloropyridin-2-yl)thiophene-2-carboxamide; N-(2-(4-fluorophenoxy)ethyl)thiophene-2-carboxamide; 2,5-dimethyl-N-phenyl-1-(thiophen-2-ylmethyl)-1H-pyrrole-3-car-boxamide; N-(3-cyanothiophen-2-yl)-4-isopropoxybenzamide; 2-(4-methoxyphenoxy)-N-(thiazol-2-yl)acetamide; 4-(4-methoxyphenyl)-N-(3-methylpyridin-2-yl)thiazol-2-amine; 4-(biphenyl-4-yl)thiazol-2-amine; 4-(4-(4-methoxyphenyl)thiazol-2-yl)-3-methylisoxazol-5-amine; N-(2-methoxyphenyl)-4-phenylthiazol-2-amine; 1-(4-amino-2-(m-tolylamino)thiazol-5-yl)-2-methylpropan-1-one; 4-(4-chlorophenyl)-1-(5H-pyrimido[5,4-b]indol-4-yl)-1H-pyrazol-3-amine; 2-(4-chlorophenyl)-6-ethyl-5-methylpyrazolo[1,5-a]pyrimidin-7(4H)-one; 5-methoxy-2-(5-phenyl-1H-pyrazol-3-yl)phenol; (3-(4-bromophenyl)-1-phenyl-1H-pyrazol-4-yl)methanol; N-(2,5-dichlorophenyl)-1-ethyl-1H-pyrazole-3-carboxamide; 4-chloro-1-methyl-N-(2-oxo-2-phenylethyl)-1H-pyrazole-3-carboxamide; N-(3-(5-tert-butyl-2-methylfuran-3-yl)-1H-pyrazol-5-yl)benzamide; N-(5-methylisoxazol-3-yl)benzo[d][1,3]dioxole-5-carboxamide; (5-(4-bromophenyl)isoxazol-3-yl)

(morpholino)methanone; N-(4-bromophenyl)-5-isopropylisoxazole-3-carboxamide; 5-(4-chloro-2-methylphenoxy)methyl)-3-(pyridin-4-yl)-1,2,4-oxadiazole; 5-(2-methoxyphenyl)-3-p-tolyl-1,2,4-oxadiazole; 5-(phenoxymethyl)-3-(pyridin-2-yl)-1,2,4-oxadiazole; 5-(2-chloro-4-methylphenyl)-3-(pyridin-3-yl)-1,2,4-oxadiazole; 3-(2-chlorophenyl)-5-p-tolyl-1,2,4-oxadiazole; 5-(piperidin-1-ylmethyl)-3-p-tolyl-1,2,4-oxadiazole; 5-(4-bromophenyl)-3-(pyridin-3-yl)-1,2,4-oxadiazole; 5-(2-bromophenyl)-3-(4-bromophenyl)-1,2,4-oxadiazole; 5-(2-bromo-5-methoxyphenyl)-3-(thiophen-2-yl)-1,2,4-oxadiazole; 3-(2-fluorophenyl)-N-(3-(piperidin-1-yl)propyl)-1,2,4-oxadiazol-5-amine; 2-(2-chlorobenzoyl)-N-(4-fluorophenyl)hydrazinecarbothioamide; 2-(methylamino)-N-phenethylbenzamide; 4-tert-butyl-N-((tetrahydrofuran-2-yl)methyl)benzamide; 2-phenyl-5-o-tolyl-1,3,4-oxadiazole; 4-(3-(4-chlorophenyl)-4,5-dihydro-1H-1,2,4-triazol-5-yl)-N,N-dimethylanil-ine; 7-methoxy-2-(4-methoxyphenyl)-1,10b-dihydrospiro[benzo[e]pyrazolo[1,5-c][1,3]oxazine-5,1'-cyclohexane]; 6-oxo-2-(4-(3-(trifluoromethyl)phenoxy)phenyl)-1,4,5,6-tetrahydropyridine-3-carbonitrile; 6-(4-methoxyphenyl)imidazo[2,1-b]thiazole; 2-(2-bromophenoxy)-N-(4H-1,2,4-triazol-3-yl)acetamide; 1-(indolin-1-yl)-2-phenoxyethanone; and 2-(4-chlorophenyl)-6,7,8,9-tetrahydrobenzo[e]imidazo[1,2-b][1,2,4]triazine, or a pharmaceutically acceptable alt thereof.

3. The composition of claim 1, wherein the agent that activates the expression and/or activity of Atoh1 is a β-catenin protein.

4. The composition of claim 1, further comprising an inhibitor of the Notch signaling pathway selected from N-[N-(3,5-difluorophenacetyl)-L-alanyl]-S-phenylglycine-t-butylester; (2S)-2-hydroxy-3-methyl-N-[(1S)-1-methyl-2-oxo-2[[(1S)-2,3,4,5-tetrahydro-3-methyl-2-oxo-1H-3-benzazepin-1-yl]amino]ethyl]butanamide; N2-[(2S)-2-(3,5-difluorophenyl)-2-hydroxyethanoyl]-N1-[(7S)-5-methyl-6-oxo-6,7-dihydro-5H-dibenzo[b,d]azepin-7-yl]-L-alaninamide; [(2S)-2{[(3,5-difluorophenyl)acetyl]amino}-N-[(3S)-1-methyl-2-oxo-5-phenyl-2,3-dihydro-1H-1,4-benzodiazepin-3-yl]propanamide]; 4-chloro-N-(2,5-difluorophenyl)-N-((1R)-{4-fluoro-2-[3-(1H-imidazol-1-yl)propyl]phenyl}ethyl)benzenesulfonamide hydrochloride; 4-[2-((1R)-1-{[(4-chlorophenyl)sulfonyl]-2,5-difluoroanilino}ethyl)-5-fluorophenyl]butanoic acid; R-flurbiprofen ([1,1'-biphenyl]-4-acetic acid, 2-fluoro-alpha-methyl); (5S)-(t-butoxycarbonylamino)-6-phenyl-(4R)hydroxy-(2R)benzylhexanoyl)-L-leu-L-phe-amide (L-685,458); 5-chloro-N-[(1S)-3,3,3-trifluoro-1-(hydroxymethyl)-2-(trifluoromethyl)propyl]thiophene-2-sulfonamide; 4-fluoro-N-[(1R,2R,4S)-1,3,3-trimethylbicyclo[2.2.1]hept-2-yl]benzenesulfonamide; (2R)-2-{[5-chloro-2-(hydroxymethyl)phenyl][(4-chlorophenyl)sulfonyl]amino}propylpropylcarbamate; 5-chloro-N-[(1S,2R)-4,4,4-trifluoro-1-(hydroxymethyl)-2-methylbutyl]thiophene-2-sulfonamide; N-{(2R,4R,5S)-2-benzyl-5-[(tert-butoxycarbonyl)aminol]-4-hydroxy-6-phenylhexanoyl}-L-leucyl-L-phenylalaninamide; L-852,647; MW167, WPE-III-31; MK0752; MRK-003; NGX-555, CZC-1040, E2012, NIC5-15, BACE Inhibitor, and CI-IF-5074.

5. The composition of claim 1, wherein the agent that inhibits the expression and/or activity of p27$^{Kip1}$ is a compound having a structure represented by a formula:

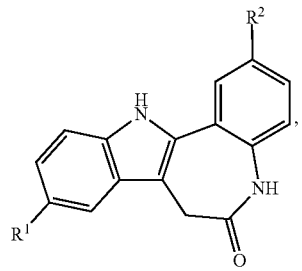

wherein $R^1$ is selected from hydrogen, halogen, —OH, —CN, —NO$_2$, —NH$_2$, —(S═O)—R$^3$, —SO —R$^3$, C1-C6 monohaloalk, C1-C6 polyhaloalkyl, C1-C6 alkoxy, C1-C6 cyanoalkyl, C1-C6 aminoalkyl, C1-C6 hydroxyalkyl, C1-C6 monoalkylamino, and C1-C6 dialkylamino; wherein $R^3$ is selected from hydrogen, —CH$_3$, —CFH$_2$, —CF$_2$H, —CF$_3$, —NH$_2$, —NH(CH$_3$), and —N(CH$_3$)$_2$; wherein $R^2$ is selected from hydrogen, halogen, —OH, —CN, —NO$_2$, —NH$_2$, —(S═O)—R$^4$, —SO$_2$—R$^4$, C1-C6 monohaloalkyl, C1-C6 polyhaloalkyl, C1-C6 alkoxy, C1-C6 cyanoalkyl, C1-C6 aminoalkyl, C1-C6 hydroxyalkyl, C1-C6 monoalkylamino, and C1-C6 dialkylamino; wherein $R^4$ is selected from hydrogen, —CH$_3$, —CFH$_2$, —CF$_2$H, —CF$_3$, —NH$_2$, —NH(CH$_3$), and —N(CH$_3$)$_2$; or a pharmaceutically acceptable salt thereof.

6. The composition of claim 1, wherein the agent that inhibits the expression and/or activity of p27$^{Kip1}$ is a compound having a structure represented by a formula:

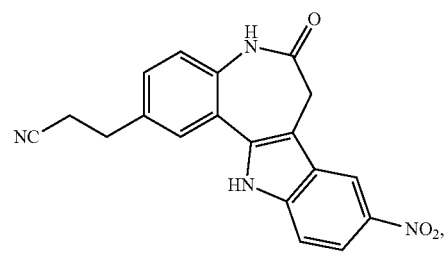

or a pharmaceutically acceptable salt thereof.

7. The composition of claim 1, wherein the agent that inhibits the expression and/or activity of p27$^{Kip1}$ is selected from:

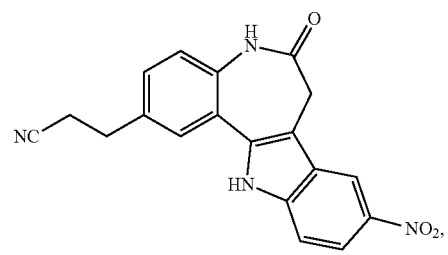 [SMILES: N#CCCc1ccc2c(c1)-c1[nH]c3ccc([N+](=O)[O-])cc3c1CC(=O)N2]

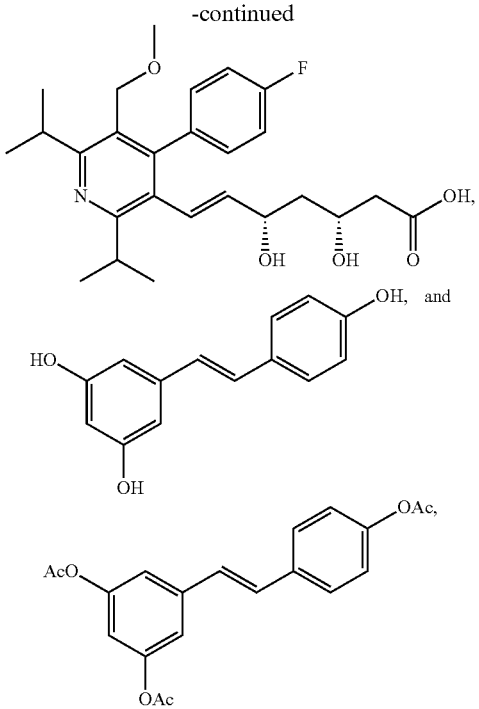

or a pharmaceutically acceptable salt thereof.

8. The composition of claim 1, wherein the pharmaceutical composition is used to treat hearing impairment.

9. A method of treating a subject who has a hearing impairment associated with loss of cochlear hair cells, the method comprising:
   a) obtaining a population of cells capable of differentiating into cochlear hair cells;
   b) contacting the population of cells with an effective amount of at least one agent that activates the expression and/or activity of Atoh1, or a pharmaceutically acceptable salt thereof, wherein the agent that activates the expression and/or activity of Atoh1 is a β-catenin protein or a compound selected from 4-(4-chlorophenyl)-1-(5H-pyrimido[5,4-b]indol-4-yl)-1H-pyrazol-3-amine; 6-chloro-1-(2-chlorobenzyloxy)-2-phenyl-1H-benzo[d]imidazole; 6-chloro-1-(2-chlorobenzyloxy)-2-(4-methoxyphenyl)-1H-benzo[d]imidazole; 6-chloro-2-(4-methoxyphenyl)-1-(4-methylbenzyloxy)-1H-benzo[d]imidazole; 6-chloro-1-(3,5-dimethylbenzyloxy)-2-(4-methoxyphenyl)-1H-benzo[d]imidazole; 6-chloro-1-(4-methoxybenzyloxy)-2-(4-methoxyphenyl)-1H-benzo[d]imidazole; 1-(4-methylbenzyloxy)-6-nitro-2-phenyl-1H-benzo[d]imidazole; 4-(1H-benzo[d]imidazol-2-yl)phenol; 2,5-dichloro-N-((1-methyl-1H-benzo[d]imidazol-2-yl)methyl)aniline; 4-(2-(1-methyl-1H-benzo[d]imidazol-2-yl)ethyl)aniline; 2-((2-methoxyphenoxy)methyl)-1H-benzo[d]imidazole; 2-((4-fluorophenoxy)methyl)-1-methyl-1H-benzo[d]imidazole; 2-(phenylthiomethyl)-1H-benzo[d]imidazole; 3-(6-methyl-1H-benzo[d]imidazol-2-yl)-2H-chromen-2-imine; 2-(o-tolyloxymethyl)-1H-benzo[d]imidazole; 2-(4-methoxyphenyl)-1-phenethyl-1H-benzo[d]imidazole; N-(6-bromobenzo[d]thiazol-2-yl)thiophene-2-carboxamide; N-(benzo[d]thiazol-2-yl)-1-methyl-1H-pyrazole-5-carboxamide; 2-(4-fluorobenzylthio)benzo[d]thiazole; 5-chloro-N-methylbenzo[d]thiazol-2-amine; N-(2-(1H-benzo[d]imidazol-2-yl)phenyl)isobutyramide; N-(6-acetamidobenzo[d]thiazol-2-yl)furan-2-carboxamide; N-(6-fluorobenzo[d]thiazol-2-yl)-3-methoxybenzamide; 2-(benzo[d]oxazol-2-ylthio)-N-(2-chlorophenyl)acetamide; 5-chloro-2-phenylbenzo[d]oxazole; 5-methyl-2-m-tolylbenzo[d]oxazole; 2-(4-isobutoxyphenyl)-3-(naphthalen-2-yl)-2,3-dihydroquinazolin-4(1H)-one-; N-(2-(2-(4-fluorophenyl)-2-oxoethylthio)-4-oxoquinazolin-3(4H)-yl)benzam-ide; 2-(4-chlorophenyl)-4-(4-methoxyphenyl)-1,4-dihydrobenzo[4,5]imidazo[1-,2-a]pyrimidine; 2-(3-pyridyl)-4-(4-bromophenyl)-1,4-dihydrobenzo[4,5]imidazo[1,2-a]pyrimi-dine; N-sec-butyl-1,7,7-trimethyl-9-oxo-8,9-dihydro-7H-furo[3,2-f]chromene-2-carboxamide; N-(3-carbamoyl-5,6-dihydro-4H-cyclopenta[b]thiophen-2-yl)benzofuran-2-car-boxamide; 3-chloro-N-(5-chloropyridin-2-yl)benzo[b]thiophene-2-carboxamide-; 3-chloro-N-((tetrahydrofuran-2-yl)methyl)benzo[b]thiophene-2-carboxamide-; N-(3-(5-chloro-3-methylbenzo[b]thiophen-2-yl)-1H-pyrazol-5-yl)acetamide; 2-(naphthalen-2-yl)-1H-indole; 2-(pyridin-2-yl)-1H-indole; N-(2-chlorophenyl)-2-(1H-indol-3-yl)-2-oxoacetamide; 2-m-tolylquinoline; 2-(4-(2-methoxyphenyl)piperazin-1-yl)quinoline; 2-(1H-benzo[d][1,2,3]triazol-1-yl)-N-(2,3-dihydro-1H-inden-2-yl)acetamide-; 1-phenethyl-1H-benzo[d][1,2,3]triazole; 7-(4-fluorobenzyloxy)-2H-chromen-2-one; N-(2,4-dichlorophenyl)-8-methoxy-2H-chromene-3-carboxam-ide; N-(3-chlorophenyl)-8-methyl-3,4-dihydroquinoline-1(2H)-carbothioamide; 7-methoxy-5-methyl-2-phenyl-4H-chromen-4-one; 2-(3,4-dimethylphenyl)quinoxaline; 4-bromo-N-(5-chloropyridin-2-yl)benzamide; 3-amino-6,7,8,9-tetrahydro-5H-cyclohepta[e]thieno[2,3-b]pyridine-2-carbox-amide; (Z)-3-methyl-N'-(nicotinoyloxy)benzimidamide; N,N-diethyl-6-methoxythieno[2,3-b]quinoline-2-carboxamide; 6-(4-methoxyphenyl)-1,2,3,4-tetrahydro-1,5-naphthyridine; 5-bromo-N-(2-(phenylthio)ethyl)nicotinamide; N-(6-methylpyridin-2-yl)-2,3-dihydrobenzo[b][1,4]dioxine-6-carboxamide; 2(4-methylbenzylthio)oxazolo[4,5-b]pyridine; N-(2-methoxyethyl)-5-p-tolylpyrimidin-2-amine; 4-(5-(benzo[b]thiophen-2-yl)pyrimidin-2-yl)morpholine; 4-(5-(4-fluorophenyl)pyrimidin-2-yl)morpholine; N-(4-bromo-3-methylphenyl)quinazolin-4-amine; N-(4-methoxyphenyl)quinazolin-4-amine; N-(3-methoxyphenyl)-9H-purin-6-amine; N,N-diethyl-1-m-tolyl-1H-pyrazolo[3,4-d]pyrimidin-4-amine; (5-(4-bromophenyl)furan-2-yl)(morpholino)methanone; (Z)-4-bromo-N'-(furan-2-carbonyloxy)benzimidamide; N-(4-iodophenyl)furan-2-carboxamide; 5(5-(2,4-difluorophenyl)furan-2-yl)-1-(methylsulfonyl)-1H-pyrazole; 1-(3-amino-5-(4-tert-butylphenyl)thiophen-2-yl)ethanone; N-(3-cyano-4,5,6,7-tetrahydrobenzo[b]thiophen-2-yl)-2-fluorobenzamide; N-(5-chloropyridin-2-yl)thiophene-2-carboxamide; N-(2-(4-fluorophenoxy)ethyl)thiophene-2-carboxamide; 2,5-dimethyl-N-phenyl-1-(thiophen-2-ylmethyl)-1H-pyrrole-3-carboxamide; N-(3-cyanothiophen-2-yl)-4-isopropoxybenzamide; 2-(4-methoxyphenoxy)-N-(thiazol-2-yl)acetamide; 4-(4-methoxyphenyl)-N-(3-methylpyridin-2-yl)thiazol-2-amine; 4-(biphenyl-4-yl)thiazol-2-amine; 4-(4-(4-methoxyphenyl)thiazol-2-yl)-3-methylisoxazol-5-amine; N-(2-methoxyphenyl)-4-phenylthiazol-2-amine; 1-(4-amino-2-(m-tolylamino)thiazol-5-yl)-2-methylpropan-1-one; 4-(4- chlorophenyl)-1-(5H-pyrimido[5,4-b]indol-4-yl)-1H-pyrazol-3-amine; 2-(4-chlorophenyl)-6-ethyl-5-methylpyrazolo[1,5-a]pyrimidin-7(4H)-one; 5-methoxy-2-(5-phenyl-1H-pyrazol-3-yl)phenol; (3-(4-bromophenyl)-1-phenyl-1H-pyrazol-4-yl)methanol; N-(2,5-dichlorophenyl)-1-ethyl-1H-pyrazole-3-carboxamide; 4-chloro-1-methyl-N-(2-oxo-2-phenylethyl)-1H-pyrazole-3-carboxamide; N-(3-(5-tert-butyl-2-methylfuran-3-yl)-1H-pyrazol-5-yl)benzamide; N-(5-methylisoxazol-3-yl)benzo[d][1,3]dioxole-5-carboxamide; (5-(4-bromophenyl)isoxazol-3-yl)(morpholino)methanone; N-(4-bromophenyl)-5-isopropylisoxazole-3-carboxamide; 5-((4-chloro-2-methylphenoxy)methyl)-3-(pyridin-4-yl)-1,2,4-oxadiazole; 5-(2-methoxyphenyl)-3-p-tolyl-1,2,4-oxadiazole; 5-(phenoxymethyl)-3-(pyridin-2-yl)-1,2,4-oxadiazole; 5-(2-chloro-4-methylphenyl)-3-(pyridin-3-yl)-1,2,4-oxadiazole; 3-(2-chlorophenyl)-5-p-tolyl-1,2,4-oxadiazole; 5-(piperidin-1-ylmethyl)-3-p-tolyl-1,2,4-oxadiazole; 5-(4-bromophenyl)-3-(pyridin-3-yl)-1,2,4-oxadiazole; 5-(2-bromophenyl)-3-(4-bromophenyl)-1,2,4-oxadiazole; 5-(2-bromo-5-methoxyphenyl)-3-(thiophen-2-yl)-1,2,4-oxadiazole; 3-(2-fluorophenyl)-N-(3-(piperidin-1-yl)propyl)-1,2,4-oxadiazol-5-amine; 2-(2-chlorobenzoyl)-N-(4-fluorophenyl)hydrazinecarbothioamide; 2-(methylamino)-N-phenethylbenzamide; 4-tert-butyl-N-((tetrahydrofuran-2-yl)methyl)benzamide; 2-phenyl-5-o-tolyl-1,3,4-oxadiazole; 4-(3-(4-chlorophenyl)-4,5-dihydro-1H-1,2,4-triazol-5-yl)-N,N-dimethylanil-ine; 7-methoxy-2-(4-methoxyphenyl)-1,10b-dihydrospiro[benzo[e]pyrazolo[1,5-c][1,3]oxazine-5,1'-cyclohexane]; 6-oxo-2-(4-(3-(trifluoromethyl)phenoxy)phenyl)-1,4,5,6-tetrahydropyridine-3-carbonitrile; 6-(4-methoxyphenyl)imidazo[2,1-b]thiazole; 2-(2-bromophenoxy)-N-(4H-1,2,4-triazol-3-yl)acetamide; 1-(indolin-1-yl)-2-phenoxyethanone; and 2-(4-chlorophenyl)-6,7,8,9-tetrahydrobenzo[e]imidazo[1,2-b][1,2,4]triazine; and at least one agent that inhibits the expression and/or activity of p27$^{Kip1}$, or a pharmaceutically acceptable salt thereof, wherein the agent that inhibits the expression and/or activity of p27$^{Kip1}$ is a compound having a structure represented by a formula:

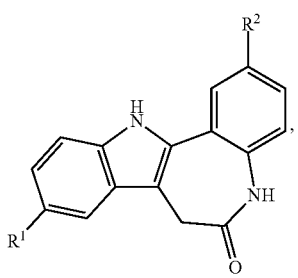

wherein R$^1$ is selected from hydrogen, halogen, —OH, —CN, —NO$_2$, —NH$_2$, —(S═O)—R$^3$, —SO$_2$—R$^3$, C1-C6 monohaloalk, C1-C6 polyhaloalkyl, C1-C6 alkoxy, C1-C6 cyanoalkyl, C1-C6 aminoalkyl, C1-C6 hydroxyalkyl, C1-C6 monoalkylamino, and C1-C6 dialkylamino; wherein R$^3$ is selected from hydrogen, —CH$_3$, —CFH$_2$, —CF$_2$H, —CF$_3$, —NH$_2$, —NH(CH$_3$), and —N(CH$_3$)$_2$; wherein R$^2$ is selected from hydrogen, halogen, —OH, —CN, —NO$_2$, —NH$_2$, —(S═O)—R$^4$, —SO$_2$—R$^4$, C1-C6 monohaloalkyl, C1-C6 polyhaloalkyl, C1-C6 alkoxy, C1-C6 cyanoalkyl, C1-C6 aminoalkyl, C1-C6 hydroxyalkyl, C1-C6 monoalkylamino, and C1-C6 dialkylamino; wherein R$^4$ is selected from hydrogen, —CH$_3$, —CFH$_2$, —CF$_2$H, —CF$_3$, —NH$_2$, —NH(CH$_3$), and —N(CH$_3$)$_2$; or a pharmaceutically acceptable salt thereof, or a compound selected from

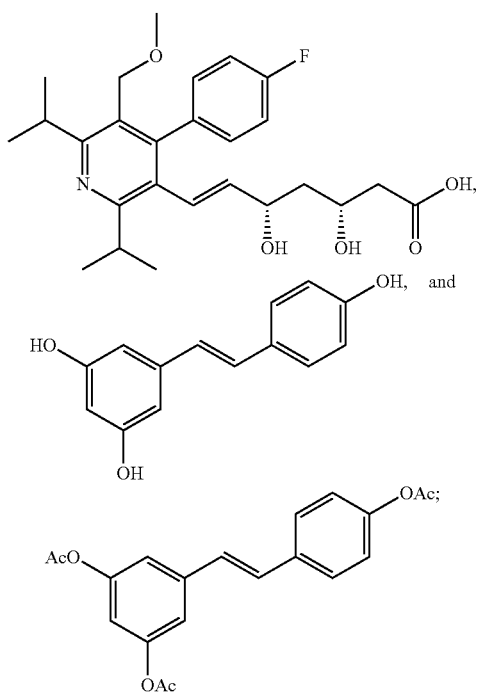

and c) administering the population of cells, or a subset thereof, to the subject's ear, thereby treating the subject.

10. The method of claim 9, wherein the subject has been diagnosed with a need for treatment of hearing impairment associated with loss of cochlear hair cells prior to the administering step.

11. The method of claim 9, further comprising identifying a subject in need of treatment for hearing impairment associated with loss of cochlear hair cells.

12. The method of claim 9, wherein administering the population of cells comprises:
a) injecting the cells into the scala tympani, the luminae of the cochlea, the auditory nerve trunk in the internal auditory meatus, or the middle ear space across the transtympanic membrane/ear drum; or
b) implanting the cells within a cochlear implant.

13. The method of claim 9, further comprising administering to the subject a therapeutically effective amount of
at least one agent that activates the expression and/or activity of Atoh1, or a pharmaceutically acceptable salt thereof, wherein the agent that activates the expression and/or activity of Atoh1 is a β-catenin protein or a compound selected from 4-(4-chlorophenyl)-1-(5H-pyrimido[5,4-b]indol-4-yl)-1H-pyrazol-3-amine; 6-chloro-1-(2-chlorobenzyloxy)-2-phenyl-1H-benzo[d]imidazole; 6-chloro-1-(2-chlorobenzyloxy)-2-(4-methoxyphenyl)-1H-benzo[d]imidazole; 6-chloro-2-

(4-methoxyphenyl)-1-(4-methylbenzyloxy)-1H-benzo[d]imidazole; 6-chloro-1-(3,5-dimethylbenzyloxy)-2-(4-methoxyphenyl)-1H-benzo[d]imidazole; 6-chloro-1-(4-methoxybenzyloxy)-2-(4-methoxyphenyl)-1H-benzo[d]imidazole; 1-(4-methylbenzyloxy)-6-nitro-2-phenyl-1H-benzo[d]imidazole; 4-(1H-benzo[d]imidazol-2-yl)phenol; 2,5-dichloro-N-((1-methyl-1H-benzo[d]imidazol-2-yl)methyl)aniline; 4-(2-(1-methyl-1H-benzo[d]imidazol-2-yl)ethyl)aniline; 2-((2-methoxyphenoxy)methyl)-1H-benzo[d]imidazole; 2-((4-fluorophenoxy)methyl)-1-methyl-1H-benzo[d]imidazole; 2-(phenylthiomethyl)-1H-benzo[d]imidazole; 3-(6-methyl-1H-benzo[d]imidazol-2-yl)-2H-chromen-2-imine; 2-(o-tolyloxymethyl)-1H-benzo[d]limidazole; 2-(4-methoxyphenyl)-1-phenethyl-1H-benzo[d]imidazole; N-(6-bromobenzo[d]thiazol-2-yl)thiophene-2-carboxamide; N-(benzo[d]thiazol-2-yl)-1-methyl-1H-pyrazole-5-carboxamide; 2-(4-fluorobenzylthio)benzo[d]thiazole; 5-chloro-N-methylbenzo[d]thiazol-2-amine; N-(2-(1H-benzo[d]imidazol-2-yl)phenyl)isobutyramide; N-(6-acetamidobenzo[d]thiazol-2-yl)furan-2-carboxamide; N-(6-fluorobenzo[d]thiazol-2-yl)-3-methoxybenzamide; 2-(benzo[d]oxazol-2-ylthio)-N-(2-chlorophenyl)acetamide; 5-chloro-2-phenylbenzo[d]oxazole; 5-methyl-2-m-tolylbenzo[d]oxazole; 2-(4-isobutoxyphenyl)-3-(naphthalen-2-yl)-2,3-dihydroquinazolin-4(1H)-one-; N-(2-(2-(4-fluorophenyl)-2-oxoethylthio)-4-oxoquinazolin-3(4H)-yl)benzam-ide; 2-(4-chlorophenyl)-4-(4-methoxyphenyl)-1,4-dihydrobenzo[4,5]imidazo[1-,2-a]pyrimidine; 2-(3-pyridyl)-4-(4-bromophenyl)-1,4-dihydrobenzo[4,5]imidazo[1,2-a]pyrimi-dine; N-sec-butyl-1,7,7-trimethyl-9-oxo-8,9-dihydro-7H-furo[3,2-f]chromene-2-carboxamide; N-(3-carbamoyl-5,6-dihydro-4H-cyclopenta[b]thiophen-2-yl)benzofuran-2-car-boxamide; 3-chloro-N-(5-chloropyridin-2-yl)benzo[b]thiophene-2-carboxam-ide-; 3-chloro-N-((tetrahydrofuran-2-yl)methyl)benzo[b]thiophene-2-carboxamide-; N-(3-(5-chloro-3-methylbenzo[b]thiophen-2-yl)-1H-pyrazol-5-yl)acetamide; 2-(naphthalen-2-yl)-1H-indole; 2-(pyridin-2-yl)-1H-indole; N-(2-chlorophenyl)-2-(1H-indol-3-yl)-2-oxoacetamide; 2-m-tolylquinoline; 2-(4-(2-methoxyphenyl)piperazin-1-yl)quinoline; 2-(1H-benzo[d][1,2,3]triazol-1-yl)-N-(2,3-dihydro-1H-inden-2-yl)acetamide-; 1-phenethyl-1H-benzo[d][1,2,3]triazole; 7-(4-fluorobenzyloxy)-2H-chromen-2-one; N-(2,4-dichlorophenyl)-8-methoxy-2H-chromene-3-carboxam-ide; N-(3-chlorophenyl)-8-methyl-3,4-dihydroquinoline-1(2H)-carbothioamide; 7-methoxy-5-methyl-2-phenyl-4H-chromen-4-one; 2-(3,4-dimethylphenyl)quinoxaline; 4-bromo-N-(5-chloropyridin-2-yl)benzamide; 3-amino-6,7,8,9-tetrahydro-5H-cyclohepta[e]thieno[2,3-b]pyridine-2-carbox-amide; (Z)-3-methyl-N'-(nicotinoyloxy)benzimidamide; N,N-diethyl-6-methoxythieno[2,3-b]quinoline-2-carboxamide; 6-(4-methoxyphenyl)-1,2,3,4-tetrahydro-1,5-naphthyridine; 5-bromo-N-(2-(phenylthio)ethyl)nicotinamide; N-(6-methylpyridin-2-yl)-2,3-dihydrobenzo[b][1,4]dioxine-6-carboxamide; 2(4-methylbenzylthio)oxazolo[4,5-b]pyridine; N-(2-methoxyethyl)-5-p-tolylpyrimidin-2-amine; 4-(5-(benzo[b]thiophen-2-yl)pyrimidin-2-yl)morpholine; 4-(5-(4-fluorophenyl)pyrimidin-2-yl)morpholine; N-(4-bromo-3-methylphenyl)quinazolin-4-amine; N-(4-methoxyphenyl)quinazolin-4-amine; N-(3-methoxyphenyl)-9H-purin-6-amine; N,N-diethyl-1-m-tolyl-1H-pyrazolo[3,4-d]pyrimidin-4-amine; (5-(4-bromophenyl)furan-2-yl)(morpholino)methanone; (Z)-4-bromo-N'-(furan-2-carbonyloxy)benzimidamide; N-(4-iodophenyl)furan-2-carboxamide; 5-(5-(2,4-difluorophenyl)furan-2-yl)-1-(methylsulfonyl)-1H-pyrazole; 1-(3-amino-5-(4-tert-butylphenyl)thiophen-2-yl)ethanone; N-(3-cyano-4,5,6,7-tetrahydrobenzo[b]thiophen-2-yl)-2-fluorobenzamide; N-(5-chloropyridin-2-yl)thiophene-2-carboxamide; N-(2-(4-fluorophenoxy)ethyl)thiophene-2-carboxamide; 2,5-dimethyl-N-phenyl-1-(thiophen-2-ylmethyl)-1H-pyrrole-3-carboxamide; N-(3-cyanothiophen-2-yl)-4-isopropoxybenzamide; 2-(4-methoxyphenoxy)-N-(thiazol-2-yl)acetamide; 4-(4-methoxyphenyl)-N-(3-methylpyridin-2-yl)thiazol-2-amine; 4-(biphenyl-4-yl)thiazol-2-amine; 4-(4-(4-methoxyphenyl)thiazol-2-yl)-3-methylisoxazol-5-amine; N-(2-methoxyphenyl)-4-phenylthiazol-2-amine; 1-(4-amino-2-(m-tolylamino)thiazol-5-yl)-2-methylpropan-1-one; 4-(4-chlorophenyl)-1-(5H-pyrimido[5,4-b]indol-4-yl)-1H-pyrazol-3-amine; 2-(4-chlorophenyl)-6-ethyl-5-methylpyrazolo[1,5-a]pyrimidin-7(4H)-one; 5-methoxy-2-(5-phenyl-1H-pyrazol-3-yl)phenol; (3-(4-bromophenyl)-1-phenyl-1H-pyrazol-4-yl)methanol; N-(2,5-dichlorophenyl)-1-ethyl-1H-pyrazole-3-carboxamide; 4-chloro-1-methyl-N-(2-oxo-2-phenylethyl)-1H-pyrazole-3-carboxamide; N-(3-(5-tert-butyl-2-methylfuran-3-yl)-1H-pyrazol-5-yl)benzamide; N-(5-methylisoxazol-3-yl)benzo[d][1,3]dioxole-5-carboxamide; (5-(4-bromophenyl)isoxazol-3-yl)(morpholino)methanone; N-(4-bromophenyl)-5-isopropylisoxazole-3-carboxamide; 5-((4-chloro-2-methylphenoxy)methyl)-3-(pyridin-4-yl)-1,2,4-oxadiazole; 5-(2-methoxyphenyl)-3-p-tolyl-1,2,4-oxadiazole; 5-(phenoxymethyl)-3-(pyridin-2-yl)-1,2,4-oxadiazole; 5-(2-chloro-4-methylphenyl)-3-(pyridin-3-yl)-1,2,4-oxadiazole; 3-(2-chlorophenyl)-5-p-tolyl-1,2,4-oxadiazole; 5-(piperidin-1-ylmethyl)-3-p-tolyl-1,2,4-oxadiazole; 5-(4-bromophenyl)-3-(pyridin-3-yl)-1,2,4-oxadiazole; 5-(2-bromophenyl)-3-(4-bromophenyl)-1,2,4-oxadiazole; 5-(2-bromo-5-methoxyphenyl)-3-(thiophen-2-yl)-1,2,4-oxadiazole; 3-(2-fluorophenyl)-N-(3-(piperidin-1-yl)propyl)-1,2,4-oxadiazol-5-amine; 2-(2-chlorobenzoyl)-N-(4-fluorophenyl)hydrazinecarbothioamide; 2-(methylamino)-N-phenethylbenzamide; 4-tert-butyl-N-((tetrahydrofuran-2-yl)methyl)benzamide; 2-phenyl-5-o-tolyl-1,3,4-oxadiazole; 4-(3-(4-chlorophenyl)-4,5-dihydro-1H-1,2,4-triazol-5-yl)-N,N-dimethylanil-ine; 7-methoxy-2-(4-methoxyphenyl)-1,10b-dihydrospiro[benzo[e]pyrazolo[1,5-c][1,3]oxazine-5,1'-cyclohexane]; 6-oxo-2-(4-(3-(trifluoromethyl)phenoxy)phenyl)-1,4,5,6-tetrahydropyridine-3-carbonitrile; 6-(4-methoxyphenyl)imidazo[2,1-b]thiazole; 2-(2-bromophenoxy)-N-(4H-1,2,4-triazol-3-yl)acetamide; 1-(indolin-1-yl)-2-phenoxyethanone; and 2-(4-chlorophenyl)-6,7,8,9-tetrahydrobenzo[e]imidazo[1,2-b][1,2,4]triazine; and at least one agent that inhibits the expression and/or activity of p27$^{Kip1}$, or a pharmaceutically acceptable salt thereof, wherein the agent that inhibits the expression and/or activity of p27$^{Kip1}$ is a compound having a structure represented by a formula:

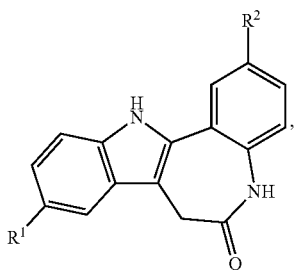

wherein R¹ is selected from hydrogen, halogen, —OH, —CN, —NO₂, —NH₂, —(S=O)—R³, —SO₂—R³, C1-C6 monohaloalk, C1-C6 polyhaloalkyl, C1-C6 alkoxy, C1-C6 cyanoalkyl, C1-C6 aminoalkyl, C1-C6 hydroxyalkyl, C1-C6 monoalkylamino, and C1-C6 dialkylamino; wherein R³ is selected from hydrogen, —CH₃, —CFH₂, —CF₂H, —CF₃, —NH₂, —NH(CH₃), and —N(CH₃)₂; wherein R² is selected from hydrogen, halogen, —OH, —CN, —NO₂, —NH₂, —(S=O)—R⁴, —SO₂—R⁴, C1-C6 monohaloalkyl, C1-C6 polyhaloalkyl, C1-C6 alkoxy, C1-C6 cyanoalkyl, C1-C6 aminoalkyl, C1-C6 hydroxyalkyl, C1-C6 monoalkylamino, and C1-C6 dialkylamino; wherein R⁴ is selected from hydrogen, —CH₃, —CFH₂, —CF₂H, —CF₃, —NH₂, —NH(CH₃), and —N(CH₃)₂; or a pharmaceutically acceptable salt thereof, or a compound selected from

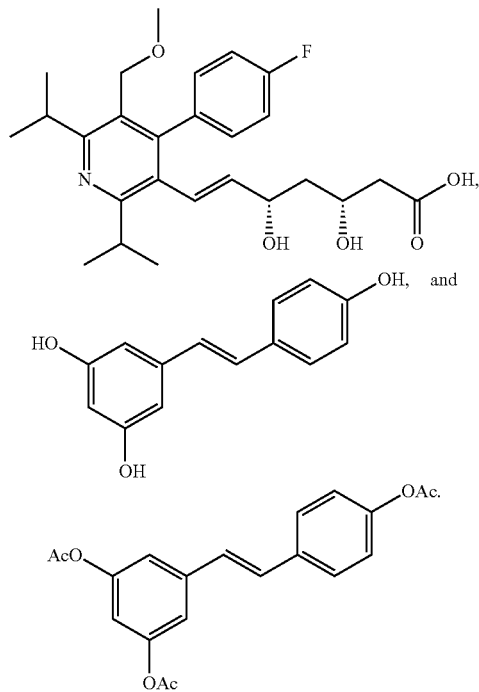

14. The method of claim 9, wherein the agent that activates the expression or activity of Atoh1 and the agent that inhibits the expression or activity of p27^{Kip1} are co-formulated.

15. The method of claim 9, wherein the agent that activates the expression or activity of Atoh1 and the agent that inhibits the expression or activity of p27^{Kip1} are co-packaged.

16. A composition comprising a population of cells made by a method comprising contacting the population of cells with an effective amount of
at least one agent that activates the expression and/or activity of Atoh1, or a pharmaceutically acceptable salt thereof, wherein the agent that activates the expression and/or activity of Atoh1 is a β-catenin protein or a compound selected from 4-(4-chlorophenyl)-1-(5H-pyrimido[5,4-b]indol-4-yl)-1H-pyrazol-3-amine; 6-chloro-1-(2-chlorobenzyloxy)-2-phenyl-1H-benzo[d]imidazole; 6-chloro-1-(2-chlorobenzyloxy)-2-(4-methoxyphenyl)-1H-benzo[d]imidazole; 6-chloro-2-(4-methoxyphenyl)-1-(4-methylbenzyloxy)-1H-benzo[d]imidazole; 6-chloro-1-(3,5-dimethylbenzyloxy)-2-(4-methoxyphenyl)-1H-benzo[d]imidazole; 6-chloro-1-(4-methoxybenzyloxy)-2-(4-methoxyphenyl)-1H-benzo[d]imidazole; 1-(4-methylbenzyloxy)-6-nitro-2-phenyl-1H-benzo[d]imidazole; 4-(1H-benzo[d]imidazol-2-yl)phenol; 2,5-dichloro-N-((1-methyl-1H-benzo[d]limidazol-2-yl)methyl)aniline; 4-(2-(1-methyl-1H-benzo[d]imidazol-2-yl)ethyl)aniline; 2-((2-methoxyphenoxy)methyl)-1H-benzo[d]imidazole; 2-((4-fluorophenoxy)methyl)-1-methyl-1H-benzo[d]imidazole; 2-(phenylthiomethyl)-1H-benzo[d]imidazole; 3-(6-methyl-1H-benzo[d]imidazol-2-yl)-2H-chromen-2-imine; 2-(o-tolyloxymethyl)-1H-benzo[d]limidazole; 2-(4-methoxyphenyl)-1-phenethyl-1H-benzo[d]imidazole; N-(6-bromobenzo[d]thiazol-2-yl)thiophene-2-carboxamide; N-(benzo[d]thiazol-2-yl)-1-methyl-1H-pyrazole-5-carboxamide; 2-(4-fluorobenzylthio)benzo[d]thiazole; 5-chloro-N-methylbenzo[d]thiazol-2-amine; N-(2-(1H-benzo[d]imidazol-2-yl)phenyl)isobutyramide; N-(6-acetamidobenzo[d]thiazol-2-yl)furan-2-carboxamide; N-(6-fluorobenzo[d]thiazol-2-yl)-3-methoxybenzamide; 2-(benzo[d]oxazol-2-ylthio)-N-(2-chlorophenyl)acetamide; 5-chloro-2-phenylbenzo[d]oxazole; 5-methyl-2-m-tolylbenzo[d]oxazole; 2-(4-isobutoxyphenyl)-3-(naphthalen-2-yl)-2,3-dihydroquinazolin-4(1H)-one-; N-(2-(2-(4-fluorophenyl)-2-oxoethylthio)-4-oxoquinazolin-3(4H)-yl)benzam-ide; 2-(4-chlorophenyl)-4-(4-methoxyphenyl)-1,4-dihydrobenzo[4,5]imidazo[1-,2-a]pyrimidine; 2-(3-pyridyl)-4-(4-bromophenyl)-1,4-dihydrobenzo[4,5]imidazo[1,2-a]pyrimi-dine; N-sec-butyl-1,7,7-trimethyl-9-oxo-8,9-dihydro-7H-furo[3,2-f]chromene-2-carboxamide; N-(3-carbamoyl-5,6-dihydro-4H-cyclopenta[b]thiophen-2-yl)benzofuran-2-car-boxamide; 3-chloro-N-(5-chloropyridin-2-yl)benzo[b]thiophene-2-carboxamide-; 3-chloro-N-((tetrahydrofuran-2-yl)methyl)benzo[b]thiophene-2-carboxamide-; N-(3-(5-chloro-3-methylbenzo[b]thiophen-2-yl)-1H-pyrazol-5-yl)acetamide; 2-(naphthalen-2-yl)-1H-indole; 2-(pyridin-2-yl)-1H-indole; N-(2-chlorophenyl)-2-(1H-indol-3-yl)-2-oxoacetamide; 2-m-tolylquinoline; 2-(4-(2-methoxyphenyl)piperazin-1-yl)quinoline; 2-(1H-benzo[d][1,2,3]triazol-1-yl)-N-(2,3-dihydro-1H-inden-2-yl)acetamide-; 1-phenethyl-1H-benzo[d][1,2,3]triazole; 7-(4-fluorobenzyloxy)-2H-chromen-2-one; N-(2,4-dichlorophenyl)-8-methoxy-2H-chromene-3-carboxam-ide; N-(3-chlorophenyl)-8-methyl-3,4-dihydroquinoline-1(2H)-carbothioamide; 7-methoxy-5-methyl-2-phenyl-4H-chromen-4-one; 2-(3,4-dimethylphenyl)quinoxaline; 4-bromo-N-(5-chloropyridin-2-yl)benzamide; 3-amino-6,7,8,9-tetrahydro-5H-cyclohepta[e]thieno[2,3-b]pyridine-2-carbox-amide; (Z)-3-methyl-N'-(nicotinoyloxy)benzimidamide; N,N- diethyl-6-methoxythieno[2,3-b]quinoline-2-carboxamide; 6-(4-methoxyphenyl)-1,2,3,4-tetrahydro-1,5-naphthyridine; 5-bromo-N-(2-(phenylthio)ethyl)nicotinamide; N-(6-methylpyridin-2-yl)-2,3-dihydrobenzo[b][1,4]dioxine-6-carboxamide; 2(4-methylbenzylthio)oxazolo[4,5-b]pyridine; N-(2-methoxyethyl)-5-p-tolylpyrimidin-2-amine; 4-(5-(benzo[b]thiophen-2-yl)pyrimidin-2-yl)morpholine; 4-(5-(4-fluorophenyl)pyrimidin-2-yl)morpholine; N-(4-bromo-3-methylphenyl)quinazolin-4-amine; N-(4-methoxyphenyl)quinazolin-4-amine; N-(3-methoxyphenyl)-9H-purin-6-amine; N,N-diethyl-1-m-tolyl-1H-pyrazolo[3,4-d]pyrimidin-4-amine; (5-(4-bromophenyl)furan-2-yl)(morpholino)methanone; (Z)-4-bromo-N'-(furan-2-carbonyloxy)benzimidamide; N-(4-iodophenyl)furan-2-carboxamide; 5(5-(2,4-difluorophenyl)furan-2-yl)-1-(methylsulfonyl)-1H-pyrazole; 1-(3-amino-5-(4-tert-butylphenyl)thiophen-2-yl)ethanone; N-(3-cyano-4,5,6,7-tetrahydrobenzo[b]thiophen-2-yl)-2-fluorobenzamide; N-(5-chloropyridin-2-yl)thiophene-2-carboxamide; N-(2-(4-fluorophenoxy)ethyl)thiophene-2-carboxamide; 2,5-dimethyl-N-phenyl-1-(thiophen-2-ylmethyl)-1H-pyrrole-3-carboxamide; N-(3-cyanothiophen-2-yl)-4-isopropoxybenzamide; 2-(4-methoxyphenoxy)-N-(thiazol-2-yl)acetamide; 4-(4-methoxyphenyl)-N-(3-methylpyridin-2-yl)thiazol-2-amine; 4-(biphenyl-4-yl)thiazol-2-amine; 4-(4-(4-methoxyphenyl)thiazol-2-yl)-3-methylisoxazol-5-amine; N-(2-methoxyphenyl)-4-phenylthiazol-2-amine; 1-(4-amino-2-(m-tolylamino)thiazol-5-yl)-2-methylpropan-1-one; 4-(4-chlorophenyl)-1-(5H-pyrimido[5,4-b]indol-4-yl)-1H-pyrazol-3-amine; 2-(4-chlorophenyl)-6-ethyl-5-methylpyrazolo[1,5-a]pyrimidin-7(4H)-one; 5-methoxy-2-(5-phenyl-1H-pyrazol-3-yl)phenol; (3-(4-bromophenyl)-1-phenyl-1H-pyrazol-4-yl)methanol; N-(2,5-dichlorophenyl)-1-ethyl-1H-pyrazole-3-carboxamide; 4-chloro-1-methyl-N-(2-oxo-2-phenylethyl)-1H-pyrazole-3-carboxamide; N-(3-(5-tert-butyl-2-methylfuran-3-yl)-1H-pyrazol-5-yl)benzamide; N-(5-methylisoxazol-3-yl)benzo[d][1,3]dioxole-5-carboxamide; (5-(4-bromophenyl)isoxazol-3-yl)(morpholino)methanone; N-(4-bromophenyl)-5-isopropylisoxazole-3-carboxamide; 5-((4-chloro-2-methylphenoxy)methyl)-3-(pyridin-4-yl)-1,2,4-oxadiazole; 5-(2-methoxyphenyl)-3-p-tolyl-1,2,4-oxadiazole; 5-(phenoxymethyl)-3-(pyridin-2-yl)-1,2,4-oxadiazole; 5-(2-chloro-4-methylphenyl)-3-(pyridin-3-yl)-1,2,4-oxadiazole; 3-(2-chlorophenyl)-5-p-tolyl-1,2,4-oxadiazole; 5-(piperidin-1-ylmethyl)-3-p-tolyl-1,2,4-oxadiazole; 5-(4-bromophenyl)-3-(pyridin-3-yl)-1,2,4-oxadiazole; 5-(2-bromophenyl)-3-(4-bromophenyl)-1,2,4-oxadiazole; 5-(2-bromo-5-methoxyphenyl)-3-(thiophen-2-yl)-1,2,4-oxadiazole; 3-(2-fluorophenyl)-N-(3-(piperidin-1-yl)propyl)-1,2,4-oxadiazol-5-amine; 2-(2-chlorobenzoyl)-N-(4-fluorophenyl)hydrazinecarbothioamide; 2-(methylamino)-N-phenethylbenzamide; 4-tert-butyl-N-((tetrahydrofuran-2-yl)methyl)benzamide; 2-phenyl-5-o-tolyl-1,3,4-oxadiazole; 4-(3-(4-chlorophenyl)-4,5-dihydro-1H-1,2,4-triazol-5-yl)-N,N-dimethylanil-ine; 7-methoxy-2-(4-methoxyphenyl)-1,10b-dihydrospiro[benzo[e]pyrazolo[1,5-c][1,3]oxazine-5,1'-cyclohexane]; 6-oxo-2-(4-(3-(trifluoromethyl)phenoxy)phenyl)-1,4,5,6-tetrahydropyridine-3-carbonitrile; 6-(4-methoxyphenyl)imidazo[2,1-b]thiazole; 2-(2-bromophenoxy)-N-(4H-1,2,4-triazol-3-yl)acetamide; 1-(indolin-1-yl)-2-phenoxyethanone; and 2-(4-chlorophenyl)-6,7,8,9-tetrahydrobenzo[e]imidazo[1,2-b][1,2,4]triazine; and at least one agent that inhibits the expression and/or activity of p27$^{Kip1}$, or a pharmaceutically acceptable salt thereof, wherein the agent that inhibits the expression and/or activity of p27$^{Kip1}$ is a compound having a structure represented by a formula:

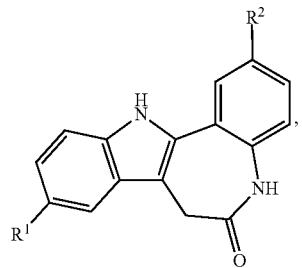

wherein R$^1$ is selected from hydrogen, halogen, —OH, —CN, —NO$_2$, —NH$_2$, —(S═O)—R$^3$, —SO$_2$—R$^3$, C1-C6 monohaloalk, C1-C6 polyhaloalkyl, C1-C6 alkoxy, C1-C6 cyanoalkyl, C1-C6 aminoalkyl, C1-C6 hydroxyalkyl, C1-C6 monoalkylamino, and C1-C6 dialkylamino; wherein R$^3$ is selected from hydrogen, —CH$_3$, —CFH$_2$, —CF$_2$H, —CF$_3$, —NH$_2$, —NH(CH$_3$), and —N(CH$_3$)$_2$; wherein R$^2$ is selected from hydrogen, halogen, —OH, —CN, —NO$_2$, —NH$_2$, —(S═O)—R$^4$, —SO$_2$—R$^4$, C1-C6 monohaloalkyl, C1-C6 polyhaloalkyl, C1-C6 alkoxy, C1-C6 cyanoalkyl, C1-C6 aminoalkyl, C1-C6 hydroxyalkyl, C1-C6 monoalkylamino, and C1-C6 dialkylamino; wherein R$^4$ is selected from hydrogen, —CH$_3$, —CFH$_2$, —CF$_2$H, —CF$_3$, —NH$_2$, —NH(CH$_3$), and —N(CH$_3$)$_2$; or a pharmaceutically acceptable salt thereof, or a compound selected from

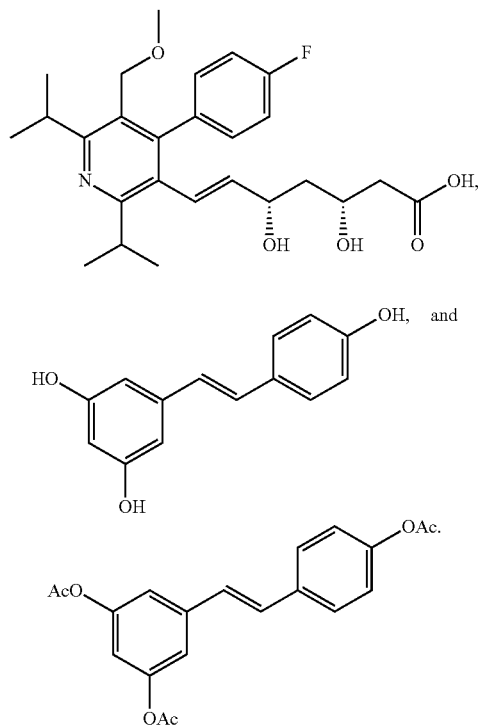

17. A pharmaceutical composition comprising β-catenin and at least one agent that activates the expression and/or activity of Atoh1, or a pharmaceutically acceptable salt thereof, wherein the agent that activates the expression and/or activity of Atoh1 is a β-catenin protein or a compound selected from 4-(4-chlorophenyl)-1-(5H-pyrimido[5,4-b]indol-4-yl)-1H-pyrazol-3-amine; 6-chloro-1-(2-chlorobenzyloxy)-2-phenyl-1H-benzo[d]imidazole; 6-chloro-1-(2-chlorobenzyloxy)-2-(4-methoxyphenyl)-1H-benzo[d]imidazole; 6-chloro-2-(4-methoxyphenyl)-1-(4-methylbenzyloxy)-1H-benzo[d]imidazole; 6-chloro-1-(3,5-dimethylbenzyloxy)-2-(4-methoxyphenyl)-1H-benzo[d]imidazole; 6-chloro-1-(4-methoxybenzyloxy)-2-(4-methoxyphenyl)-1H-benzo[d]imidazole; 1-(4-methylbenzyloxy)-6-nitro-2-phenyl-1H-benzo[d]imidazole; 4-(1H-benzo[d]imidazol-2-yl)phenol; 2,5-dichloro-N-((1-methyl-1H-benzo[d]imidazol-2-yl)methyl)aniline; 4-(2-(1-methyl-1H-benzo[d]imidazol-2-yl)ethyl)aniline; 2-((2-methoxyphenoxy)methyl)-1H-benzo[d]imidazole; 2-((4-fluorophenoxy)methyl)-1-methyl-1H-benzo[d]imidazole; 2-(phenylthiomethyl)-1H-benzo[d]imidazole; 3-(6-methyl-1H-benzo[d]imidazol-2-yl)-2H-chromen-2-imine; 2-(o-tolyloxymethyl)-1H-benzo[d]imidazole; 2-(4-methoxyphenyl)-1-phenethyl-1H-benzo[d]imidazole; N-(6-bromobenzo[d]thiazol-2-yl)thiophene-2-carboxamide; N-(benzo[d]thiazol-2-yl)-1-methyl-1H-pyrazole-5-carboxamide; 2-(4-fluorobenzylthio)benzo[d]thiazole; 5-chloro-N-methylbenzo[d]thiazol-2-amine; N-(2-(1H-benzo[d]imidazol-2-yl)phenyl)isobutyramide; N-(6-acetamidobenzo[d]thiazol-2-yl)furan-2-carboxamide; N-(6-fluorobenzo[d]thiazol-2-yl)-3-methoxybenzamide; 2-(benzo[d]oxazol-2-ylthio)-N-(2-chlorophenyl)acetamide; 5-chloro-2-phenylbenzo[d]oxazole; 5-methyl-2-m-tolylbenzo[d]oxazole; 2-(4-isobutoxyphenyl)-3-(naphthalen-2-yl)-2,3-dihydroquinazolin-4(1H)-one-; N-(2-(2-(4-fluorophenyl)-2-oxoethylthio)-4-oxoquinazolin-3(4H)-yl)benzam-ide; 2-(4-chlorophenyl)-4-(4-methoxyphenyl)-1,4-dihydrobenzo[4,5]imidazo[1-,2-a]pyrimidine; 2-(3-pyridyl)-4-(4-bromophenyl)-1,4-dihydrobenzo[4,5]imidazo[1,2-a]pyrimidine; N-sec-butyl-1,7,7-trimethyl-9-oxo-8,9-dihydro-7H-furo[3,2-f]chromene-2-carboxamide; N-(3-carbamoyl-5,6-dihydro-4H-cyclopenta[b]thiophen-2-yl)benzofuran-2-carboxamide; 3-chloro-N-(5-chloropyridin-2-yl)benzo[b]thiophene-2-carboxamide; 3-chloro-N-((tetrahydrofuran-2-yl)methyl)benzo[b]thiophene-2-carboxamide-; N-(3-(5-chloro-3-methylbenzo[b]thiophen-2-yl)-1H-pyrazol-5-yl)acetamide; 2-(naphthalen-2-yl)-1H-indole; 2-(pyridin-2-yl)-1H-indole; N-(2-chlorophenyl)-2-(1H-indol-3-yl)-2-oxoacetamide; 2-m-tolylquinoline; 2-(4-(2-methoxyphenyl)piperazin-1-yl)quinoline; 2-(1H-benzo[d][1,2,3]triazol-1-yl)-N-(2,3-dihydro-1H-inden-2-yl)acetamide-; 1-phenethyl-1H-benzo[d][1,2,3]triazole; 7-(4-fluorobenzyloxy)-2H-chromen-2-one; N-(2,4-dichlorophenyl)-8-methoxy-2H-chromene-3-carboxamide; N-(3-chlorophenyl)-8-methyl-3,4-dihydroquinoline-1(2H)-carbothioamide; 7-methoxy-5-methyl-2-phenyl-4H-chromen-4-one; 2-(3,4-dimethylphenyl)quinoxaline; 4-bromo-N-(5-chloropyridin-2-yl)benzamide; 3-amino-6,7,8,9-tetrahydro-5H-cyclohepta[e]thieno[2,3-b]pyridine-2-carbox-amide; (Z)-3-methyl-N'-(nicotinoyloxy)benzimidamide; N,N-diethyl-6-methoxythieno[2,3-b]quinoline-2-carboxamide; 6-(4-methoxyphenyl)-1,2,3,4-tetrahydro-1,5-naphthyridine; 5-bromo-N-(2-(phenylthio)ethyl)nicotinamide; N-(6-methylpyridin-2-yl)-2,3-dihydrobenzo[b][1,4]dioxine-6-carbox-amide; 2(4-methylbenzylthio)oxazolo[4,5-b]pyridine; N-(2-methoxyethyl)-5-p-tolylpyrimidin-2-amine; 4-(5-(benzo[b]thiophen-2-yl)pyrimidin-2-yl)morpholine; 4-(5-(4-fluorophenyl)pyrimidin-2-yl)morpholine; N-(4-bromo-3-methylphenyl)quinazolin-4-amine; N-(4-methoxyphenyl)quinazolin-4-amine; N-(3-methoxyphenyl)-9H-purin-6-amine; N,N-diethyl-1-m-tolyl-1H-pyrazolo[3,4-d]pyrimidin-4-amine; (5-(4-bromophenyl)furan-2-yl)(morpholino)methanone; (Z)-4-bromo-N'-(furan-2-carbonyloxy)benzimidamide; N-(4-iodophenyl)furan-2-carboxamide; 5(5-(2,4-difluorophenyl)furan-2-yl)-1-(methylsulfonyl)-1H-pyrazole; 1-(3-amino-5-(4-tert-butylphenyl)thiophen-2-yl)ethanone; N-(3-cyano-4,5,6,7-tetrahydrobenzo[b]thiophen-2-yl)-2-fluorobenzamide; N-(5-chloropyridin-2-yl)thiophene-2-carboxamide; N-(2-(4-fluorophenoxy)ethyl)thiophene-2-carboxamide; 2,5-dimethyl-N-phenyl-1-(thiophen-2-ylmethyl)-1H-pyrrole-3-carboxamide; N-(3-cyanothiophen-2-yl)-4-isopropoxybenzamide; 2-(4-methoxyphenoxy)-N-(thiazol-2-yl)acetamide; 4-(4-methoxyphenyl)-N-(3-methylpyridin-2-yl)thiazol-2-amine; 4-(biphenyl-4-yl)thiazol-2-amine; 4-(4-(4-methoxyphenyl)thiazol-2-yl)-3-methylisoxazol-5-amine; N-(2-methoxyphenyl)-4-phenylthiazol-2-amine; 1-(4-amino-2-(m-tolylamino)thiazol-5-yl)-2-methylpropan-1-one; 4-(4-chlorophenyl)-1-(5H-pyrimido[5,4-b]indol-4-yl)-1H-pyrazol-3-amine; 2-(4-chlorophenyl)-6-ethyl-5-methylpyrazolo[1,5-a]pyrimidin-7(4H)-one; 5-methoxy-2-(5-phenyl-1H-pyrazol-3-yl)phenol; (3-(4-bromophenyl)-1-phenyl-1H-pyrazol-4-yl)methanol; N-(2,5-dichlorophenyl)-1-ethyl-1H-pyrazole-3-carboxamide; 4-chloro-1-methyl-N-(2-oxo-2-phenylethyl)-1H-pyrazole-3-carboxamide; N-(3-(5-tert-butyl-2-methylfuran-3-yl)-1H-pyrazol-5-yl)benzamide; N-(5-methylisoxazol-3-yl)benzo[d][1,3]dioxole-5-carboxamide; (5-(4-bromophenyl)isoxazol-3-yl)(morpholino)methanone; N-(4-bromophenyl)-5-isopropylisoxazole-3-carboxamide; 5-((4-chloro-2-methylphenoxy)methyl)-3-(pyridin-4-yl)-1,2,4-oxadiazole; 5-(2-methoxyphenyl)-3-p-tolyl-1,2,4-oxadiazole; 5-(phenoxymethyl)-3-(pyridin-2-yl)-1,2,4-oxadiazole; 5-(2-chloro-4-methylphenyl)-3-(pyridin-3-yl)-1,2,4-oxadiazole; 3-(2-chlorophenyl)-5-p-tolyl-1,2,4-oxadiazole; 5-(piperidin-1-ylmethyl)-3-p-tolyl-1,2,4-oxadiazole; 5-(4-bromophenyl)-3-(pyridin-3-yl)-1,2,4-oxadiazole; 5-(2-bromophenyl)-3-(4-bromophenyl)-1,2,4-oxadiazole; 5-(2-bromo-5-methoxyphenyl)-3-(thiophen-2-yl)-1,2,4-oxadiazole; 3-(2-fluorophenyl)-N-(3-(piperidin-1-yl)propyl)-1,2,4-oxadiazol-5-amine; 2-(2-chlorobenzoyl)-N-(4-fluorophenyl)hydrazinecarbothioamide; 2-(methylamino)-N-phenethylbenzamide; 4-tert-butyl-N-((tetrahydrofuran-2-yl)methyl)benzamide; 2-phenyl-5-o-tolyl-1,3,4-oxadiazole; 4-(3-(4-chlorophenyl)-4,5-dihydro-1H-1,2,4-triazol-5-yl)-N,N-dimethylanil-ine; 7-methoxy-2-(4-methoxyphenyl)-1,10b-dihydrospiro[benzo[e]pyrazolo[1,5-c][1,3]oxazine-5,1'-cyclohexane]; 6-oxo-2-(4-(3-(trifluoromethyl)phenoxy)phenyl)-1,4,5,6-tetrahydropyridine-3-carbonitrile; 6-(4-methoxyphenyl)imidazo[2,1-b]thiazole; 2-(2-bromophenoxy)-N-(4H-1,2,4-triazol-3-yl)acetamide; 1-(indolin-1-yl)-2-phenoxyethanone; and 2-(4-chlorophenyl)-6,7,8,9-tetrahydrobenzo[e]imidazo[1,2-b][1,2,4]triazine.

18. The composition of claim 17, wherein β-catenin is a β-catenin protein or fragment thereof.

19. The composition of claim 17, wherein β-catenin is a nucleotide encoding a β-catenin protein.

20. The composition of claim 17, wherein the pharmaceutical composition is used to treat hearing impairment.

* * * * *

UNITED STATES PATENT AND TRADEMARK OFFICE
CERTIFICATE OF CORRECTION

PATENT NO.        : 9,572,815 B2
APPLICATION NO.   : 14/774597
DATED             : February 21, 2017
INVENTOR(S)       : Jian Zuo et al.

It is certified that error appears in the above-identified patent and that said Letters Patent is hereby corrected as shown below:

In the Specification

In Column 1, Line 15 – Line 21:
Replace: "This invention was made with U.S. Government support under grant numbers GM086415, DC06471 and CA21765 awarded by the National Institutes of Health (NIH) and grant numbers N000140911014, N000141210191, and N000141210775, awarded by the Office of Naval Research. The U.S. Government has certain rights in the invention."
With: -- This invention was made with government support under grants GM086415, DC006471 and CA021765 awarded by the National Institutes of Health and grants N00014-09-V-1014, N00014-12-V-0191 and N00014-12-V-0775 awarded by the Office of Naval Research. The government has certain rights in the invention. --

Signed and Sealed this
Tenth Day of July, 2018

Andrei Iancu
*Director of the United States Patent and Trademark Office*

SEQUENCE LISTING

```
<160> NUMBER OF SEQ ID NOS: 4

<210> SEQ ID NO 1
<211> LENGTH: 1020
<212> TYPE: DNA
<213> ORGANISM: Homo sapiens
<220> FEATURE:
<221> NAME/KEY: misc_feature
<222> LOCATION: (1)..(1020)
<223> OTHER INFORMATION: Nucleotide sequnce for human Atoh1

<400> SEQUENCE: 1
atgtcccgcc tgctgcatgc agaagagtgg gctgaagtga aggagttggg agaccaccat      60
cgccagcccc agccgcatca tctcccgcaa ccgccgccgc cgccgcagcc acctgcaact     120
ttgcaggcga gagagcatcc cgtctacccg cctgagctgt ccctcctgga cagcaccgac     180
ccacgcgcct ggctggctcc cactttgcag ggcatctgca cggcacgcgc cgcccagtat     240
ttgctacatt ccccggagct gggtgcctca gaggccgctg cgccccggga cgaggtggac     300
ggccgggggg agctggtaag gaggagcagc ggcggtgcca gcagcagcaa gagccccggg     360
ccggtgaaag tgcgggaaca gctgtgcaag ctgaaaggcg gggtggtggt agacgagctg     420
ggctgcagcc gccaacgggc cccttccagc aaacaggtga atggggtgca gaagcagaga     480
cggctagcag ccaacgccag ggagcggcgc aggatgcatg gctgaacca  cgccttcgac     540 cagctgcgca atgttatccc gtcgttcaac aacgacaaga agctgtccaa atatgagacc     600
ctgcagatgg cccaaatcta catcaacgcc ttgtccgagc tgctacaaac gcccagcgga     660
ggggaacagc caccgccgcc tccagcctcc tgcaaaagcg accaccacca ccttcgcacc     720
gcggcctcct atgaaggggg cgcgggcaac gcgaccgcag ctggggctca gcaggcttcc     780
ggagggagcc agcggccgac cccgcccggg agttgccgga ctcgcttctc agccccagct     840
tctgcgggag ggtactcggt gcagctggac gctctgcact tctcgacttt cgaggacagc     900
gccctgacag cgatgatggc gcaaaagaat ttgtctcctt ctctcccggg gagcatcttg     960
cagccagtgc aggaggaaaa cagcaaaact tcgcctcggt cccacagaag cgacggggaa    1020

<210> SEQ ID NO 2
<211> LENGTH: 354
<212> TYPE: PRT
<213> ORGANISM: Homo sapiens
<220> FEATURE:
<221> NAME/KEY: MISC_FEATURE
<222> LOCATION: (1)..(354)
<223> OTHER INFORMATION: Protein is human Atoh1
<220> FEATURE:
```

```
<221> NAME/KEY: MISC_FEATURE
<222> LOCATION: (1)..(354)
<223> OTHER INFORMATION: Protein sequence for human Atoh1

<400> SEQUENCE: 2
```

| | | | | | | | | | | | | | | |
|---|---|---|---|---|---|---|---|---|---|---|---|---|---|---|
| Met | Ser | Arg | Leu | Leu | His | Ala | Glu | Glu | Trp | Ala | Glu | Val | Lys | Glu | Leu |
| 1 | | | | 5 | | | | | 10 | | | | | 15 | |

| Gly | Asp | His | His | Arg | Gln | Pro | Gln | Pro | His | His | Leu | Pro | Gln | Pro | Pro |
|---|---|---|---|---|---|---|---|---|---|---|---|---|---|---|---|
| | | | 20 | | | | 25 | | | | 30 | | | | |

Pro Pro Pro Gln Pro Pro Ala Thr Leu Gln Ala Arg Glu His Pro Val
          35              40              45

Tyr Pro Pro Glu Leu Ser Leu Leu Asp Ser Thr Asp Pro Arg Ala Trp
 50              55              60

Leu Ala Pro Thr Leu Gln Gly Ile Cys Thr Ala Arg Ala Ala Gln Tyr
 65              70              75              80

Leu Leu His Ser Pro Glu Leu Gly Ala Ser Glu Ala Ala Ala Pro Arg
                 85              90              95

Asp Glu Val Asp Gly Arg Gly Glu Leu Val Arg Arg Ser Ser Gly Gly
                100             105             110

Ala Ser Ser Ser Lys Ser Pro Gly Pro Val Lys Val Arg Glu Gln Leu
                115             120             125

Cys Lys Leu Lys Gly Gly Val Val Val Asp Glu Leu Gly Cys Ser Arg
                130             135             140

Gln Arg Ala Pro Ser Ser Lys Gln Val Asn Gly Val Gln Lys Gln Arg
145             150             155             160

Arg Leu Ala Ala Asn Ala Arg Glu Arg Arg Arg Met His Gly Leu Asn
                165             170             175

His Ala Phe Asp Gln Leu Arg Asn Val Ile Pro Ser Phe Asn Asn Asp
                180             185             190

Lys Lys Leu Ser Lys Tyr Glu Thr Leu Gln Met Ala Gln Ile Tyr Ile
                195             200             205

Asn Ala Leu Ser Glu Leu Leu Gln Thr Pro Ser Gly Gly Glu Gln Pro
                210             215             220

Pro Pro Pro Pro Ala Ser Cys Lys Ser Asp His His His Leu Arg Thr
225             230             235             240

Ala Ala Ser Tyr Glu Gly Gly Ala Gly Asn Ala Thr Ala Ala Gly Ala
                245             250             255

Gln Gln Ala Ser Gly Gly Ser Gln Arg Pro Thr Pro Pro Gly Ser Cys
                260             265             270

Arg Thr Arg Phe Ser Ala Pro Ala Ser Ala Gly Gly Tyr Ser Val Gln
                275             280             285

Leu Asp Ala Leu His Phe Ser Thr Phe Glu Asp Ser Ala Leu Thr Ala
                290             295             300

Met Met Ala Gln Lys Asn Leu Ser Pro Ser Leu Pro Gly Ser Ile Leu
305             310             315             320

Gln Pro Val Gln Glu Glu Asn Ser Lys Thr Ser Pro Arg Ser His Arg
                325             330             335

Ser Asp Gly Glu Phe Ser Pro His Ser His Tyr Ser Asp Ser Asp Glu
                340             345             350

Ala Ser

```
<210> SEQ ID NO 3
<211> LENGTH: 2400
<212> TYPE: DNA
<213> ORGANISM: Homo sapiens
```

```
<220> FEATURE:
<221> NAME/KEY: misc_feature
<222> LOCATION: (1)..(2400)
<223> OTHER INFORMATION: Nucleotide sequence for human p27Kip1

<400> SEQUENCE: 3
cttcttcgtc agcctccctt ccaccgccat attgggccac taaaaaaagg gggctcgtct     60
tttcggggtg ttttttctccc cctcccctgt ccccgcttgc tcacggctct gcgactccga    120
cgccggcaag gtttggagag cggctgggtt cgcgggaccc gcgggcttgc acccgcccag    180
actcggacgg gctttgccac cctctccgct tgcctggtcc cctctcctct ccgccctccc    240
gctcgccagt ccatttgatc agcggagact cggcggccgg gccggggctt ccccgcagcc    300
cctgcgcgct cctagagctc gggccgtggc tcgtcggggt ctgtgtcttt tggctccgag    360
ggcagtcgct gggcttccga gaggggttcg ggctgcgtag gggcgctttg ttttgttcgg    420
ttttgttttt ttgagagtgc gagagaggcg gtcgtgcaga cccgggagaa agatgtcaaa    480
cgtgcgagtg tctaacggga gccctagcct ggagcggatg gacgccaggc aggcggagca    540
ccccaagccc tcggcctgca ggaacctctt cggcccggtg gaccacgaag agttaacccg    600
ggacttggag aagcactgca gagacatgga agaggcgagc cagcgcaagt ggaatttcga    660
ttttcagaat cacaaacccc tagagggcaa gtacgagtgg caagaggtgg agaagggcag    720
cttgcccgag ttctactaca gaccccgcg gcccccaaa ggtgcctgca aggtgccggc    780
gcaggagagc caggatgtca gcgggagccg cccggcggcg cctttaattg gggctccggc    840
taactctgag gacacgcatt tggtggaccc aaagactgat ccgtcggaca gccagacggg    900
gttagcggag caatgcgcag gaataaggaa gcgacctgca accgacgatt cttctactca    960
aaacaaaaga gccaacagaa cagaagaaaa tgtttcagac ggttccccaa atgccggttc    1020
tgtggagcag acgcccaaga agcctggcct cagaagacgt caaacgtaaa cagctcgaat    1080
taagaatatg tttccttgtt tatcagatac atcactgctt gatgaagcaa ggaagatata    1140
catgaaaatt ttaaaaatac atatcgctga cttcatggaa tggacatcct gtataagcac    1200
tgaaaaacaa caacacaata acactaaaat tttaggcact cttaaatgat ctgcctctaa    1260
aagcgttgga tgtagcatta tgcaattagg ttttcctta tttgcttcat tgtactacct    1320
gtgtatatag tttttacctt ttatgtagca cataaacttt ggggaaggga gggcagggtg    1380
gggctgagga actgacgtgg agcggggtat gaagagcttg ctttgattta cagcaagtag    1440
ataaatattt gacttgcatg aagagaagca attttgggga agggtttgaa ttgttttctt    1500
taaagatgta atgtccctttt cagagacagc tgatacttca tttaaaaaaa tcacaaaaat    1560
ttgaacactg gctaaagata attgctattt attttacaa gaagtttatt ctcatttggg    1620
agatctggtg atctcccaag ctatctaaag tttgttagat agctgcatgt ggcttttta    1680 aaaaagcaac agaaacctat cctcactgcc ctccccagtc tctcttaaag ttggaattta    1740
ccagttaatt actcagcaga atggtgatca ctccaggtag tttggggcaa aaatccgagg    1800
tgcttgggag ttttgaatgt taagaattga ccatctgctt ttattaaatt tgttgacaaa    1860
attttctcat tttcttttca cttcgggctg tgtaaacaca gtcaaaataa ttctaaatcc    1920
ctcgatattt ttaaagatct gtaagtaact tcacattaaa aaatgaaata ttttttaatt    1980
taaagcttac tctgtccatt tatccacagg aaagtgttat ttttcaagga aggttcatgt    2040
agagaaaagc acacttgtag gataagtgaa atggatacta catctttaaa cagtatttca    2100
ttgcctgtgt atggaaaaac catttgaagt gtacctgtgt acataactct gtaaaaacac    2160
```

```
tgaaaaatta tactaactta tttatgttaa aagattttt ttaatctaga caatatacaa    2220
gccaaagtgg catgttttgt gcatttgtaa atgctgtgtt gggtagaata ggttttcccc    2280
tcttttgtta aataatatgg ctatgcttaa aaggttgcat actgagccaa gtataatttt    2340
ttgtaatgtg tgaaaaagat gccaattatt gttacacatt aagtaatcaa taaagaaaac    2400

<210> SEQ ID NO 4
<211> LENGTH: 198
<212> TYPE: PRT
<213> ORGANISM: Homo sapiens
<220> FEATURE:
<221> NAME/KEY: MISC_FEATURE
<222> LOCATION: (1)..(198)
<223> OTHER INFORMATION: Protein sequence for human p27Kip1

<400> SEQUENCE: 4

Met Ser Asn Val Arg Val Ser Asn Gly Ser Pro Ser Leu Glu Arg Met
 1               5                  10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
        195
```